(12) United States Patent
Brook et al.

(10) Patent No.: US 7,750,036 B2
(45) Date of Patent: Jul. 6, 2010

(54) CARVEDILOL SALTS, CORRESPONDING COMPOSITIONS, METHODS OF DELIVERY AND/OR TREATMENT

(75) Inventors: Christopher S. Brook, King of Prussia, PA (US); Pingyun Y. Chen, Indianapolis, IN (US); Wei Chen, Woodbury, MN (US); Qunying Dai, King of Prussia, PA (US); Philip C. Dell'Orco, King of Prussia, PA (US); Clifford S. Labaw, King of Prussia, PA (US); Ann Marie Diederich, King of Prussia, PA (US); Choon K. Oh, Collegeville, PA (US); Claire Hisler, Meyzieu (FR); David H. Igo, Research Triangle Park, NC (US); Lee M. Katrincic, King of Prussia, PA (US); Li-Jen Ping, King of Prussia, PA (US); Paul G. Spoors, King of Prussia, PA (US); Jun Wang, King of Prussia, PA (US); Christopher Werner, King of Prussia, PA (US)

(73) Assignee: SB Pharmco Puerto Rico Inc., Hato Rey, PR (US)

( * ) Notice: Subject to any disclaimer, the term of this patent is extended or adjusted under 35 U.S.C. 154(b) by 1353 days.

(21) Appl. No.: 10/997,230

(22) Filed: Nov. 24, 2004

(65) Prior Publication Data

US 2005/0277689 A1 Dec. 15, 2005

(51) Int. Cl.
  A61K 31/403 (2006.01)
  C07D 209/82 (2006.01)
(52) U.S. Cl. ........................ 514/411; 548/440
(58) Field of Classification Search ................ 514/411; 548/440
See application file for complete search history.

(56) References Cited

U.S. PATENT DOCUMENTS

| | | | |
|---|---|---|---|
| 4,503,067 A * | 3/1985 | Wiedemann et al. | ........ 514/411 |
| 4,697,022 A | 9/1987 | Leinert | |
| 4,824,963 A | 4/1989 | Leinert | |
| 4,888,179 A | 12/1989 | Applegren | |
| 4,985,454 A | 1/1991 | Leinert | |
| 5,071,868 A | 12/1991 | Leinert | |
| 5,308,862 A | 5/1994 | Ohlstein | |
| 5,312,828 A | 5/1994 | Finkeistein | |
| 5,393,772 A | 2/1995 | Yue et al. | |
| 5,405,863 A | 4/1995 | Barone et al. | |
| 5,453,436 A | 9/1995 | Ohlstein | |
| 5,643,939 A | 7/1997 | Ohlstein | |
| 5,760,069 A | 6/1998 | Lukas-Laskey et al. | |
| 5,902,821 A | 5/1999 | Lukas-Laskey et al. | |
| 6,096,777 A | 8/2000 | Feuerstein et al. | |
| 6,214,854 B1 | 4/2001 | Wang et al. | |
| 6,358,990 B1 | 3/2002 | Howlett et al. | |
| 6,403,579 B1 | 6/2002 | Heller | |
| 6,515,010 B1 | 2/2003 | Franchini et al. | |
| 6,699,997 B2 | 3/2004 | Hildesheim et al. | |
| 6,852,337 B2 | 2/2005 | Gabel et al. | |
| 7,056,942 B2 | 6/2006 | Hildesheim et al. | |
| 7,126,008 B2 | 10/2006 | Hildesheim et al. | |
| 7,268,156 B2 | 9/2007 | Brook et al. | |
| RE40,000 E | 1/2008 | Lukas-Laskey et al. | |
| RE40,707 E | 5/2009 | Lukas-Laskey et al. | |
| 2001/0036959 A1 | 11/2001 | Gabel et al. | |
| 2001/0036960 A1 | 11/2001 | Decker et al. | |
| 2002/0052367 A1 | 5/2002 | Heller | |
| 2002/0068740 A1 | 6/2002 | Mylari | |
| 2002/0099013 A1 | 7/2002 | Piccariello et al. | |
| 2002/0099046 A1 | 7/2002 | Scott | |
| 2002/0107279 A1 | 8/2002 | Barone et al. | |
| 2002/0115655 A1 | 8/2002 | Mehanna et al. | |
| 2002/0143045 A1 | 10/2002 | Hildesheim et al. | |

(Continued)

FOREIGN PATENT DOCUMENTS

WO   WO98/02157   1/1998

(Continued)

OTHER PUBLICATIONS

U.S. Appl. No. 10/513,234, filed May 3, 2002 PCT/US03/14021 Filed: May 3, 2002 WO03/092626 Pub. Date: Nov. 13, 2003, Oh.
U.S. Appl. No. 10/513,235, filed Nov. 2, 2004 PCT/US03/14020 Filed: May 3, 2002 WO03/092626 Pub. Date: Nov. 13, 2003, Oh et al.
U.S. Appl. No. 10/518,206, filed Dec. 16, 2004 PCT/US03/20346 Filed: Jun. 27, 2002 WO04/002472 Pub. Date: Jan. 8, 2004, Chen et al.
U.S. Appl. No. 10/997,230, filed Nov. 24, 2004 PCT/US04/039528 Filed: Nov. 24, 2004 WO05/051383 Pub. Date: Jun. 9, 2005, Brook et al.

(Continued)

Primary Examiner—Kamal A Saeed
Assistant Examiner—Janet L Coppins
(74) Attorney, Agent, or Firm—Grace Hsu; John Lemanowicz

(57) ABSTRACT

The present invention relates to a salt of carvedilol and/or corresponding solvates thereof, compositions containing such carvedilol and/or corresponding solvates thereof, and/or methods of using the aforementioned compound(s) in the treatment of certain disease states in mammals, in particular man.

The present invention further relates to carvedilol phosphate salts, and/or solvates thereof, which include a novel crystalline form of carvedilol dihydrogen phosphate (i.e., which is the dihydrogen phosphate salt of 1-(carbazol-4-yloxy-3-[[2-(o-methoxyphenoxy)ethyl]amino]-2-propanol) and/or carvedilol hydrogen phosphate, etc.) and/or other corresponding solvates thereof, compositions containing these carvedilol phosphate salts and/or solvates, and methods of using the aforementioned salts and/or solvates to treat hypertension, congestive heart failure and angina, etc.

48 Claims, 130 Drawing Sheets

U.S. PATENT DOCUMENTS

| | | |
|---|---|---|
| 2002/0169199 A1 | 11/2002 | Gruber et al. |
| 2003/0004205 A1 | 1/2003 | Gabel et al. |
| 2003/0004206 A1 | 1/2003 | Decker et al. |
| 2003/0035836 A1 | 2/2003 | Shanghvi et al. |
| 2003/0036559 A1 | 2/2003 | Beyer et al. |
| 2003/0050301 A1 | 3/2003 | Mylari |
| 2003/0054041 A1 | 3/2003 | Lemmens et al. |
| 2003/0166702 A1 | 9/2003 | Kor et al. |
| 2004/0019096 A1 | 1/2004 | Oh et al. |
| 2004/0152756 A1 | 8/2004 | Chen et al. |
| 2004/0186158 A1 | 9/2004 | Oh |
| 2004/0220250 A1 | 11/2004 | Oh |
| 2005/0009897 A1 | 1/2005 | Anderson et al. |
| 2005/0148779 A1 | 7/2005 | Oh et al. |
| 2005/0169994 A1 | 8/2005 | Burke et al. |
| 2007/0142451 A1 | 6/2007 | Chen et al. |
| 2007/0238774 A1 | 10/2007 | Brook et al. |
| 2007/0244181 A1 | 10/2007 | Brook et al. |
| 2007/0244182 A1 | 10/2007 | Brook et al. |
| 2007/0259940 A1 | 11/2007 | Brook et al. |
| 2008/0096951 A1 | 4/2008 | Chen et al. |
| 2008/0262069 A1 | 10/2008 | Brook et al. |

FOREIGN PATENT DOCUMENTS

| | | |
|---|---|---|
| WO | WO99/05105 A1 | 2/1999 |
| WO | WO99/52526 | 10/1999 |
| WO | WO00/04902 | 2/2000 |
| WO | WO00/32174 | 6/2000 |
| WO | WO01/74356 | 10/2001 |
| WO | WO01/87837 A1 | 11/2001 |
| WO | WO02/00216 A1 | 1/2002 |
| WO | WO02/092078 | 11/2002 |
| WO | WO03/007962 | 1/2003 |
| WO | WO03/024426 | 3/2003 |
| WO | WO03/024429 | 3/2003 |
| WO | WO03/028645 | 4/2003 |
| WO | WO03/028718 | 4/2003 |
| WO | WO2004/009120 | 1/2004 |
| WO | WO2004/016249 | 2/2004 |
| WO | WO2004/041252 | 5/2004 |
| WO | WO2004/056336 | 7/2004 |

OTHER PUBLICATIONS

PCT/US04/039614 Filed: Nov. 24, 2004 WO05/051322 Pub. Date: Jun. 9, 2005, Pub. Date: Aug. 11, 2005, Castan et al.

U.S. Appl. No. 11/137,261, filed May 25, 2005, Burke et al., CIP U.S. Appl. No. 10/996,904, filed Nov. 24, 2004.

Phadnis et al., "Identification of Drugs in Pharmaceutical Dosage Forms by X-Ray Powder Diffractometry", J. of Pharm. and Biomed. Analysis, 1997,15, 929-943.

Taday et al., "Using Terahertz Pulse Spectroscopy to Study the Crystalline Structure of a Drug: A Case Study of the Polymorphs of Ranitidine Hydrochloride", J. of Pharm. Sci., 2003, vol. 92, No. 4, 831-838 (2003).

Chakravarty et al., Crystal Forms of Tolbutamide from Acetonitrile and 1-Octanol: Effect of Solvent, Humidity and Compression Pressure, Intern. 'l J. of Pharmaceutics, 2005, 288, 335-348.

TransForm Pharmaceuticals, "Carvedilol Phosphate Solid Form Screening, Final Report", Apr. 19, 2004, pp. 1-67.

KSR v. Teleflex, Wikipedia, The Free Encyclopedia, pp. 1-3 (see Footnote 6 at p. 3, lines 14-17).

Berge et. al., "Pharmaceutical Salts", J. Pharm. Sciences, 66: 1-19, 1977.

Shanker et al., "Selection of Appropriate Salt Form(s) for New Drug Candidates", Pharm. Res. 11:S-236, 1995.

Bryn et al., "Pharmaceutical Solids: A Strategic Approach to Regulatory Considerations", Pharmaceutical Research (1995), 12 (7), pp. 945-954.

Davies et al., Changing the Salt Form of a Drug Affects Its Clinical Efficacy and Safety, The Pharmaceutical Journal (2001), 266(7), pp. 322-323.

U.S. Office Action of U.S. Appl. No. 11/767,573, Dated: Mar. 31, 2008 and Dec. 10, 2008.

U.S. Office Action of U.S. Appl. No. 11/767,581, Dated: Apr. 10, 2008 andNov. 26, 2008.

U.S. Office Action of U.S. Appl. No. 11/767,586, Dated: Mar. 31, 2008 and Dec 1, 2008.

U.S. Office Action of U.S. Appl. No. 11/767,566, Dated: Apr. 4, 2008 and Dec. 18, 2008.

U.S. Office Action of U.S. Appl. No. 10/483,217, Dated: Jul. 18, 2006.

U.S. Office Actions of U.S. Appl. No. 10/512,628, Dated: Oct. 4, 2007 and Mar. 30, 2007.

U.S. Office Actions of U.S. Appl. No. 10/518,206, Dated: Dec. 5, 2005 and Jul. 13, 2006.

U.S.P.T.O. Biotechnology/Chemical/Pharmaceutical Customer Partnership Meeting, Jun. 13, 2006, Slide Lecture on: Polymorphs in Pharmaceutical Products, Presenter: Christopher Low, tQAS, TC1600.

U.S.P.T.O. Board of Patent Appeals and Interferences Decision: Ex parte Buchi Reddy Reguri and Sudhakar Sunkari ("Ex parte Buchi"), Appeal 2007-0313, U.S. Appl. No. 10/414,447, Technology Center 1600, Decided: Sep. 6, 2007.

Swedberg, Karl et al., "Prolongation of Survival in Congestive Cardiomyopathy by Beta Receptor Blockade," Lancet 1374-1376 (Jun. 30, 2979).

Pritchard, B.N.C. and Tomlinson b., "Choice of Antihypertensive Drug Therapy," American Heart Journal; 114 (4): 1030-40 (Oct. 1987).

Das Gupta, et al., "Improvement in congestive heart failure following chronic therapy with a new vasodilating bctablockcr Carvcdilol," Circulation, vol. 80 No. 4, Suppl 2, II-117 (1989).

DiBanco, Robert et al., "A comparison of Oral Milrinone, Digoxin, and Their Combination in the Treatment of Patients with Chronic Heart Failure," New England J. Med., vol. 320, No. 11, 677-683 (Mar. 16, 1989).

Das Gupta, P. et al., "Value of carvedilol in congestive heart failure secondary to coronary artery disease," American Journal of Cardiology, vol. 66, No. 15, pp. 1118-1123, (Nov. 1, 1990).

Krukemyer, J., "Use of Beta-Adrenergic Blocking Agents in Congestive Heart Failure," Clin Pharm 9(11):853-63 (Nov. 1990).

Strein, K. and Sponer, G, "experimental and clinical pharmacology of carvedilol and other drugs combining vasodilation and beta-adrenoceptor antagonism in a single molecule," z Kariol 79 Suppl. 3, pp. 89-98 (1990).

Das Gupta, P. et al., "The effects of intravenous carvedilol, a new multiple action vasodilatory beta-blocker, in congestive heart failure.," J Cardiovasc Pharmacol, vol. 18, Suppl. 4, pp. S 12-S 16 (1991).

Di Lenarda, Andrea, "Acute Hemodynamic Effects of Carvedilol Versus Metoprolol in Idiopathic Dilated Cardiomyopathy.," Abstract—JACC vol. 17(2), 142A (Feb. 1991).

Hamburger, S.A., et al., "Carvedilol (Kredex®) reduces infact size in a canine model of acute myocardial infarction," Pharmacology, vol. 43, pp. 113-120 (1991).

Ruffolo, R., et al., "Carvedilol (Kredex®): A Novel Multiple Action Cardiovascular Agent,," Drugs of Today 27(7): 465-492 (1991).

Bristow, M.R. et al., "Effects of carvedilol on adrenergic receptor pharmacology in human ventricular myocardium and lymphocytes," Clinical Investig 70 Suppl 1: S105-13 (1992).

Das Gupta, P. et al., "Can intravenous beta-blockade predict long-term hemodynamic benefit in chronic congestive heart failure secondary to ischemic heart disease?" J. Cardiovasc Pharmacol, vol. 19, Suppl. I, pp. S62-S67 (1992).

De Cree, J. et al., "Comparative cardiac haemodynamics of bisoprolol, celiprolol, carvedilol and nebivolol in normal volunteers," Int J Clin Pharmacol Res., vol. 12, No. 4, pp. 159-163 (1992).

Feuerstein, G.Z., et al., "Myocardial protection with Carvedilol," J Cardiovasc Pharmacol, vol. 19, Suppl. 1, pp. S138-S141 (1992).

Senior, R.; Muller-Beckmann, b., Das Gupta, P., van der Does, R. and Lahiri, A. "Effects of carvedilol on ventricular arrhythmias," J Cardiovasc Pharmacol 19 Suppl. 1:S117-121 (1992).

Sponer, G. et al., "Vasodilatory action of Carvedilol," J Cardiovasc Pharmacol 19 Suppl 1:S5-11 (1992).

Bristow, M.R., "Pathophysiologic and Pharmacologic Rationales for Clinical Management of Chronic Heart Failure with Beta-Blocking Agents," Am J Cardiol 71(9):12C-22C (1993).

Cheng, H.-Y., et al., "Physical chemical investigation of antioxidant properties of carvedilol a cadioprotective drug," International Congress Series No. 1058, Frontiers of reactive oxygen species in biology and medicine, 349-350 (1994).

Feuerstein, G.z., et al., "Myocardiol protection by the novel vasodilating beta-blocker, carvedilol: potential relevance of anti-oxidant activity," J Hypertens, vol. 11, No. Suppl. 4, pp. S41-S48 (Jun. 1993).

Fowler, M.B., "Controlled trials with beta blockers in heart failure: metoprolol as the prototype," Am J Cardiol vol. 71, No. 9, pp. 45C-53C (Mar. 25, 1993).

Kelly, David T., "Carvedilol in Heart Failure," Cardiology 82 (suppl3): 45-49 (1993).

Krum, Henry et al., "Controlled Clinical Trials in Heart Failure I: Beta-Blockers," JACC vol. 21, No. 2: 114A, Abstract 725-1 (Feb. 1993).

Lessem, J. N. and Lukas, M.A., "Development of a multiaction beta blocker. Scientific challenges and regulatory needs," Cardiology vol. 82, Suppl 3, pp. 50-58 (1993).

McTavish, Donna, et al., "Carvedilol: A Review of its Pharmacodyanamic and Pharmacokinetic Properties, and Therapeutic Efficacy," Drugs, vol. 45, No. 2, pp. 232-258 (Feb. 1993).

Ohlstein, E.H. et al., "Carvedilol, a cardiovascular drug, prevents vascular smooth muscle cell proliferation, migration, and neointimal formation following vascular injury," Proc Natl. Acad, Sci U.S.A., vol. 90, No. 13, pp. 6189-6193 (Jul. 1993).

Olsen, Stephanie et al., "Controlled Clinical Trials in Heart Failure I: Beta Blockers," JACC vol. 21, No. 2:141A, Abstract 725-2 (Feb. 1993).

Metra, M. et al., "Effects of acute and chronic Carvedilol on resting and exercise hemodynamics of patients with idiopathic cardiomyopathy," JACC vol. 21, No. 2:141A, Abstract 725-3 (Feb. 1993).

Rosendorff, C., "Beta-blocking agents with vasodilator activity," J Hypertens Suppl vol. 11, No. 4, pp. S37-S40 (Jun. 1993).

Ruffolo, R.R. et al., "Preclinical and clinical pharmacology of Carvedilol," J Hum Hypertens vol. 7 Suppl. 1, pp. S2-S15 (Feb. 1993).

Waagstein, Finn, "Beneficial Effects of metoprolol in idiopathic dilated cardiomyopathy," Lancet, vol. 342, 1441-46 (Dec. 11, 1993).

Unknown, "SB to file seven NDAs launch Havrix hepatitis A vaccine in 1995; No major drugs come off patent through 2000: Genomics work as synergy with diagnostics—BBS," F-C-D Reports—"The Pink Sheet", vol. 56, No. 51, pp. 17-18 (Dec. 19, 1994).

CIBIS Investigators and Committees, "A Randomized Trial of Beta-Blockade in Heart Failure—The Cardiac Insufficiency Bisoprolol Study (CIBIS)," Circulation, vol. 90(4), 1765-1773 (1994).

Doughty, R.N. et al., "Beta-Blockers in Heart Failure: Promising or Proved?" J Am Coll Cardiol 23(3):814-21 (1994).

Hampton, J. R., "Choosing the right beta-blocker. A guide to selection," Drugs 48(4):549-68 (Oct. 1994).

Hjalmarson, Ake et al., "The Role of Beta-Blockers in the Treatment of Cardiomyopathy and Ischaemic Heart Failure," Drugs 47 (Suppl. 4): 31-40 (1994).

Louis, W.J. et al., "A risk-benefit assessment of carvedilol in the treatment of vardiovascular disorders," Drugs Safety 11(2):86-93 (Aug. 1994).

Metra, Marco et al., "Effects of Short- and Long-Term Carvedilol Administration on Rest and Exercise Hemodynamic Variables, Exercise Capacity and Clinical Conditions in Patients witih Idiopathic Dilated Cardiomyopathy," J Am Coll Cardiol vol. 24, No. 7 1678-87 (Dec. 1994).

Unknown, "Smithkline Expands Testing of Carvedilol Due to Effectiveness, "Wall St. J. (Midwest Ed) 76(82):B7 (1995).

Unknown, "Survival Chance Improved—BBS," Manufacturing Chemist 66(12):13 (Dec. 1995).

Unkown, "Low dose carvedilol trial success," Pharmaceutical Journal 255(6868):719 (Nov. 1995).

Unknown, "SmithKline Beecham COREG (carvedilol) decreases mortality by 67%—BBS," F-D-C Reports—"The Pink Sheet" vol. 57, No. 47: (T & G 14- T & G 15) (Nov. 20, 1995).

Unknown, "Success halts US trials of carvedilol—BBS," Pharmaceutical Journal, vol. 254, No. 6828, p. 216 (Feb. 18, 1995).

Unknown, "SmithKline expands testing on carvedilol due to effectiveness—BBS," Wall Street Journal, vol. 225, No. 28 p. B6 (Feb. 9, 1995).

Unknown, "Smithkline Beecham/Boehringer Mannheim, UK/Germany: Carvedilol marketed," Bulletin International d'Informations (Droit et Pharmacie) No. 10, pp. 82-83 (Oct. 23, 1995).

Unknown, "SmithKline Beecham to stop its placebo controlled trials for carvedilol in the US," European Chemical News vol. 63, No. 1654, p. 23 (Feb. 1995).

Unknown, "Boerhringer Mannheim and SmithKline Beecham strengthen collaborations to market Carvedilol worldwide," Press Release, p. 1 (Oct. 5, 1995).

Unknown, "SmithKline Beecham: unexpected success halts drug trial," Chemistry and Industry (London): No. 4, p. 123 (Feb. 20, 1995).

Green, Daniel, "UK Company News: SB heart drug proves effective," Financial Times, p. 26 (Feb. 9, 1995).

Australia—New Zealand Heart Failure Research Collaborative Group, "Effects of carvedilol, a vasodilator-beta blocker, in patients with congestive heart failure due to ischemic heart disease," Circulation vol. 92, No. 2, pp. 212-218 (Jul. 15, 1995).

Colucci, W.S. et al., "Carvedilol inhibits clinical progression in patients with mild heart failure—BIO," Circulation, vol. 92, No. 9, Suppl., p. I-395, Abstract 1884 (1995).

Ghali, J.K., "Carvedilol Therapy in Heart Failure—I," J Am Coll Cardiol 26(5):1399 (1995).

Bristow, M.R. et al., "The B-Blocking Agents Metopolol And Carvedilol Affect Cardiac Adrenergic Drive Differently In Subjects With Heart Failure From Idiopathic Dilated Cardiomyopathy," JACC, 21(2), 314A (Feb. 1993) (Abstract).

Diehm, C., Antihypertensive Therapy In Arterial Occlusive Disease, Vasa Suppl., 33, 71-4 (1991) (English Summary).

Olsen, S.L., et al., "B-Blocker Related Improvement In Submaximal Exercise Tolerance In Heart Failure From Idiopathic Dilated Cardiomyopathy (IDC)", JACC, 19, Mar. 1, 1992, 146A, Abstract 747-5.

Carbajal, E.V., "Carvedilol Therapy In Heart Failure—II" J Am Coll Cardiol 26(5):1399-1400 (1995).

Lee, Y.C., "Carvedilol Therapy In Heart Failure—III and Reply," J Am Coll Cardiol 26(5): 1400-1401 (1995).

Feuerstein et al., "Carvedilol Update III: Rationale For Use In Congestive Heart Failure," Drugs Of Today, vol. 31 (Suppl. F) pp. 1-23 (Feb. 1995).

Krum, Henry et al., "Double0Blind, Placebo-Controlled Study Of The Long-Term Efficacy Of Carvedilol In Patients With Severe Chronic Heart Failure," Circulation 92(6): 1499-1506 (1995).

Lahiri, A. et al., "Reduction Of Adverse Cardiac Events By Carvedilol After Acute Myocardial Infarction," European Heart Journal 16(Abst.Suppl.), p. 36, Abstract P306 (1995).

Olsen, S.L. et al., "Carvedilol Improves Left Ventricular Function And Symptoms In Chronic Heart Failure: A Double-Blind Randomized Study," J Am Coll Cardiol 25(6):1225-31 (1995).

Raftery, E.B., "Vasodilating Beta-Blockers In Heart Failure," Eur Heart J 16 Suppl F:32-7 Erratum in Eur Heart J 16(10): 1451 (1995).

Sackner-Bemstein, J. And Mancin, D.M., "Rationale For Treatment Of Patients With Chronic Heart Failure With Adrenergic Blockade," JAMA vol. 274, No. 18, pp. 1462-1467 (1995).

Tham, T.C.K. et al., "The Dose Dependency Of The Alpha- And Beta- Adrenoceptor Antagonist Activity Of Carvedilol In Man," Br J Clin Pharmacol 40(1): 19-23 (1995).

Welter, E.A. And Semchuk, W.M., "The Role Of Beta-Blockers In Congestive Heart Failure," J Can Pharm Hosp 48(6):328-35 (1995).

White, M. et al., "What Patient With Congestive Heart Failure Respond To Beta-Blocking Agents: A Meta-Analysis," Journal Of Heart And Lung Transplantation vol. 14, No. 1, p. S85, Abstract 196 (1995).

Winslow, R., "Experimental Smithkline Drug Shown To Combat Congestive Heart Failure—BBS," Wall Street Journal vol. 226, No. 95, p. B 14 (1995).

Bonarjee, V.V. And Dickstein, K., "Novel Drugs And Current Therapeutic Approaches In The Treatment Of Heart Failure," Drugs 51(3): 347-58 (1996).

Dracup, K., "Heart Failure Secondary To Left Ventricular Systolic Dysfunction. Therapeutic Advances And Treatment Recommendations," Nurse Pract 21(9):57,58,61,65-68 (1996).

Feuerstein, G.Z. And Ruffolo, R.R., "Carvedilol, A Novel Vasodilating Beta-Blocker With The Potential For Cardiovascular Organ Protection," Eur Heart J 17 Suppl B:24-9 (1996).

Krum, H. et al., "Changes In Plasma Endothelin-1 Levels Reflect Clinical Response To Beta-Blockade In Chronic Heart Failure," Am Heart J 131(2):337-41 (1996).

Packer, M. et al., "The Effect Of Carvedilol On Morbidity And Mortality In Patients With Chronic Heart Failure. U.S. Carvedilol Heart Failure Study Group," N Engl J Med Med 334(21):1349-55 (1996).

Raftery, E.B. "The Preventative Effects Of Vasodilating Beta-Blockers In Cardiovascular Disease," Eur Heart J 17 Suppl B:30-8 (1996).

Sharpe, N., Beta-Blockers In Heart Failure. Future Directions, Eur Heart J 17 Suppl B:39-42 (Apr. 1996).

Beta-Blocker Evaluation Of Survival Trial Investigators, "A Trial Of The Beta-Blocker Bucindolol In Patients With Advanced Chronic Heart Failure," New England J. Med. 344(22), 1659-1667 (2001).

Ruffolo, R.R. et al., "Cardioprotective Potential Of Carvedilol," Cardiology, 82(Supp13), 24-28 (1993).

Cohn, J. N. et al., "Effect Of Vasodilator Therapy On Mortality In Chronic Congestive Heart Failure," New England J. Med. 314(24), 1547-52 (1986).

Whitfield, H.N. et al., "The Effect Of Adrenergic Blocking Drugs On Outflow Resistance" Brit. J. Urology, 47, 823-827 (1976).

Caine, M. et al., "The Use Of Alpha-Adrenergic Blockers In Benign Prostatic Obstruction," Brit. J. Urology, 48, 255-263 (1976).

Buchwald, A. et al., Z. Kardiol, 79, 424-28 (1990) (English Abstract).

Tepper, D., "Multicenter Oral Carvedilol Heart Failure Assessment (MOCHA)," Frontiers in CHF 2(1), 39-40 (1996).

Waagstein, F. et al., "Effect Of Chronic Beta-Adrenergic Receptor Blockade In Congestive Cardiomyopathy," Brit. Heart J., 37, 1022-36 (1975).

Waagstein F. et al., "Beta-Blockers In Dilated Cardiomyopathies: They Work," Eur Heart J., 4(Supp A), 173-178 (1983).

Swedberg, K. et al., "Beneficial Effects Of Long-Term Beta-Blockade In Congestive Cardiomyopathy," Brit Heart J., 44, 117-33 (1980).

Swedberg, K. et al., "Adverse Effects Of Beta-Blockade Withdrawal In Patients With Congestive Cardiomyopathy," Brit Heart J., 44, 134-42 (1980).

Drexler, H. et al., Characterization Of Skeletal Muscle β-Adrenergic Receptors In Patients With Chronic Heart Failure, Circulation 80(4), II-116 (1989) (Abstract).

Sponer, G. et al., "Pharmocological Profile Of β-Adrenoceptor Blockers With Vasodilating Properties, Especially Carvedilol—Rationale For Clinical Use," Clin. Investig., 70, S20-S26 (1992).

Lessem, J.N., Weber, M.A., "Antihypertensive Treatment With A Dual-Acting Beta-Blocker In The Elderly," J. Hypertens Suppl., 11(4), S29-36 (1993).

Harder S. et al., "Lack Of Pharmacokinetic Interaction Between Carvedilol And Digitoxin Or Phenprocoumon," Eur. J. Clin Pharmacol, 44(6), 583-6 (1993).

Australia/New Zealand Heart Failure Research Collaborative Group, "Randomised Placebo-Controlled Trial Of Carvedilol In Patients With Congestive Heart Failure Due To Ischaemic Heart Disease," Lancet, 349, 375-80 (1997).

Cleland et al., "Clinical Trials Update From The American College Of Cardiology: Darbepoetin Alfa, Asteroid Universae, Paediatric Carvedilol, Unload And Iceland," Euopean Journal Of Heart Failure, 8, pp. 326-329, 2006.

Shaddy et al., "The Pediatric Randomized Carvedilol Trial In Children With Chronic Heart Failure: Rationale And Design," American Heart Journal, vol. 144, No. 3, pp. 383-389, (2002).

Eggertsen et al., Eur. J. Clinical Pharmacology, (1984), 27: 19-22.

Schnurr et al., Journal Of Cardiovascular Pharmacology, (1987), 19(Suppl. 11)S101-S107.

* cited by examiner

FT-IR Spectrum of Carvedilol Mandelate

FT-Raman Spectrum of Carvedilol Lactate pH-solubility profile for carvedilol.

Mean plasma profiles in beagle dogs following intra-colonic administration of a carvedilol solution containing Captisol or carvedilol in aqueous suspension.

Dissolution/Solubility profile of carvedilol phosphate in pH7.1 Tris buffer (for comparison, carvedilol free base has a solubility of ~20-30 ug/mL at this pH).

Mean plasma profiles in beagle dogs following oral administration of the formulations listed in Table 16.

Mean plasma profiles following oral administration of Companion capsules filled with four formulations at 10 mg strength to Beagle dogs.

CARVEDILOL SALTS, CORRESPONDING COMPOSITIONS, METHODS OF DELIVERY AND/OR TREATMENT

FIELD OF THE INVENTION

The present invention relates to salts of carvedilol, corresponding anhydrous forms or solvates thereof, pharmaceutical compositions, and/or methods of using the aforementioned compound(s) in treatment of certain disease states in mammals, in particular man.

The present invention further relates to a novel crystalline salt or solvate form of carvedilol, a salt of 1-(carbazol-4-yloxy-3-[[2-(o-methoxyphenoxy)ethyl]amino]-2-propanol), corresponding pharmaceutical compositions (i.e., containing such salts, anhydrous forms or solvates thereof, etc.) and methods of using the aforementioned compound(s) and/or pharmaceutical compositions to treat cardiovascular diseases, which may include, but are not limited to hypertension, congestive heart failure, and angina.

BACKGROUND OF THE INVENTION

The compound, 1-(carbazol-4-yloxy-3-[[2-(o-methoxyphenoxy)ethyl]-amino]-2-propanol is known as Carvedilol. Carvedilol is depicted by the following chemical structure:

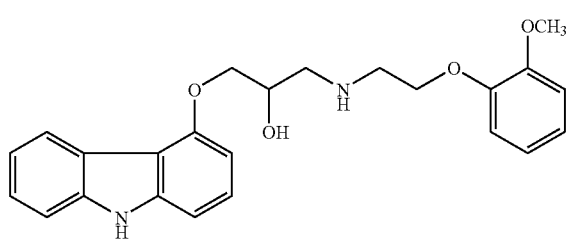

Carvedilol is disclosed in U.S. Pat. No. 4,503,067 to Wiedemann et al. (i.e., assigned to Boehringer Mannheim, GmbH, Mannheim-Waldhof, Fed. Rep. of Germany), which was issued on Mar. 5, 1985.

Currently, carvedilol is synthesized as free base for incorporation in medication that is available commercially. The aforementioned free base form of Carvedilol is a racemic mixture of R(+) and S(−) enantiomers, where non-selective β-adrenoreceptor blocking activity is exhibited by the S(−) enantiomer and α-adrenergic blocking activity is exhibited by both R(+) and S(−) enantiomers. Those unique features or characteristics associated with such a racemic Carvedilol mixture contributes to two complementary pharmacologic actions: i.e., mixed venous and arterial vasodilation and non-cardioselective, beta-adrenergic blockade.

Carvedilol is used for treatment of hypertension, congestive heart failure and angina. The currently commercially available carvedilol product is a conventional, tablet prescribed as a twice-a-day (BID) medication in the United States.

Carvedilol contains an α-hydroxyl secondary amine functional group, which has a pKa of 7.8. Carvedilol exhibits predictable solubility behaviour in neutral or alkaline media, i.e. above a pH of 9.0, the solubility of carvedilol is relatively low (<1 μg/mL). The solubility of carvedilol increases with decreasing pH and reaches a plateau near pH=5, i.e. where saturation solubility is about 23 μg/mL at pH=7 and about 100 μg/mL at pH=5 at room temperature. At lower pH values (i.e., at a pH of 1 to 4 in various buffer systems), solubility of carvedilol is limited by the solubility of its protonated form or its corresponding salt formed in-situ. For example, a hydrochloride salt of carvedilol generated in situ an acidic medium, which simulates gastric fluid, is less soluble in such medium.

In addition, the presence of the α-hydroxyl secondary amine group in the Carvedilol chemical structure confers a propensity upon the compound to chemically react with excipients normally included in a dosage form to aid manufacture, maintain quality, or enhances dissolution rate. For example, the α-hydroxyl secondary amine group of Carvedilol can react with aldehydes or ester functional groups through nucleophilic reactions. Common chemical functional group residues associated with conventionally used excipients, include ester, aldehyde and/or other chemical residue functional groups. This often results in marginal or unacceptable chemical stability upon storage.

In light of the foregoing, novel salt forms of carvedilol with greater aqueous solubility, chemical stability, etc. would offer many potential benefits for provision of medicinal products containing the drug carvedilol.

Such benefits would include products with the ability to achieve desired or prolonged drug levels in a systemic system by sustaining absorption along the gastrointestinal tract of mammals (i.e., such as humans), particularly in regions of neutral pH, where a drug, such as carvedilol, has minimal solubility.

Surprisingly, it has now been shown that novel crystalline forms of carvedilol salts, may be isolated as a pure crystalline solid, which exhibit much higher aqueous solubility than the corresponding free base or other prepared crystalline carvedilol salts.

This novel crystalline form also has potential to improve the stability of carvedilol in formulations due to the fact that the secondary amine functional group attached to the carvedilol core structure, a moiety pivotal to degradation processes, is protonated as a salt.

In light of the above, a need exists to develop different carvedilol salt forms and/or different corresponding compositions, respectively, which have greater aqueous solubility, chemical stability, sustained or prolonged drug or absorption properties (i.e., such as in neutral gastrointestinal tract pH regions, etc.).

There also exists a need to develop methods of treatment for cardiovascular diseases and/or associated disorders, which may include, but are not limited to hypertension, congestive heart failure or angina, etc., which comprises administration of the such carvedilol salt forms, and/or corresponding pharmaceutical compositions.

The present invention is directed to overcoming these and other problems encountered in the art.

SUMMARY OF THE INVENTION

The present invention relates to a salt of carvedilol and/or corresponding solvates thereof, pharmaceutical compositions containing such carvedilol and/or corresponding solvates thereof, and/or methods of using the aforementioned compound(s) and/or pharmaceutical compositions in the treatment of certain disease states in mammals, in particular man.

The present invention further relates to carvedilol salt forms, which may, but are not limited to include novel crystalline salt forms of carvedilol mandelate, carvedilol lactate, carvedilol maleate, carvedilol sulfate, carvedilol glutarate, carvedilol mesylate, carvedilol phosphate, carvedilol citrate, carvedilol hydrogen bromide, carvedilol oxalate, carvedilol hydrochloride, carvedilol hydrogen bromide, carvedilol benzoate, and/or corresponding anhydrous, solvates, thereof.

The present invention relates to a pharmaceutical composition, which contain such aforementioned carvedilol salt forms, and/or corresponding anhydrous, solvates thereof, and/or pharmaceutically acceptable adjuvants, carriers, excipients.

The present invention further relates to a method of treating hypertension, congestive heart failure and angina, which comprises administering to a subject in need thereof an effective amount of a carvedilol salt form (which include corresponding novel crystalline forms, anhydrous forms, solvates thereof) and/or such aforementioned corresponding pharmaceutical compositions (i.e., which contain such carvedilol salt forms, anhydrous, solvates thereof).

BRIEF DESCRIPTION OF THE FIGURES

Carvedilol Phosphate Salts

Carvedilol HBr Salts

Figure 30:
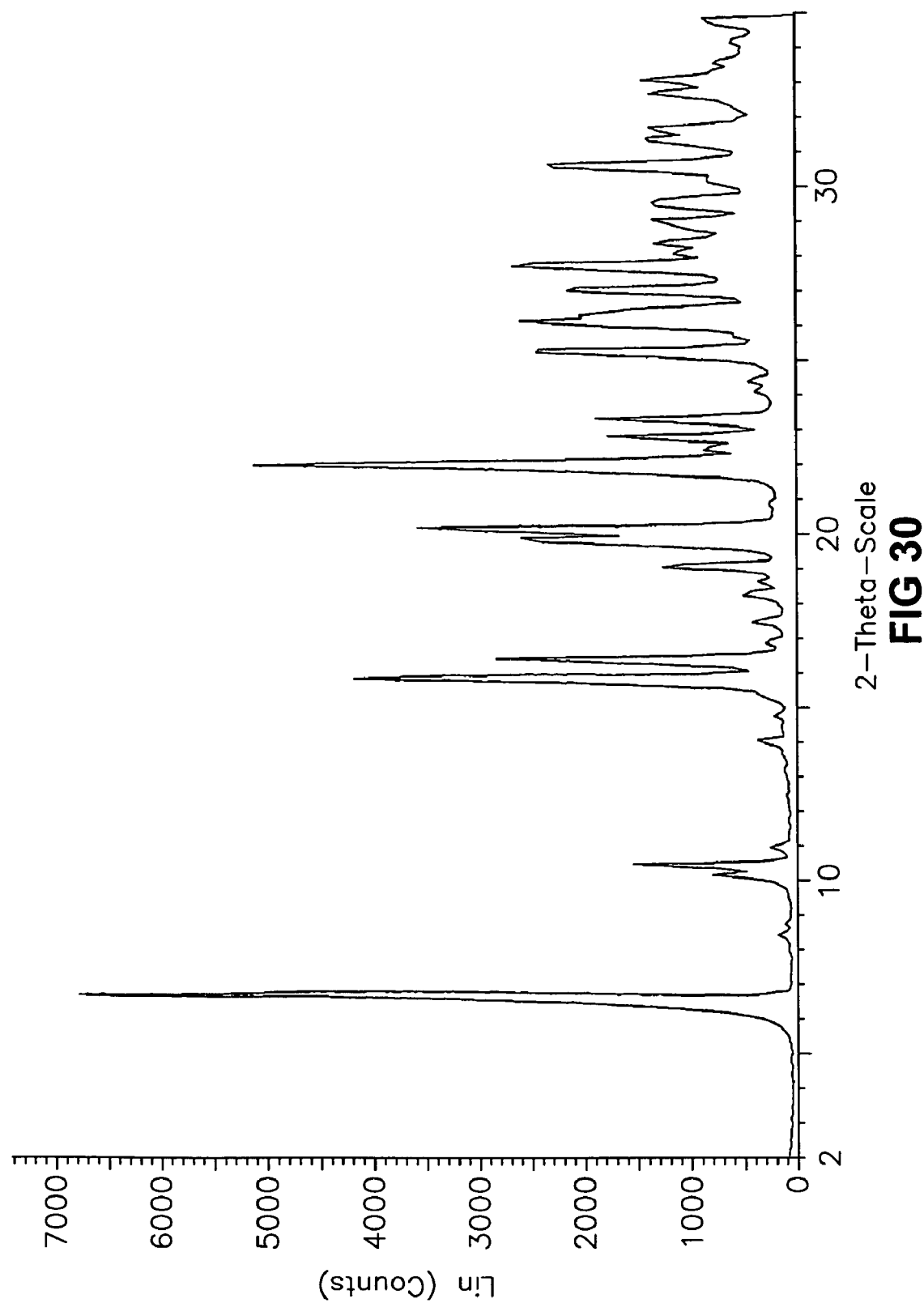

FIG. 30 is an x-ray powder diffractogram for carvedilol hydrobromide monohydrate.

Figure 31:
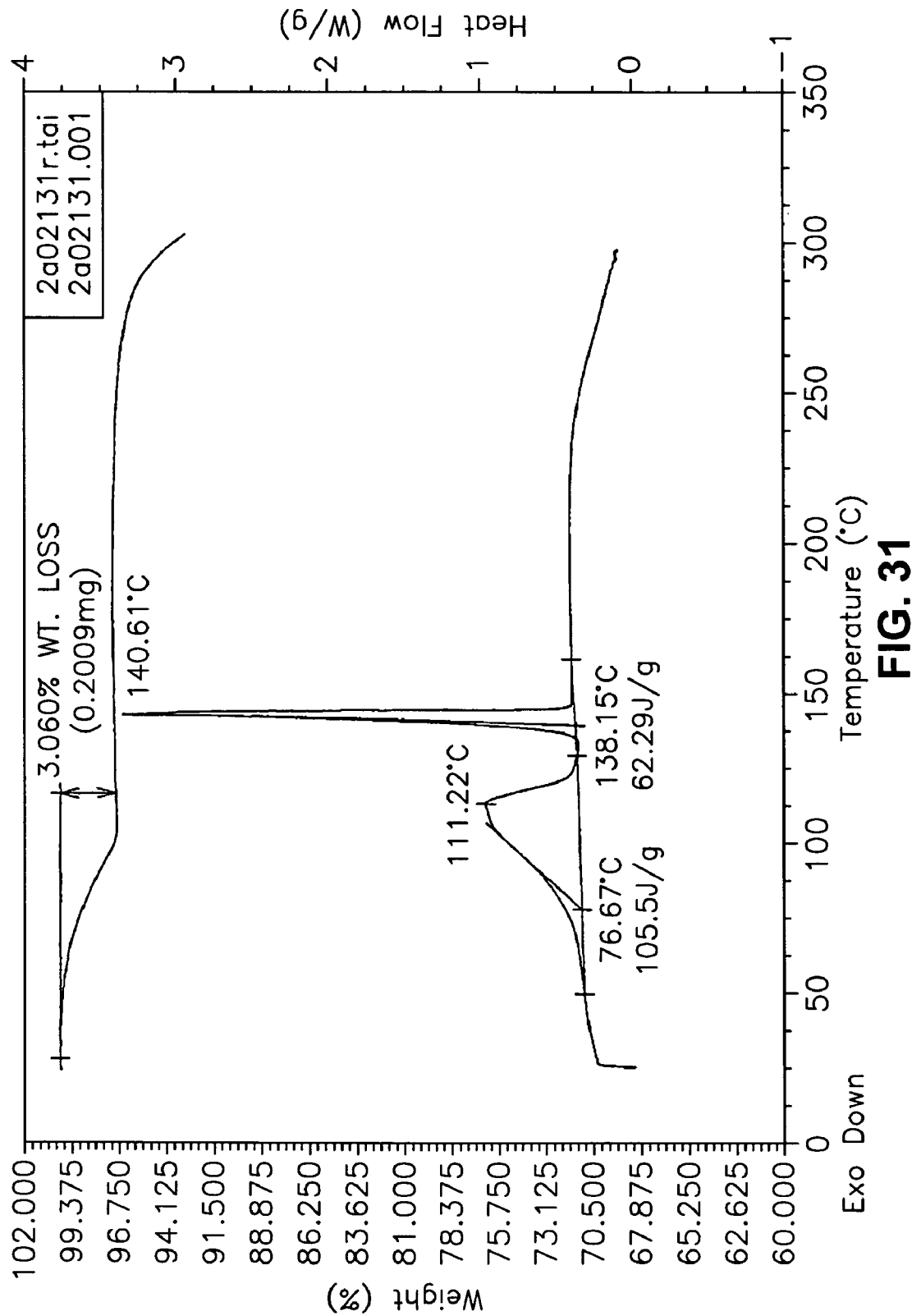

FIG. 31 is a differential scanning calorimetry thermogram for carvedilol hydrobromide monohydrate.

Figure 32:
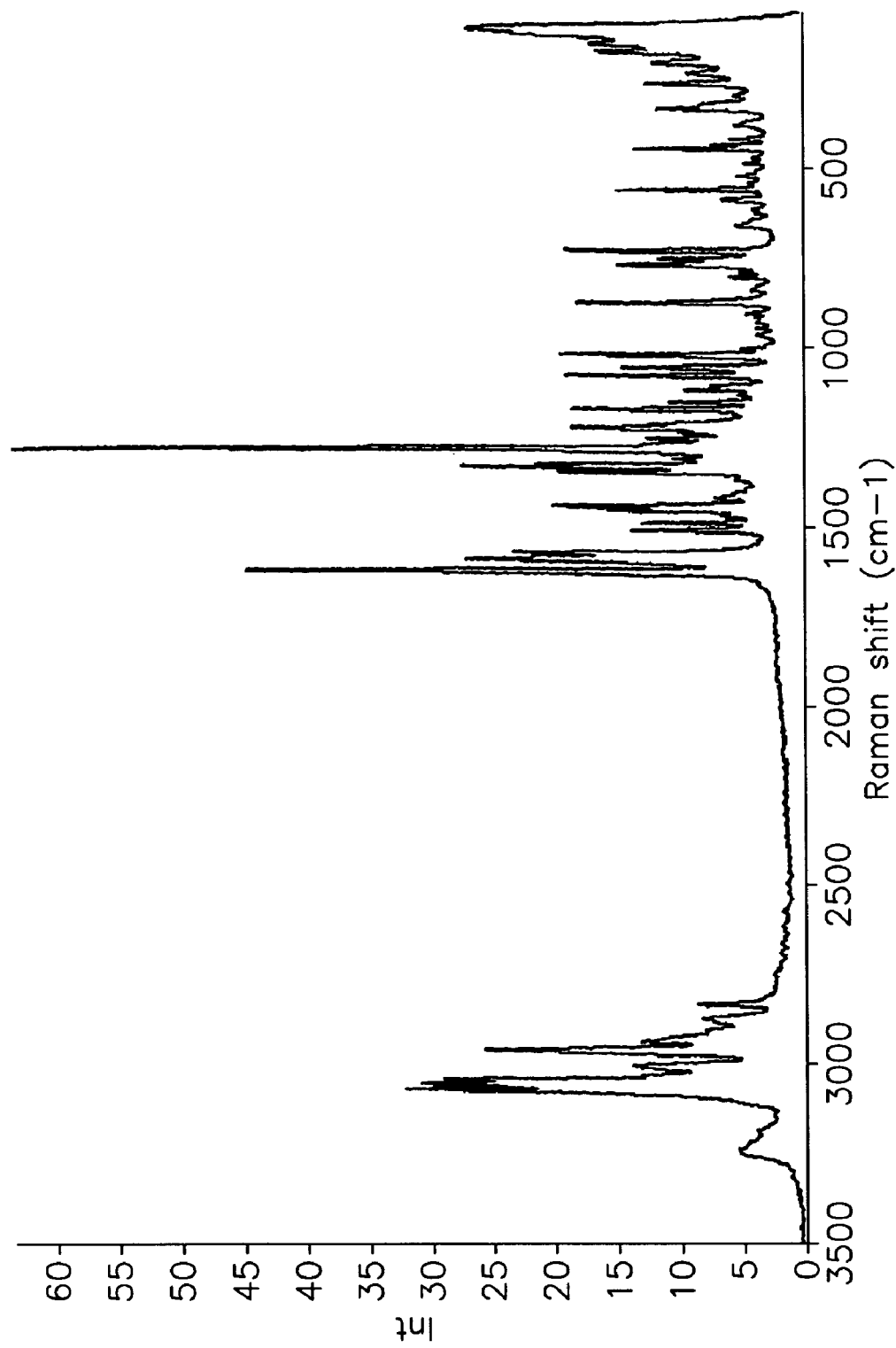

FIG. 32 is an FT-Raman spectrum for carvedilol hydrobromide monohydrate.

Figure 33:
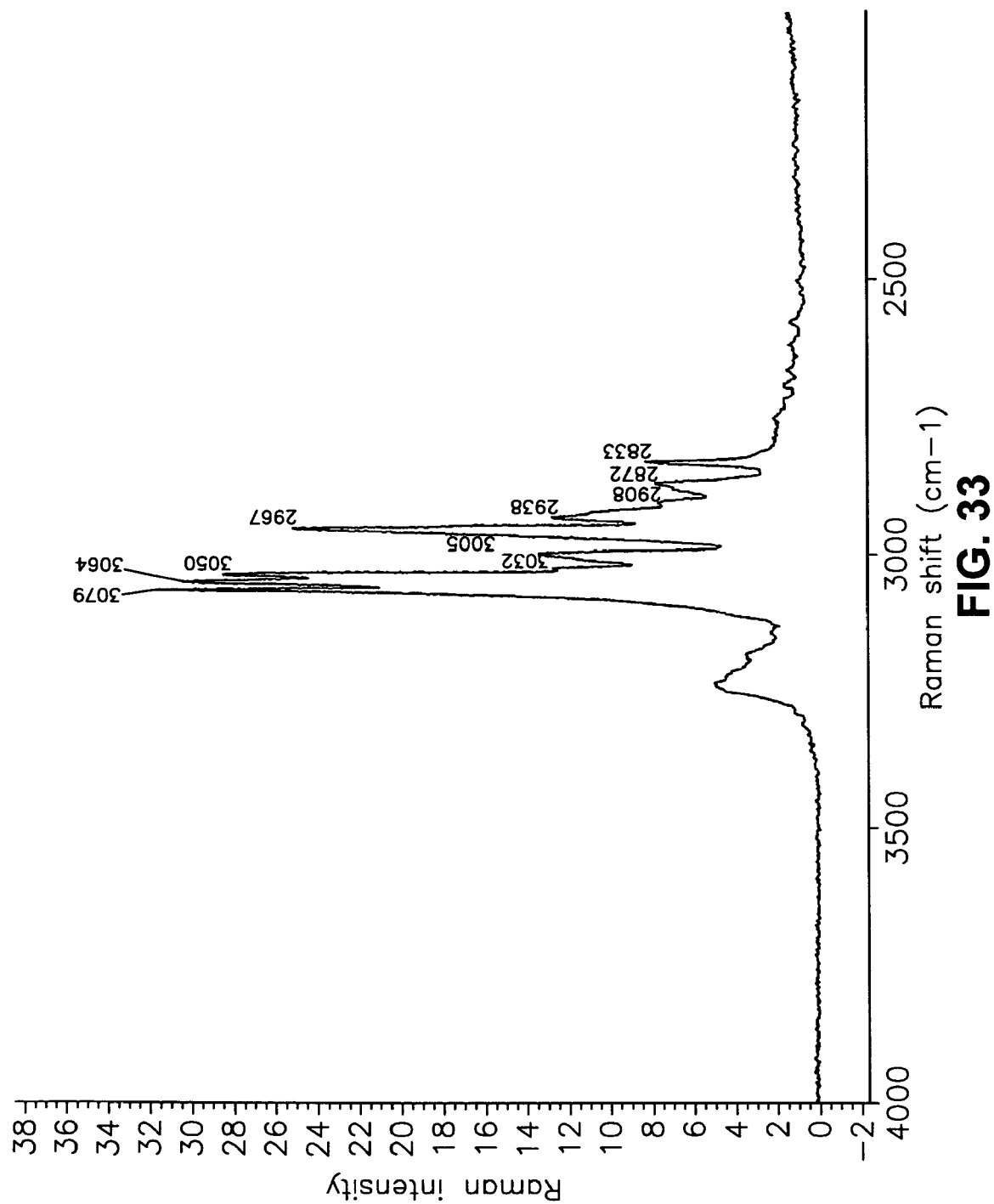

FIG. 33 is an FT-Raman spectrum for carvedilol hydrobromide monohydrate in the 4000-2000 $cm^{-1}$ region of the spectrum.

Figure 34:
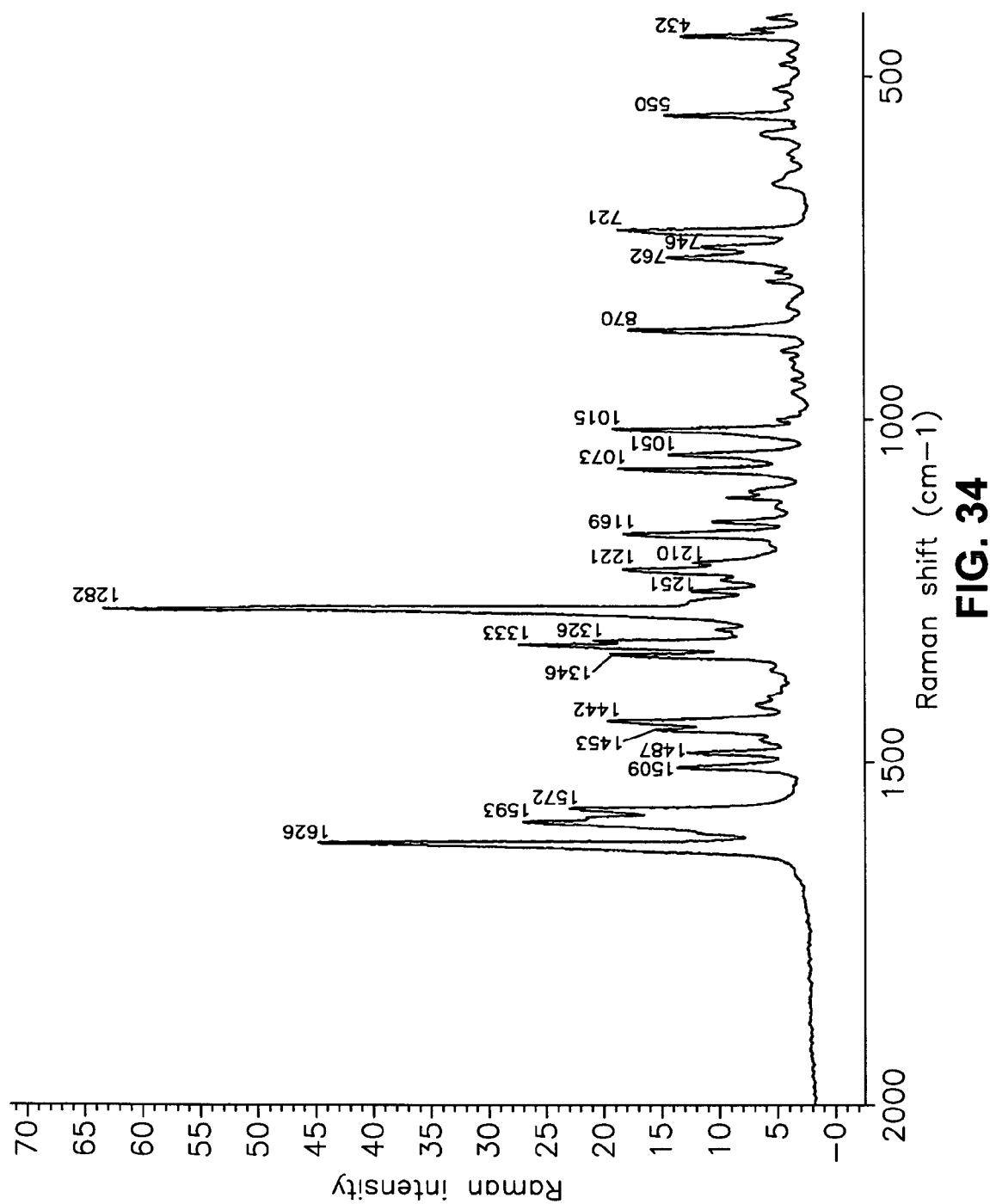

FIG. 34 is an FT-Raman spectrum for carvedilol hydrobromide monohydrate in the 2000-400 $cm^{-1}$ region of the spectrum.

Figure 35:
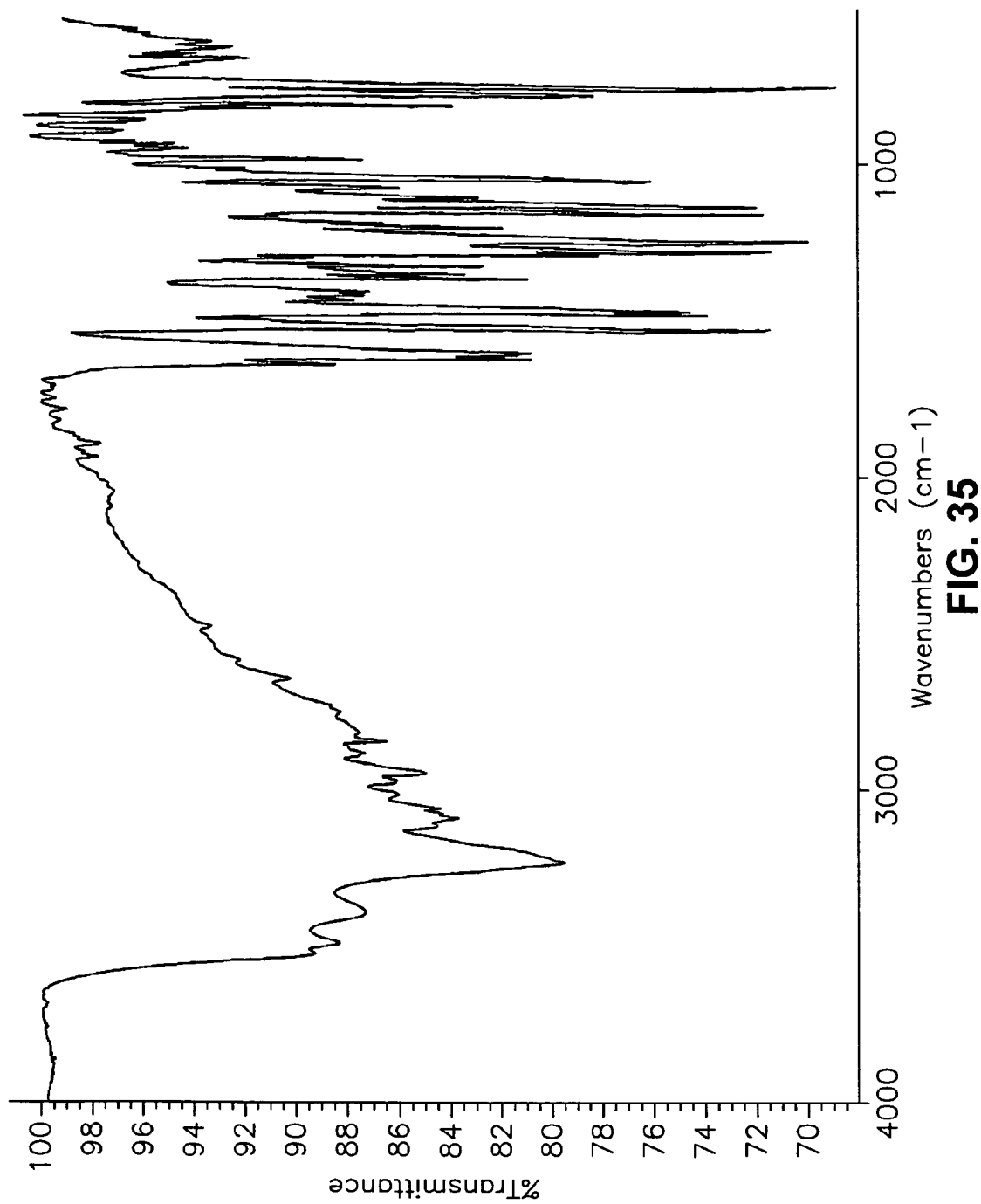

FIG. 35 is an FT-IR spectrum for carvedilol hydrobromide monohydrate.

Figure 36:
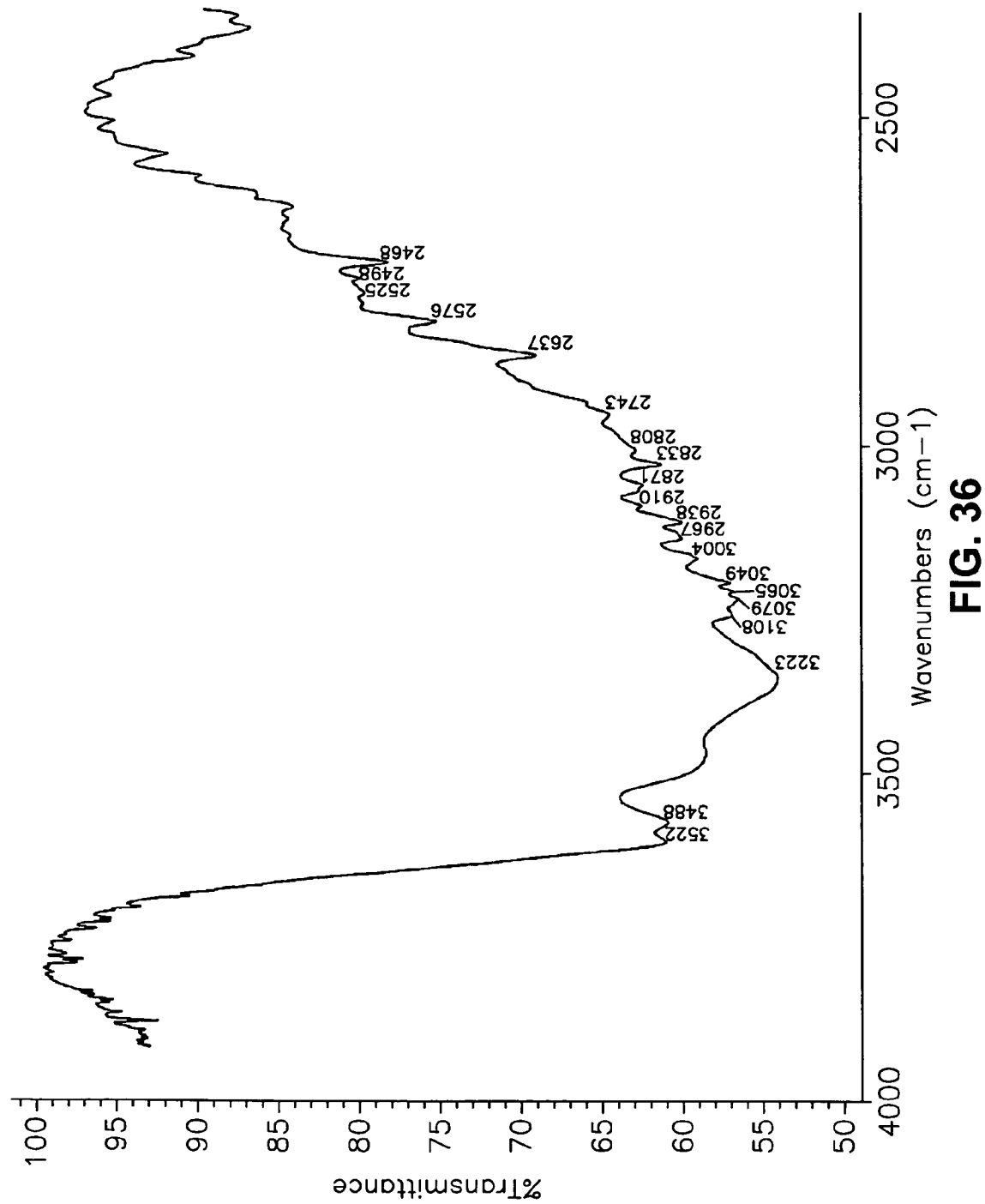

FIG. 36 is an FT-IR spectrum for carvedilol hydrobromide monohydrate in the 4000-2000 $cm^{-1}$ region of the spectrum.

Figure 37:
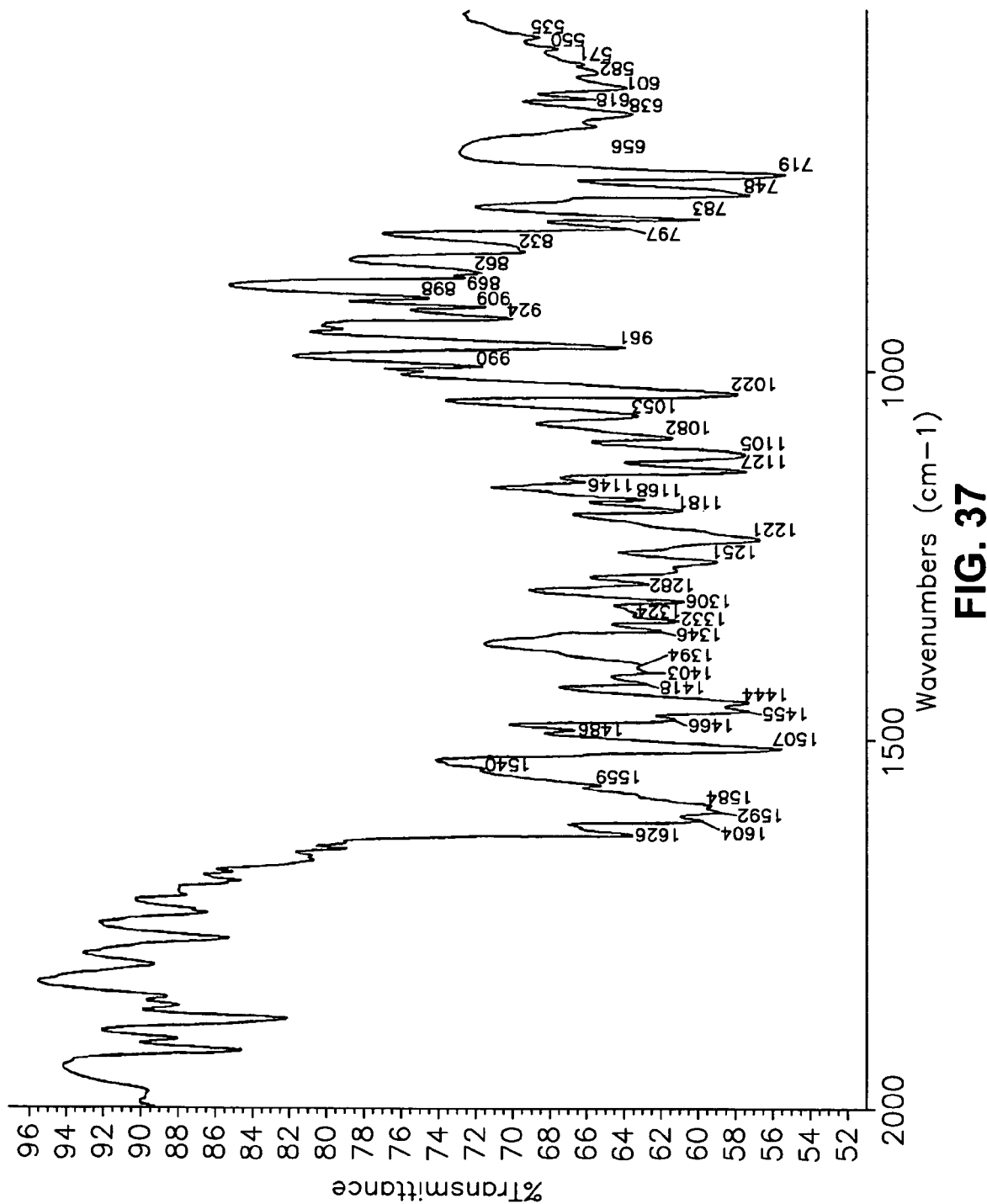

FIG. 37 is an FT-IR spectrum for carvedilol hydrobromide monohydrate in the 2000-500 $cm^{-1}$ region of the spectrum.

Figure 38:
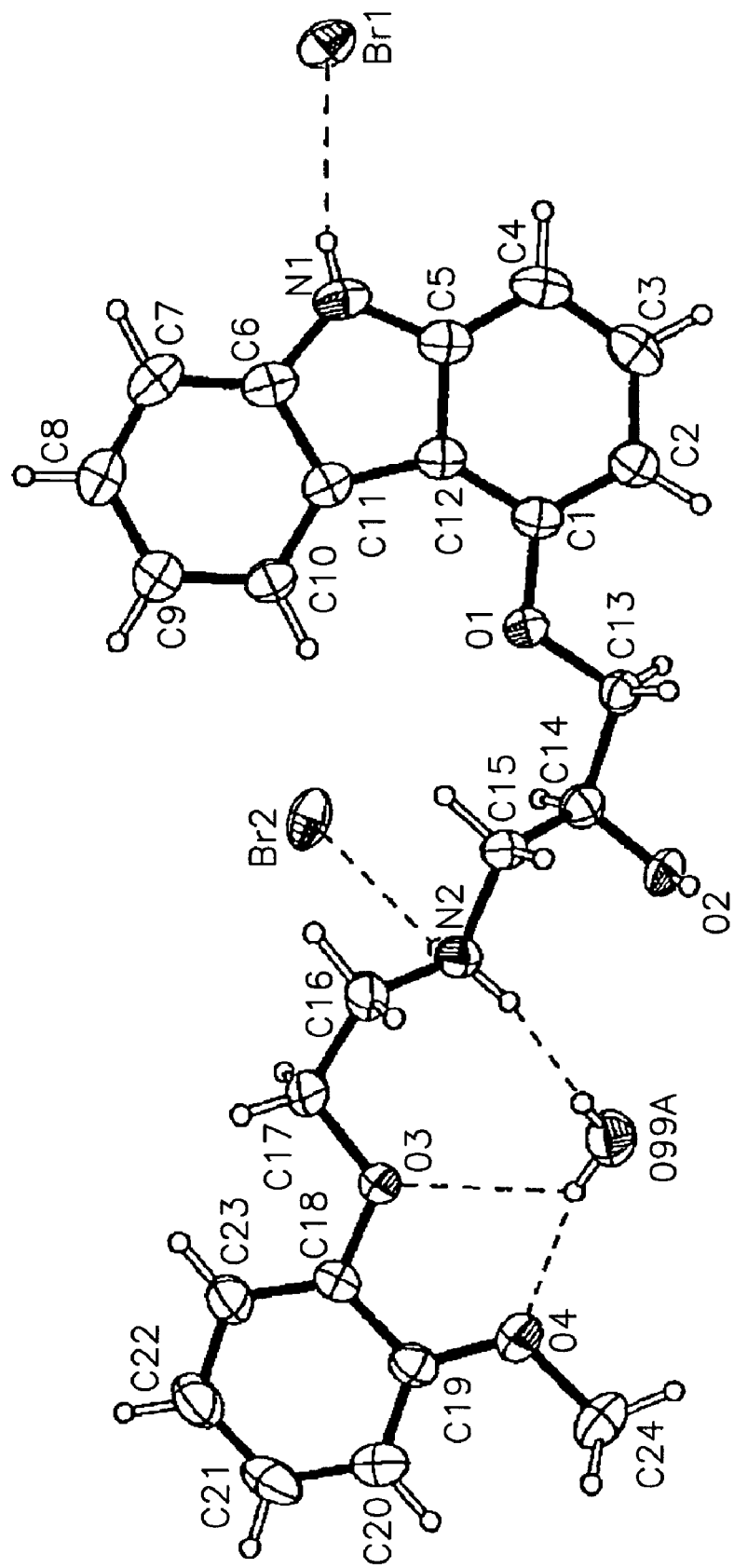

FIG. 38 is a view of a single molecule of carvedilol hydrobromide monohydrate. The hydroxyl group and the water molecule are disordered.

Figure 39:
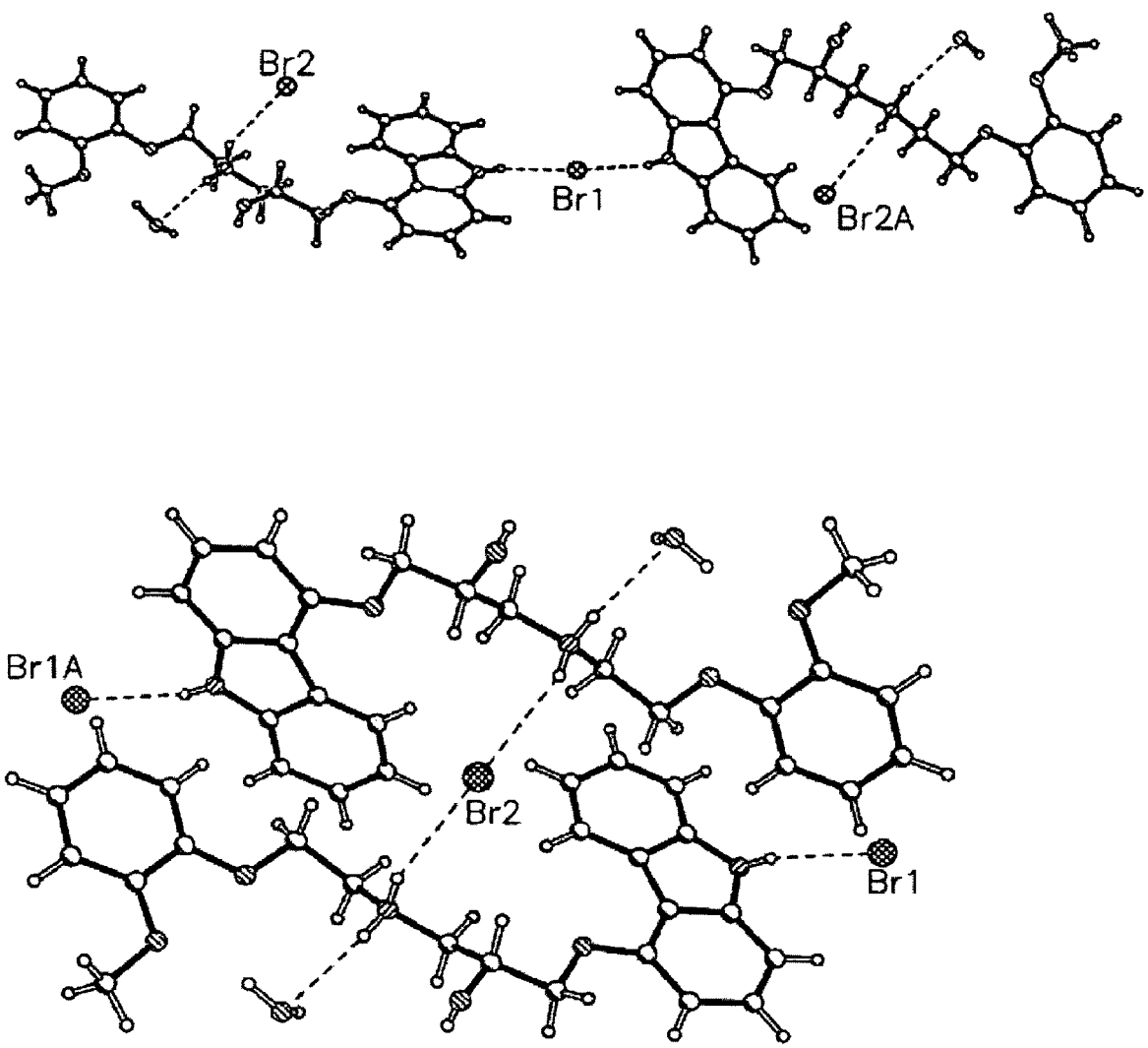

FIG. 39 are views of molecules of carvedilol hydrobromide monohydrate showing the N—H...Br...H—N interactions. The top view focuses on Br1 and the bottom view focuses on Br2. The interaction between the carvedilol cation and the bromine anion is unusual. Each carvedilol molecule makes two chemically different contacts to the bromine anions. Each bromine anion sits on a crystallographic special position (that is, on a crystallographic two-fold axis) which means that there are two half bromine anions interacting with each carvedilol cation.

Figure 40:
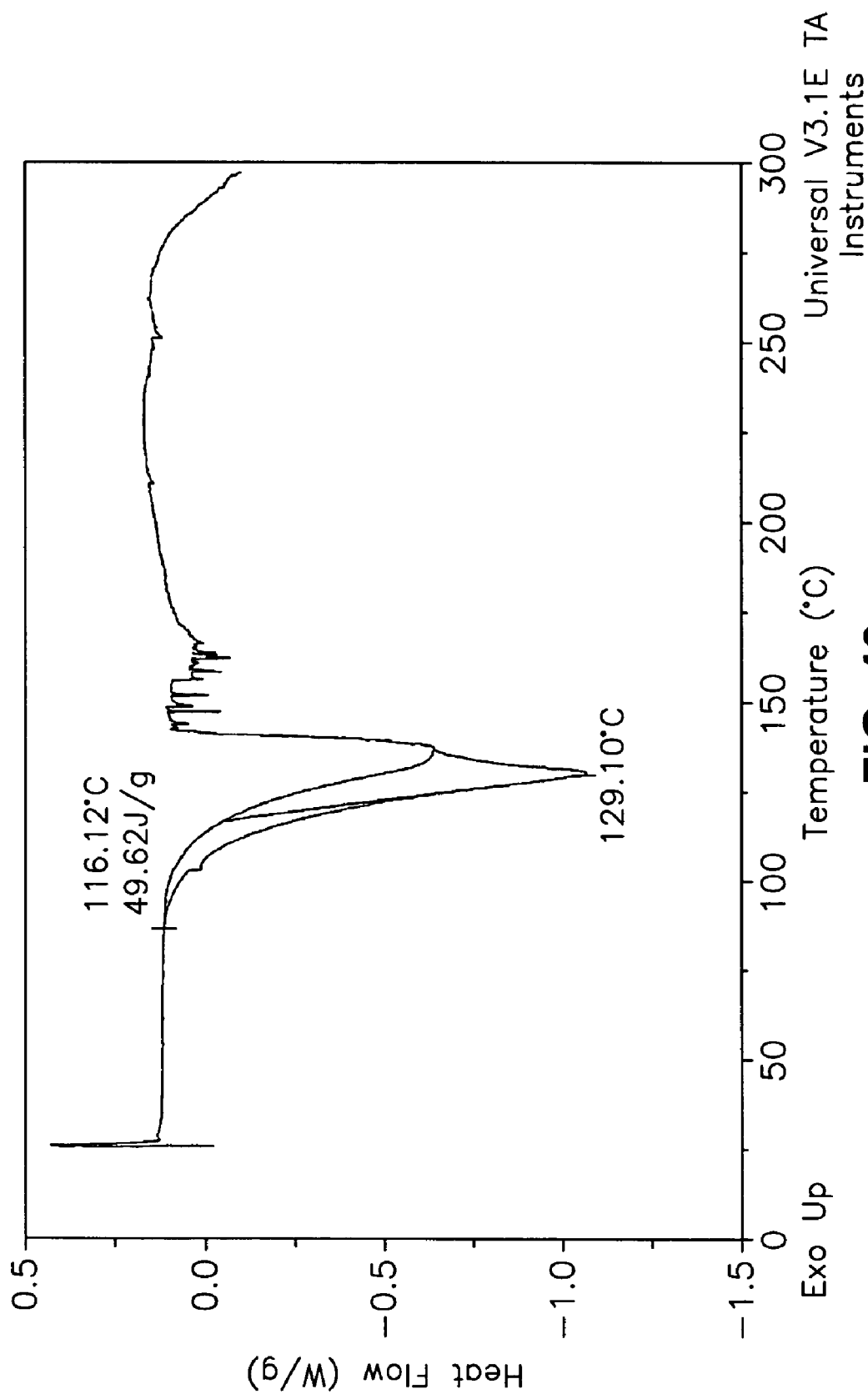

FIG. 40 is a differential scanning calorimetry thermogram for carvedilol hydrobromide dioxane solvate.

Figure 41:
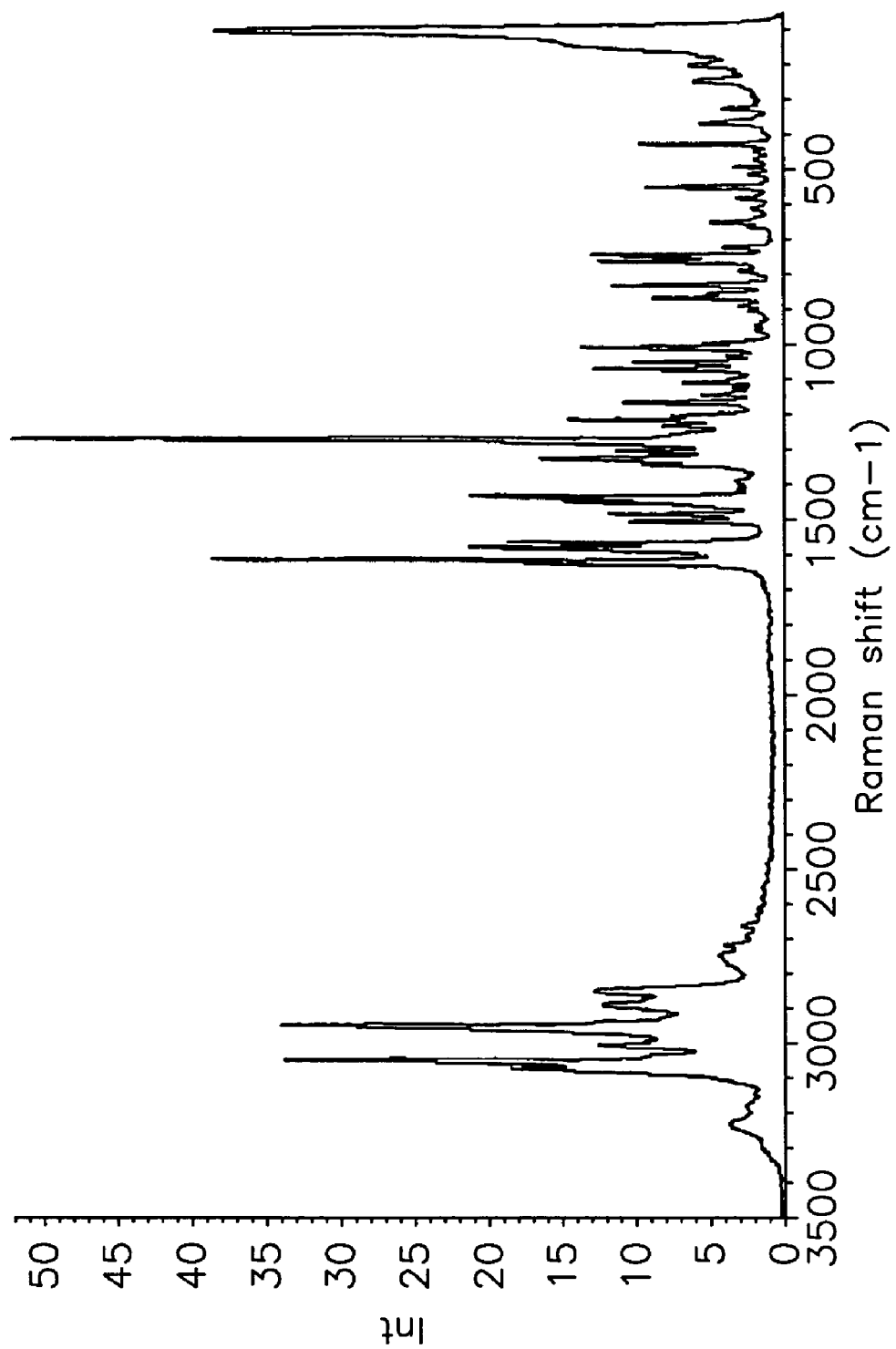

FIG. 41 is an FT-Raman spectrum for carvedilol hydrobromide dioxane solvate.

Figure 42:
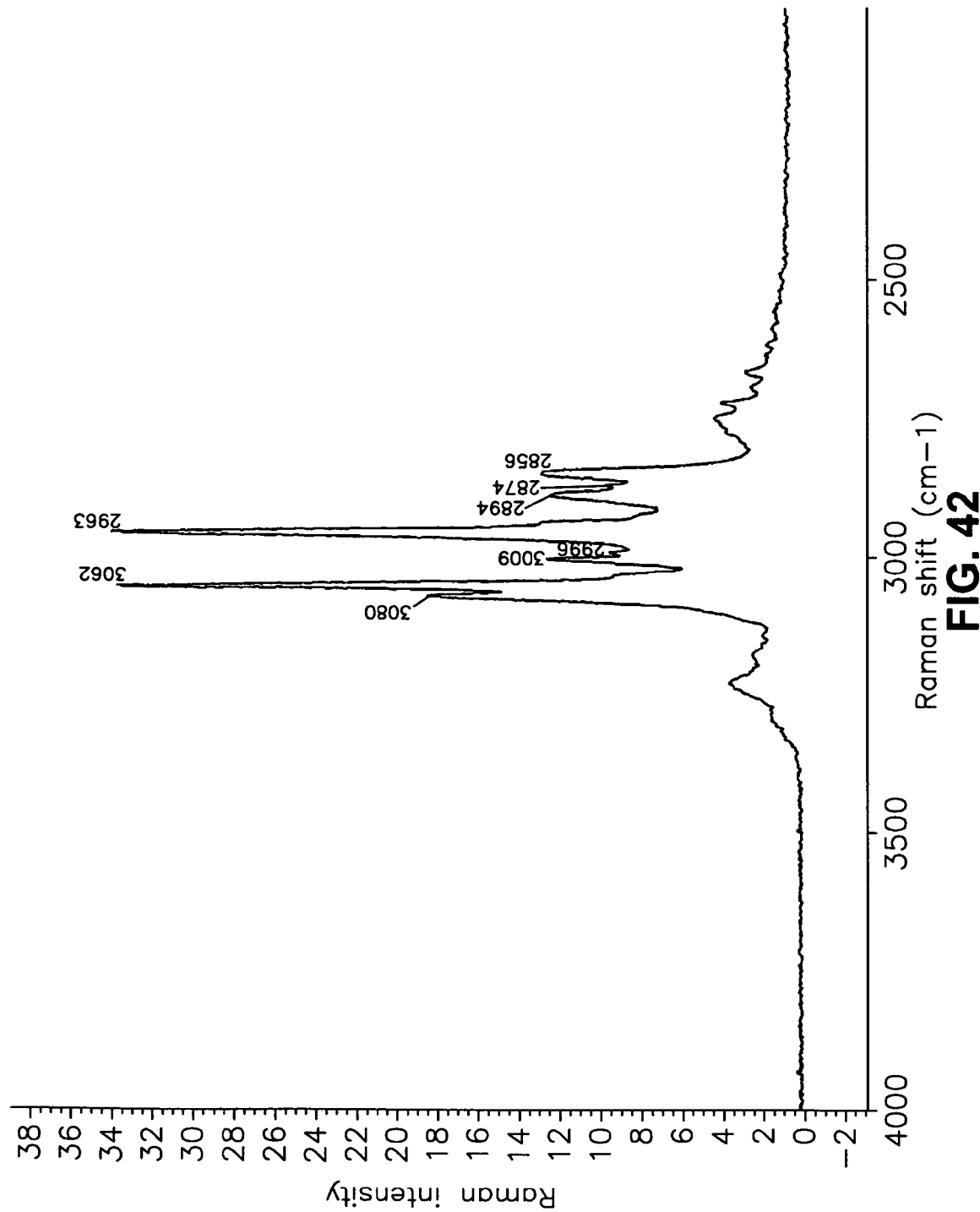

FIG. 42 is an FT-Raman spectrum for carvedilol hydrobromide dioxane solvate in the 4000-2000 $cm^{-1}$ region of the spectrum.

Figure 43:
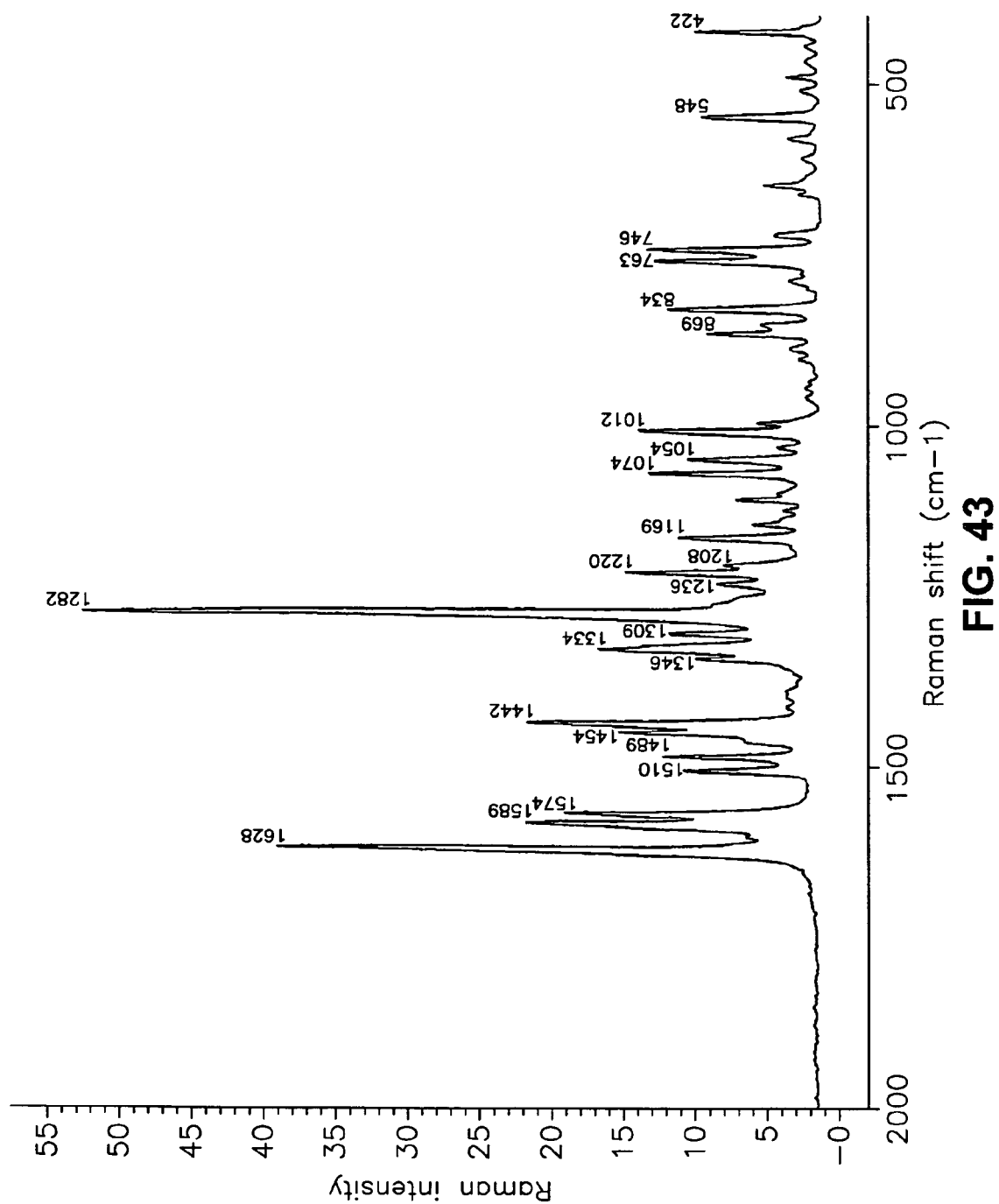

FIG. 43 is an FT-Raman spectrum for carvedilol hydrobromide dioxane solvate in the 2000-400 $cm^{-1}$ region of the spectrum.

Figure 44:
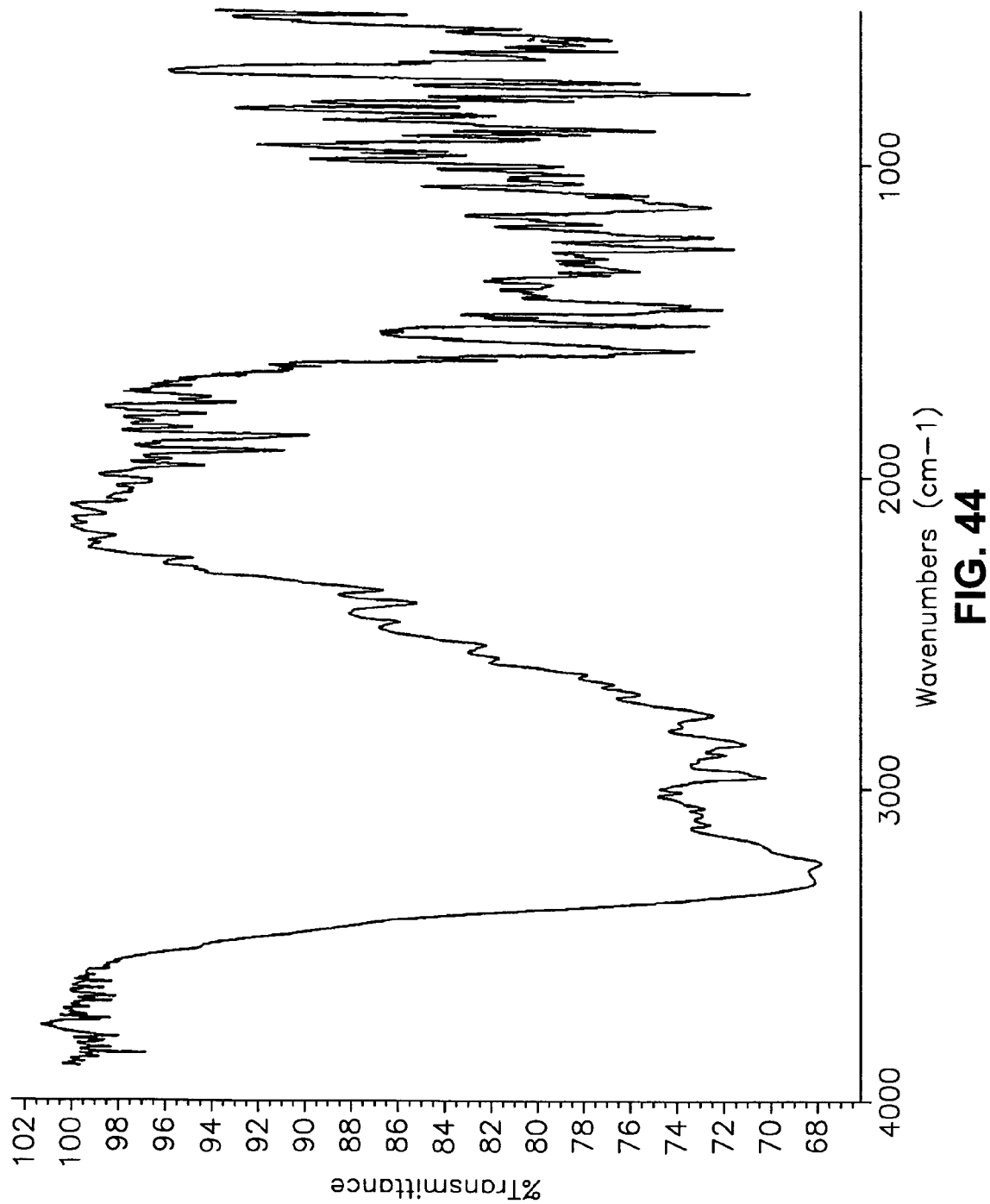

FIG. 44 is an FT-IR spectrum for carvedilol hydrobromide dioxane solvate.

Figure 45:
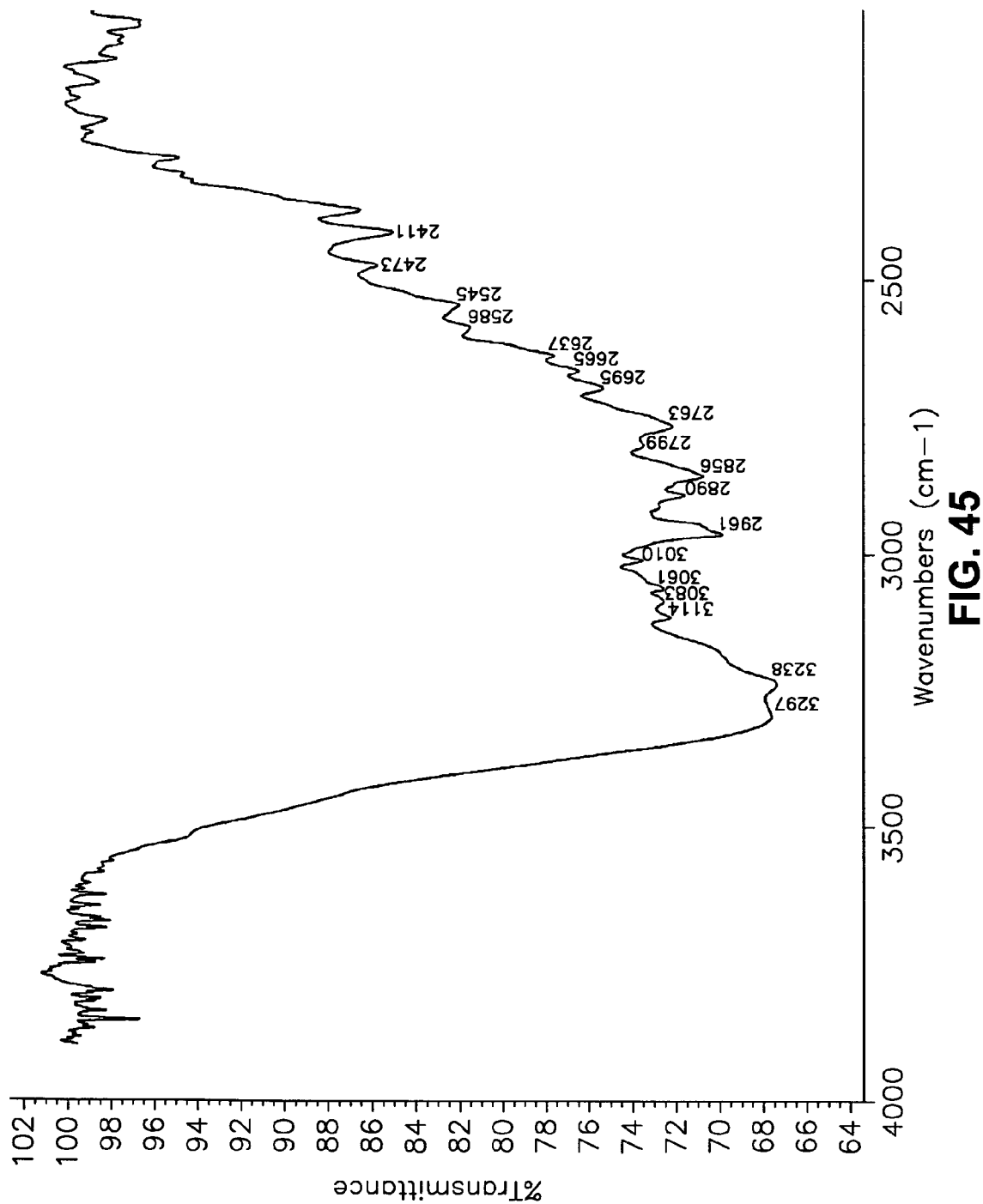

FIG. 45 is an FT-IR spectrum for carvedilol hydrobromide dioxane solvate in the 4000-2000 cm$^{-1}$ region of the spectrum.

Figure 46:
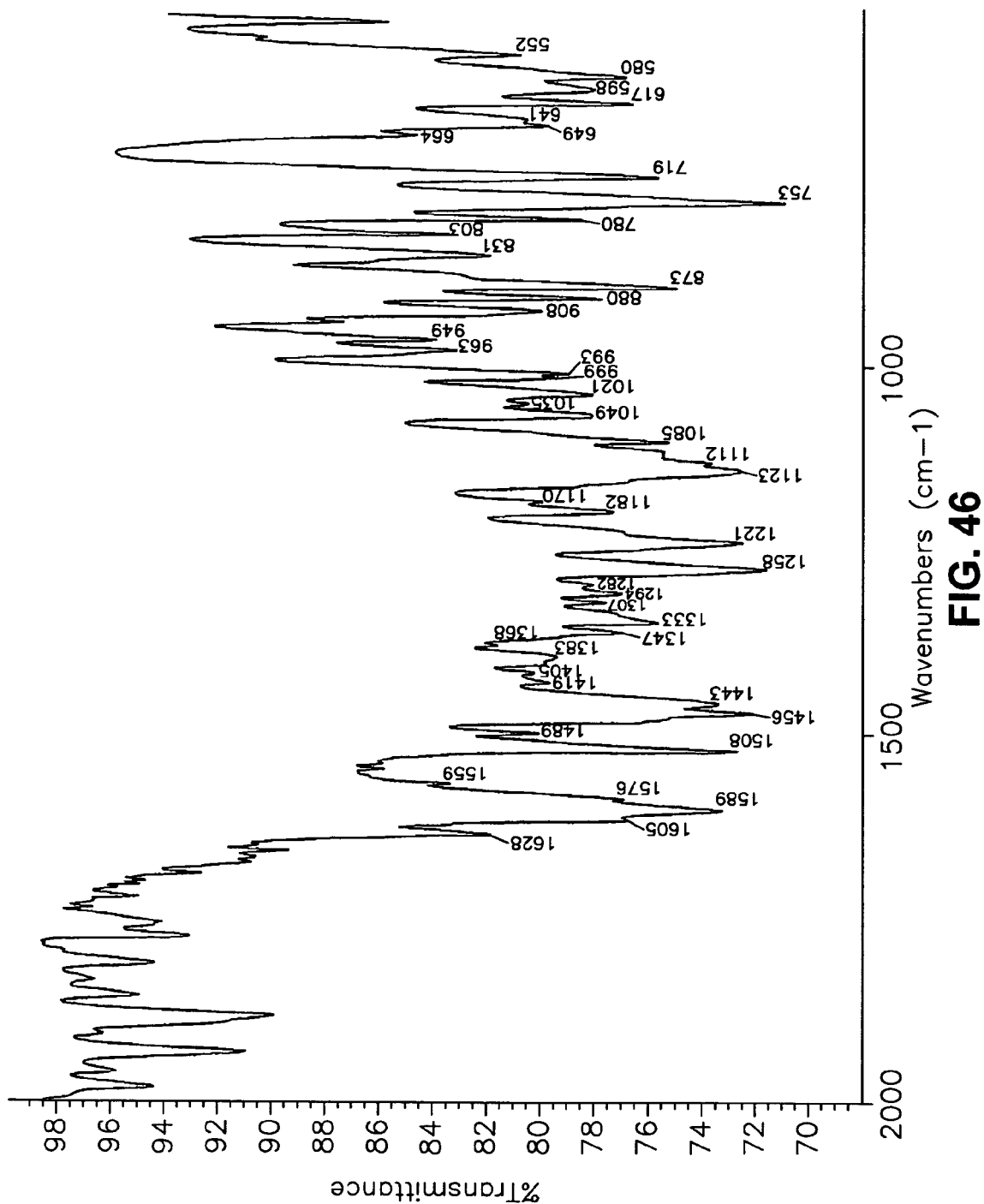

FIG. 46 is an FT-IR spectrum for carvedilol hydrobromide dioxane solvate in the 2000-500 cm$^{-1}$ region of the spectrum.

Figure 47:
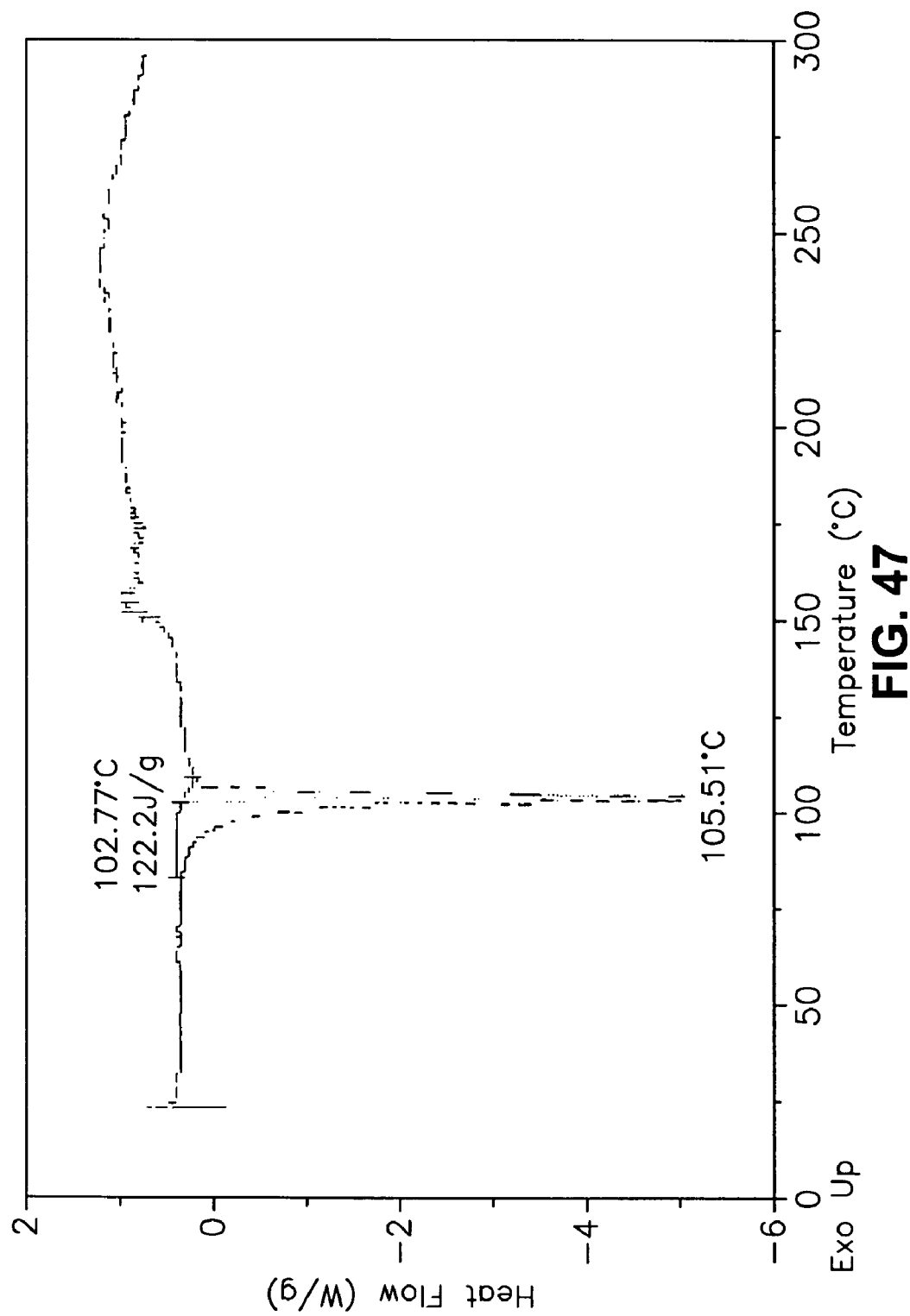

FIG. 47 is a differential scanning calorimetry thermogram for carvedilol hydrobromide 1-pentanol solvate.

Figure 48:
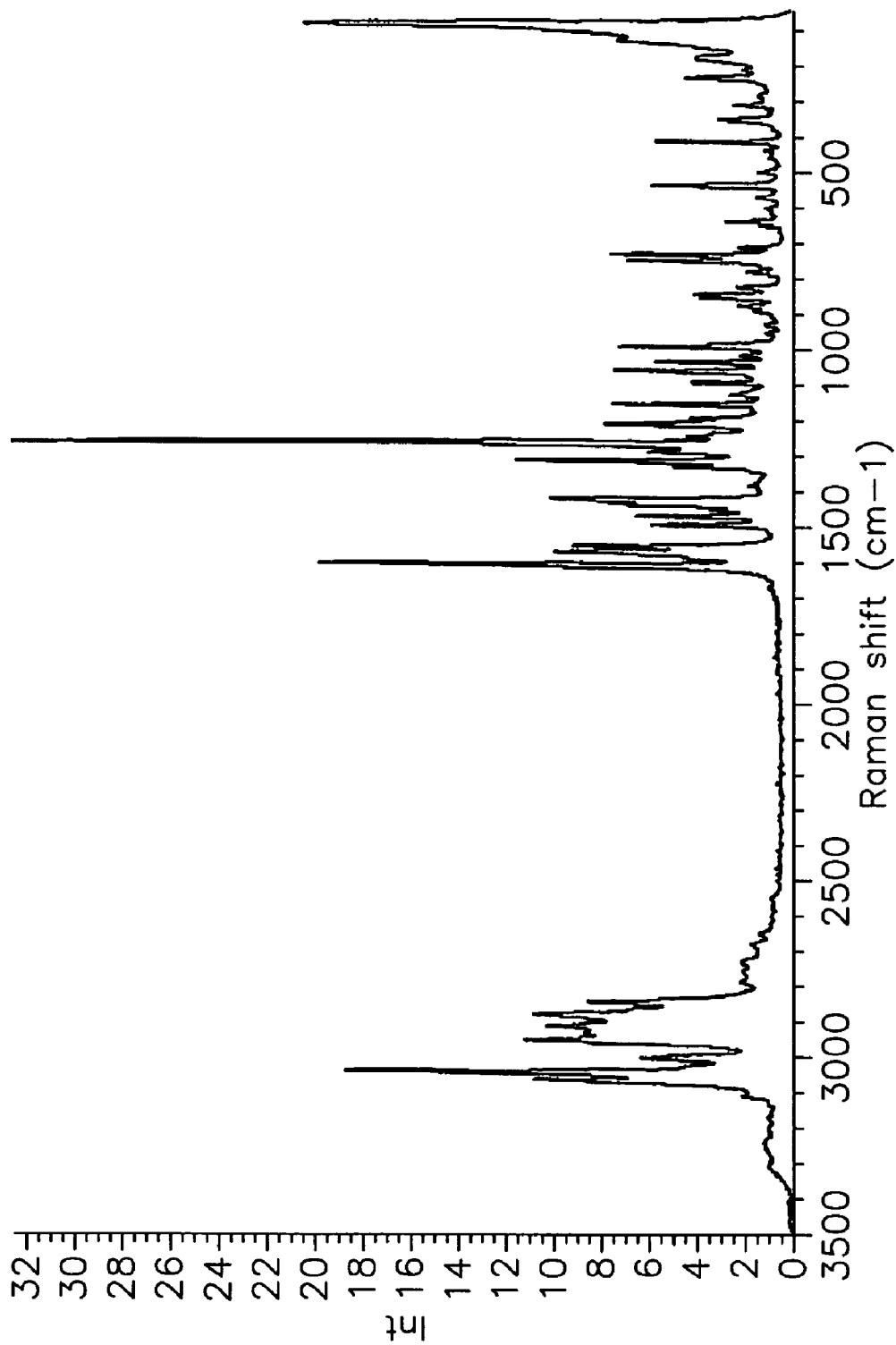

FIG. 48 is an FT-Raman spectrum for carvedilol hydrobromide 1-pentanol solvate.

Figure 49:
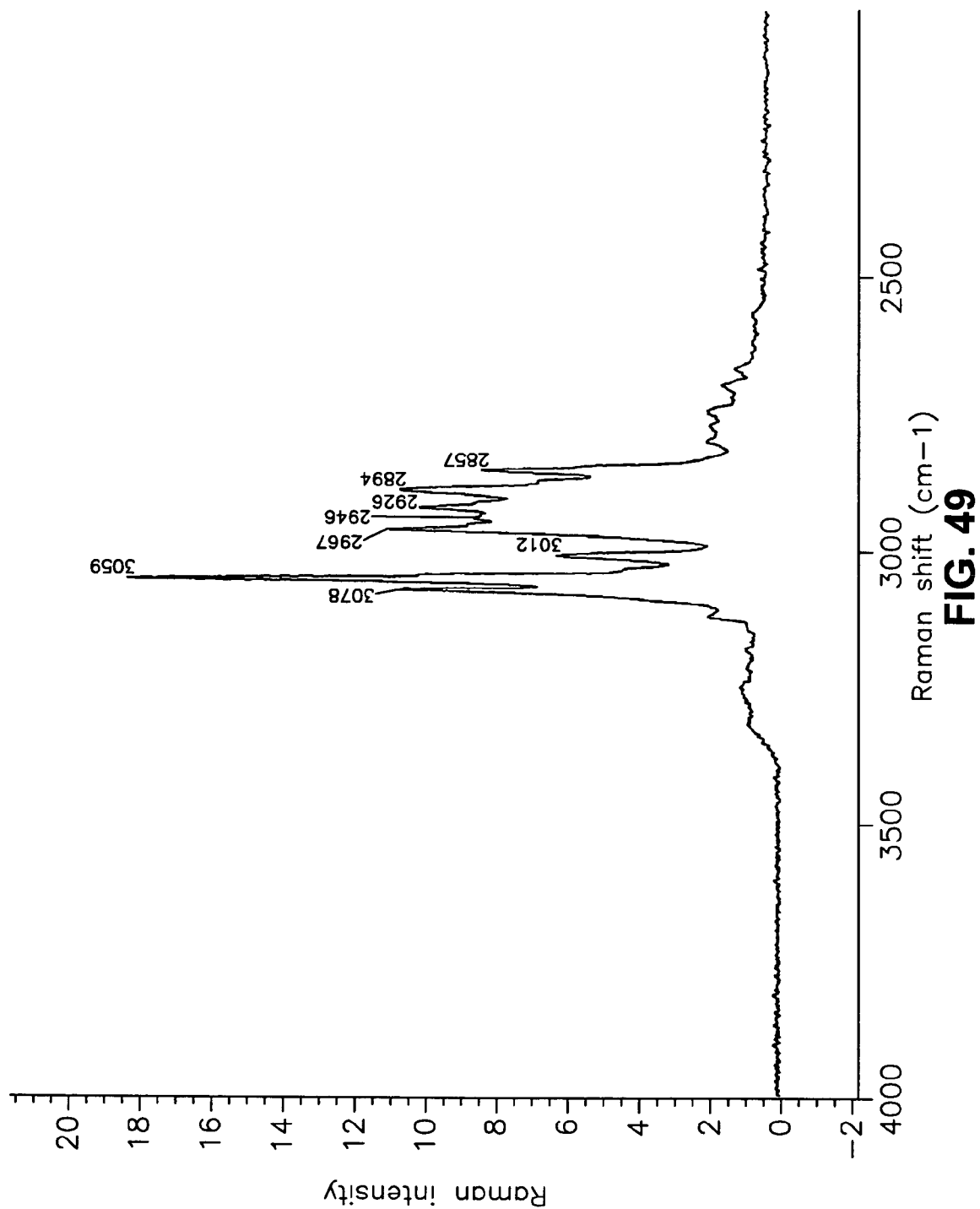

FIG. 49 is an FT-Raman spectrum for carvedilol hydrobromide 1-pentanol solvate in the 4000-2000 cm$^{-1}$ region of the spectrum.

Figure 50:
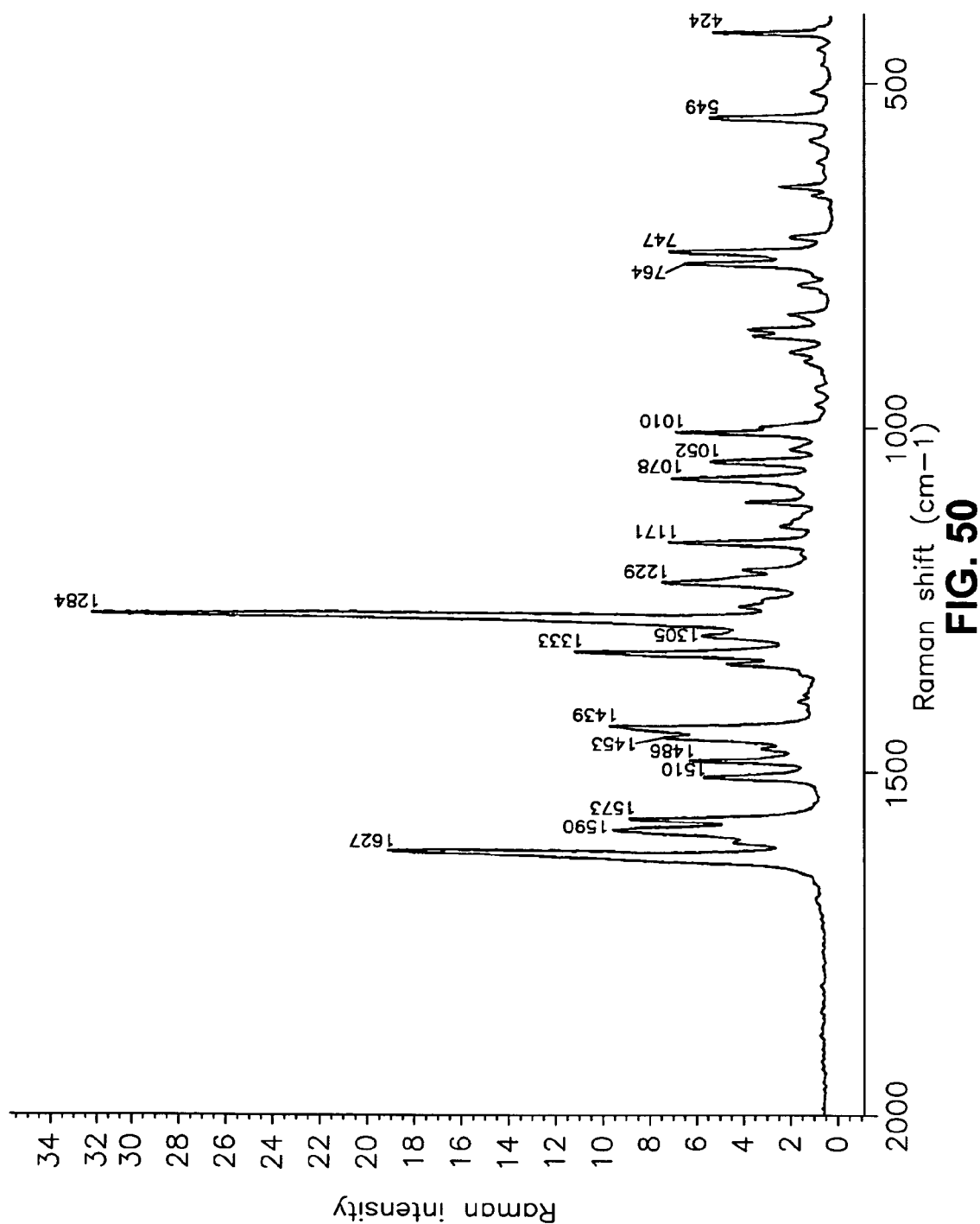

FIG. 50 is an FT-Raman spectrum for carvedilol hydrobromide 1-pentanol solvate in the 2000-400 cm$^{-1}$ region of the spectrum.

Figure 51:
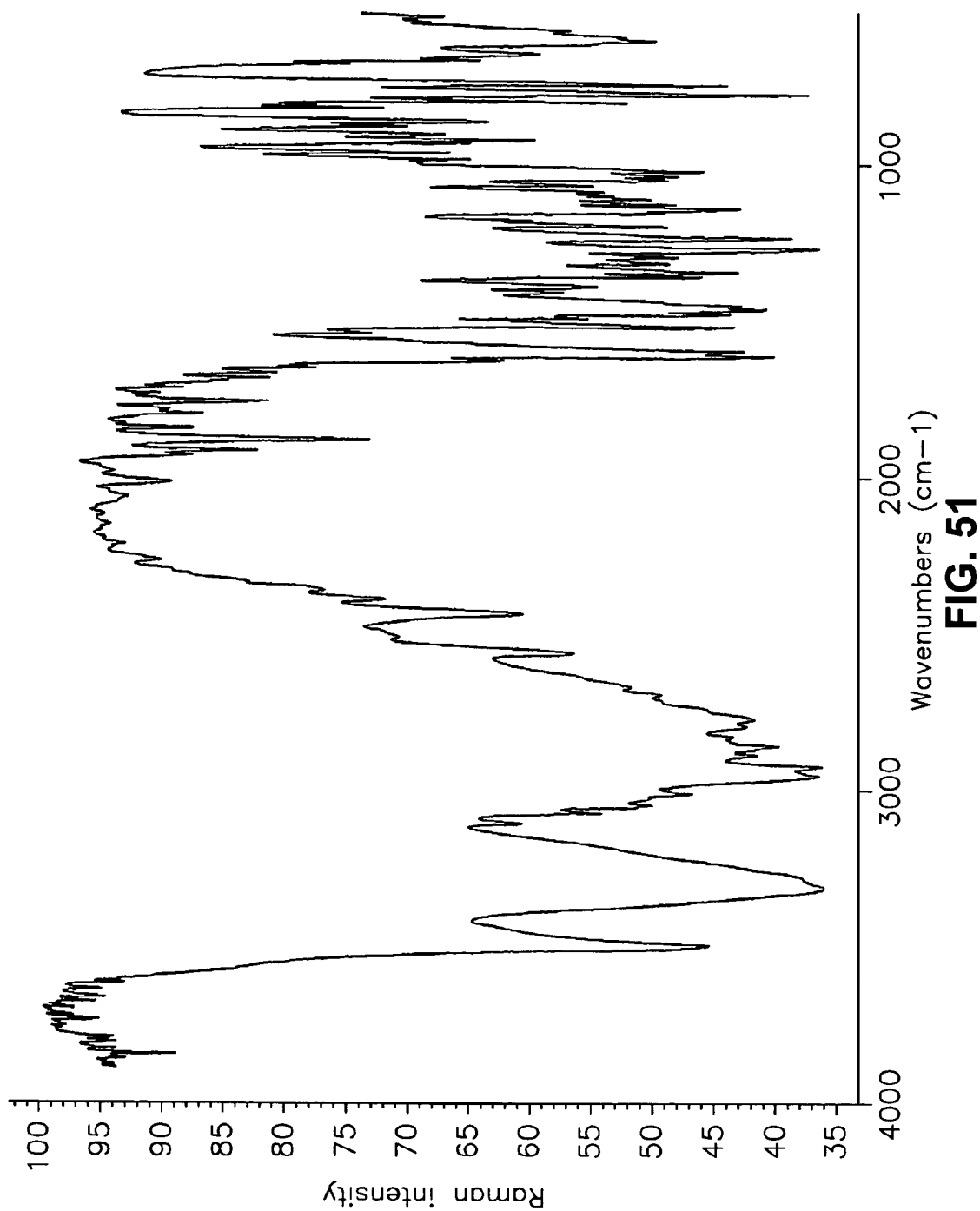

FIG. 51 is an FT-IR spectrum for carvedilol hydrobromide 1-pentanol solvate.

Figure 52:
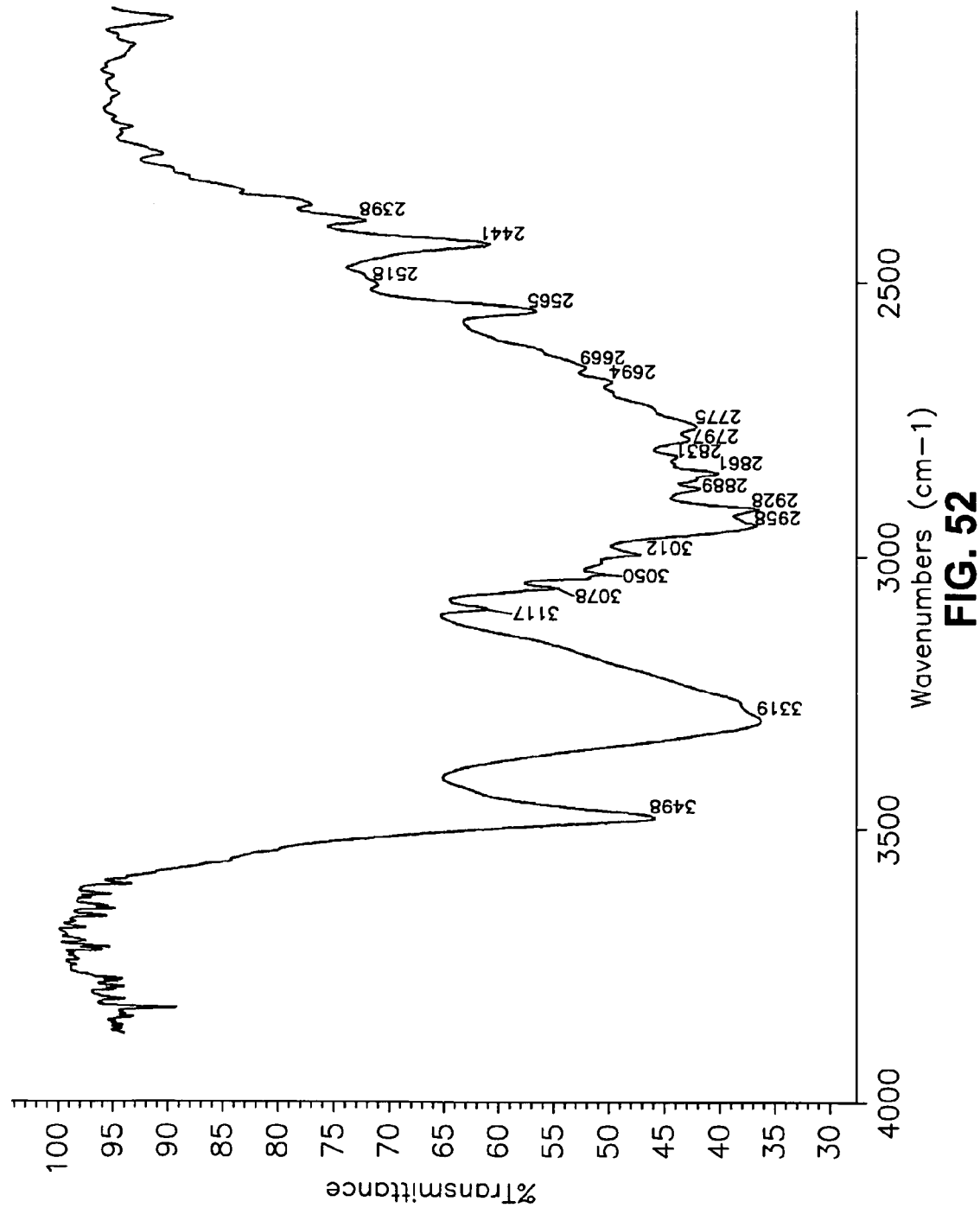

FIG. 52 is an FT-IR spectrum for carvedilol hydrobromide 1-pentanol solvate in the 4000-2000 cm$^{-1}$ region of the spectrum.

Figure 53:
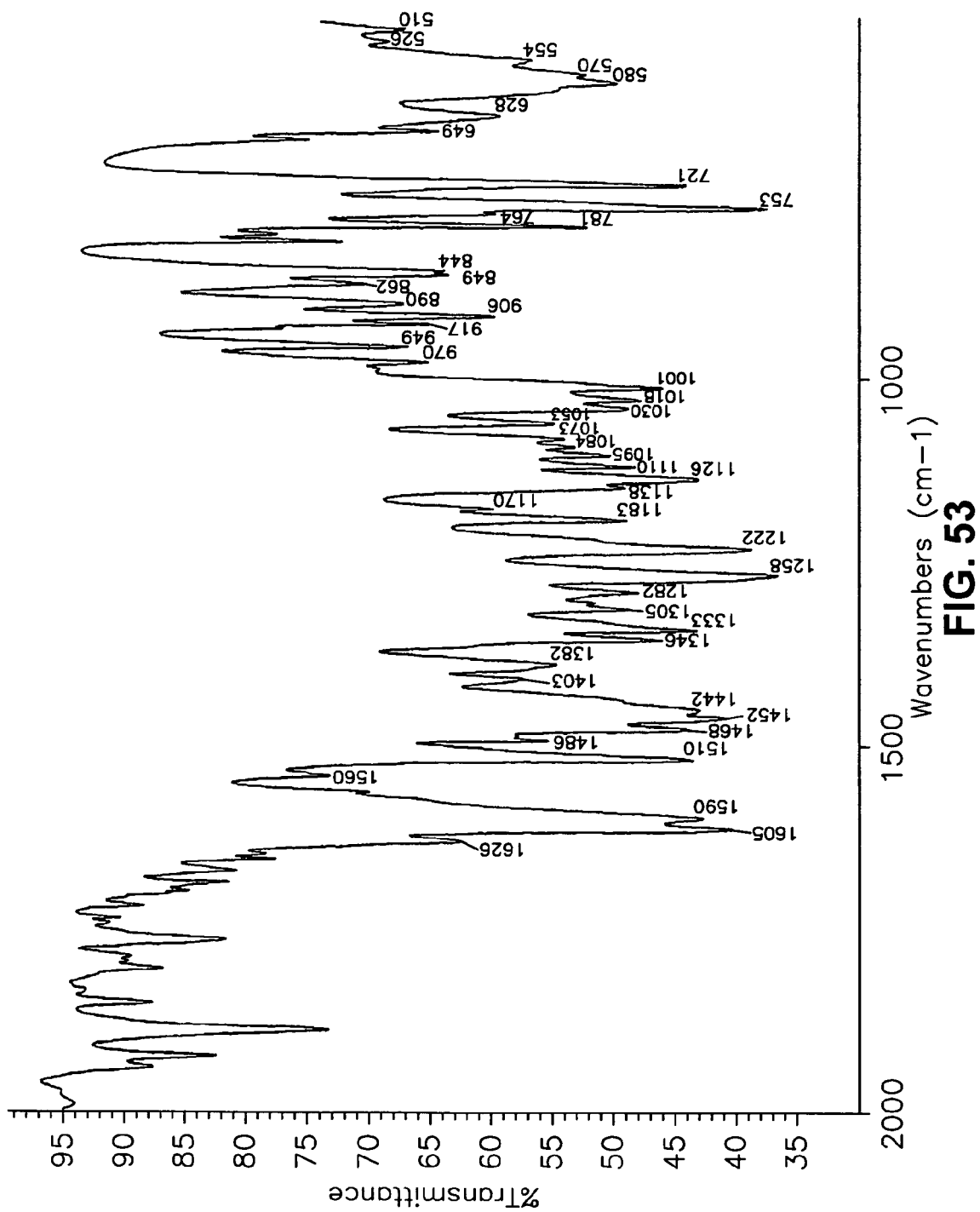

FIG. 53 is an FT-IR spectrum for carvedilol hydrobromide 1-pentanol solvate in the 2000-500 cm$^{-1}$ region of the spectrum.

Figure 54:
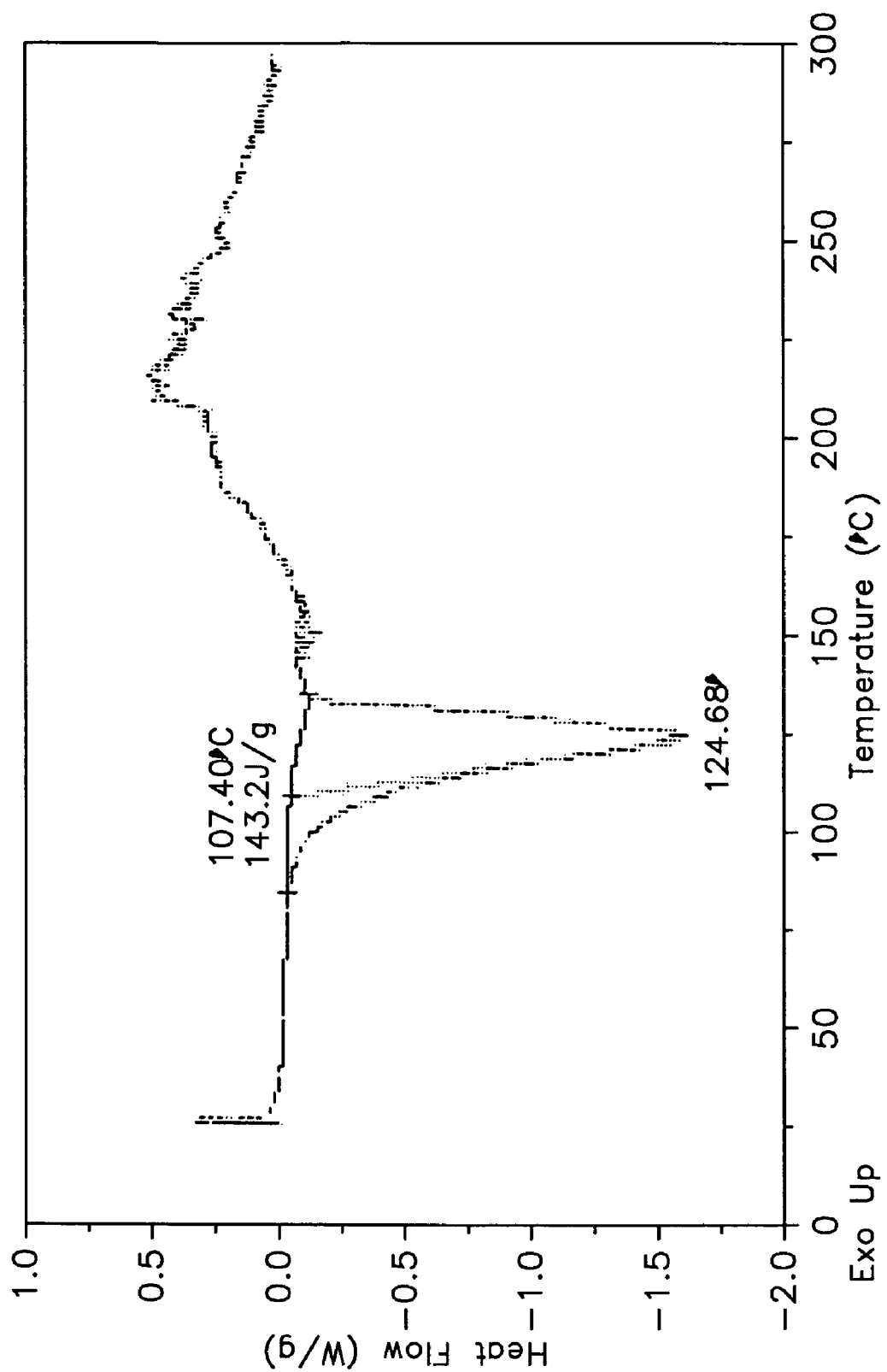

FIG. 54 is a differential scanning calorimetry thermogram for carvedilol hydrobromide 2-methyl-1-propanol solvate.

Figure 55:
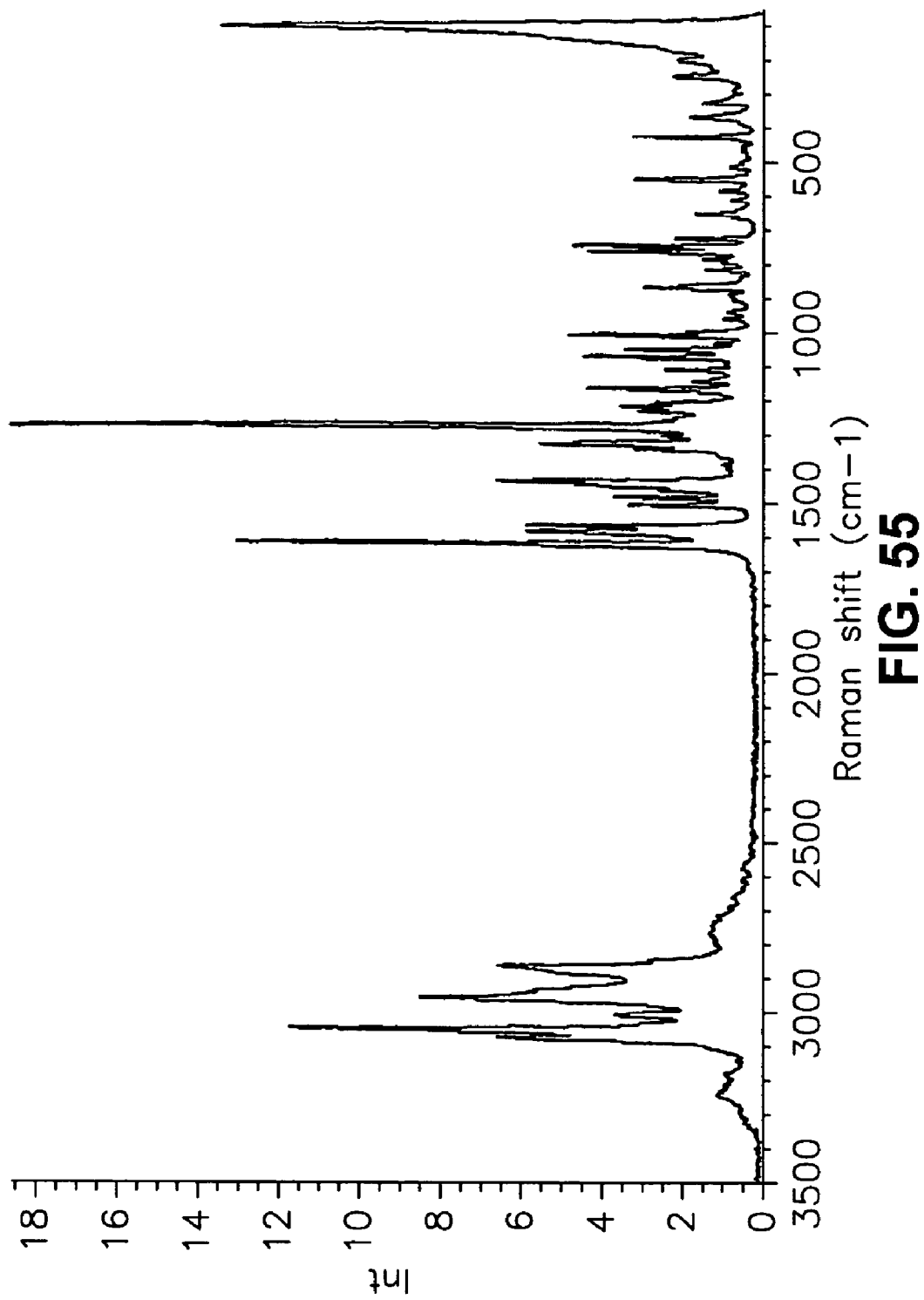

FIG. 55 is an FT-Raman spectrum for carvedilol hydrobromide 2-methyl-1-propanol solvate.

Figure 56:
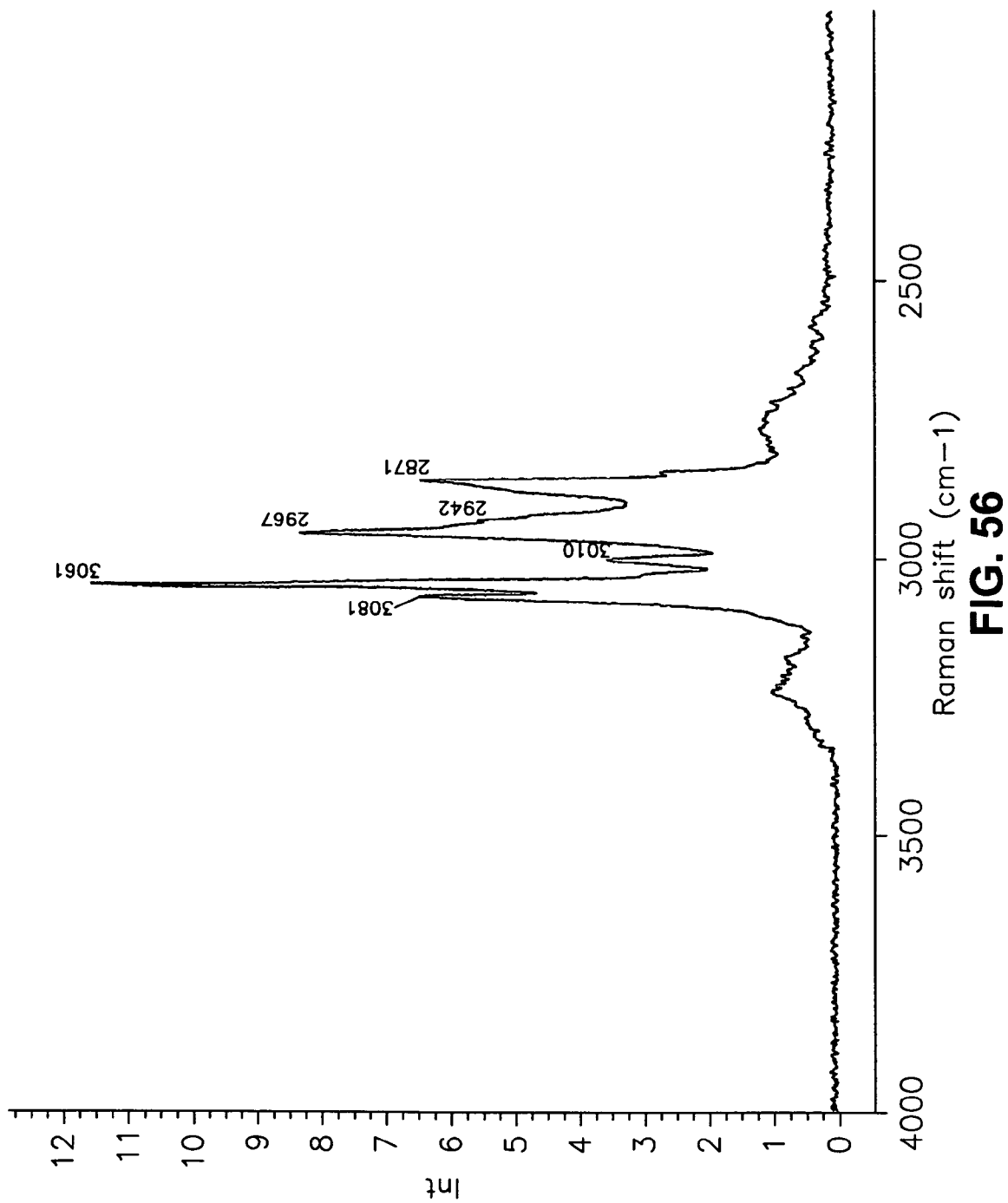

FIG. 56 is an FT-Raman spectrum for carvedilol hydrobromide 2-methyl-1-propanol solvate in the 4000-2000 cm$^{-1}$ region of the spectrum.

Figure 57:
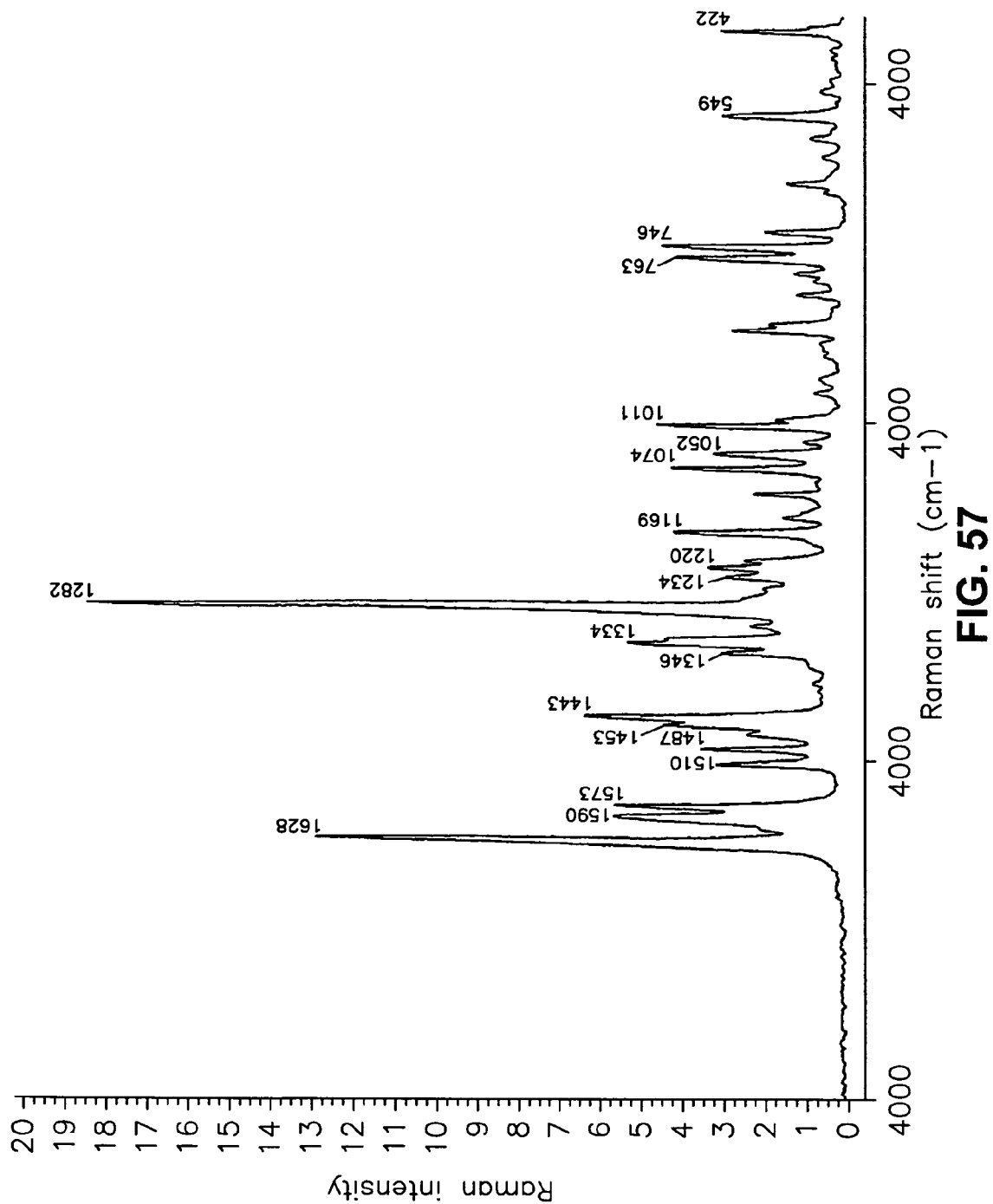

FIG. 57 is an FT-Raman spectrum for carvedilol hydrobromide 2-methyl-1-propanol solvate in the 2000-400 cm$^{-1}$ region of the spectrum.

Figure 58:
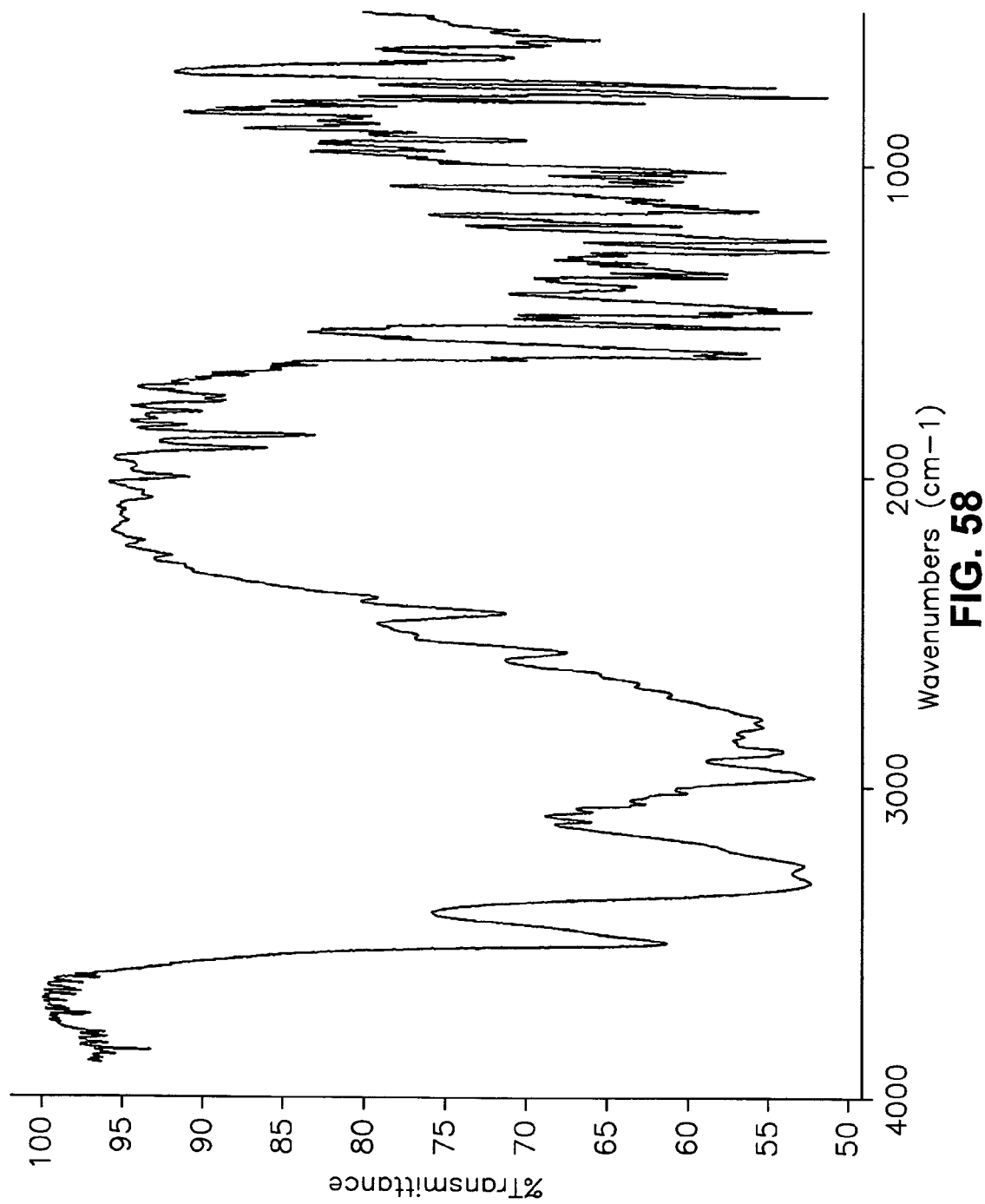

FIG. 58 is an FT-IR spectrum for carvedilol hydrobromide 2-methyl-1-propanol solvate.

Figure 59:
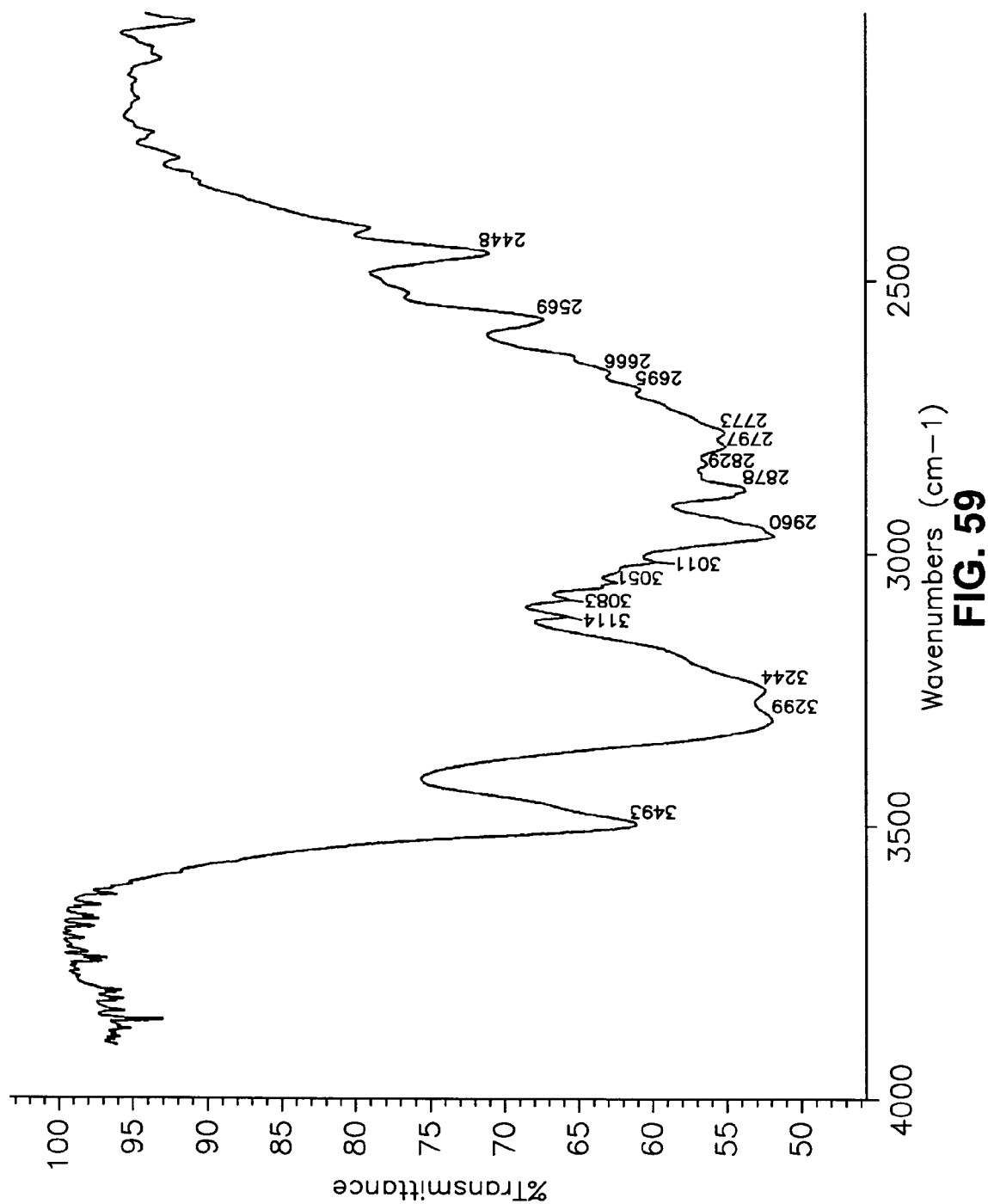

FIG. 59 is an FT-IR spectrum for carvedilol hydrobromide 2-methyl-1-propanol solvate in the 4000-2000 cm$^{-1}$ region of the spectrum.

Figure 60:
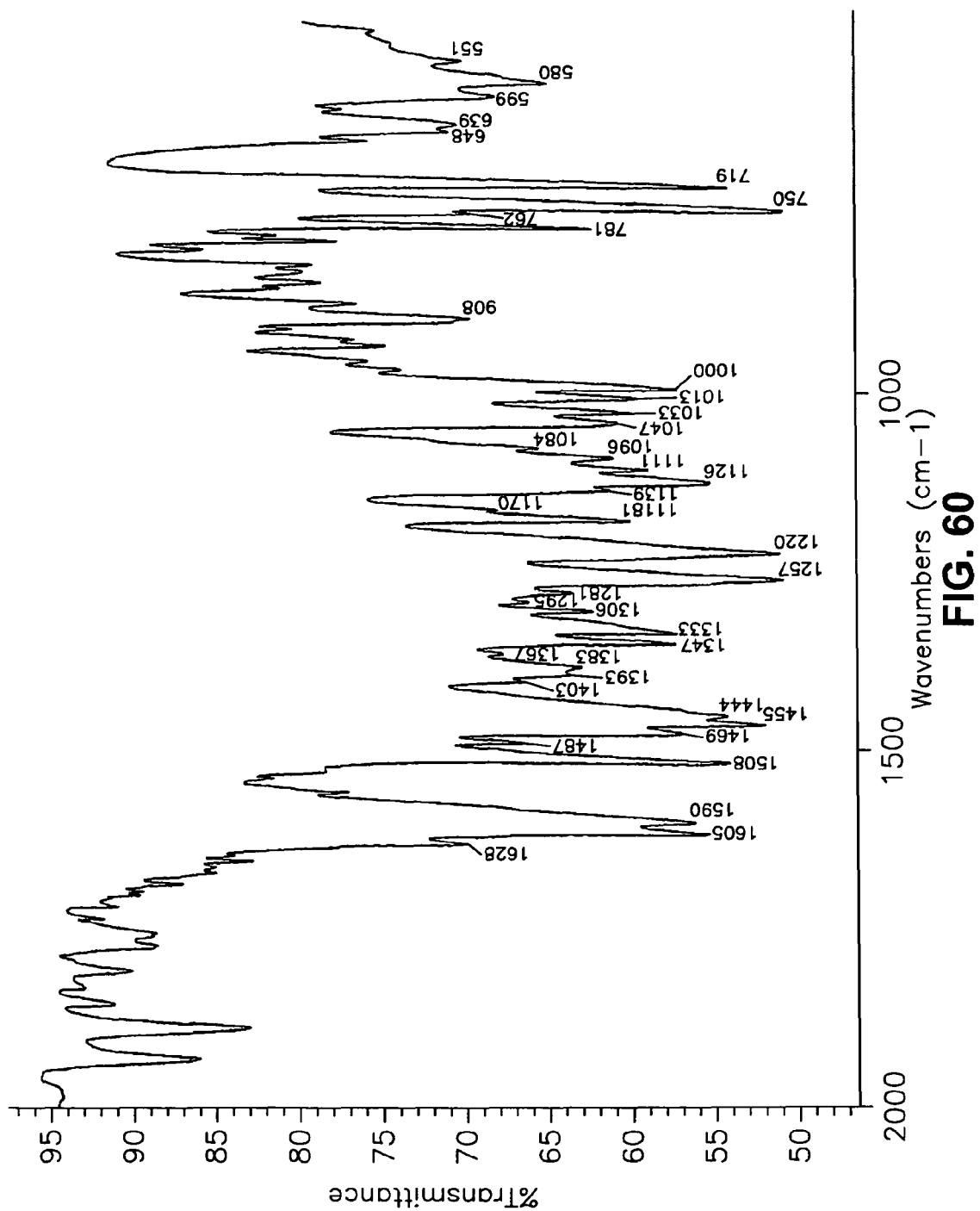

FIG. 60 is an FT-IR spectrum for carvedilol hydrobromide 2-methyl-1-propanol solvate in the 2000-500 cm$^{-1}$ region of the spectrum.

Figure 61:
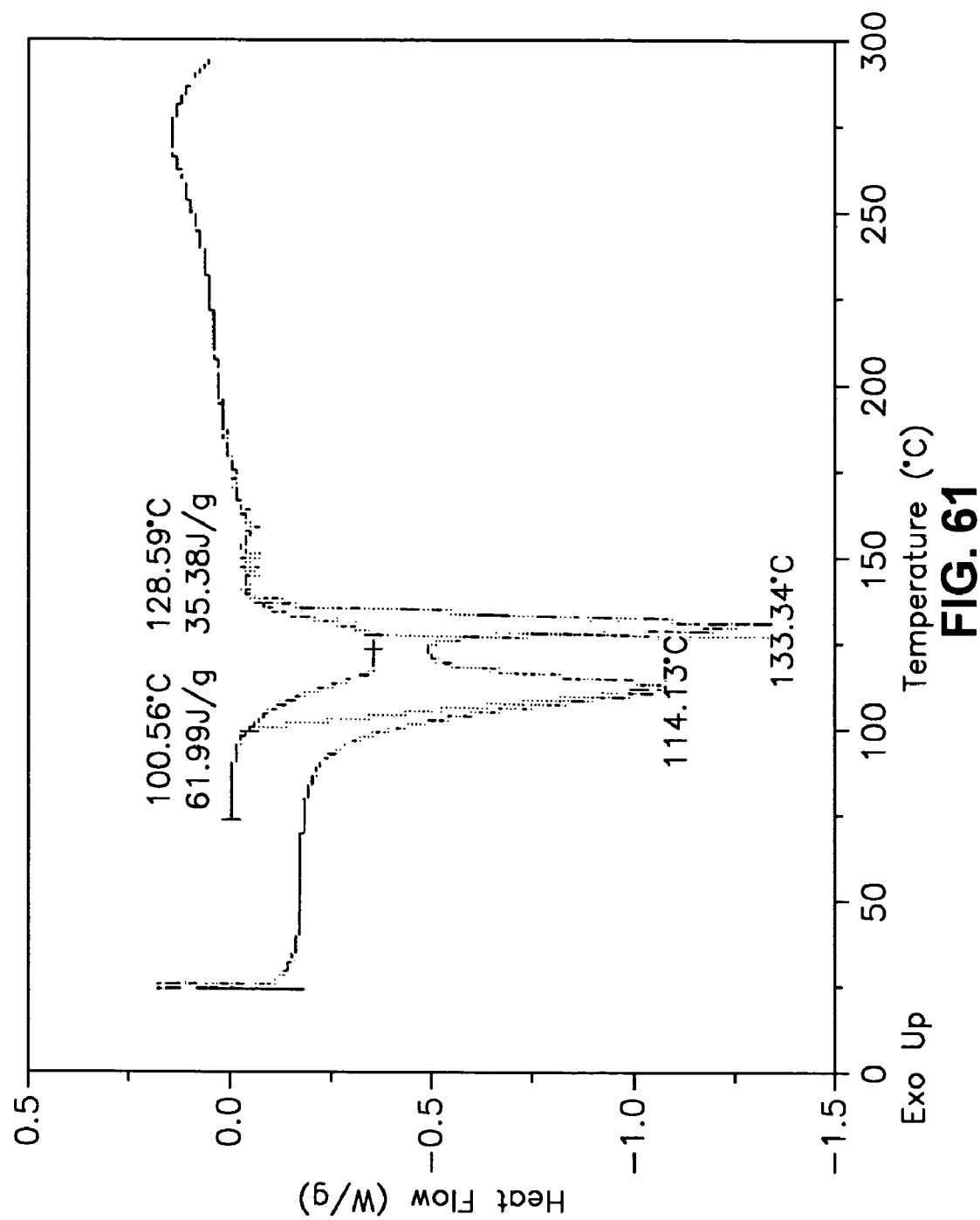

FIG. 61 is a differential scanning calorimetry thermogram for carvedilol hydrobromide trifluoroethanol solvate.

Figure 62:
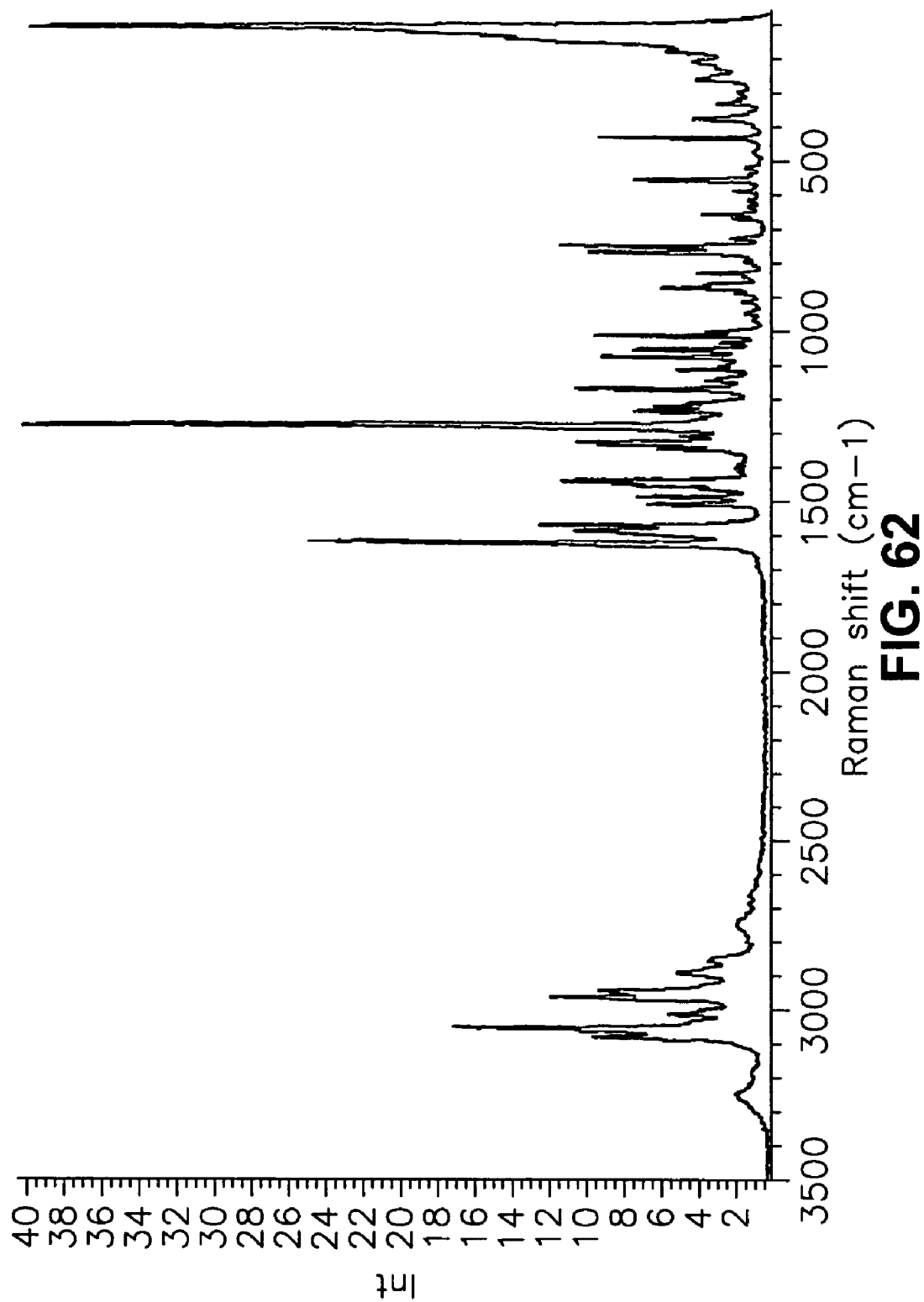

FIG. 62 is an FT-Raman spectrum for carvedilol hydrobromide trifluoroethanol solvate.

Figure 63:
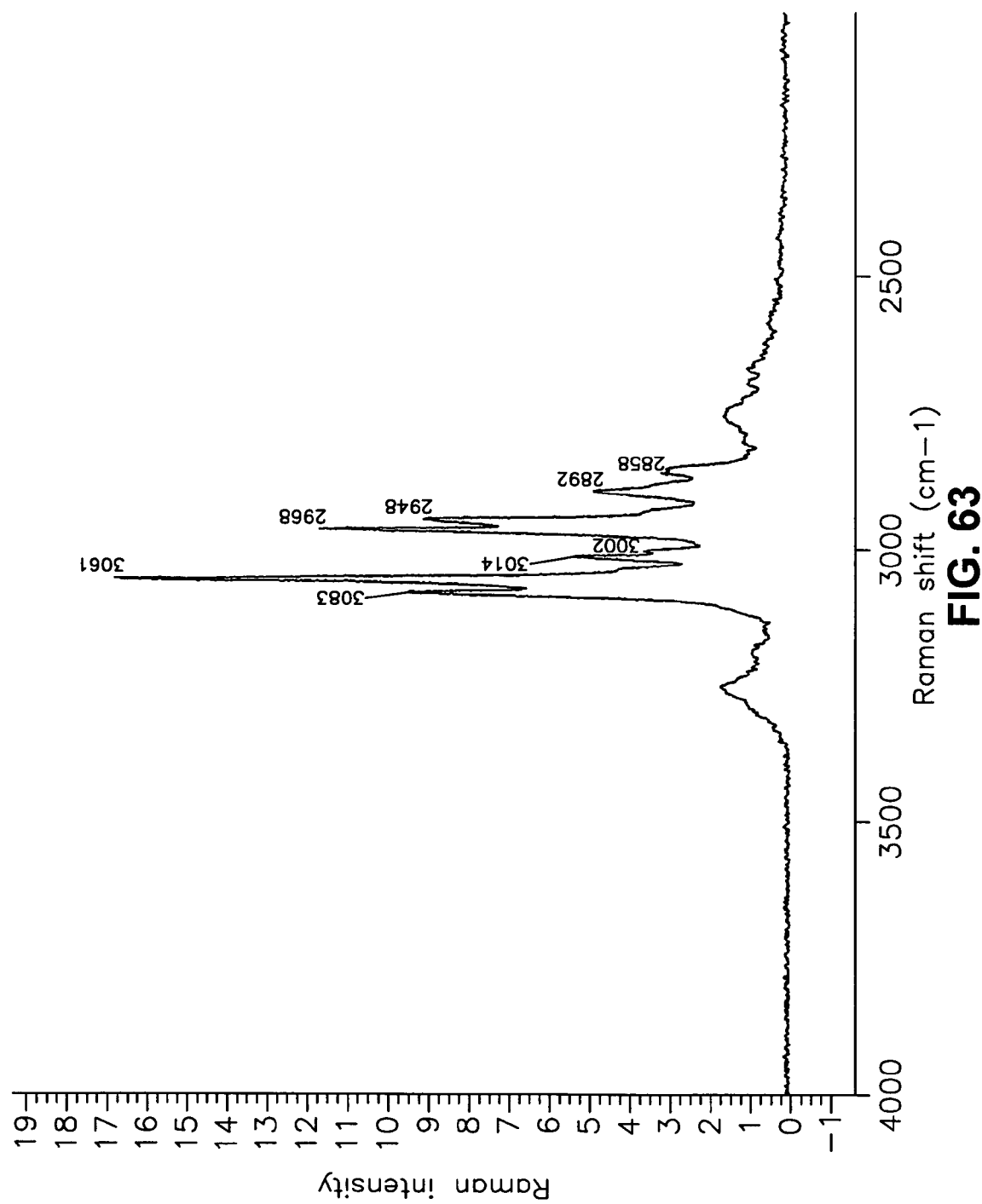

FIG. 63 is an FT-Raman spectrum for carvedilol hydrobromide trifluoroethanol solvate in the 4000-2000 cm$^{-1}$ region of the spectrum.

Figure 64:
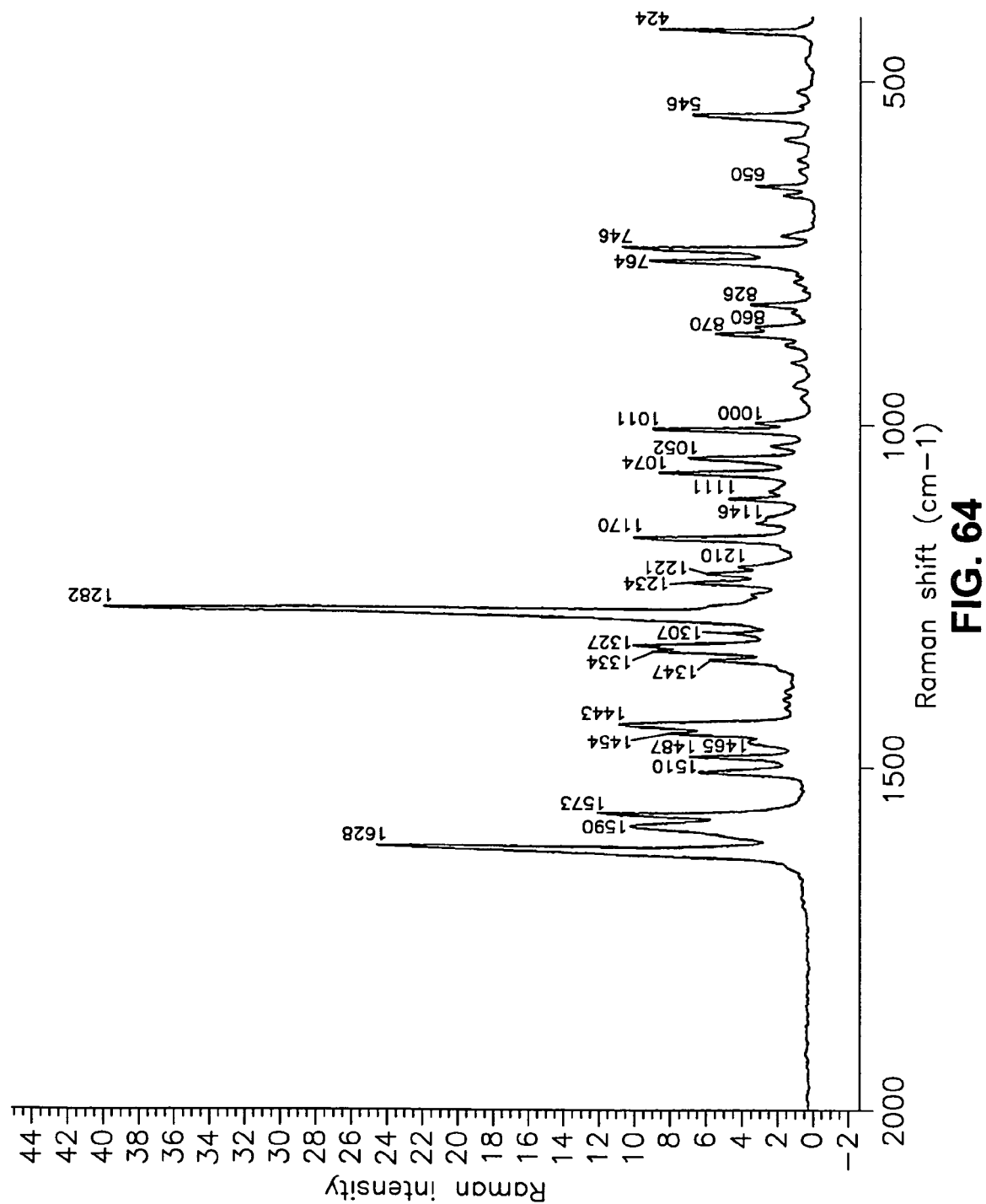

FIG. 64 is an FT-Raman spectrum for carvedilol hydrobromide trifluoroethanol solvate in the 2000-400 cm$^{-1}$ region of the spectrum.

Figure 65:
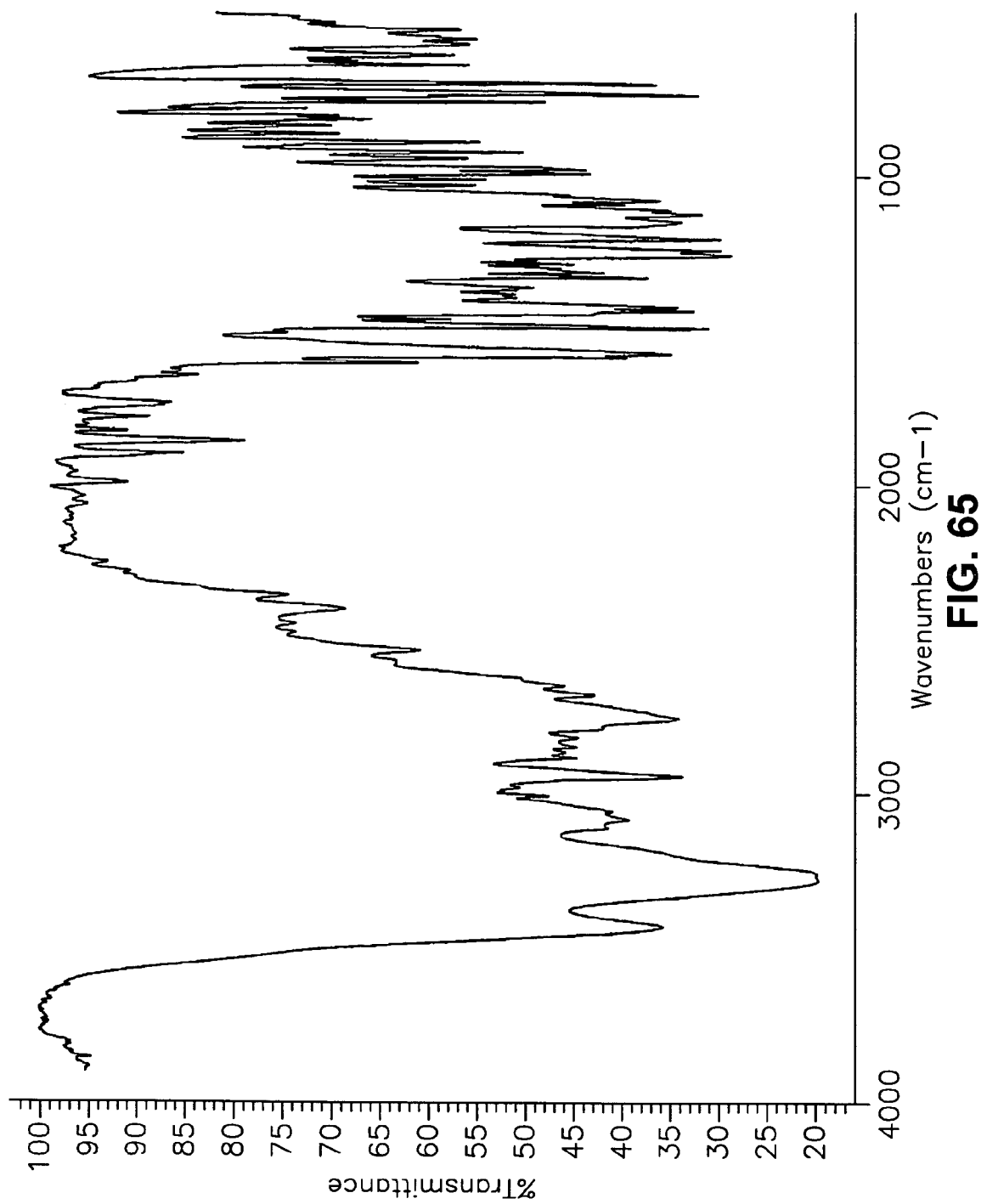

FIG. 65 is an FT-IR spectrum for carvedilol hydrobromide trifluoroethanol solvate.

Figure 66:
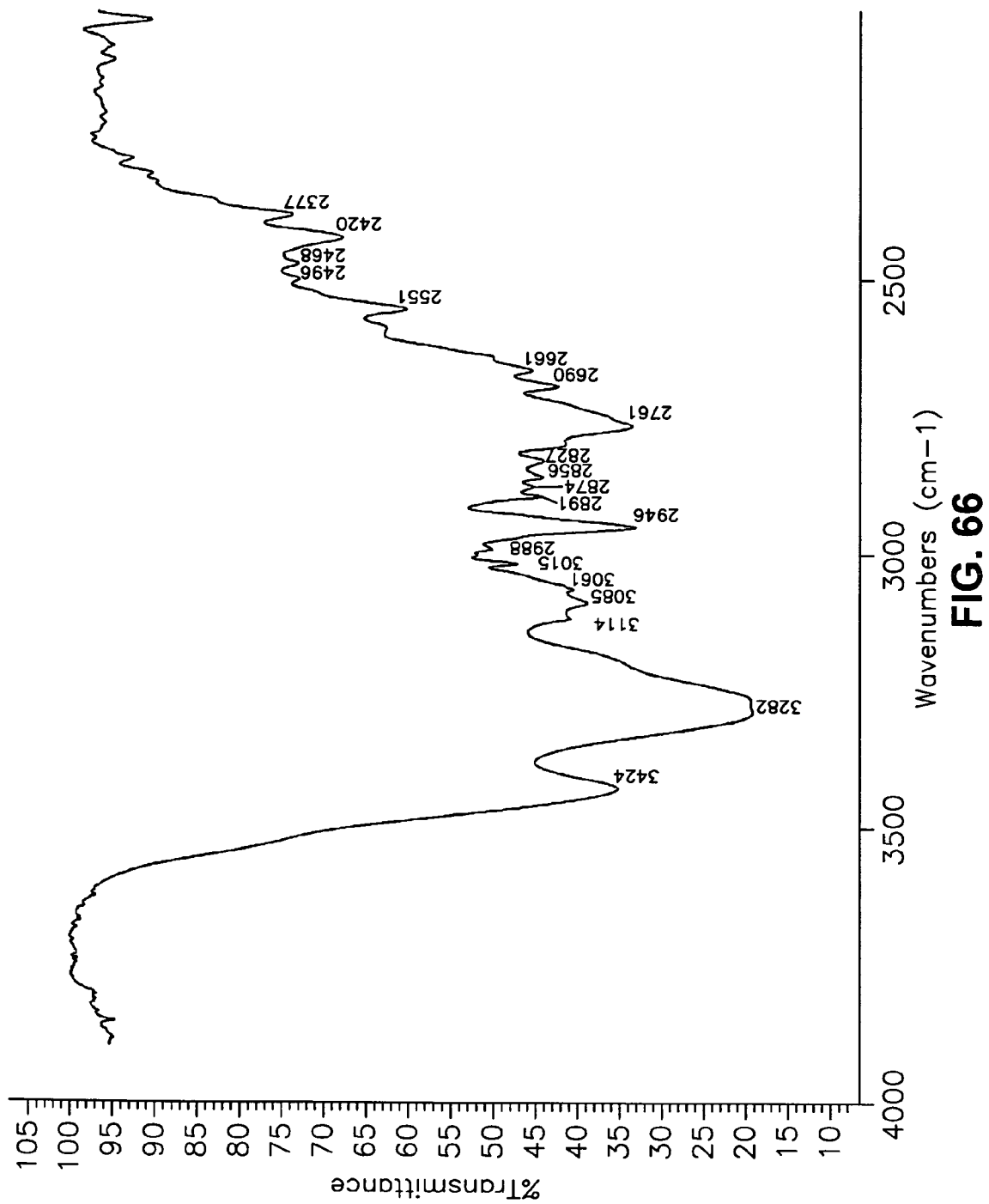

FIG. 66 is an FT-IR spectrum for carvedilol hydrobromide trifluoroethanol solvate in the 4000-2000 cm$^{-1}$ region of the spectrum.

Figure 67:
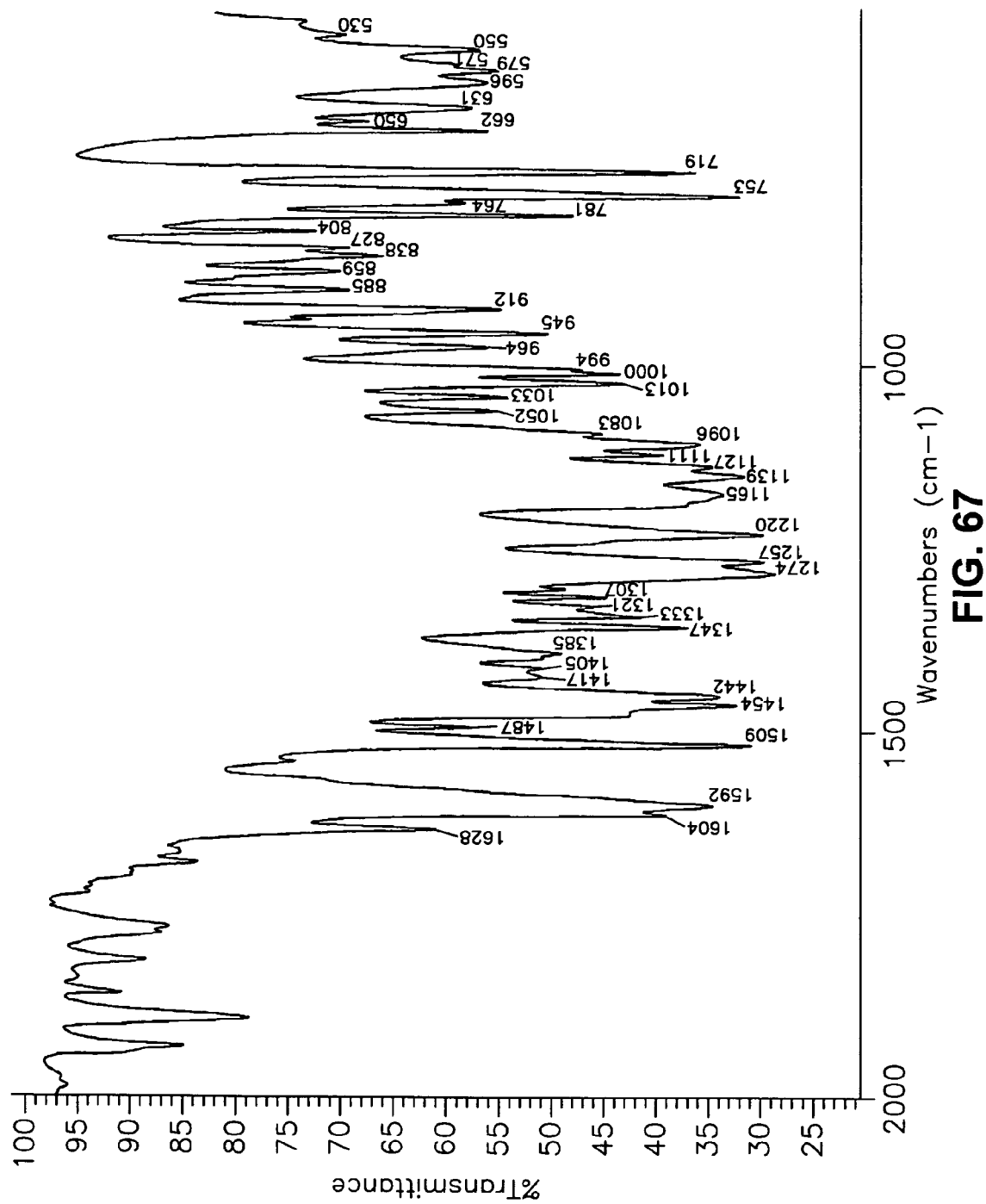

FIG. 67 is an FT-IR spectrum for carvedilol hydrobromide trifluoroethanol solvate in the 2000-500 cm$^{-1}$ region of the spectrum.

Figure 68:
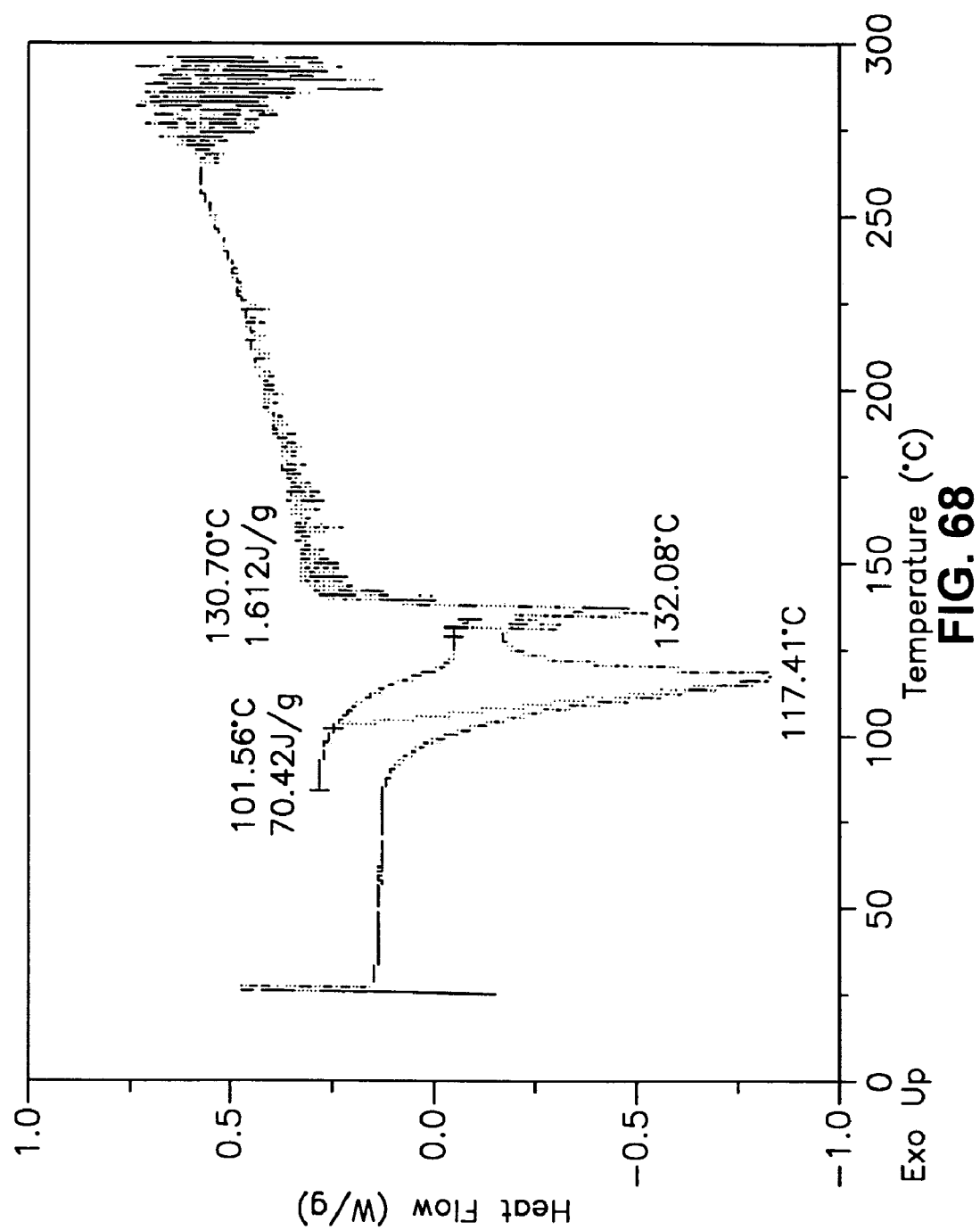

FIG. 68 is a differential scanning calorimetry thermogram for carvedilol hydrobromide 2-propanol solvate.

Figure 69:
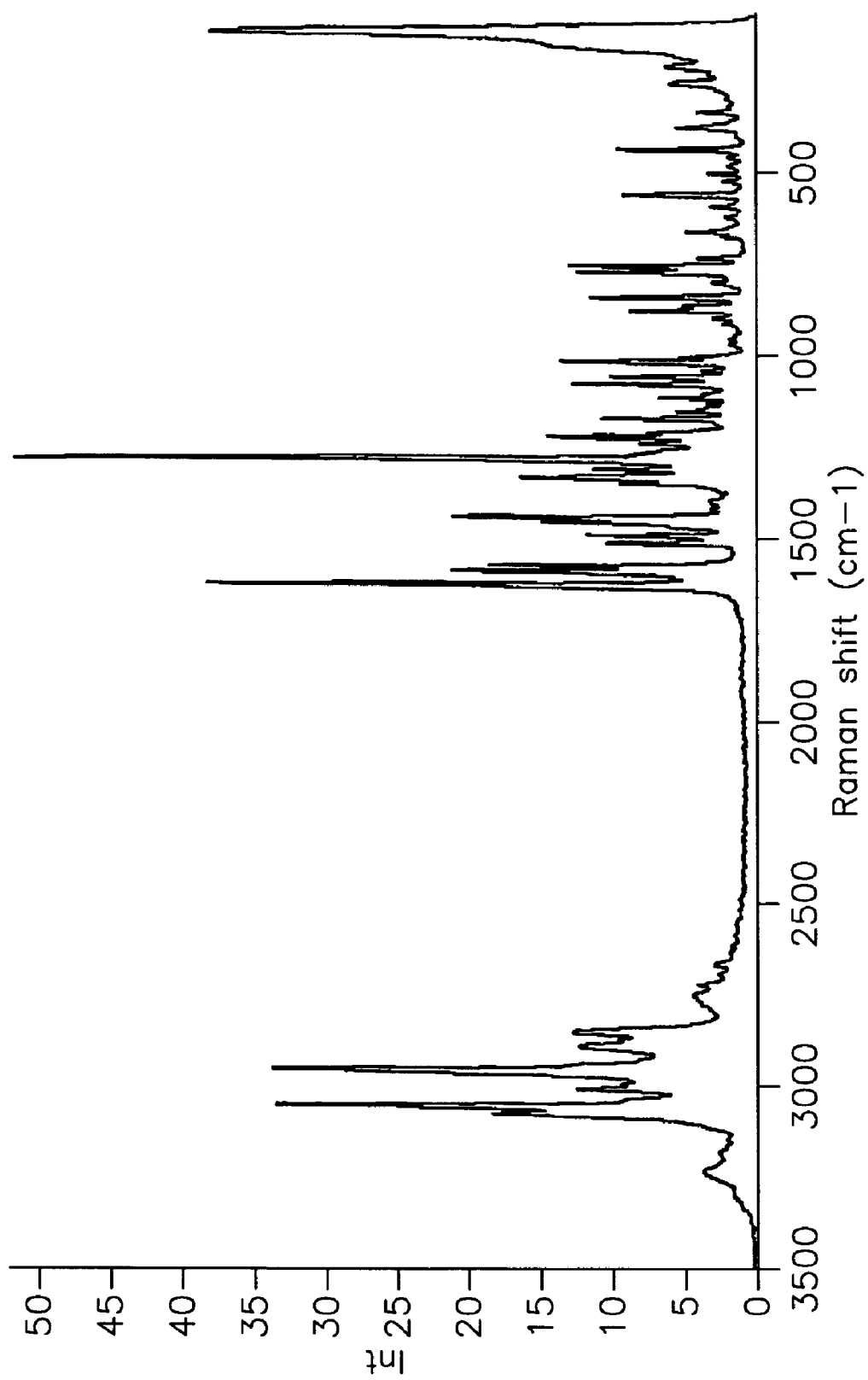

FIG. 69 is an FT-Raman spectrum for carvedilol hydrobromide 2-propanol solvate.

Figure 70:
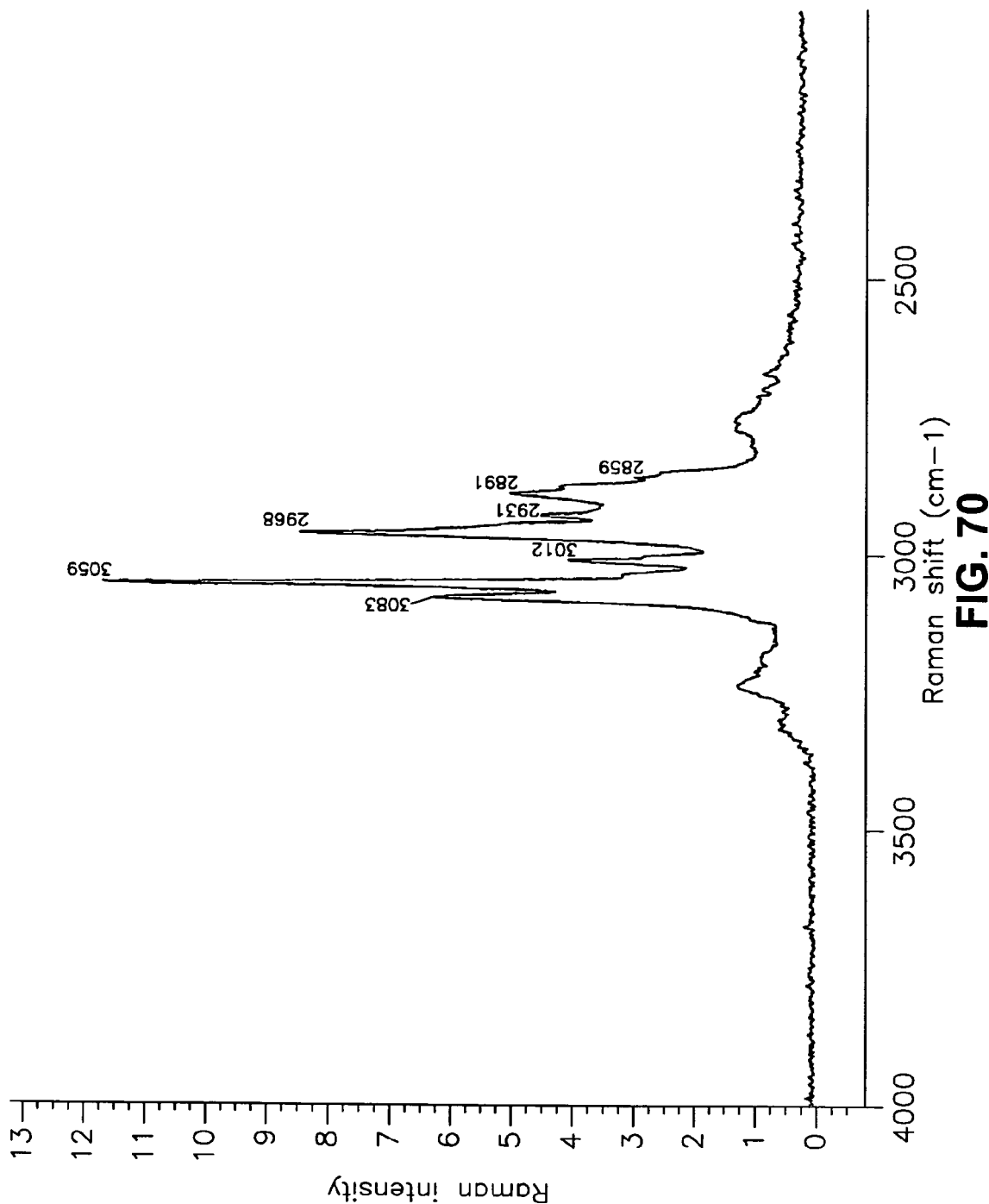

FIG. 70 is an FT-Raman spectrum for carvedilol hydrobromide 2-propanol solvate in the 4000-2000 cm$^{-1}$ region of the spectrum.

Figure 71:
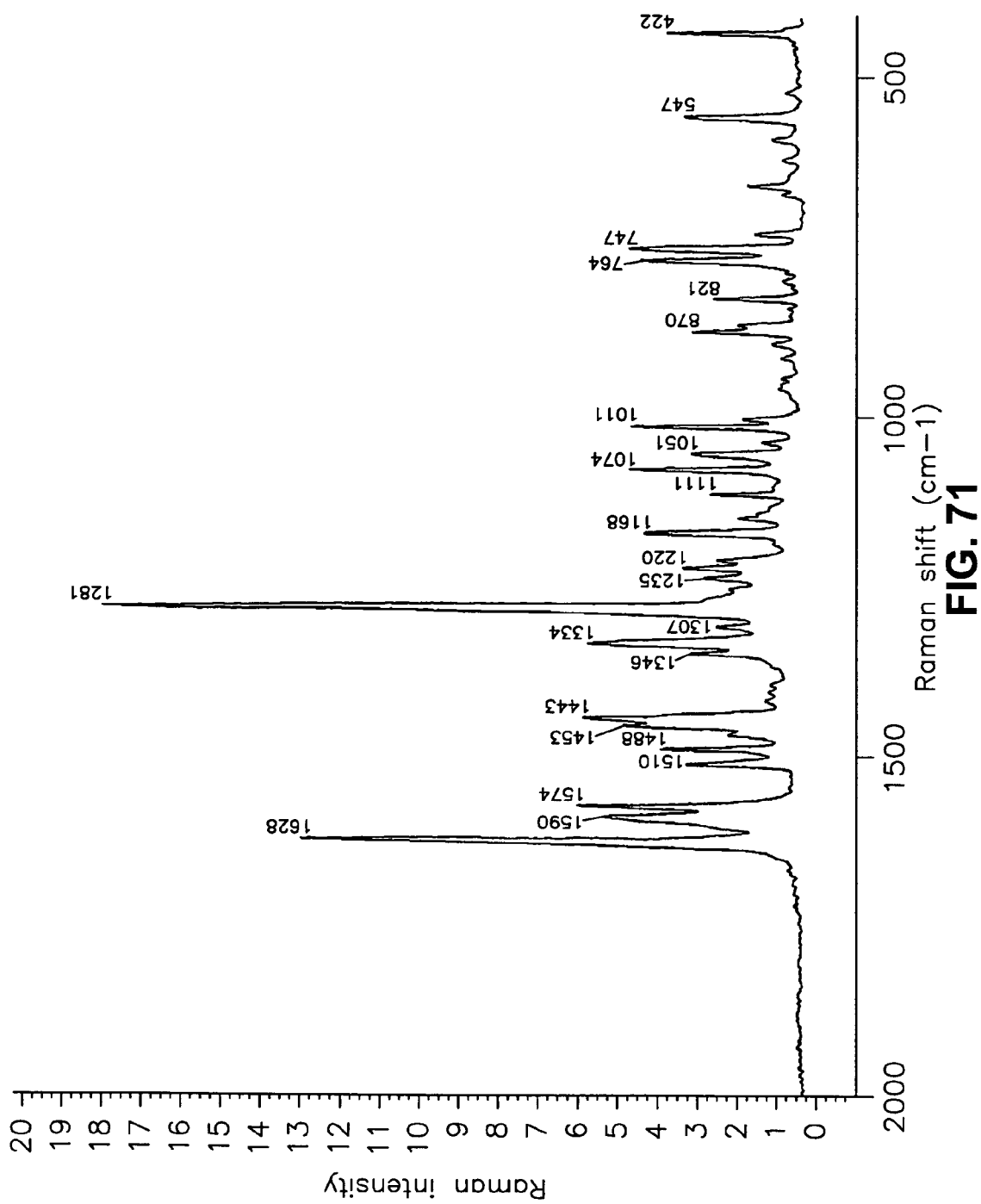

FIG. 71 is an FT-Raman spectrum for carvedilol hydrobromide 2-propanol solvate in the 2000-400 cm$^{-1}$ region of the spectrum.

Figure 72:
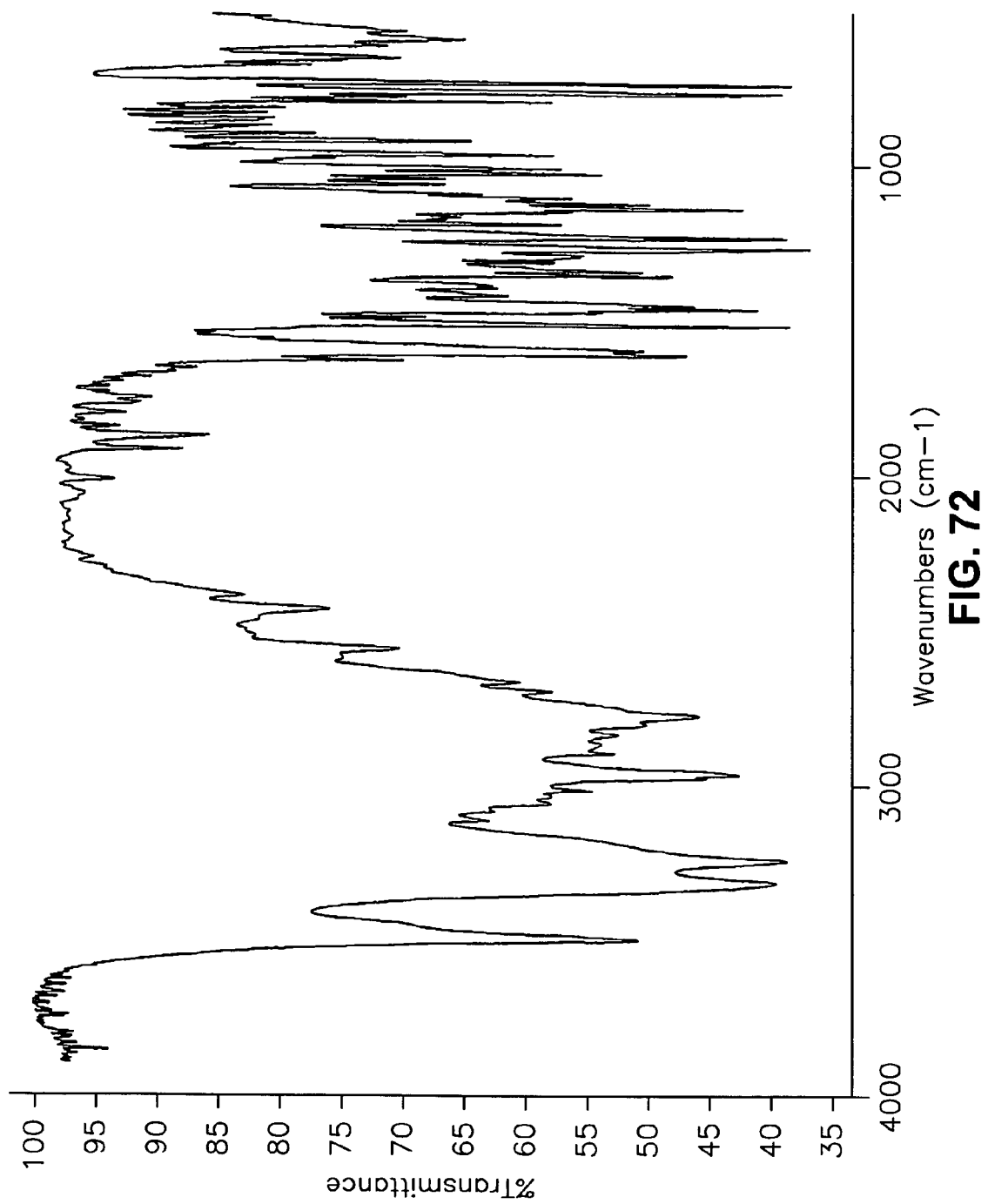

FIG. 72 is an FT-IR spectrum for carvedilol hydrobromide 2-propanol solvate.

Figure 73:
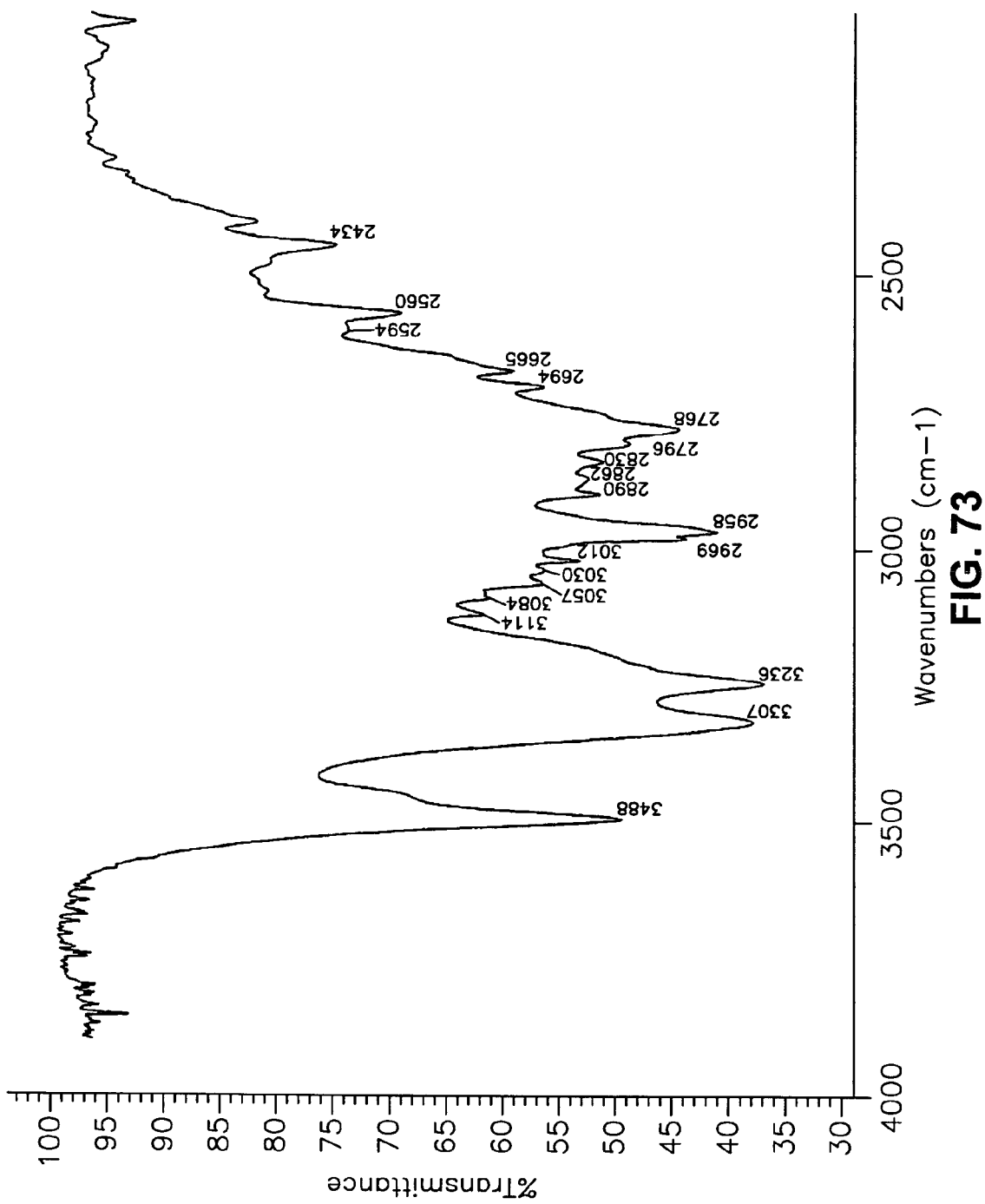

FIG. 73 is an FT-IR spectrum for carvedilol hydrobromide 2-propanol solvate in the 4000-2000 cm$^{-1}$ region of the spectrum.

Figure 74:
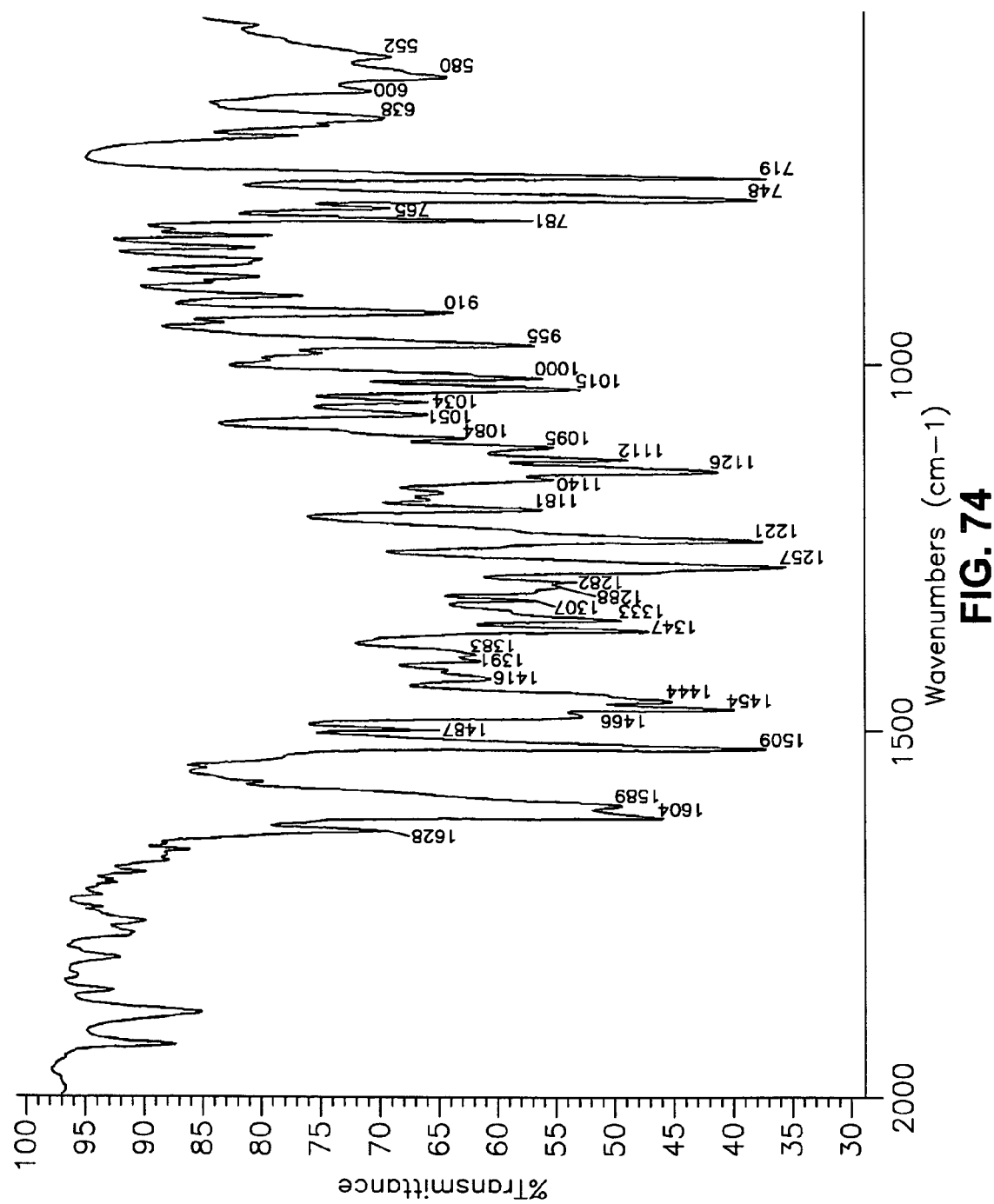

FIG. 74 is an FT-IR spectrum for carvedilol hydrobromide 2-propanol solvate in the 2000-500 cm$^{-1}$ region of the spectrum.

Figure 75:
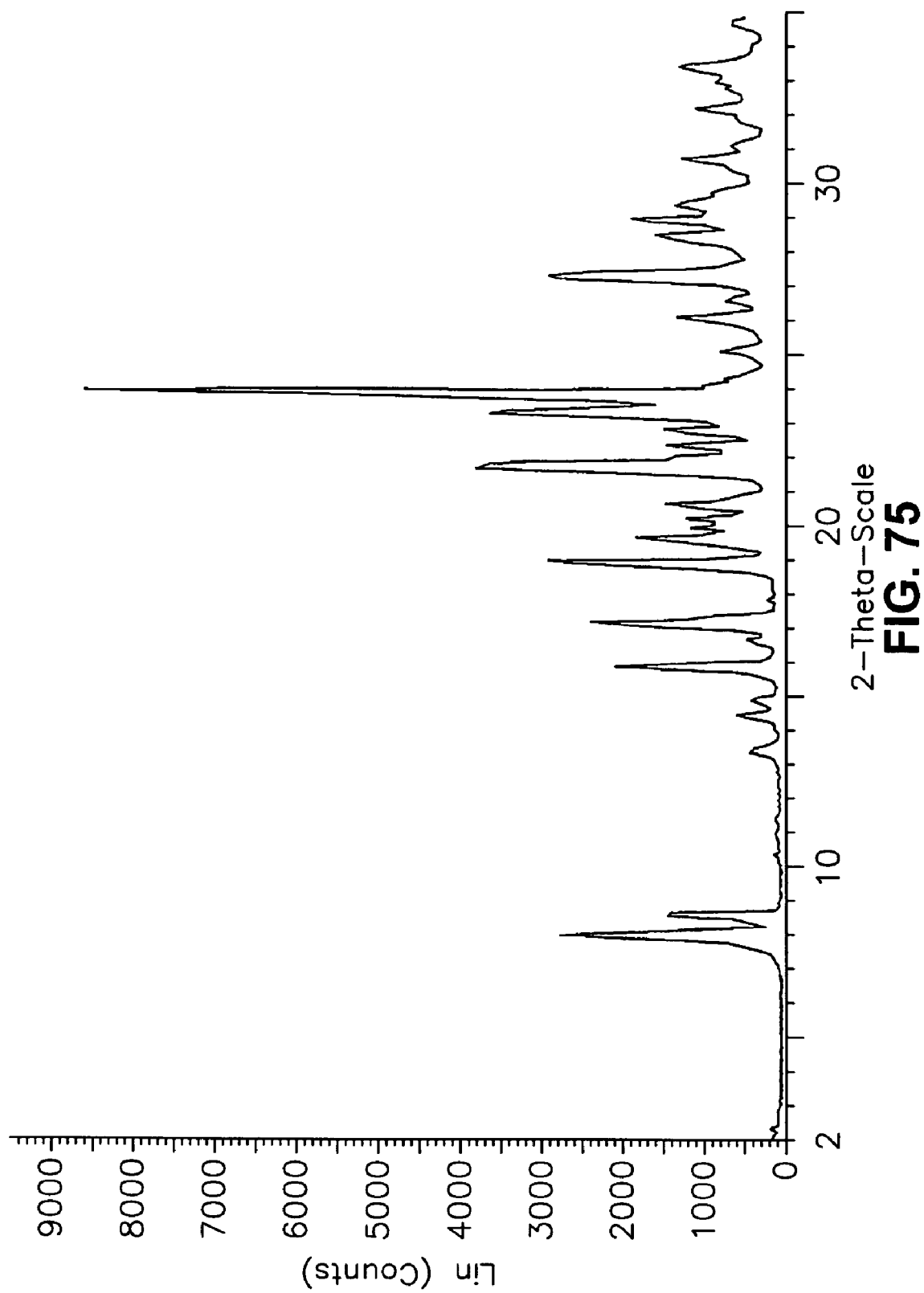

FIG. 75 is an x-ray powder diffractogram for carvedilol hydrobromide n-propanol solvate #1.

Figure 76:
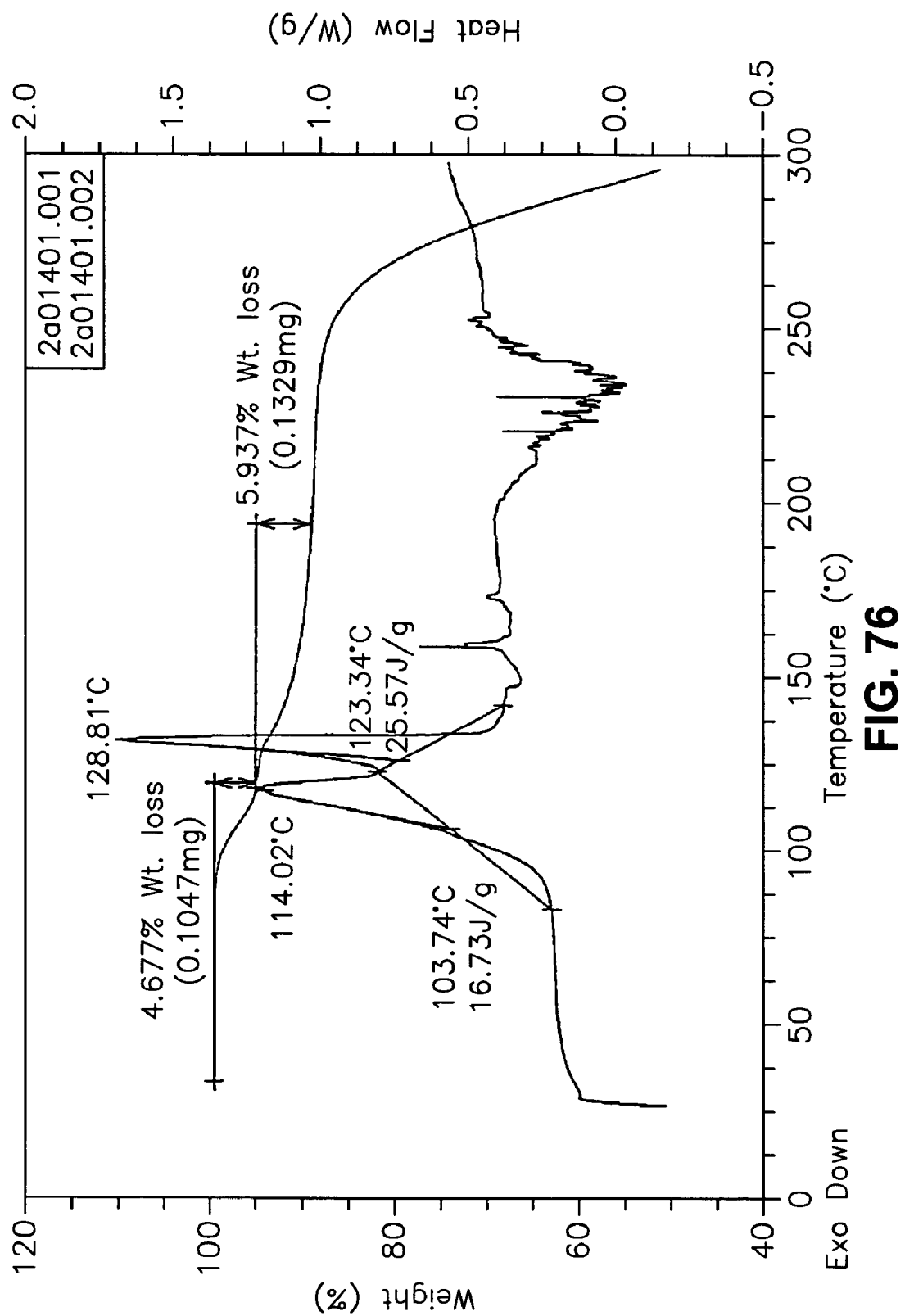

FIG. 76 shows the thermal analysis results for carvedilol hydrobromide n-propanol solvate #1.

Figure 77:
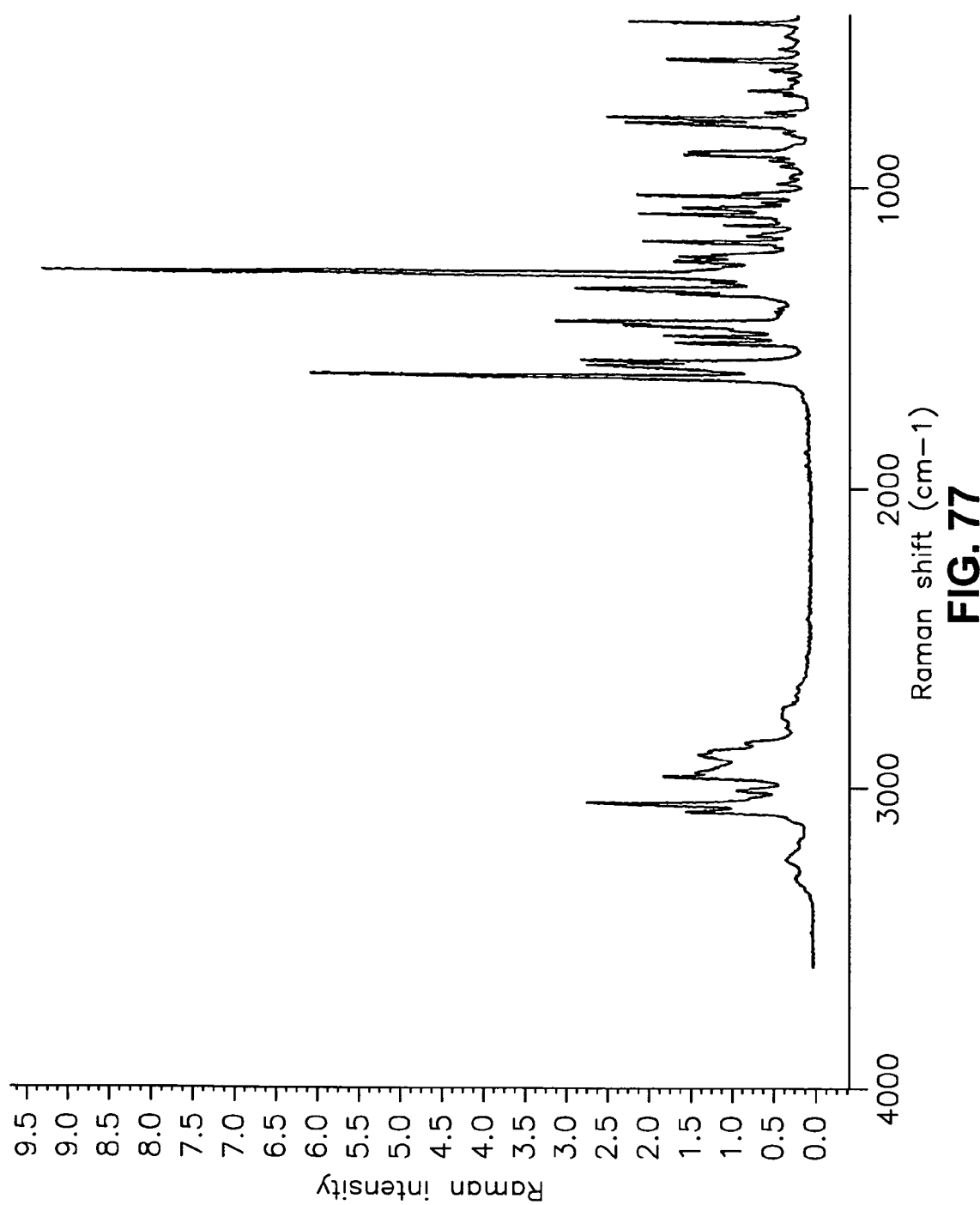

FIG. 77 is an FT-Raman spectrum for carvedilol hydrobromide n-propanol solvate #1.

Figure 78:
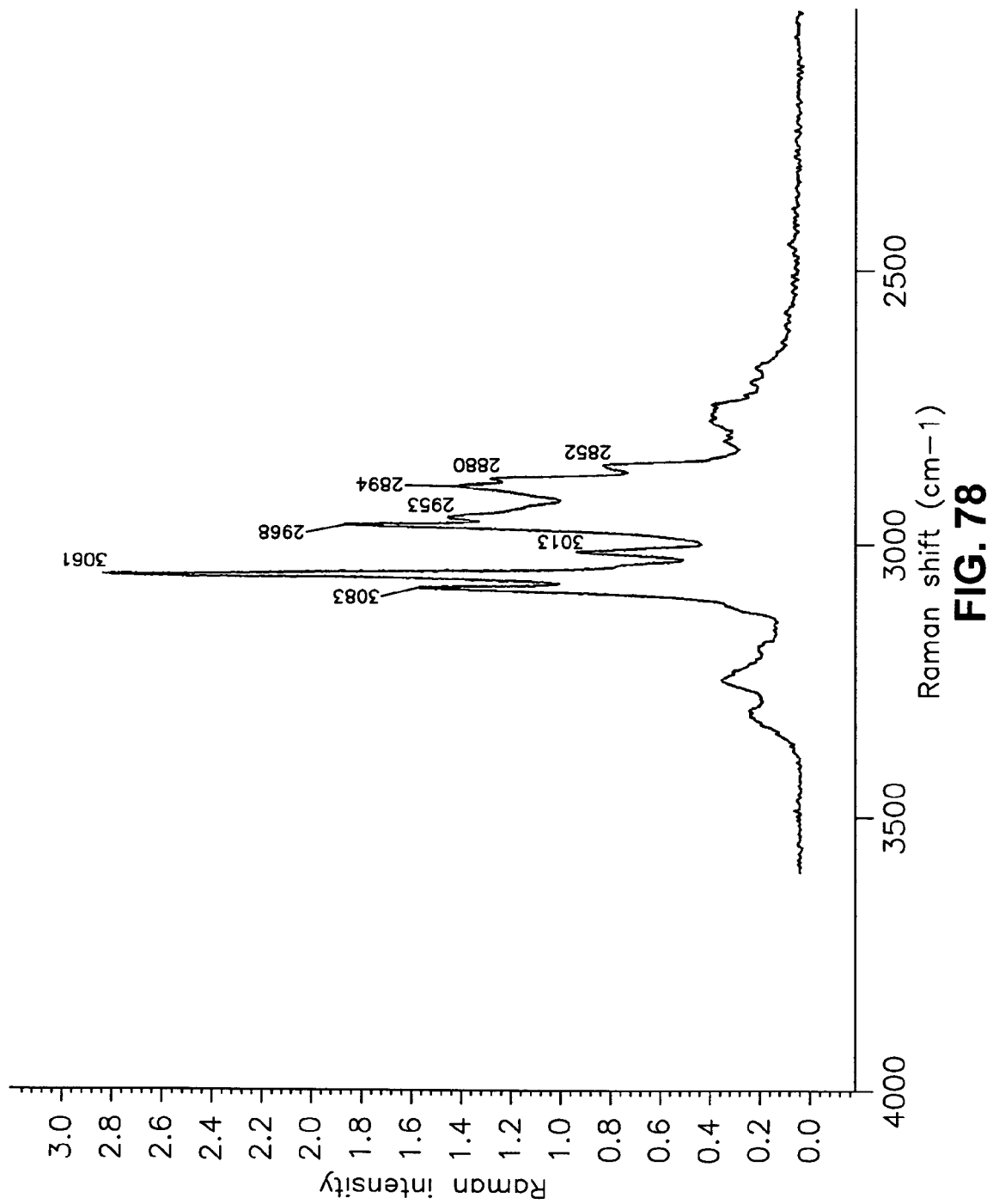

FIG. 78 is an FT-Raman spectrum for carvedilol hydrobromide n-propanol solvate #1 in the 4000-2000 cm$^{-1}$ region of the spectrum.

Figure 79:
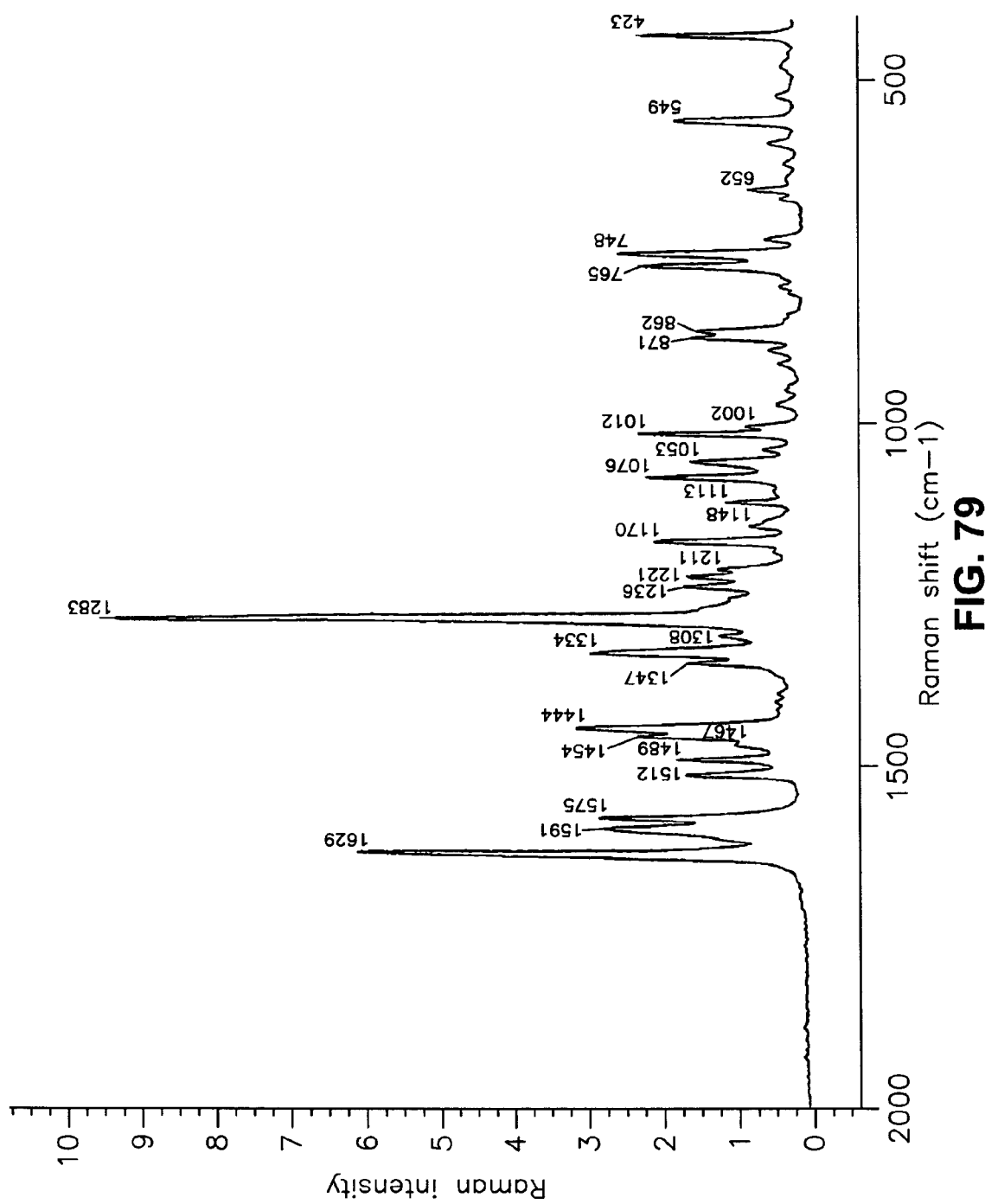

FIG. 79 is an FT-Raman spectrum for carvedilol hydrobromide n-propanol solvate #1 in the 2000-400 cm$^{-1}$ region of the spectrum.

Figure 80:
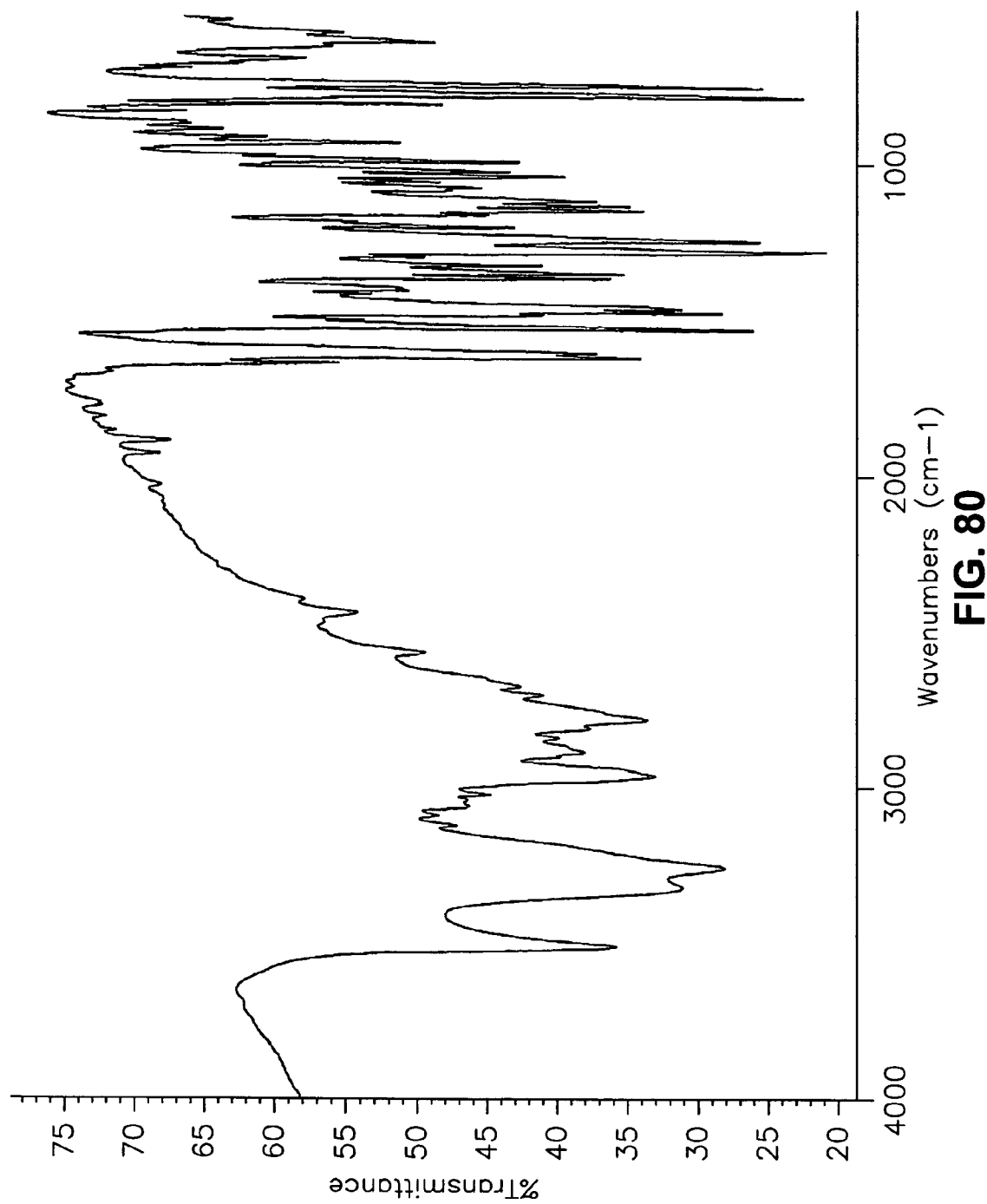

FIG. 80 is an FT-IR spectrum for carvedilol hydrobromide n-propanol solvate #1.

Figure 81:
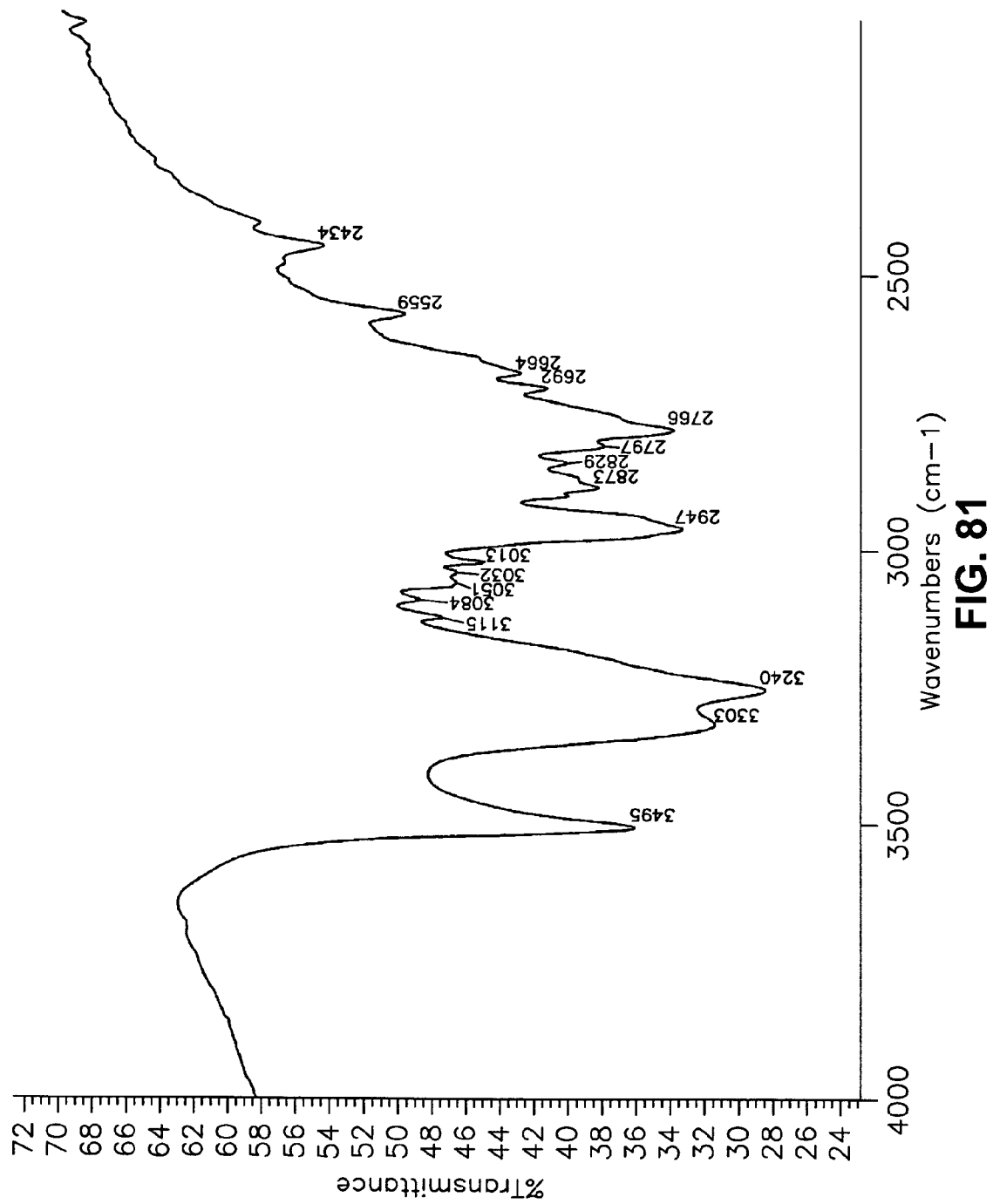

FIG. 81 is an FT-IR spectrum for carvedilol hydrobromide n-propanol solvate #1 in the 4000-2000 cm$^{-1}$ region of the spectrum.

Figure 82:
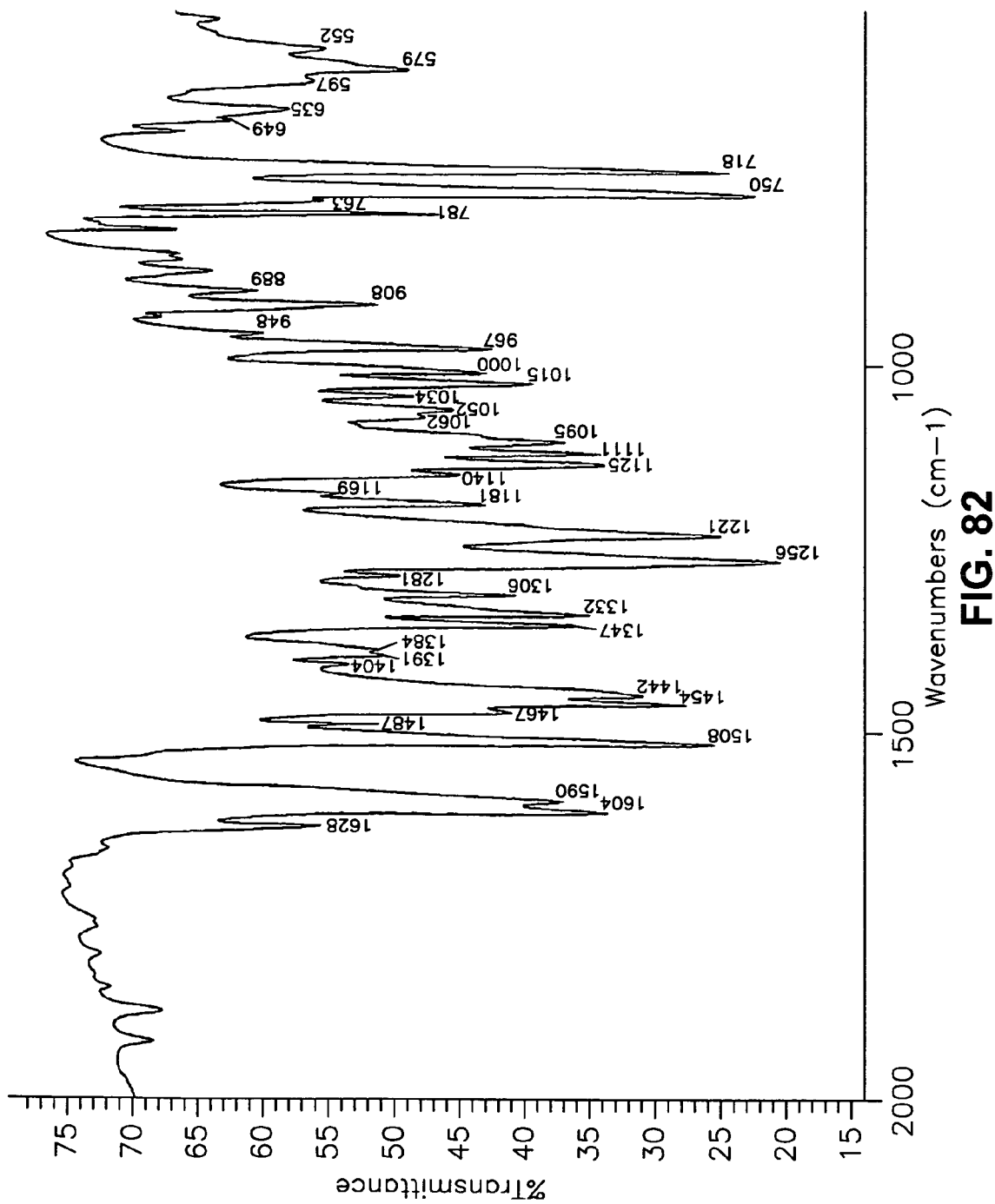

FIG. 82 is an FT-IR spectrum for carvedilol hydrobromide n-propanol solvate #1 in the 2000-500 cm$^{-1}$ region of the spectrum.

Figure 83:
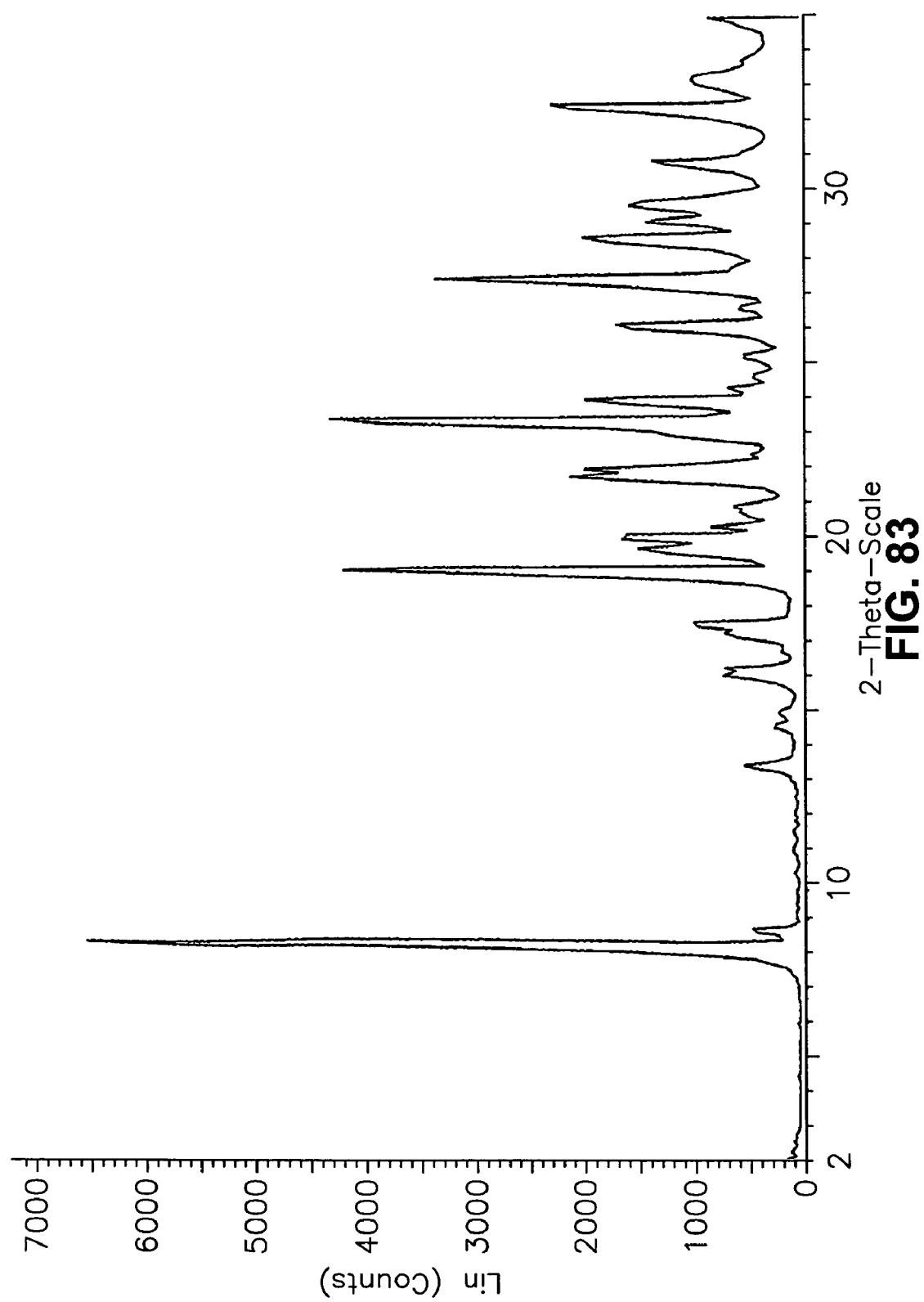

FIG. 83 is an x-ray powder diffractogram for carvedilol hydrobromide n-propanol solvate #2.

Figure 84:
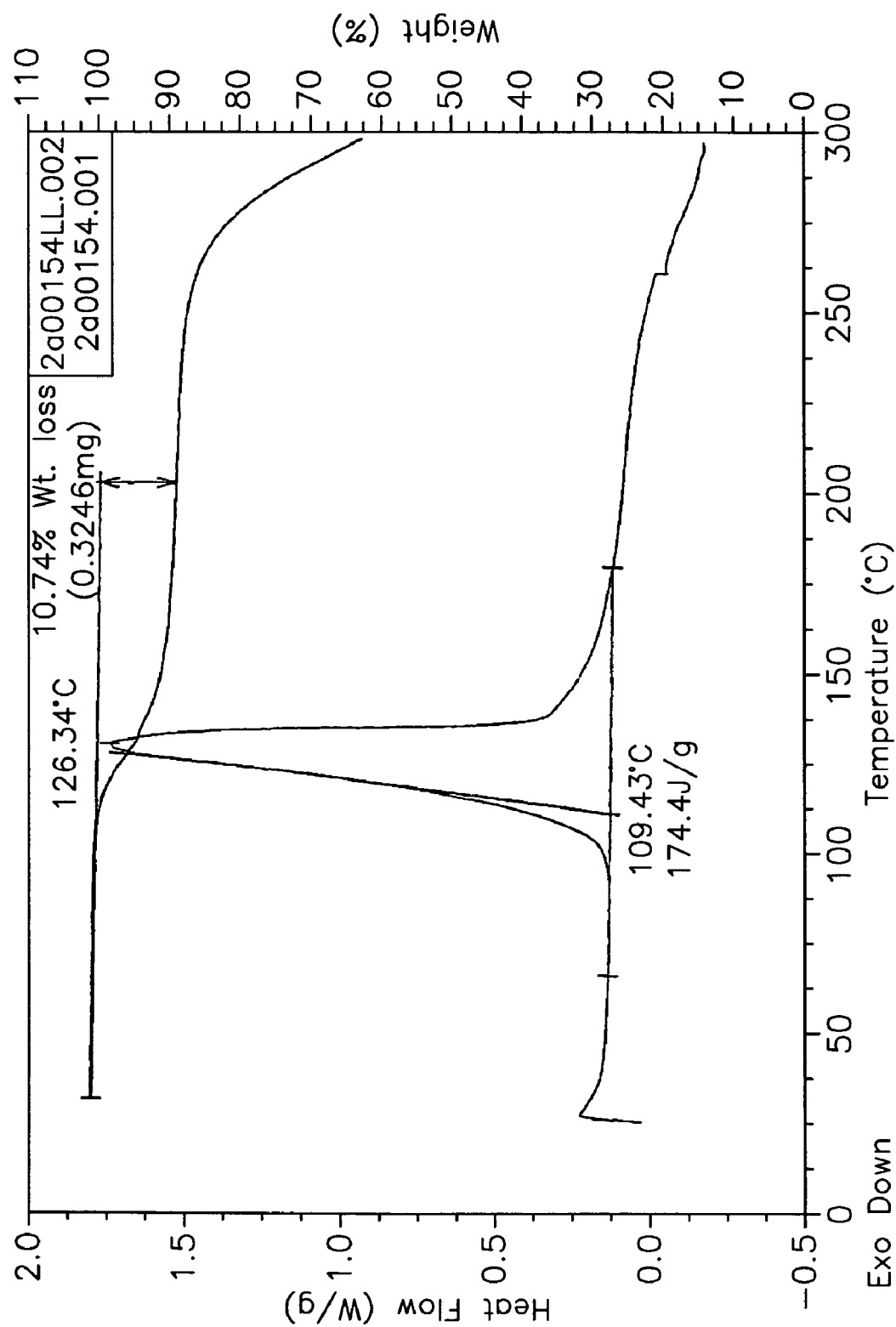

FIG. 84 shows the thermal analysis results for carvedilol hydrobromide n-propanol solvate #2.

Figure 85:
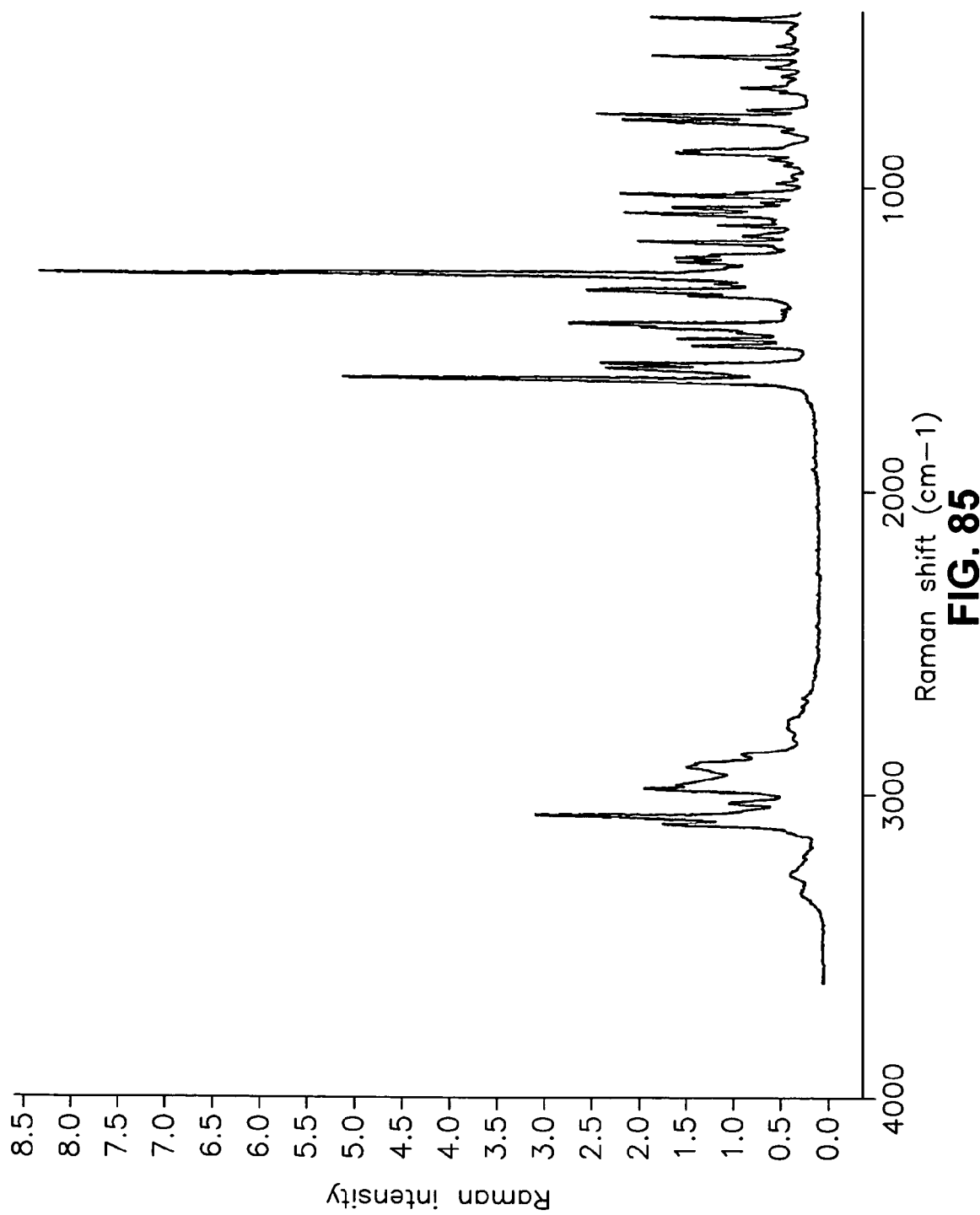

FIG. 85 is an FT-Raman spectrum for carvedilol hydrobromide n-propanol solvate #2.

Figure 86:
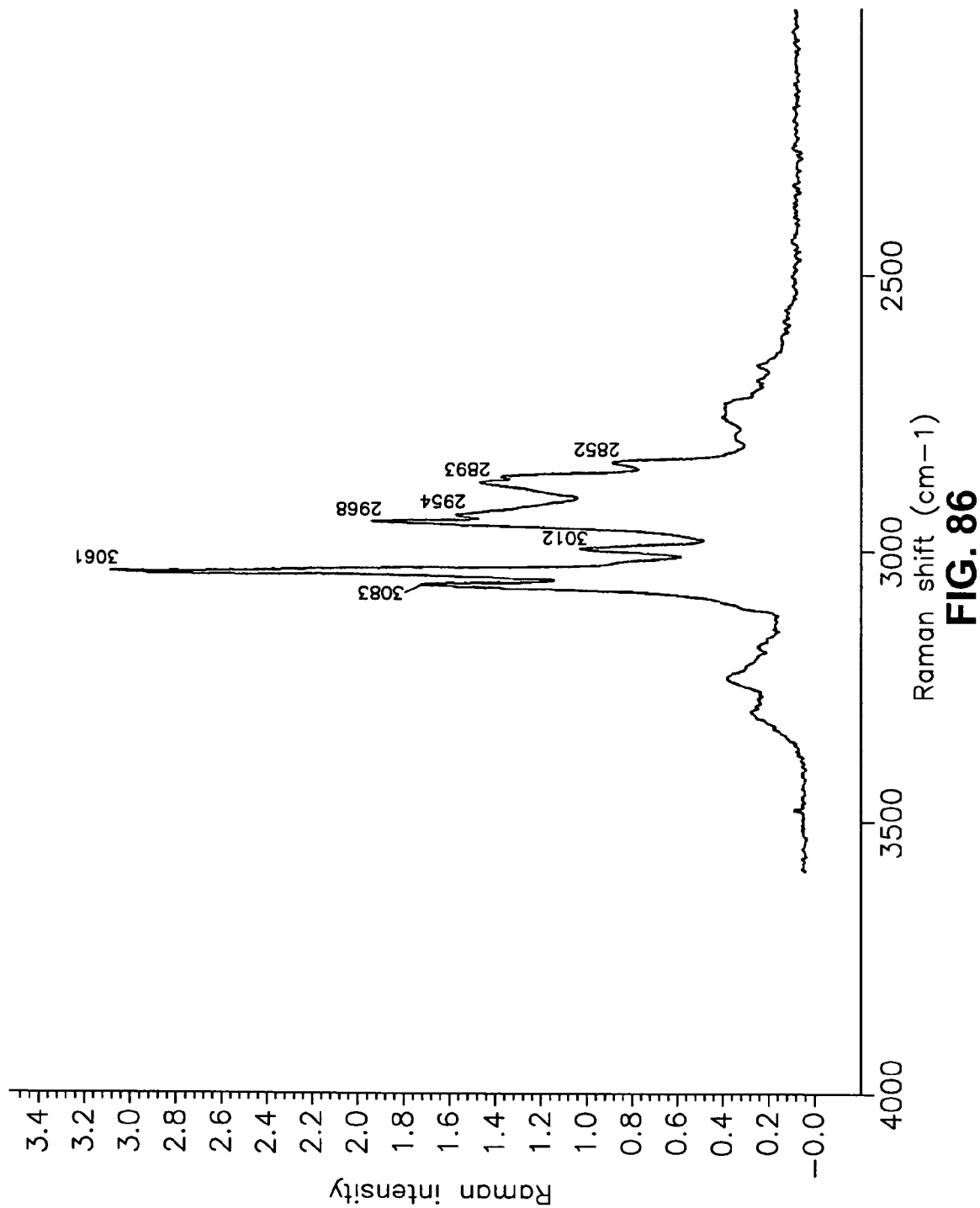

FIG. 86 is an FT-Raman spectrum for carvedilol hydrobromide n-propanol solvate #2 in the 4000-2000 cm$^{-1}$ region of the spectrum.

Figure 87:
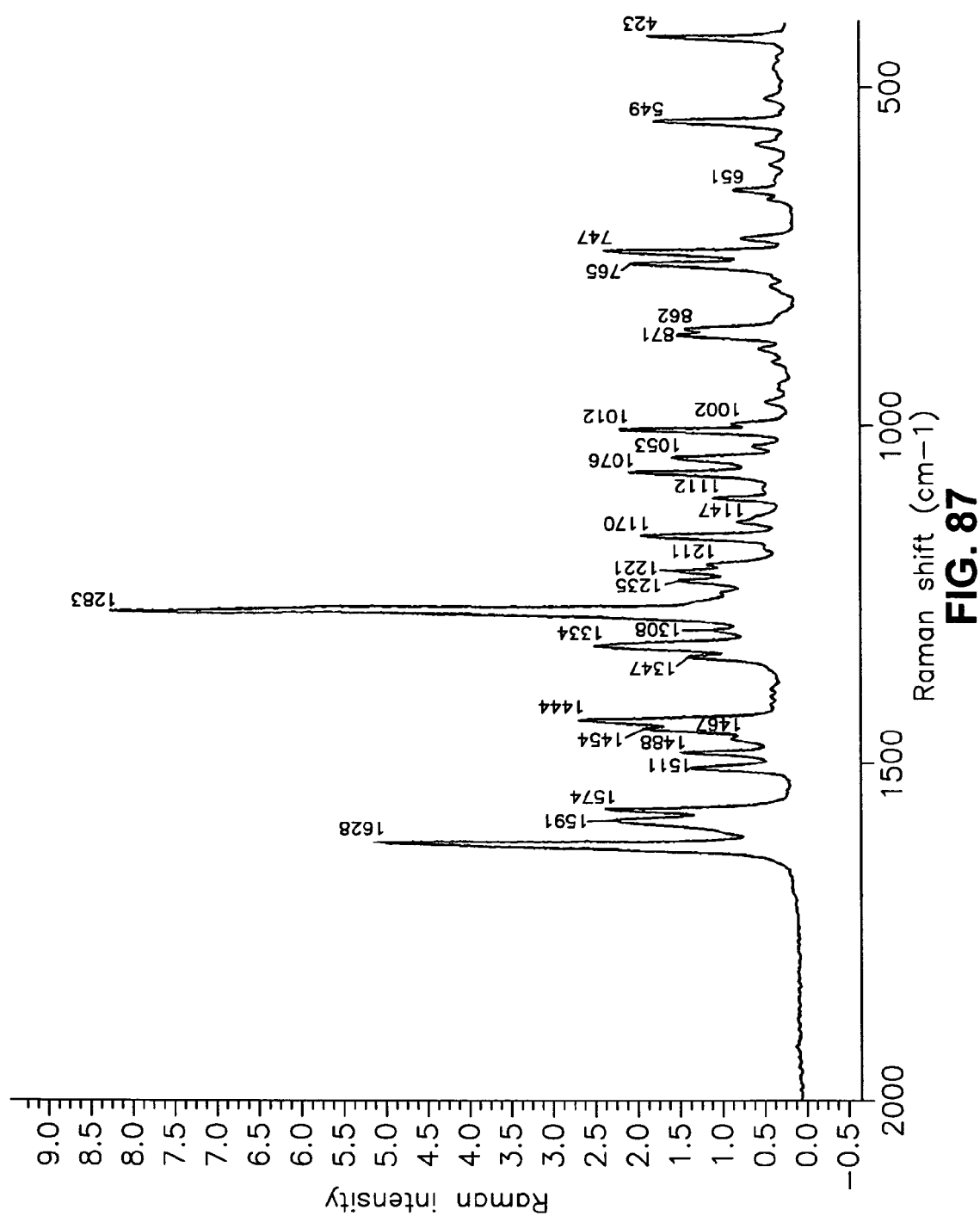

FIG. 87 is an FT-Raman spectrum for carvedilol hydrobromide n-propanol solvate #2 in the 2000-400 cm$^{-1}$ region of the spectrum.

Figure 88:
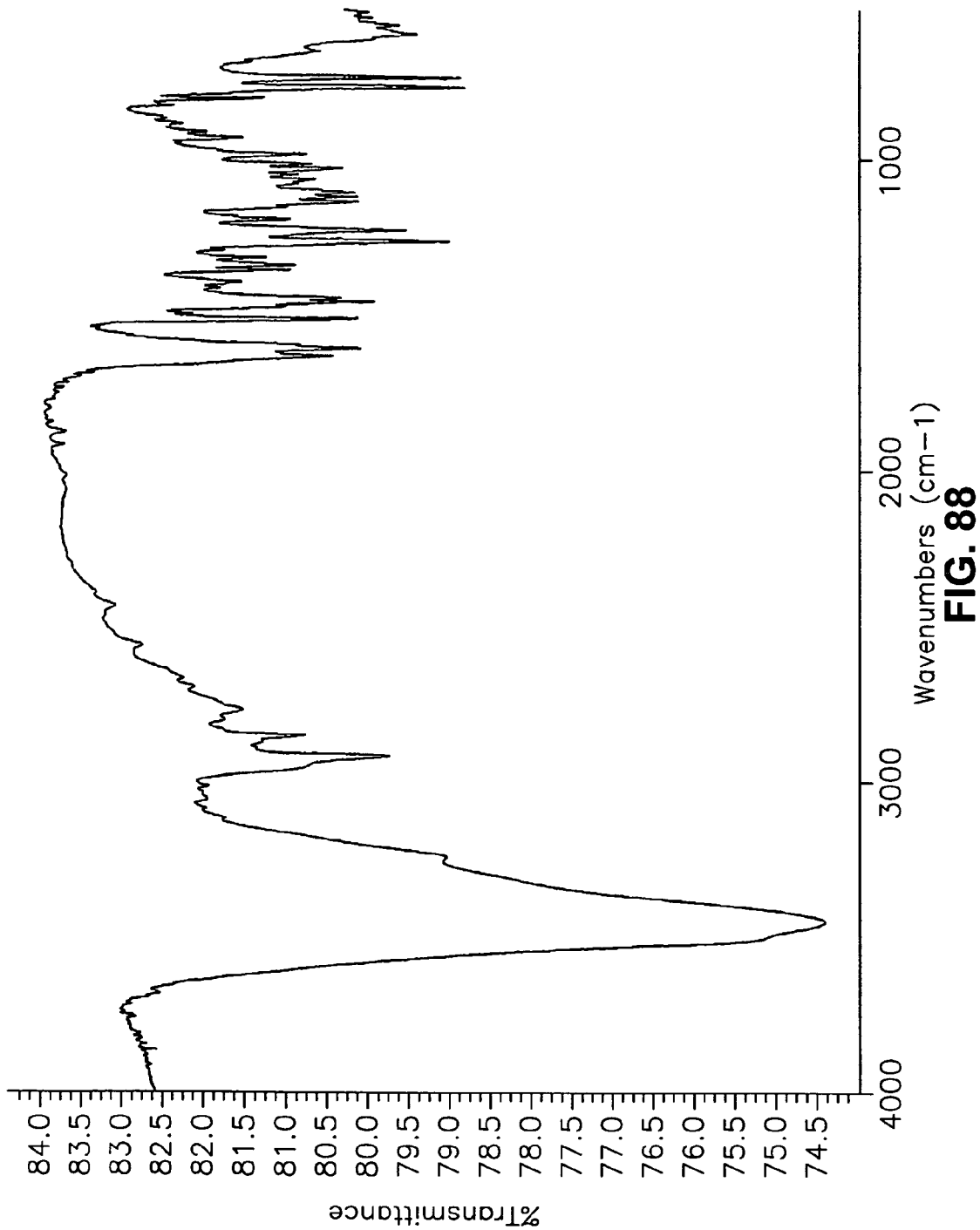

FIG. 88 is an FT-IR spectrum for carvedilol hydrobromide n-propanol solvate #2.

Figure 89:
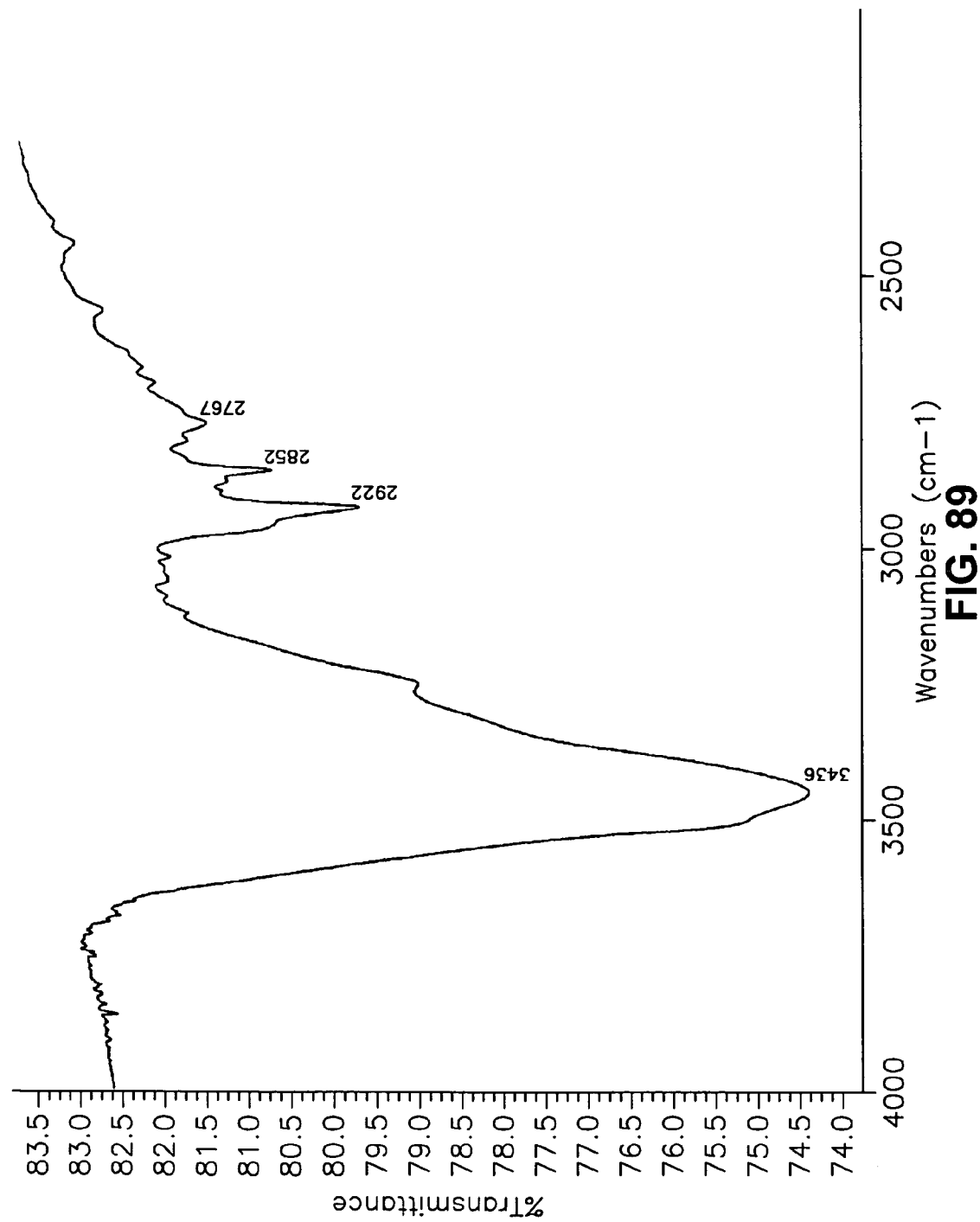

FIG. 89 is an FT-IR spectrum for carvedilol hydrobromide n-propanol solvate #2 in the 4000-2000 cm$^{-1}$ region of the spectrum.

Figure 90:
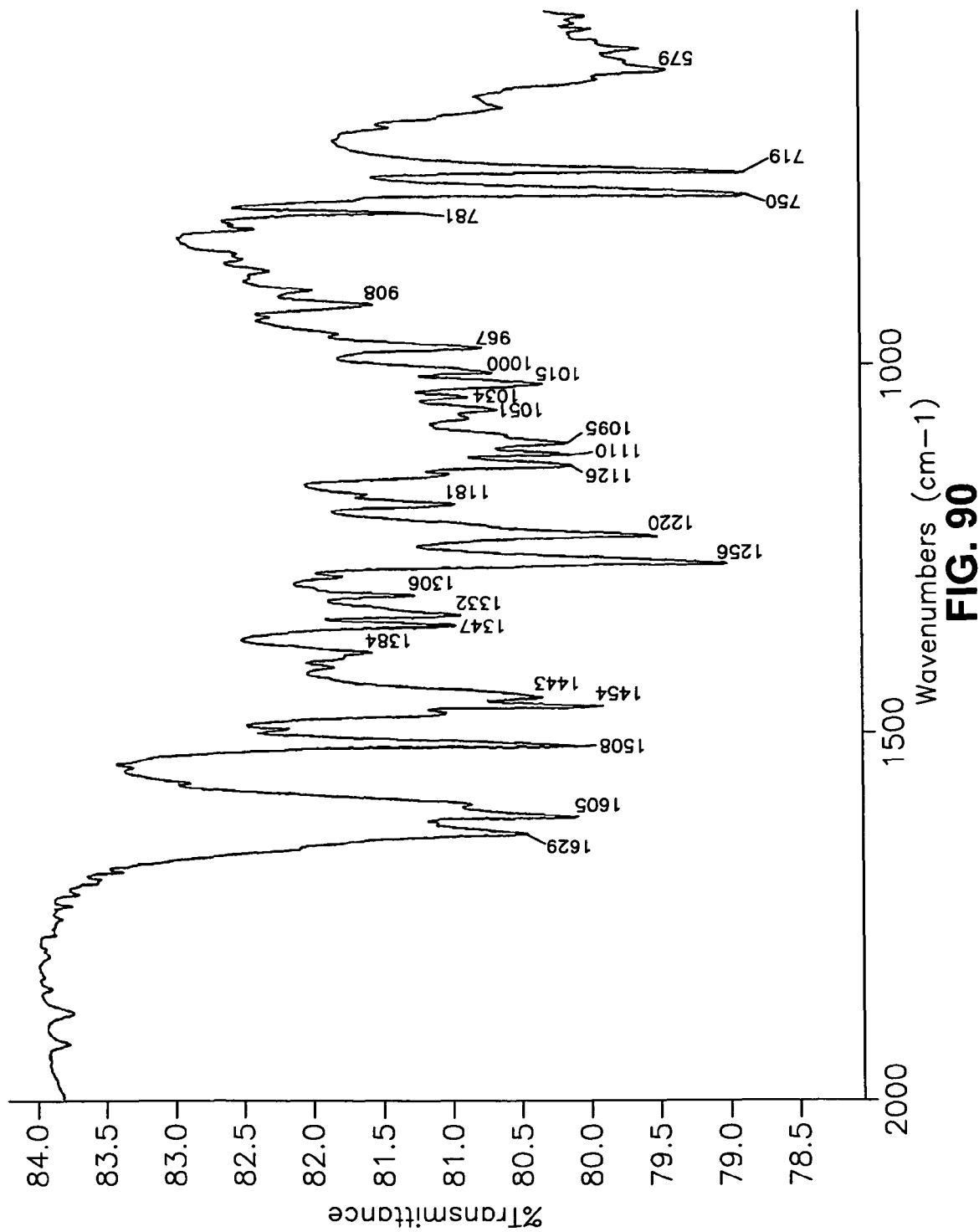

FIG. 90 is an FT-IR spectrum for carvedilol hydrobromide n-propanol solvate #2 in the 2000-500 cm$^{-1}$ region of the spectrum.

Figure 91:
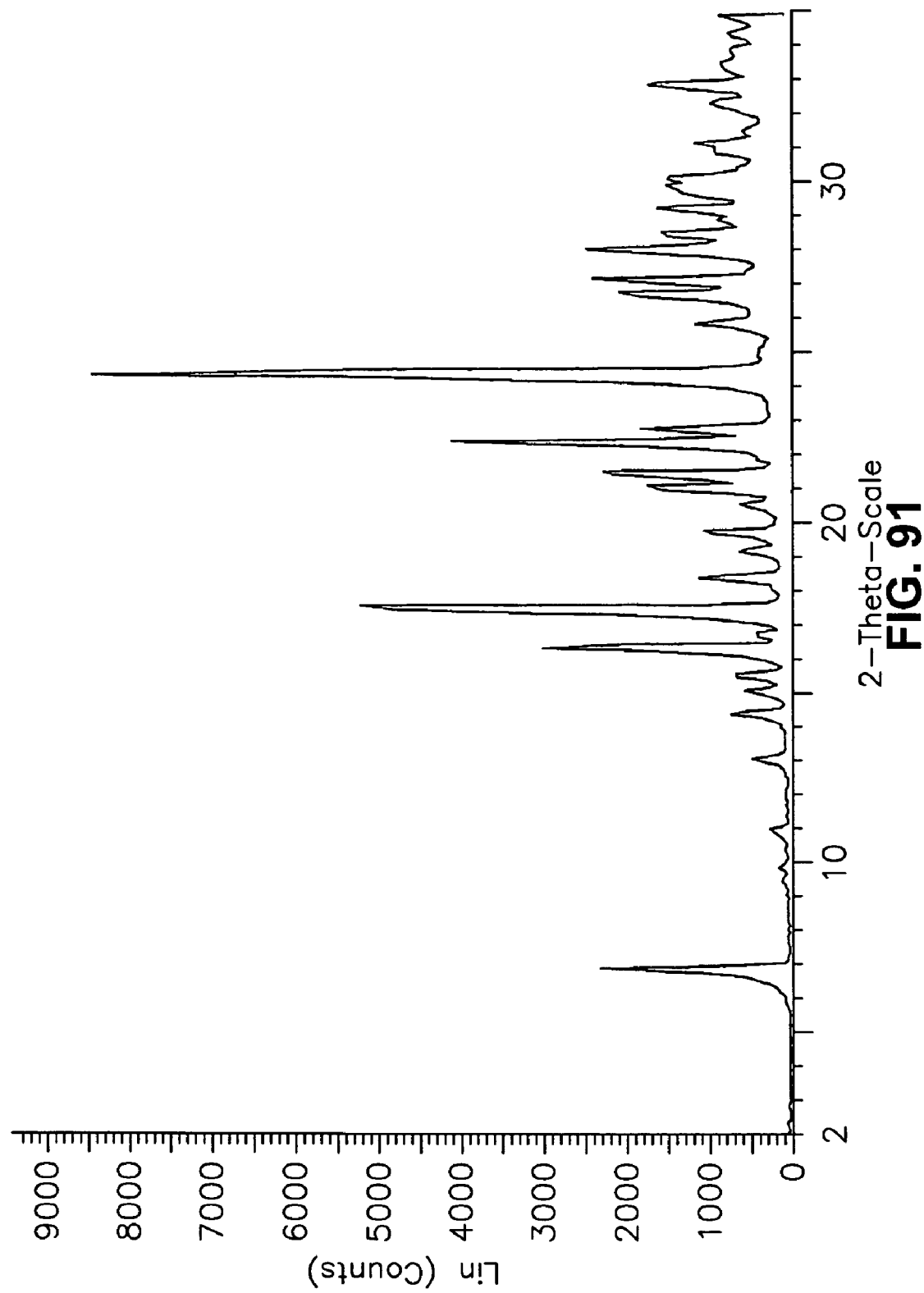

FIG. 91 is an x-ray powder diffractogram for carvedilol hydrobromide anhydrous.

Figure 92:
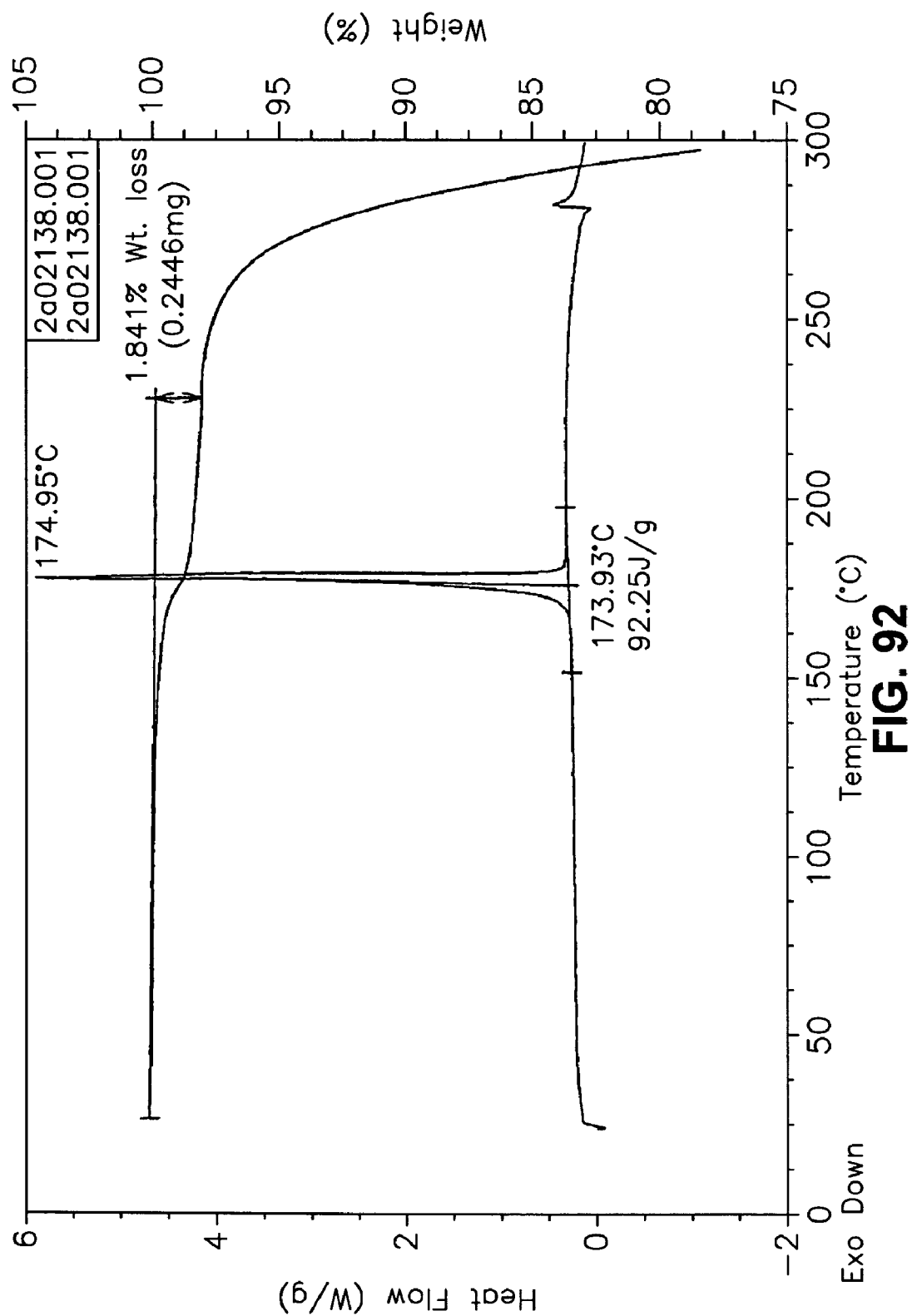

FIG. 92 shows the thermal analysis results for carvedilol hydrobromide anhydrous.

Figure 93:
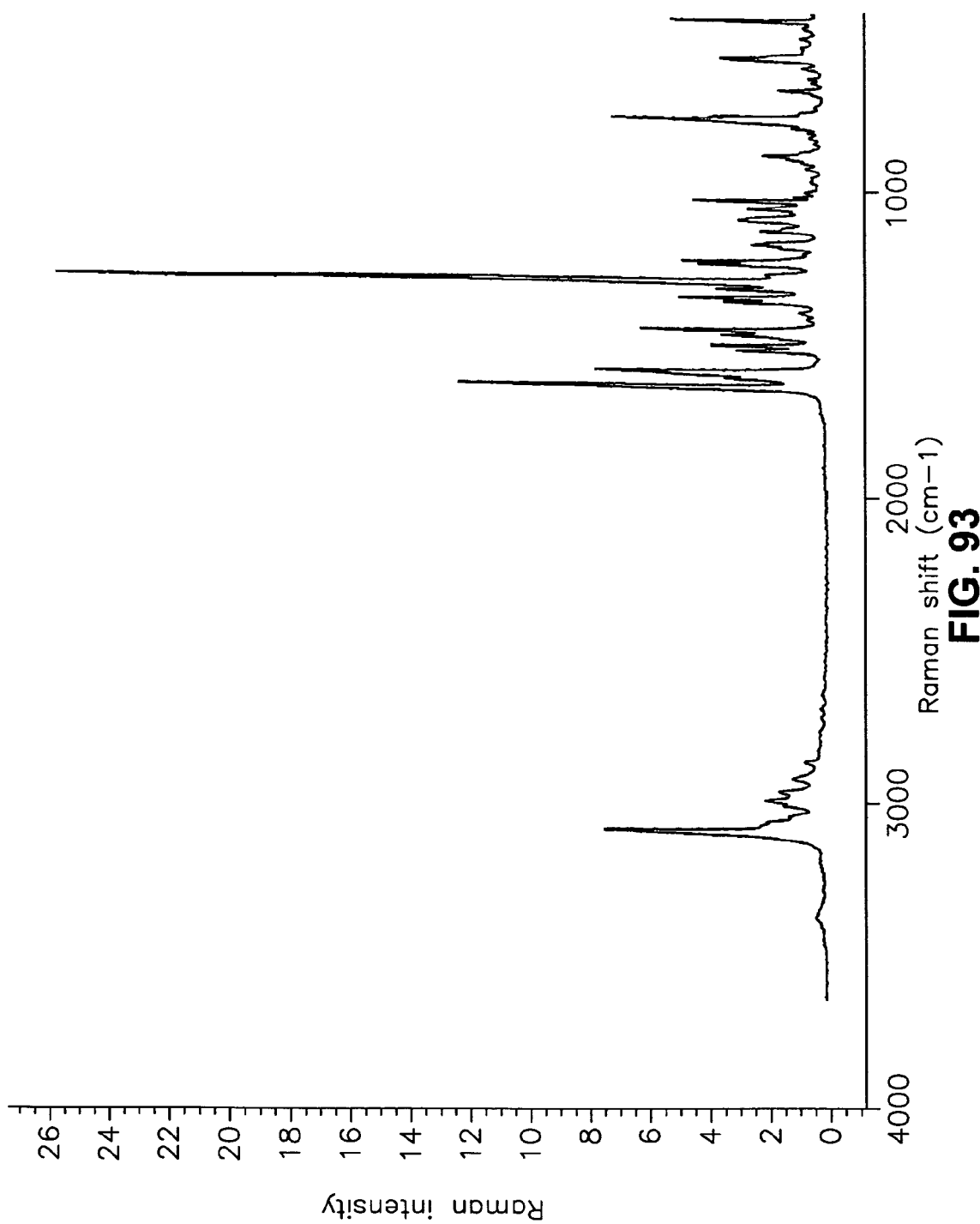

FIG. 93 is an FT-Raman spectrum for carvedilol hydrobromide anhydrous.

Figure 94:
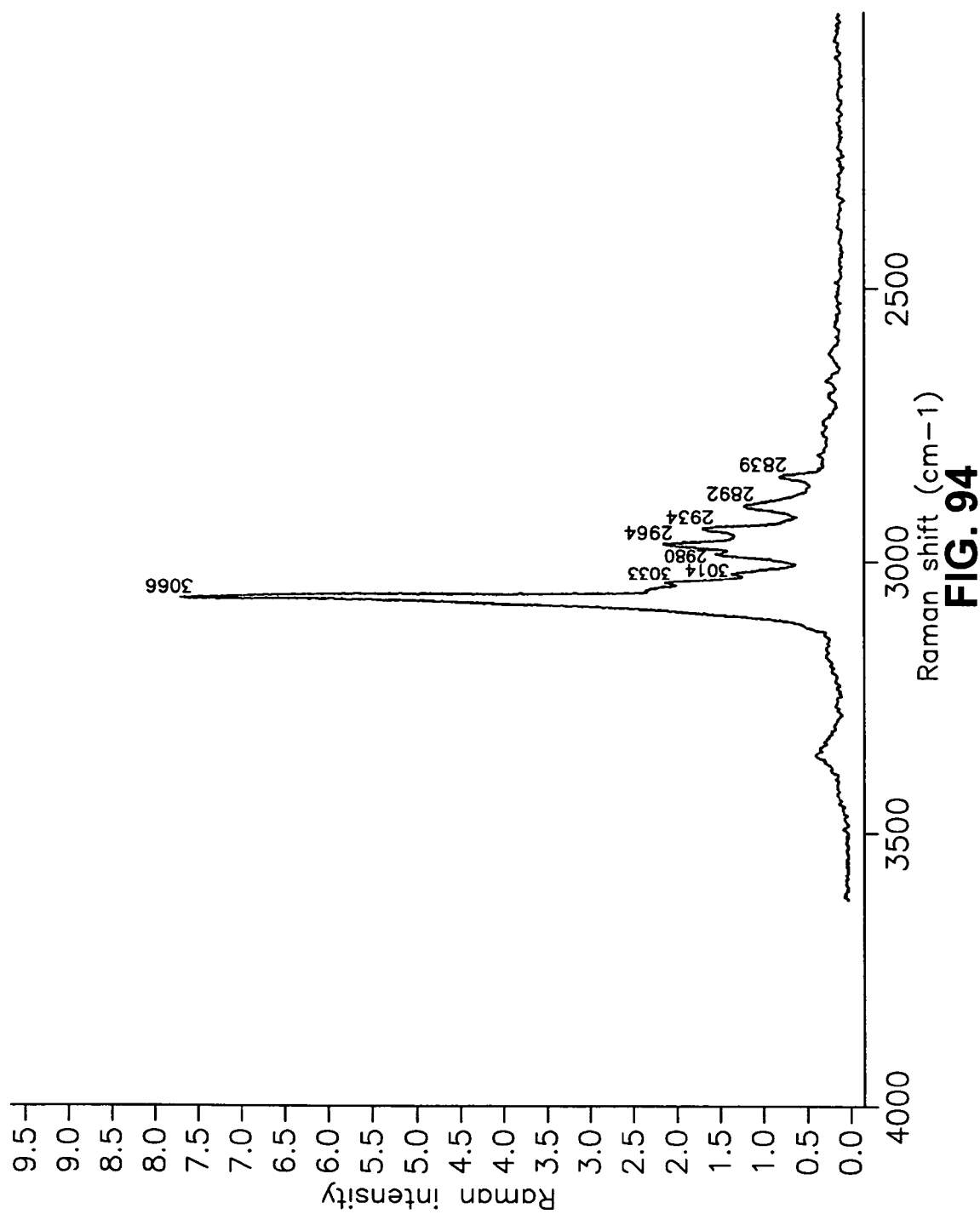

FIG. 94 is an FT-Raman spectrum for carvedilol hydrobromide anhydrous forms in the 4000-2000 cm$^{-1}$ region of the spectrum.

Figure 95:
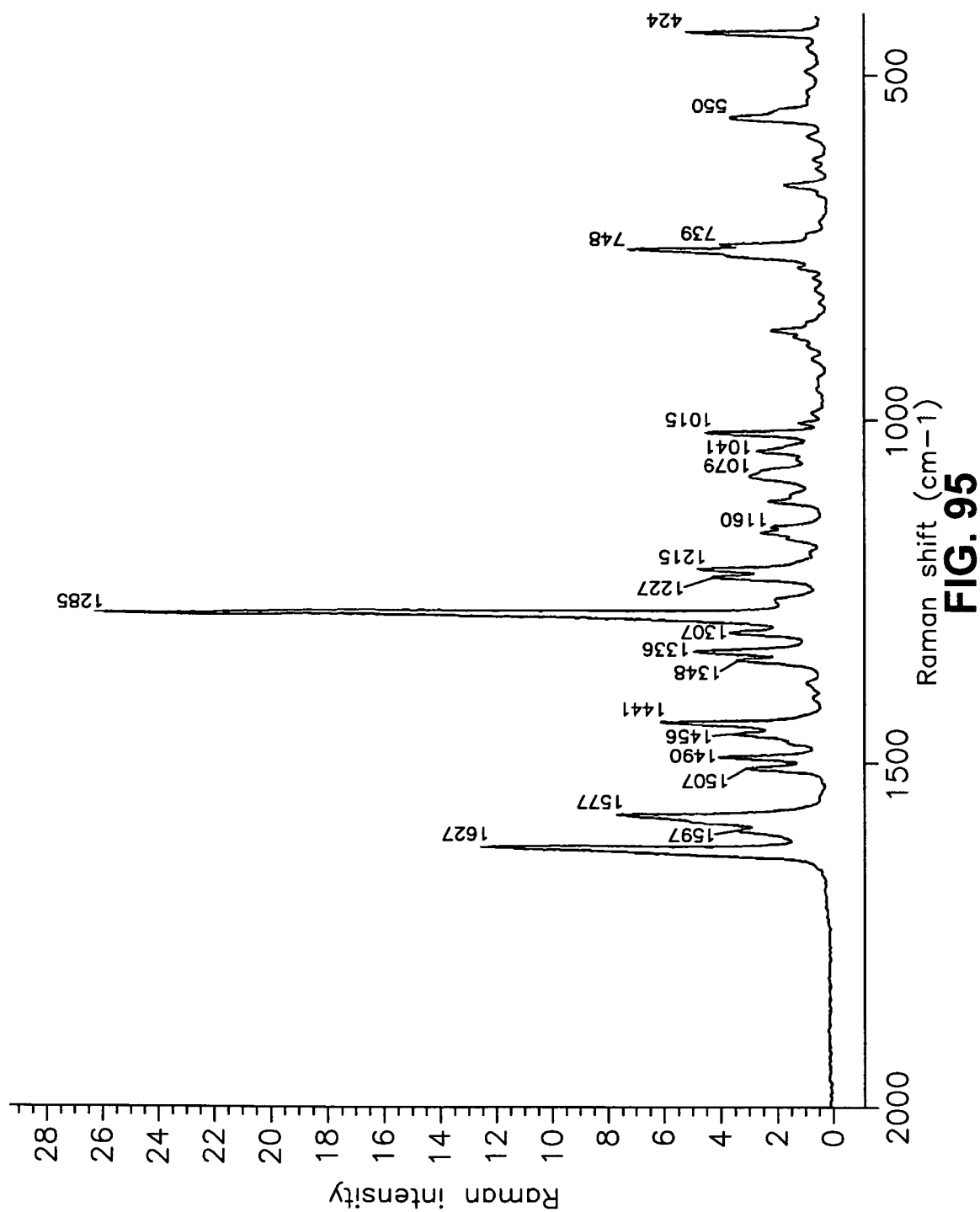

FIG. 95 is an FT-Raman spectrum for carvedilol hydrobromide anhydrous forms in the 2000-400 cm$^{-1}$ region of the spectrum.

Figure 96:
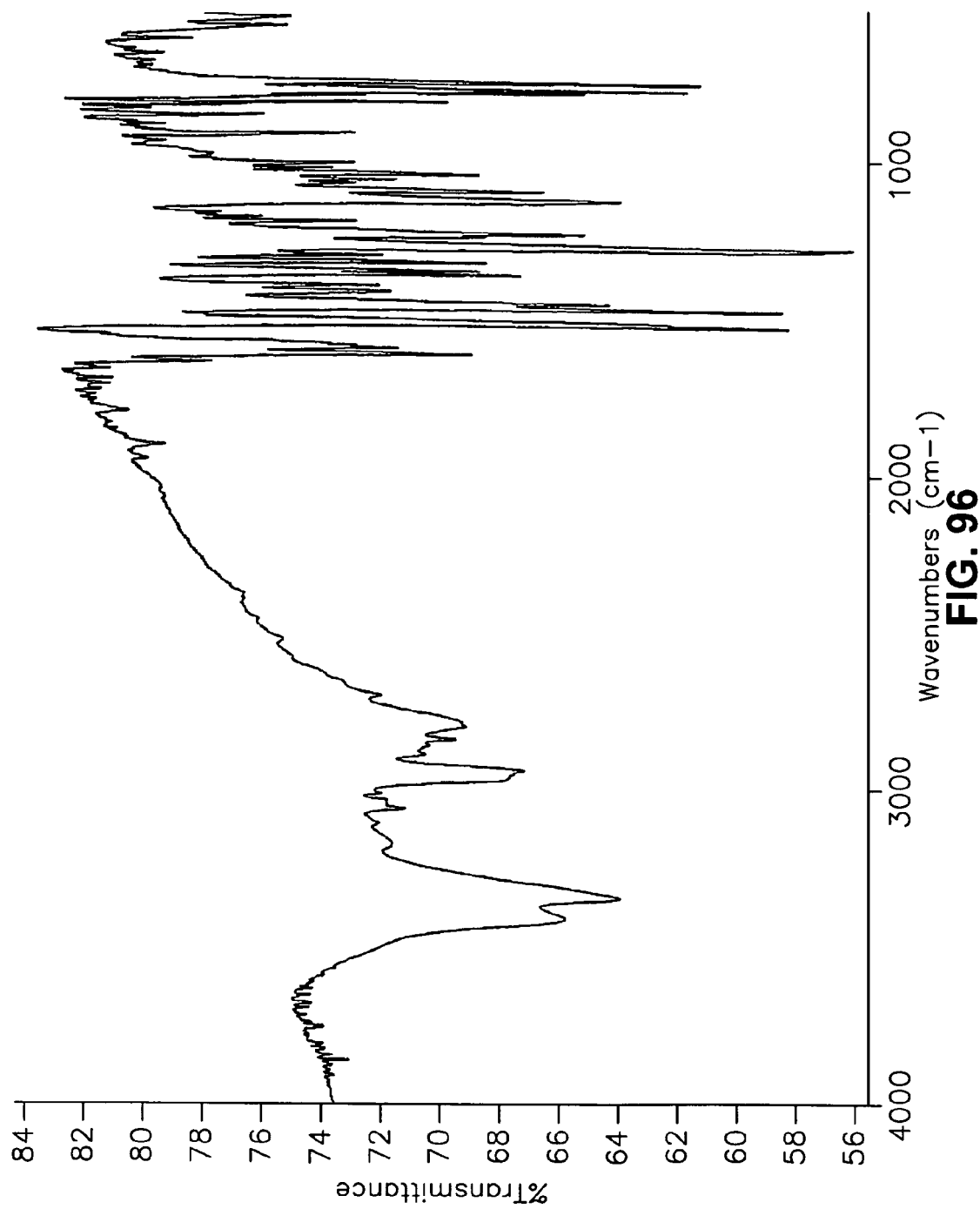

FIG. 96 is an FT-IR spectrum for carvedilol hydrobromide anhydrous.

Figure 97:
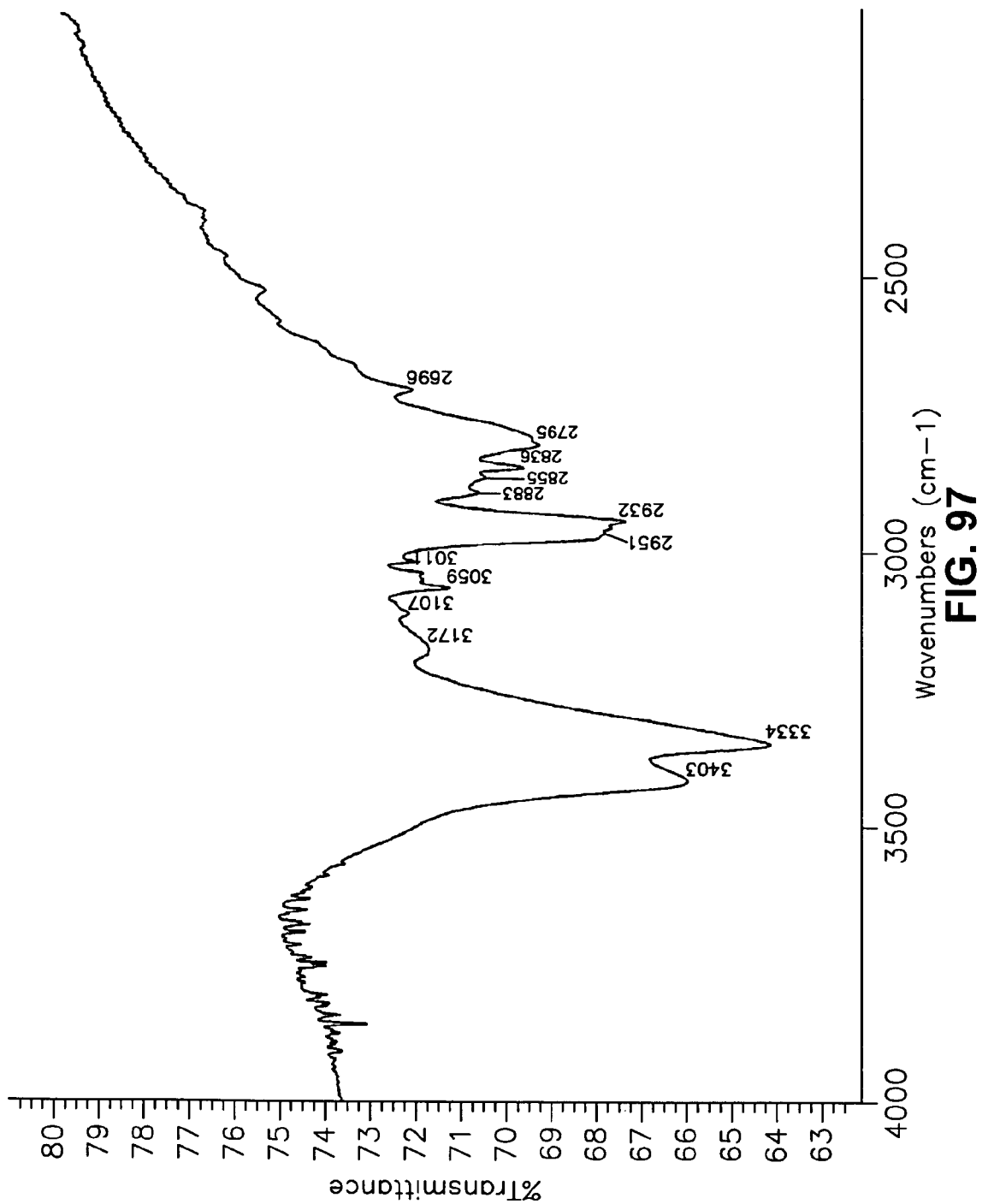

FIG. 97 is an FT-IR spectrum for carvedilol hydrobromide anhydrous forms in the 4000-2000 cm$^{-1}$ region of the spectrum.

Figure 98:
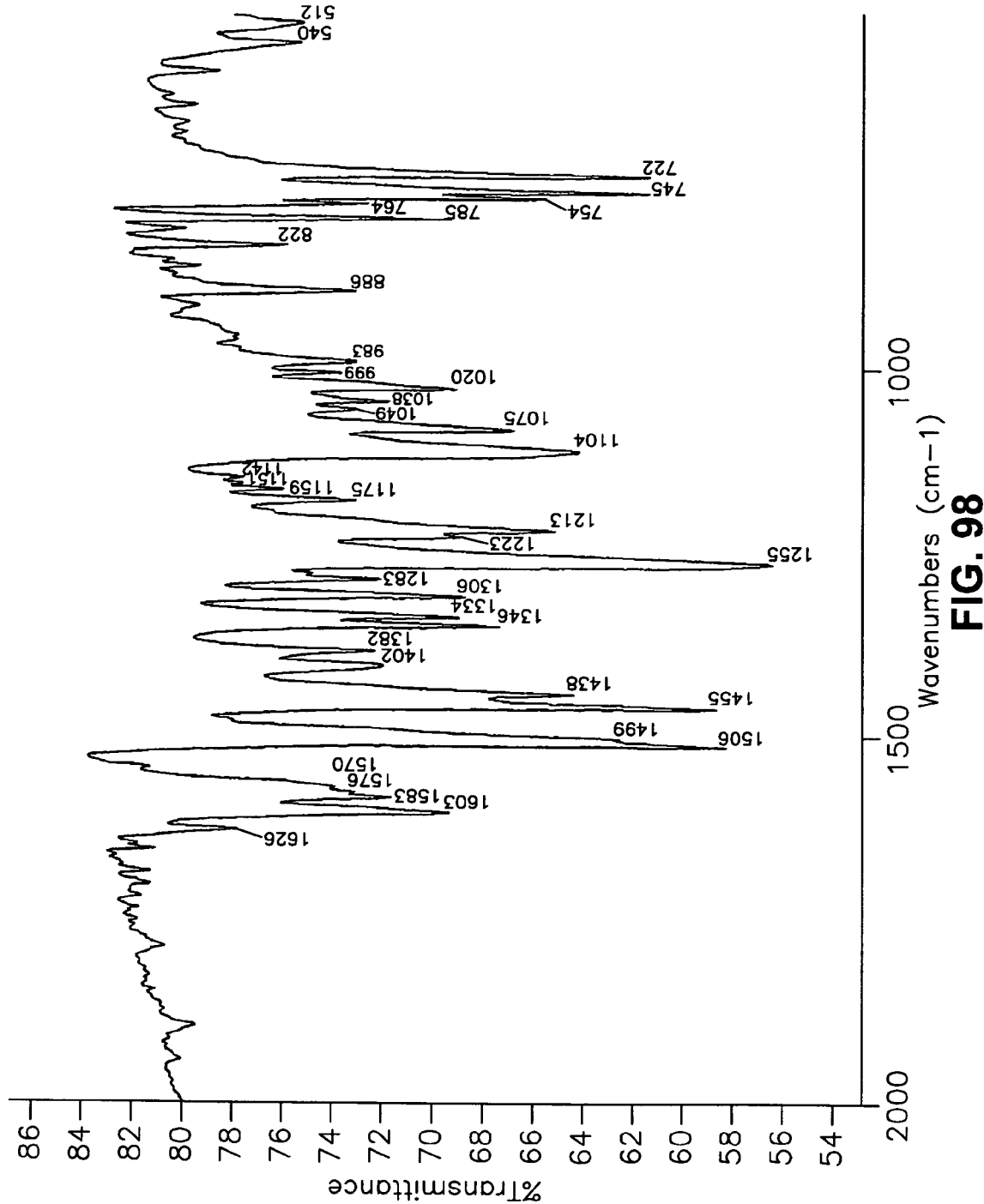

FIG. 98 is an FT-IR spectrum for carvedilol hydrobromide anhydrous forms in the 2000-500 cm$^{-1}$ region of the spectrum.

Figure 99:
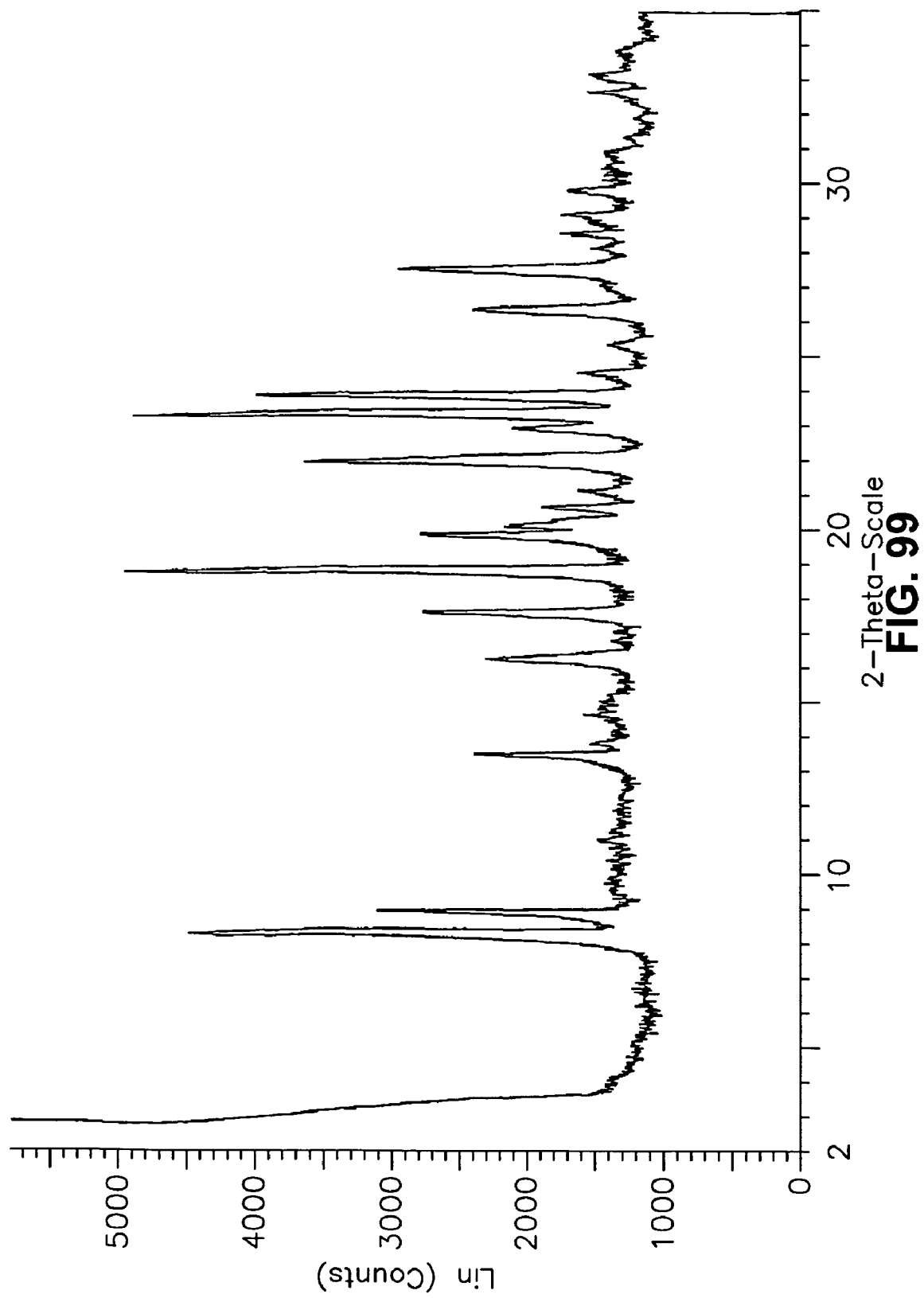

FIG. 99 is an x-ray powder diffractogram for carvedilol hydrobromide ethanol solvate.

Figure 100:
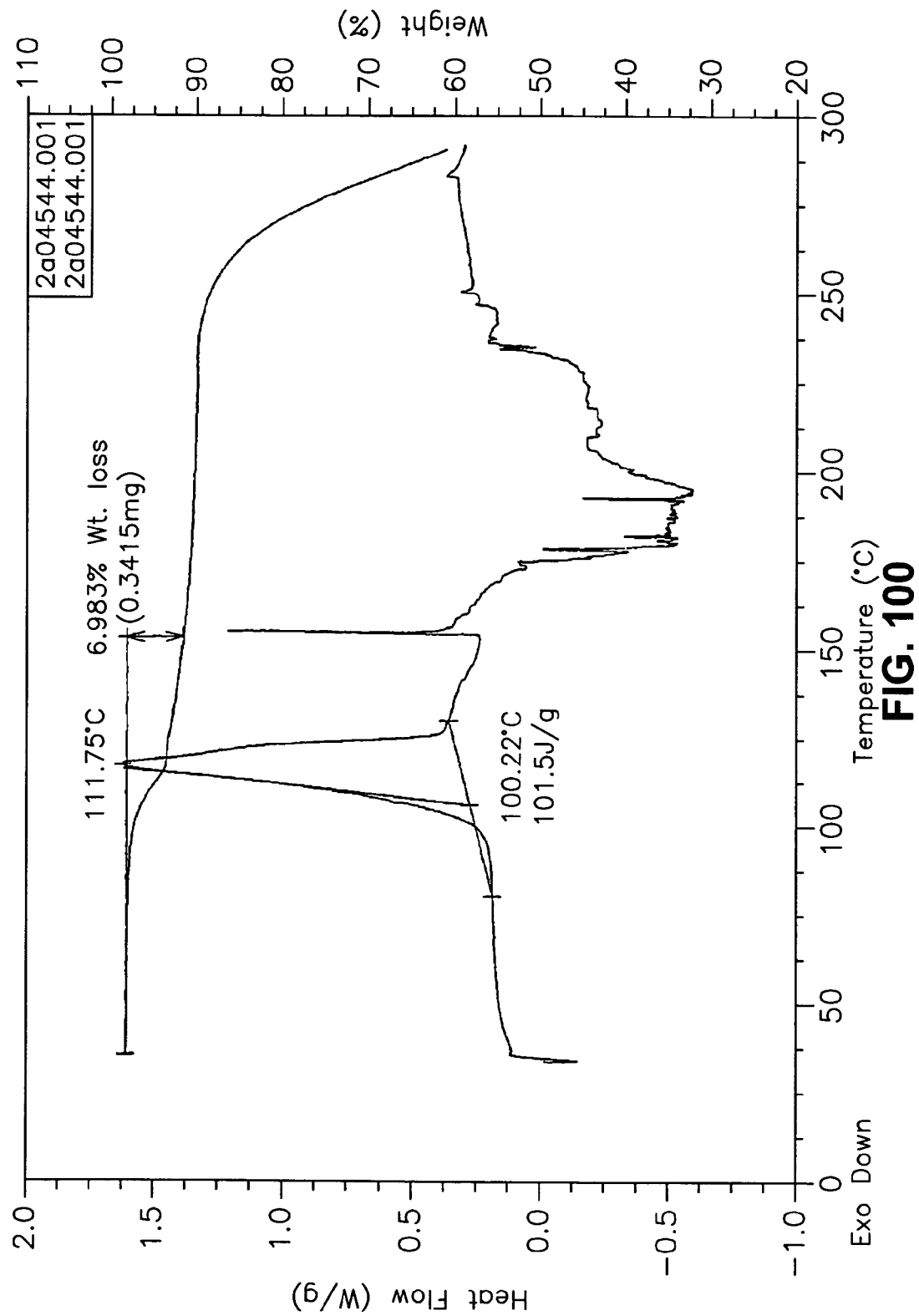

FIG. 100 shows the thermal analysis results for carvedilol hydrobromide ethanol solvate.

Figure 101:
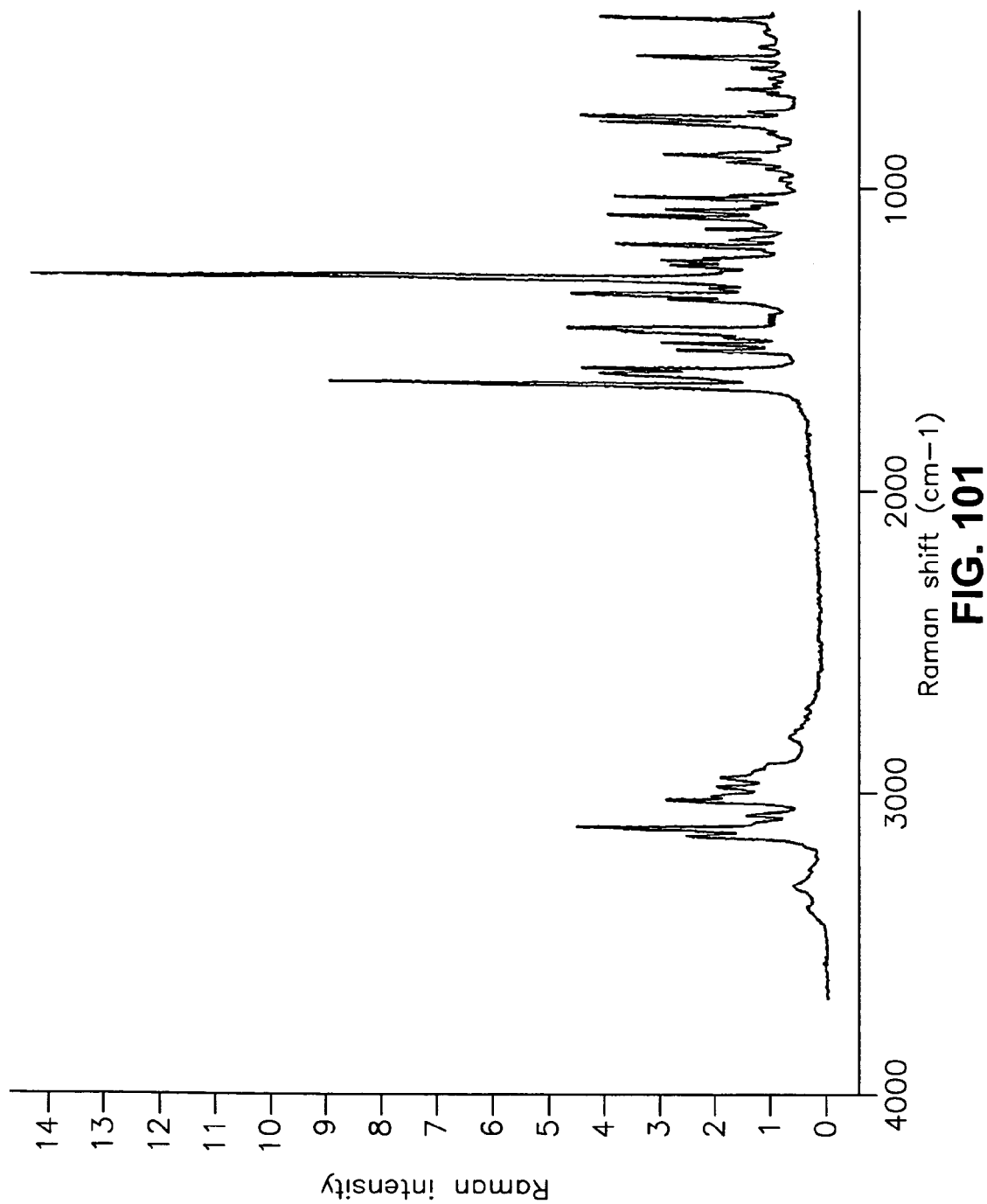

FIG. 101 is an FT-Raman spectrum for carvedilol hydrobromide ethanol solvate.

Figure 102:
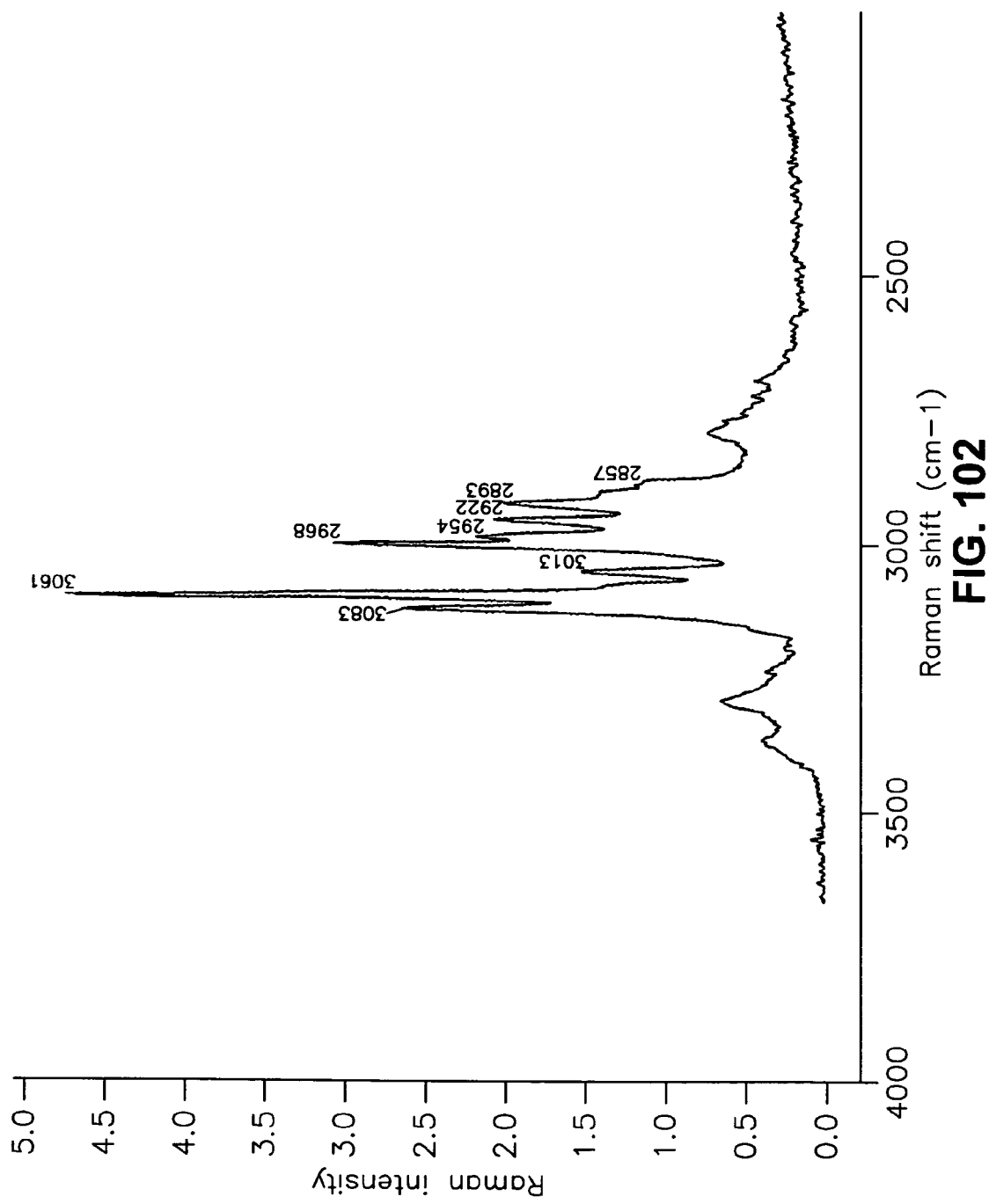

FIG. 102 is an FT-Raman spectrum for carvedilol hydrobromide ethanol solvate in the 4000-2000 cm$^{-1}$ region of the spectrum.

Figure 103:
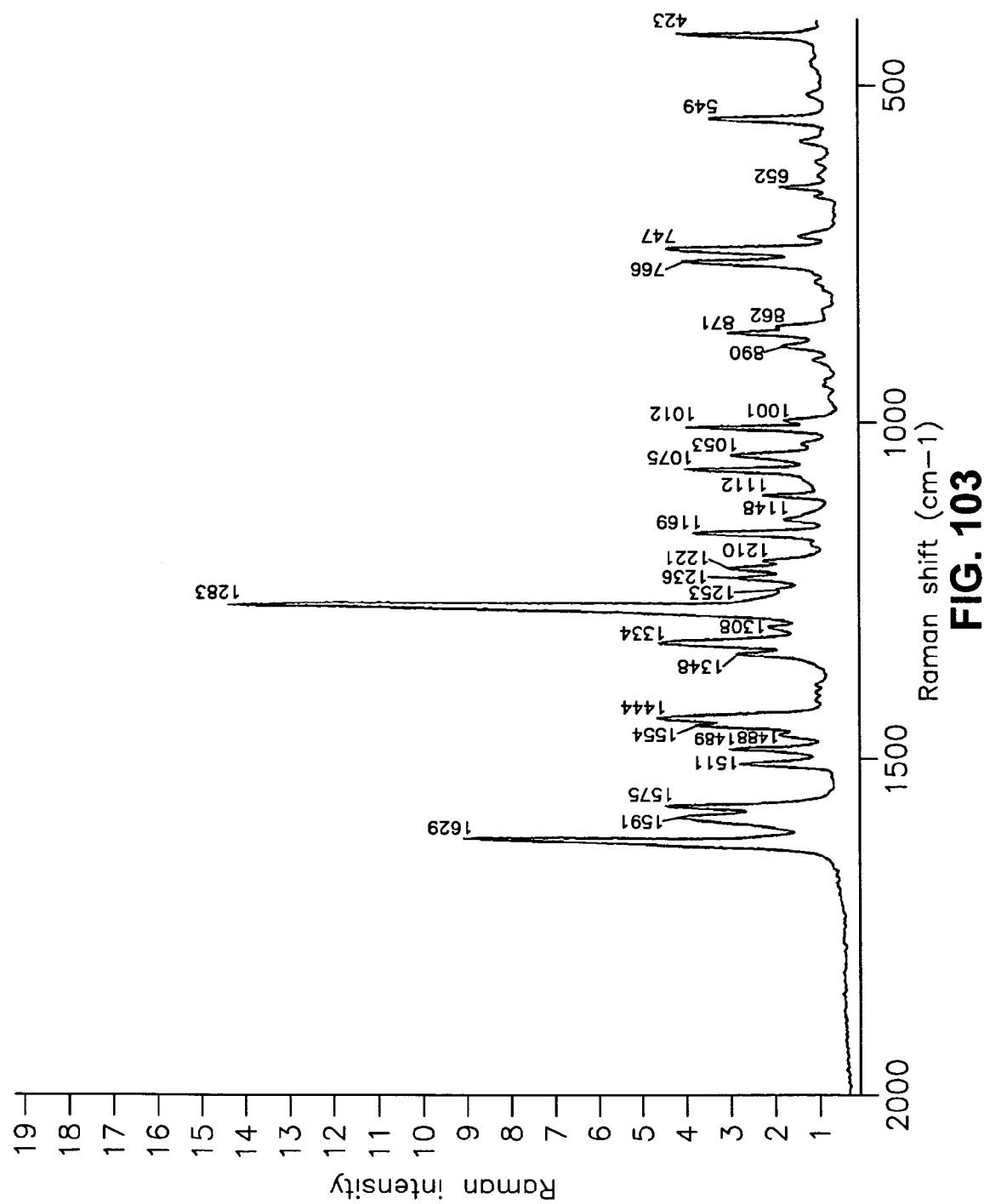

FIG. 103 is an FT-Raman spectrum for carvedilol hydrobromide ethanol solvate in the 2000-400 cm$^{-1}$ region of the spectrum.

Figure 104:
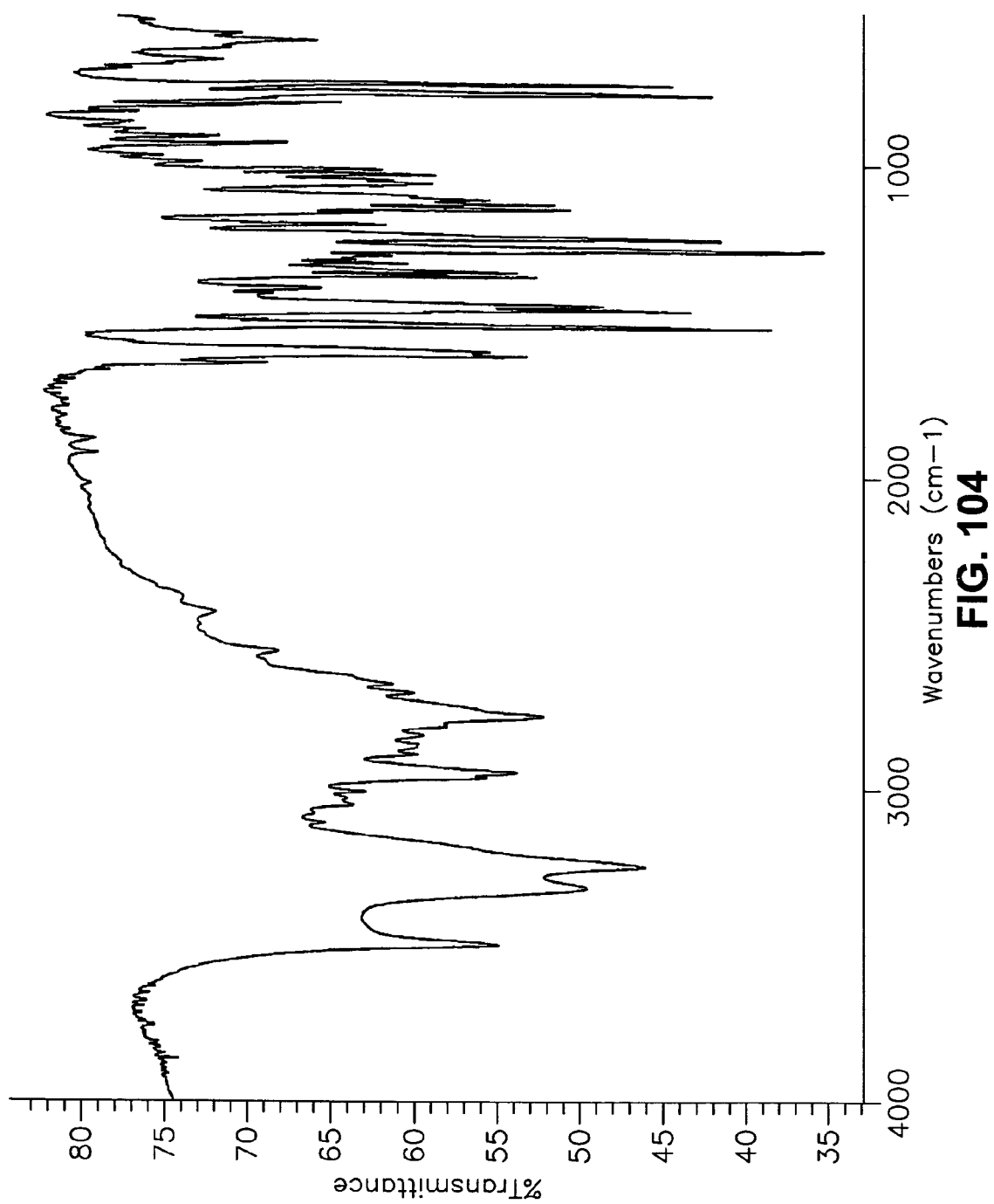

FIG. 104 is an FT-IR spectrum for carvedilol hydrobromide ethanol solvate.

Figure 105:
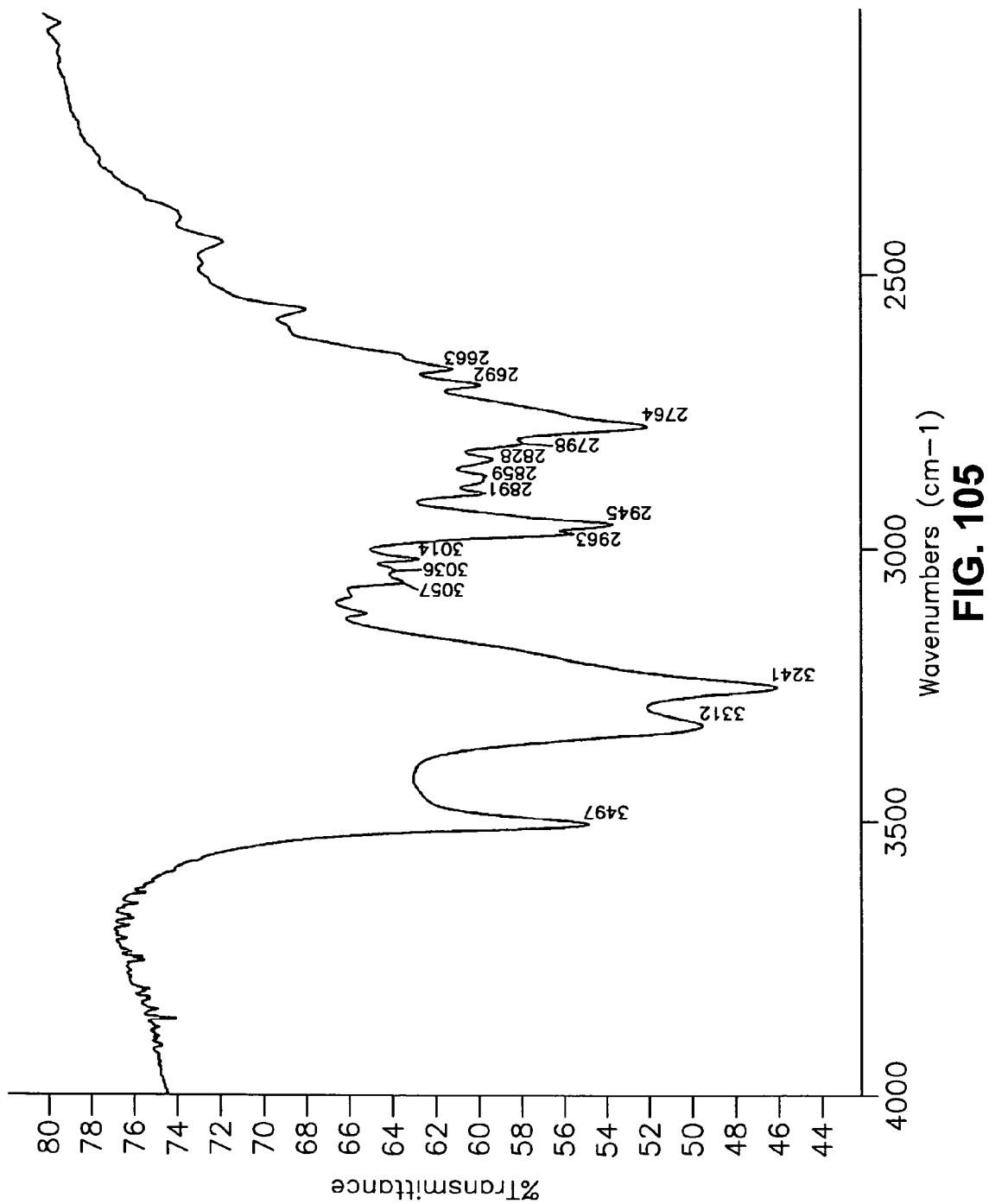

FIG. 105 is an FT-IR spectrum for carvedilol hydrobromide ethanol solvate in the 4000-2000 cm$^{-1}$ region of the spectrum.

Figure 106:
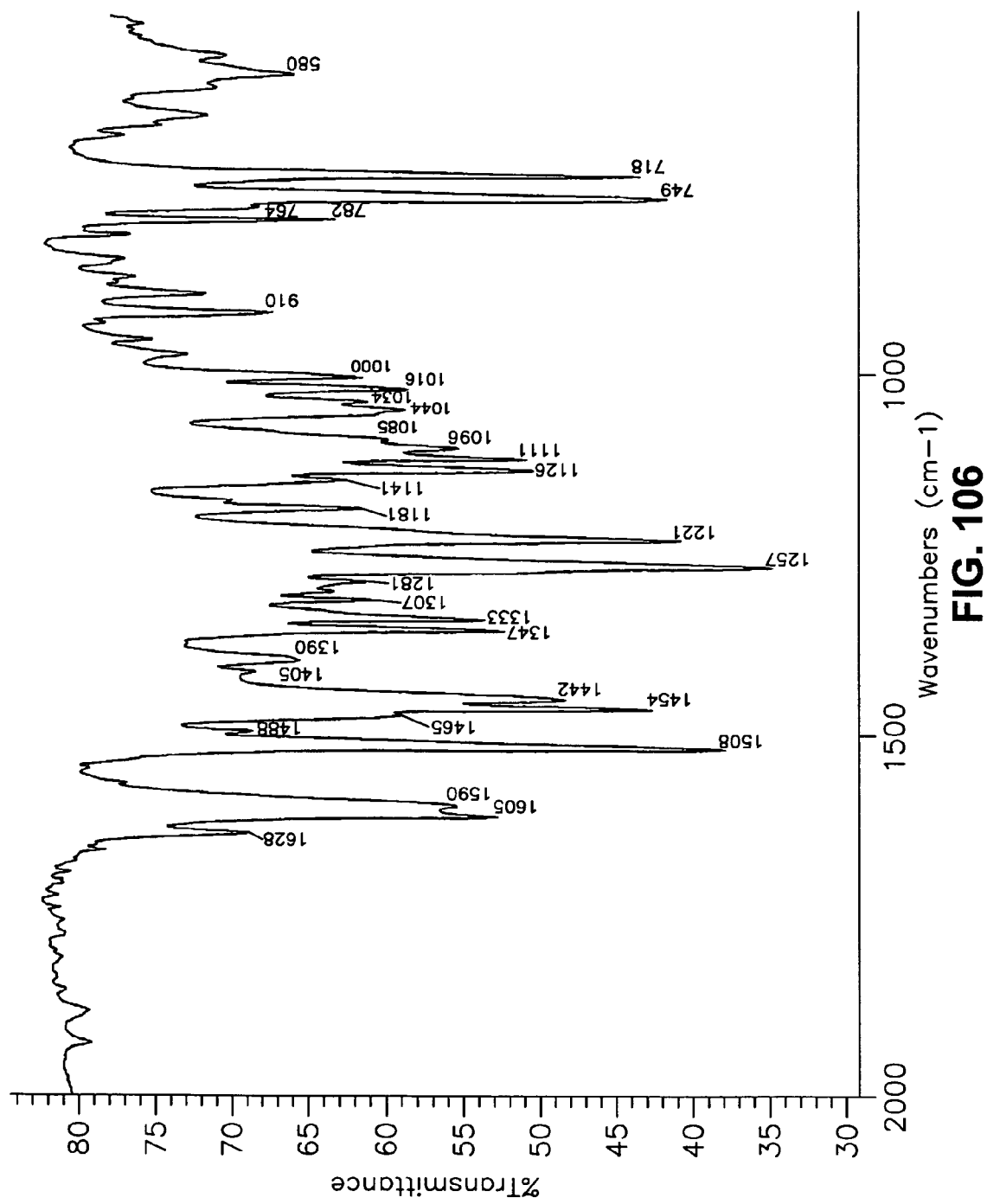

FIG. 106 is an FT-IR spectrum for carvedilol hydrobromide ethanol solvate in the 2000-500 cm$^{-1}$ region of the spectrum.

Figure 107:
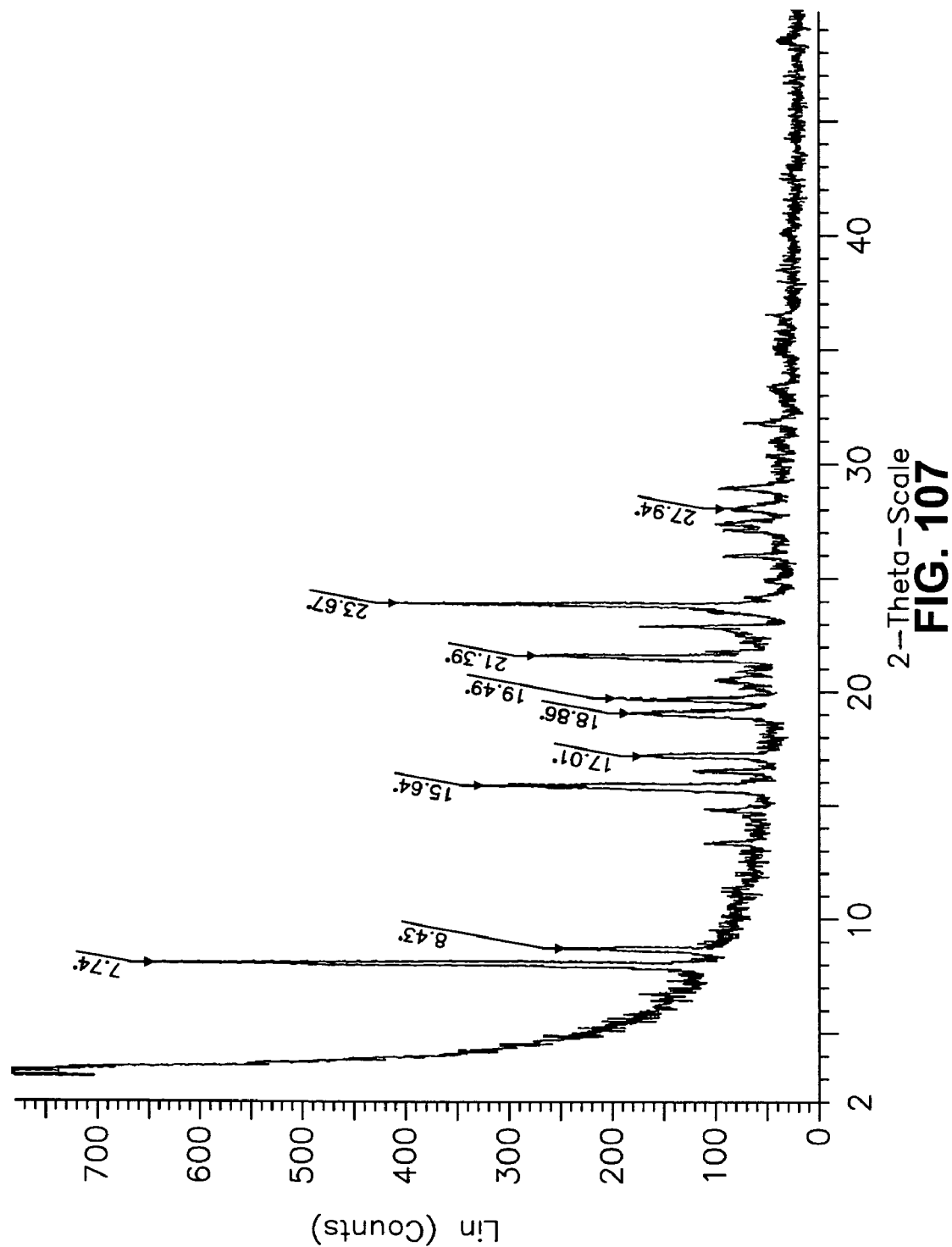

FIG. 107 is an x-ray powder diffractogram for carvedilol hydrobromide dioxane solvate.

Figure 108:
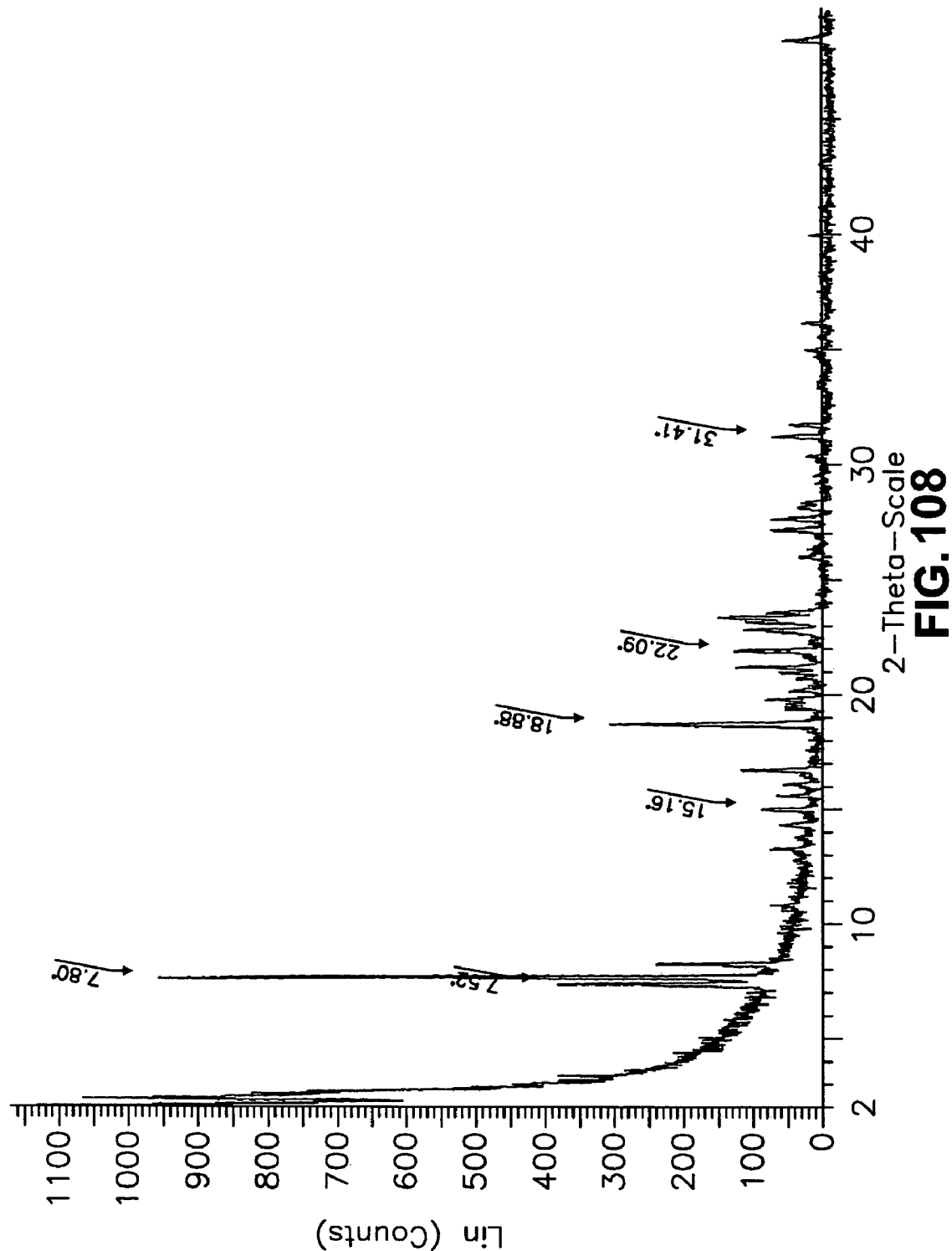

FIG. 108 is an x-ray powder diffractogram for carvedilol hydrobromide 1-pentanol solvate.

Figure 109:
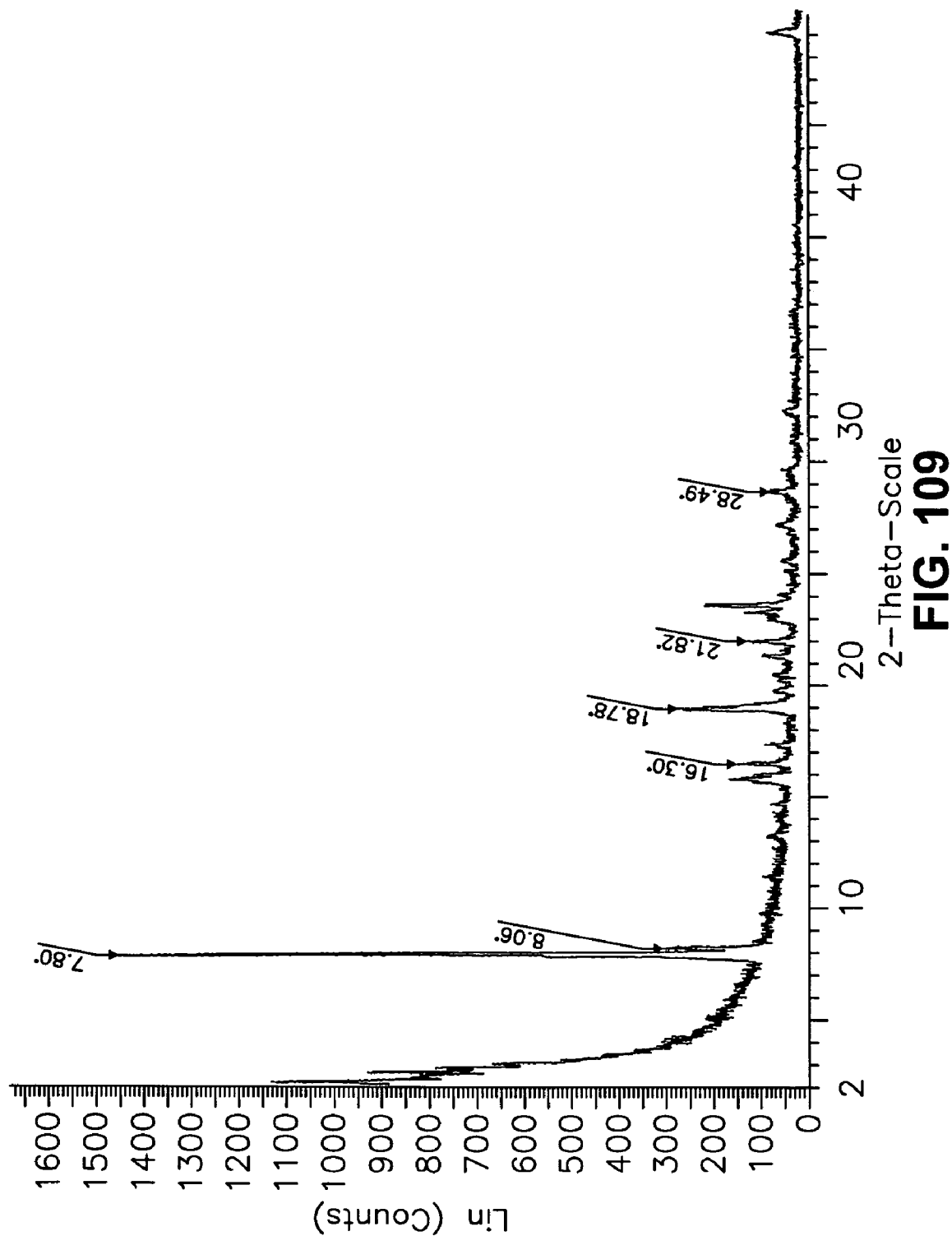

FIG. 109 is an x-ray powder diffractogram for carvedilol hydrobromide 2-methyl-1-propanol solvate.

Figure 110:
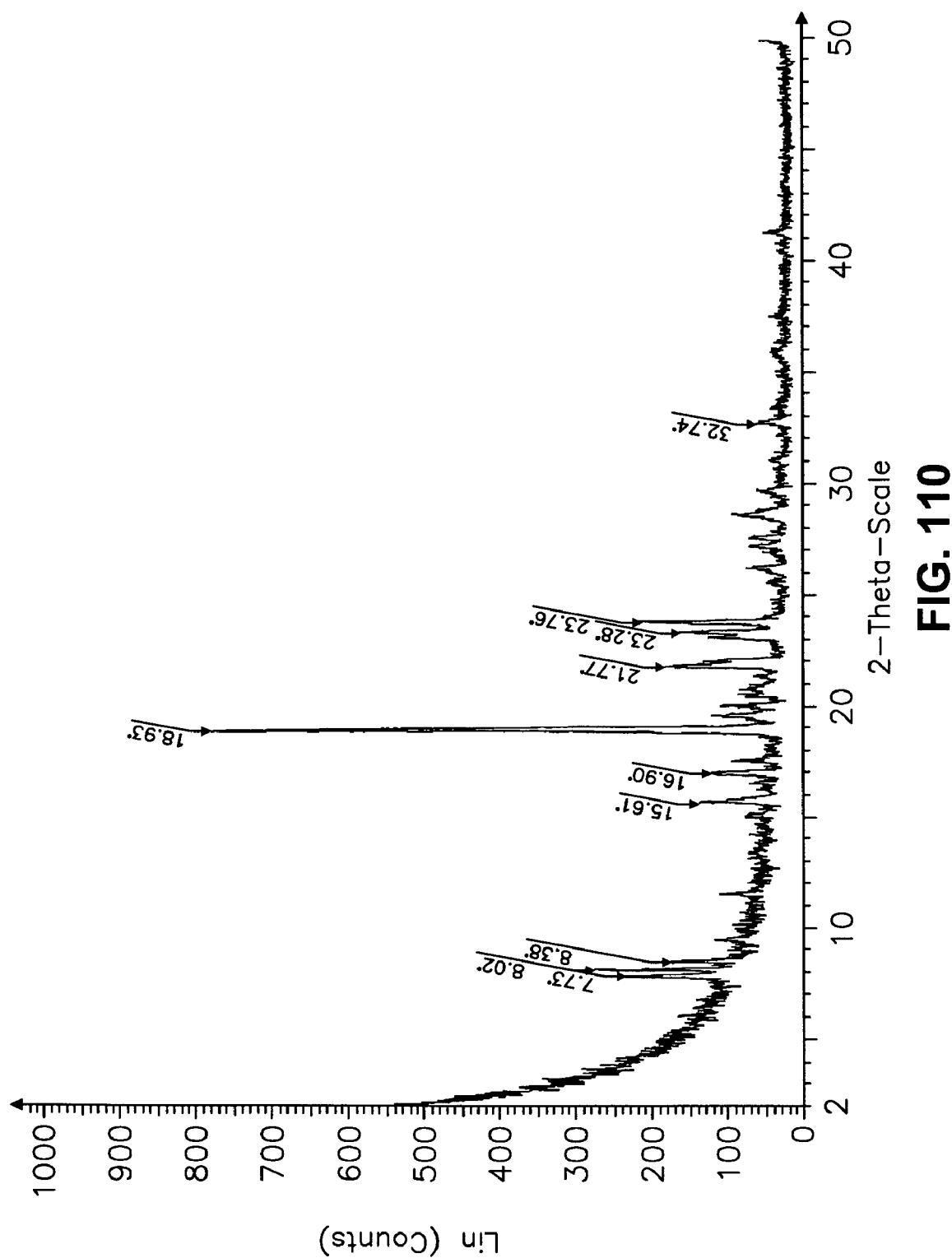

FIG. 110 is an x-ray powder diffractogram for carvedilol hydrobromide trifluoroethanol solvate.

Figure 111:
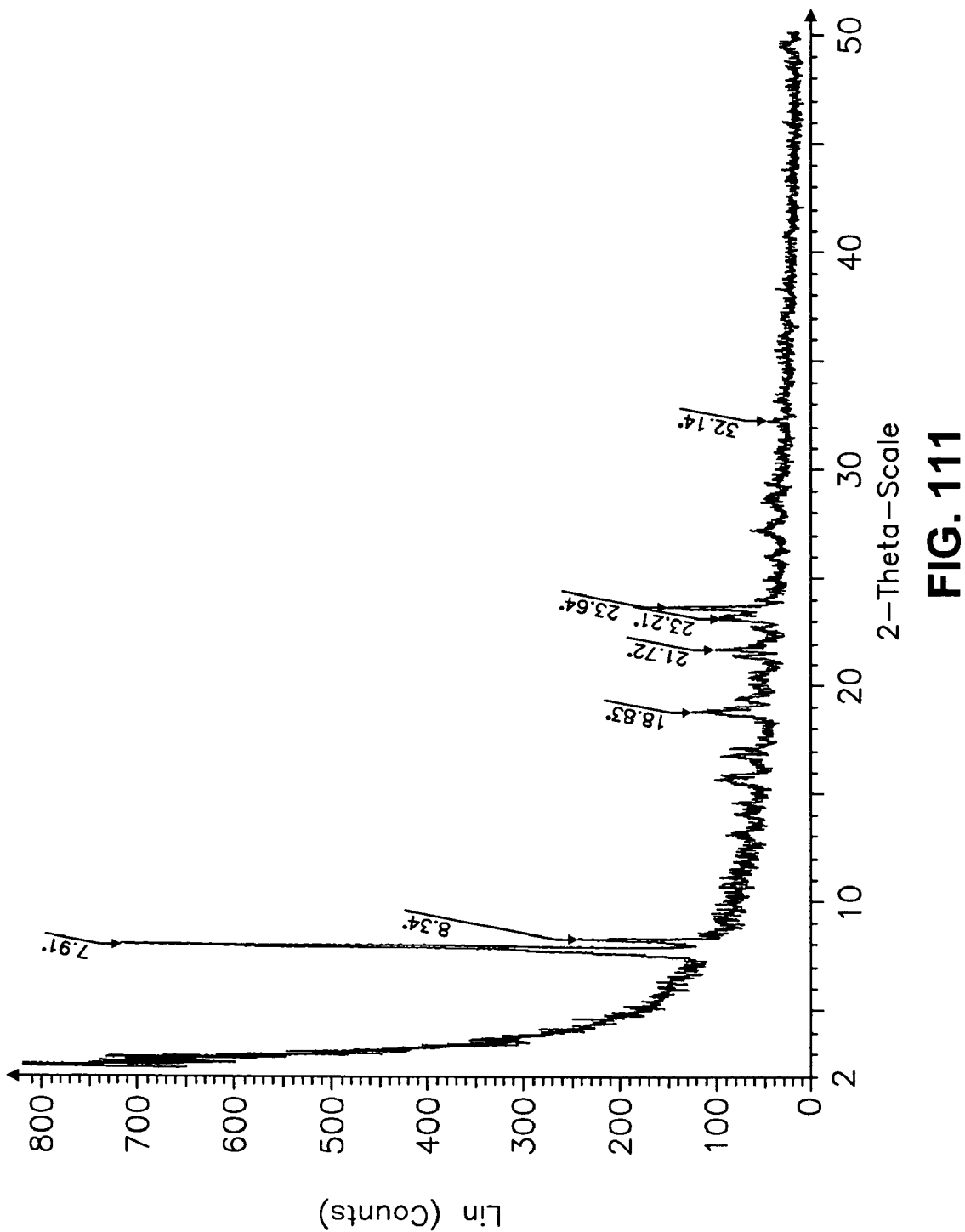

FIG. 111 is an x-ray powder diffractogram for carvedilol hydrobromide 2-propanol solvate.

Carvedilol Citrate Salts

Figure 112:
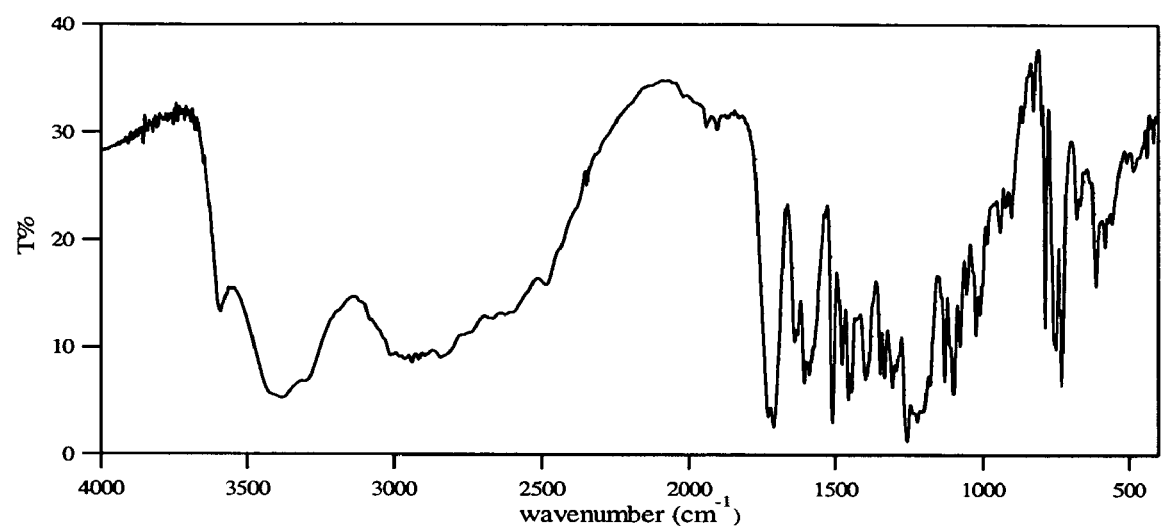

FIG. 112 is a FT-IR spectrum of carvedilol monocitrate salt.

Figure 113:
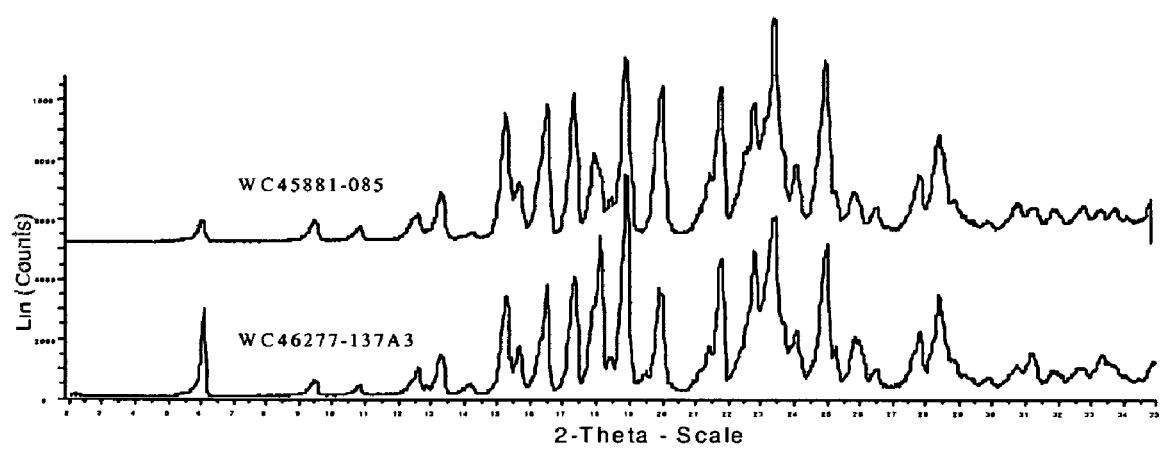

FIG. 113 depicts XRPD patterns of two different batches of Carvedilol monocitrate salt.

Carvedilol Mandelate Salts

Figure 114:
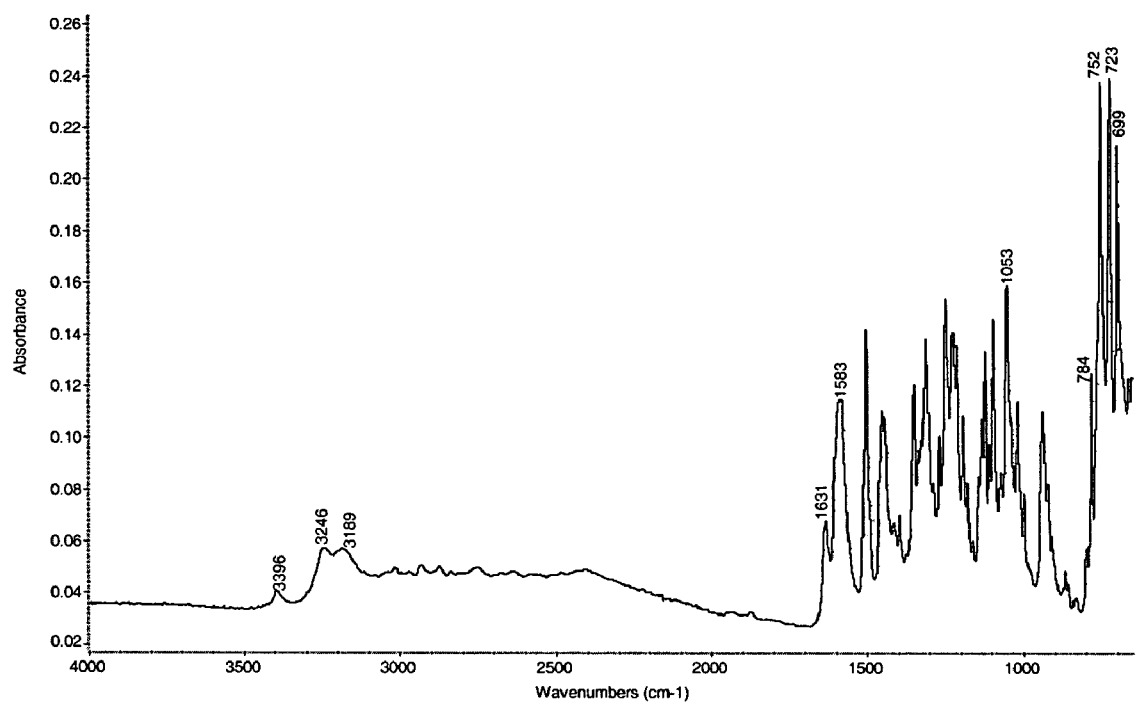

FIG. 114 is a FT-IR spectrum of carvedilol mandelate salt.

Figure 115:
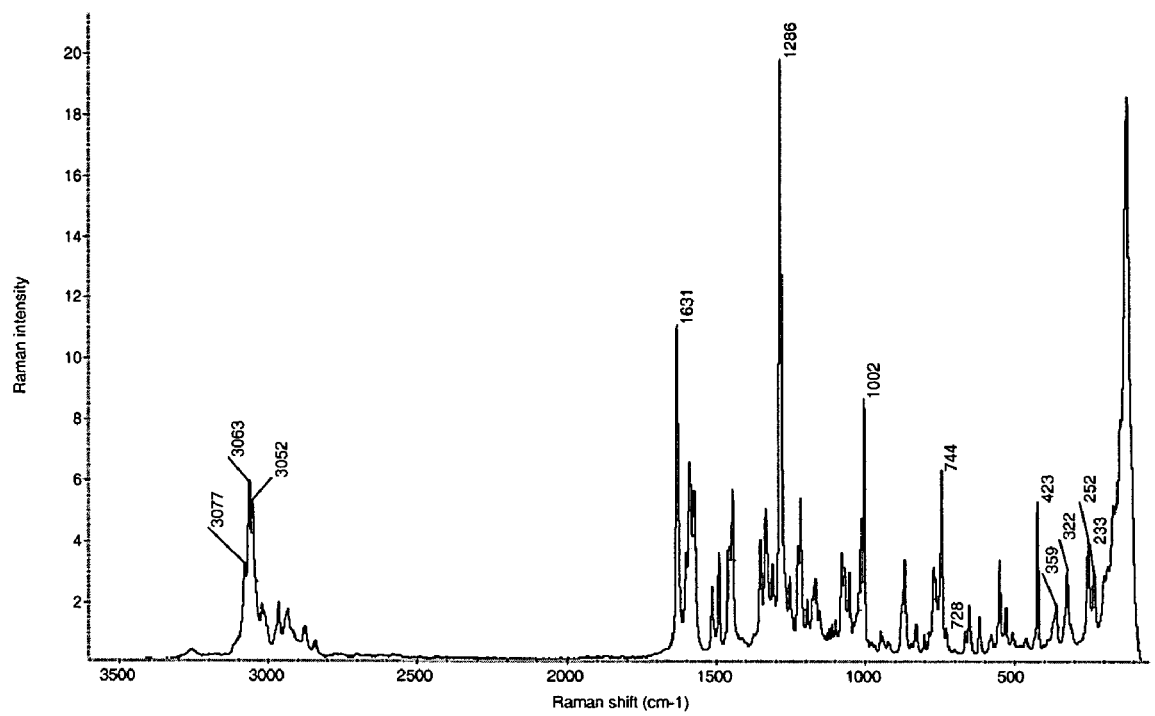

FIG. 115 is a FT-Raman spectrum of carvedilol mandelate salt.

Carvedilol Lactate Salts

Figure 116:
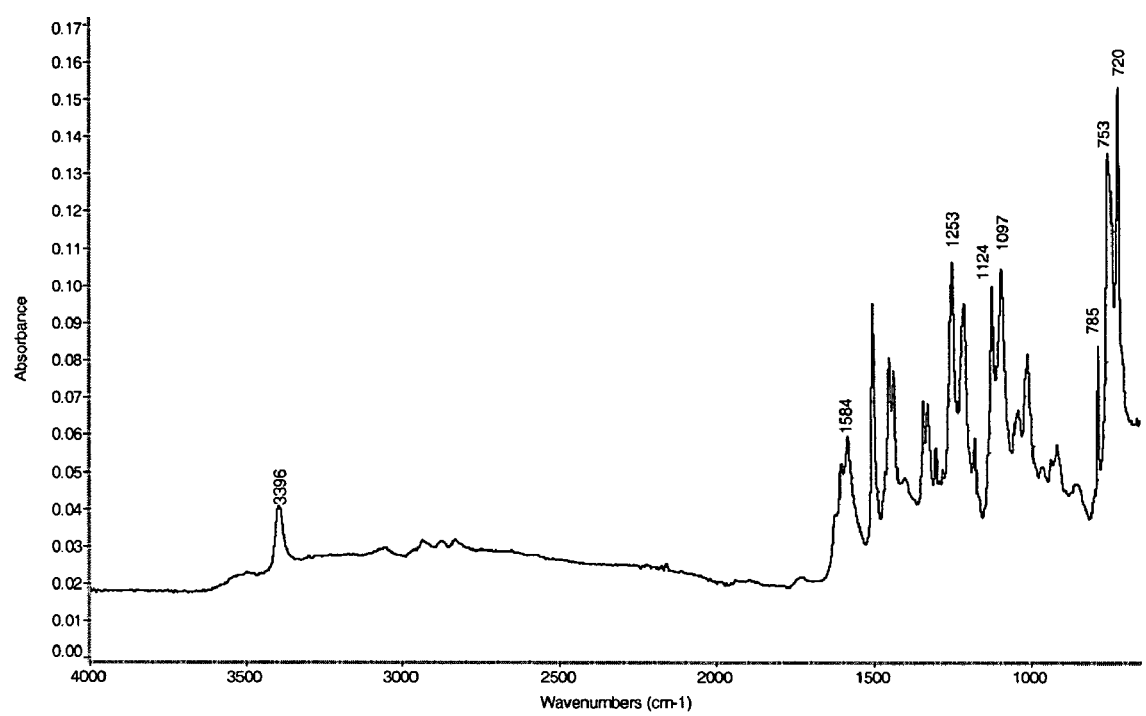

FIG. 116 is a FT-IR spectrum of carvedilol lactate salt.

Figure 117:
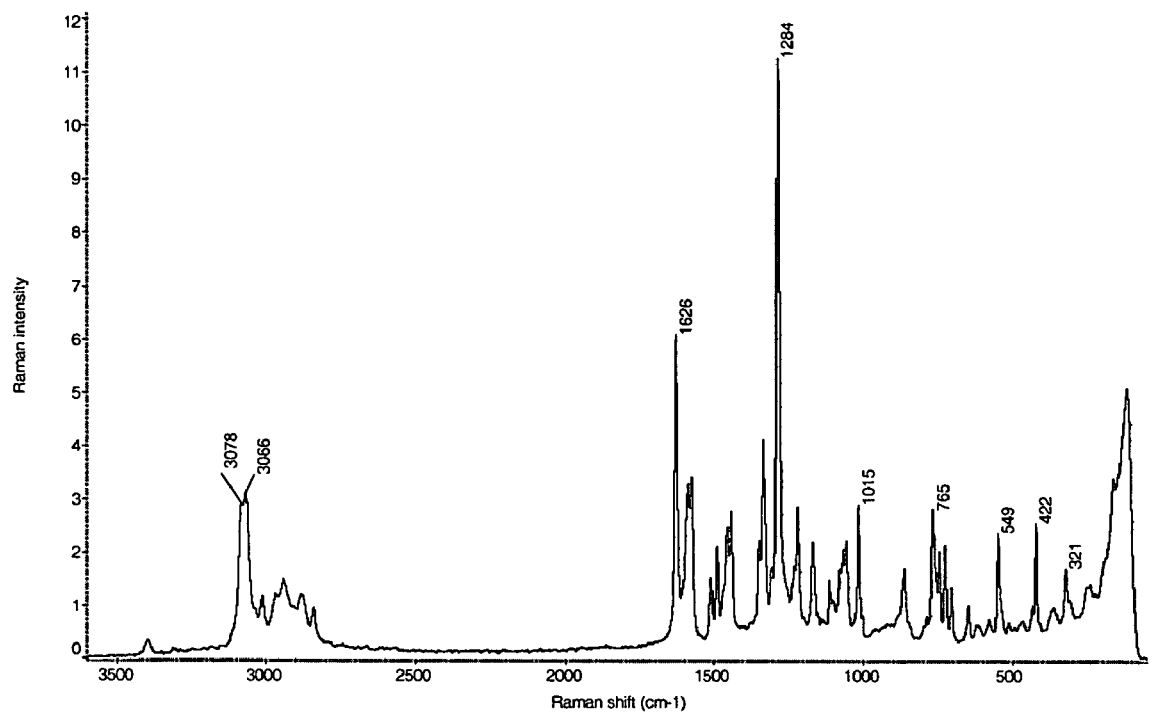

FIG. 117 is a FT-Raman spectrum of carvedilol lactate salt.

Carvedilol Maleate Salts

Figure 118:
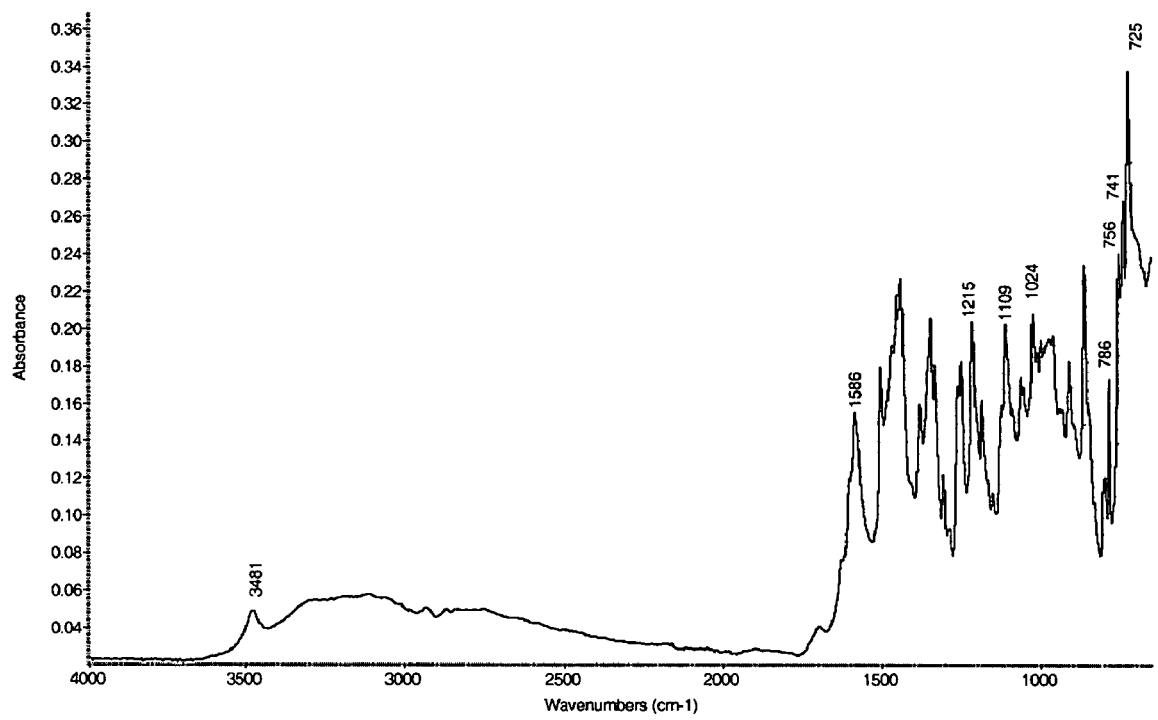

FIG. 118 is a FT-IR spectrum of carvedilol maleate salt.

Figure 119:
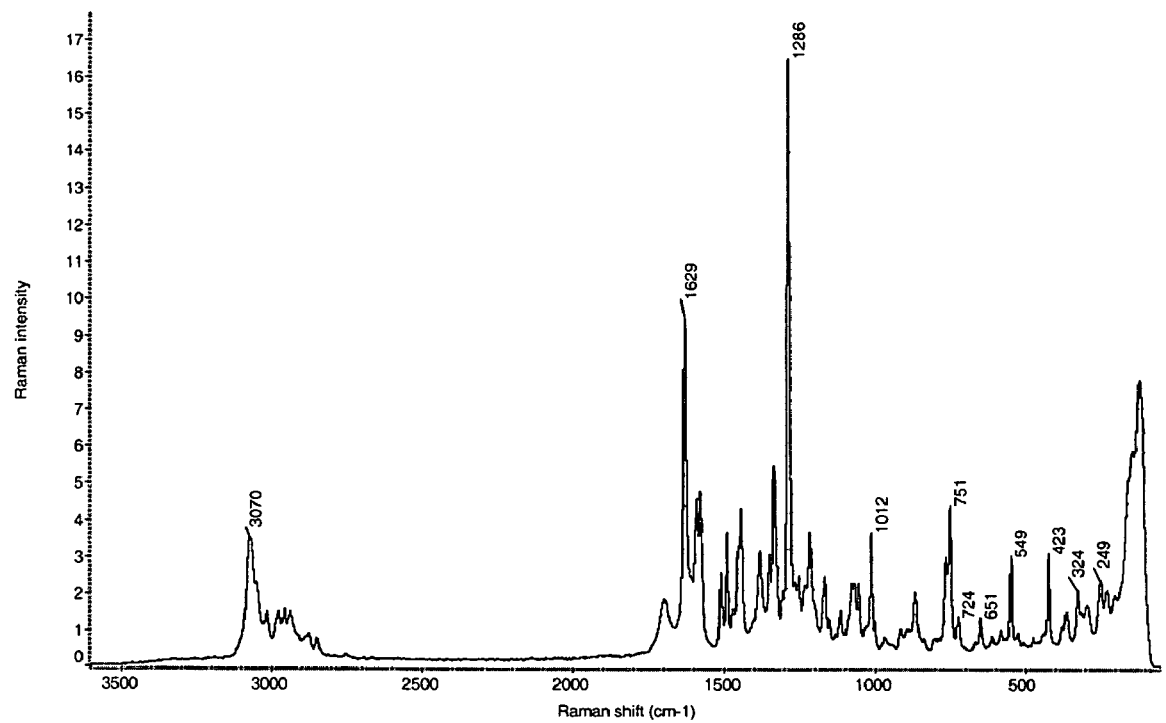

FIG. 119 is a FT-Raman spectrum of carvedilol maleate salt.

Carvedilol Sulfate Salts

Figure 120:
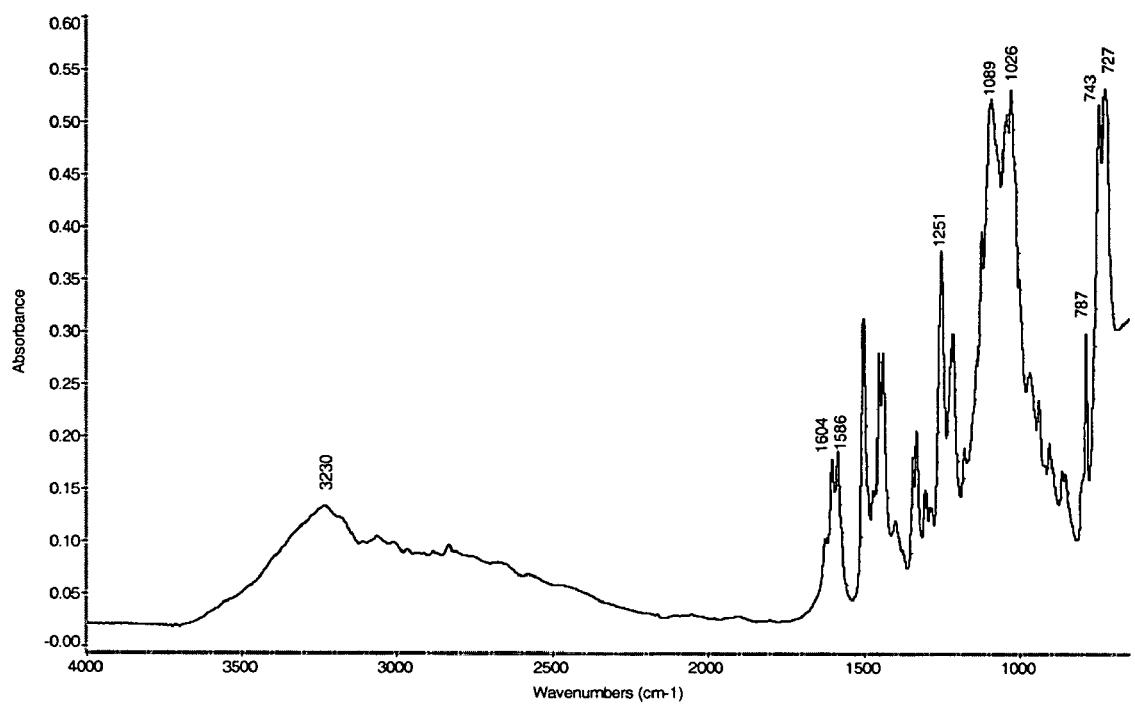

FIG. 120 is a FT-IR spectrum of carvedilol sulfate salt.

Figure 121:
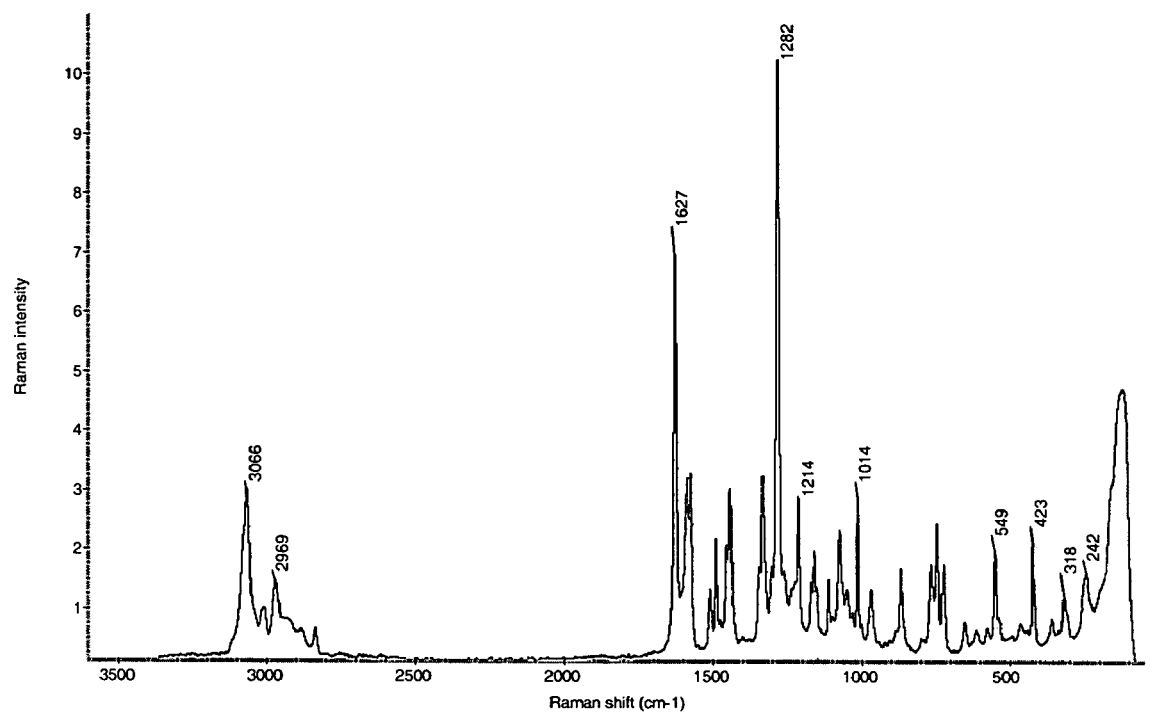

FIG. 121 is a FT-Raman spectrum of carvedilol sulfate salt.

Carvedilol Glutarate Salts

Figure 122:
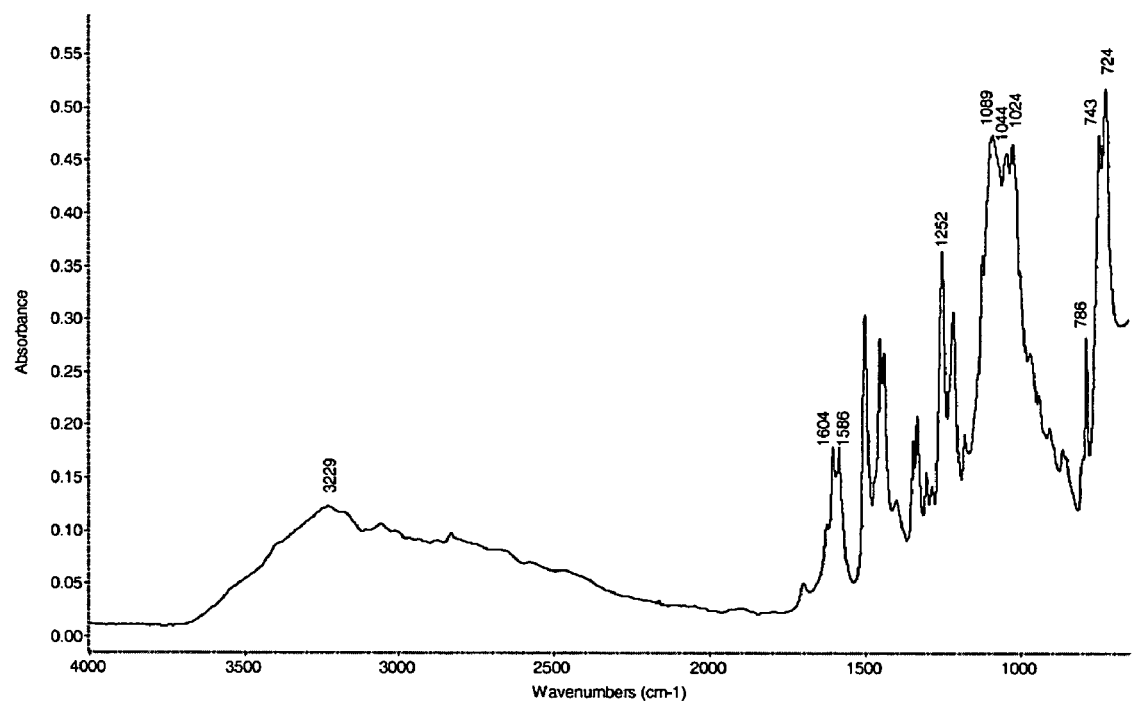

FIG. 122 is a FT-IR spectrum of carvedilol glutarate salt.

Figure 123:
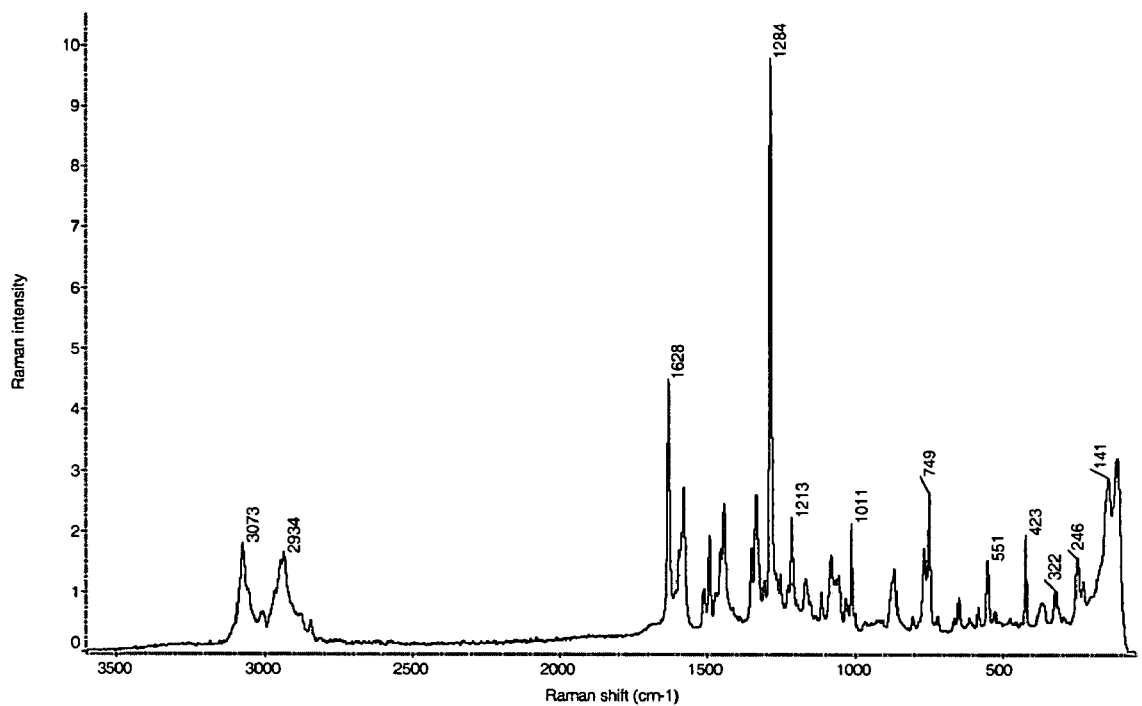

FIG. 123 is a FT-Raman spectrum of carvedilol glutarate salt.

Carvedilol Benzoate Salts

Figure 124:
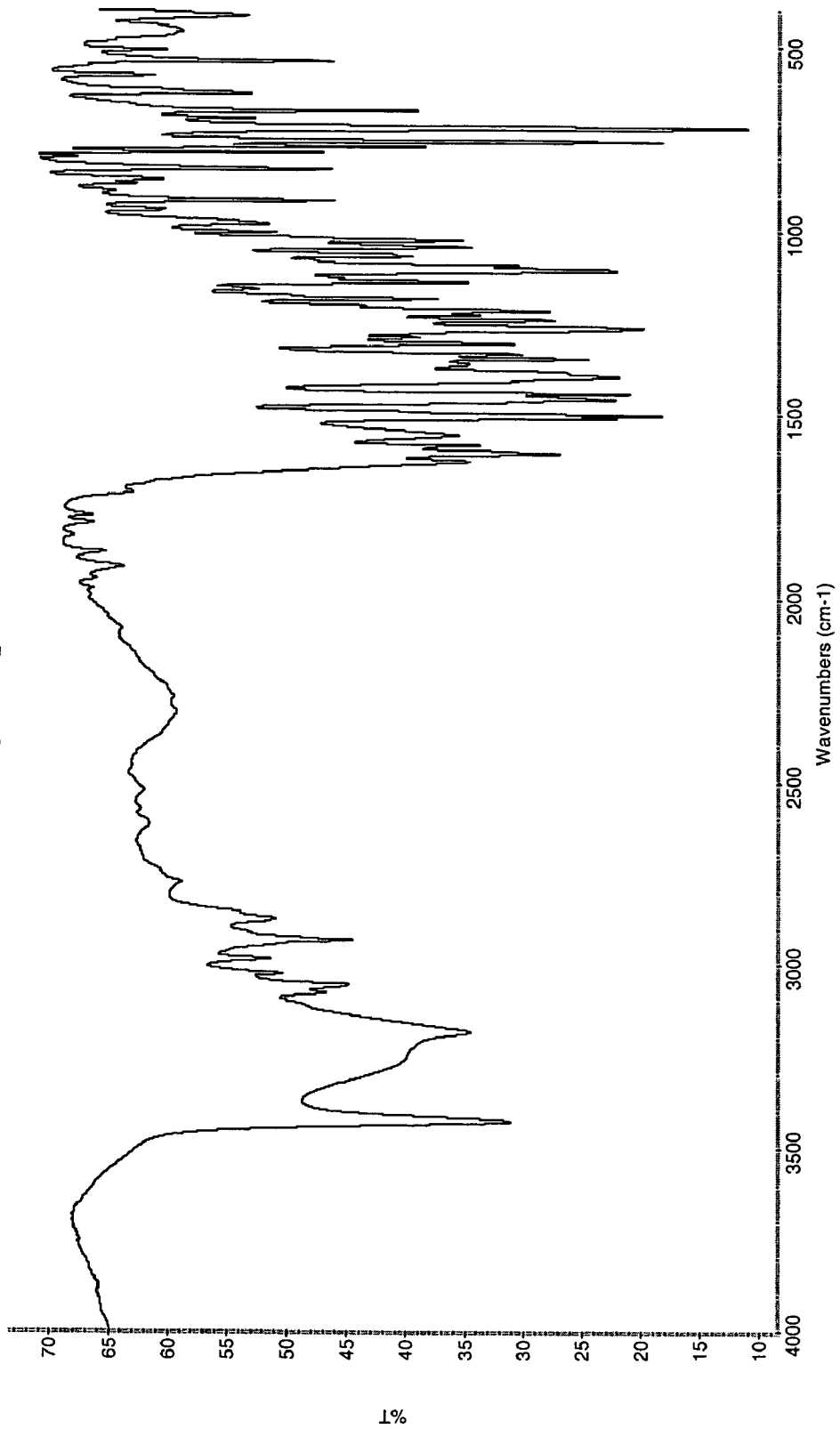

FIG. 124 is a FT-IR spectrum of carvedilol benzoate salt.

Figure 125:
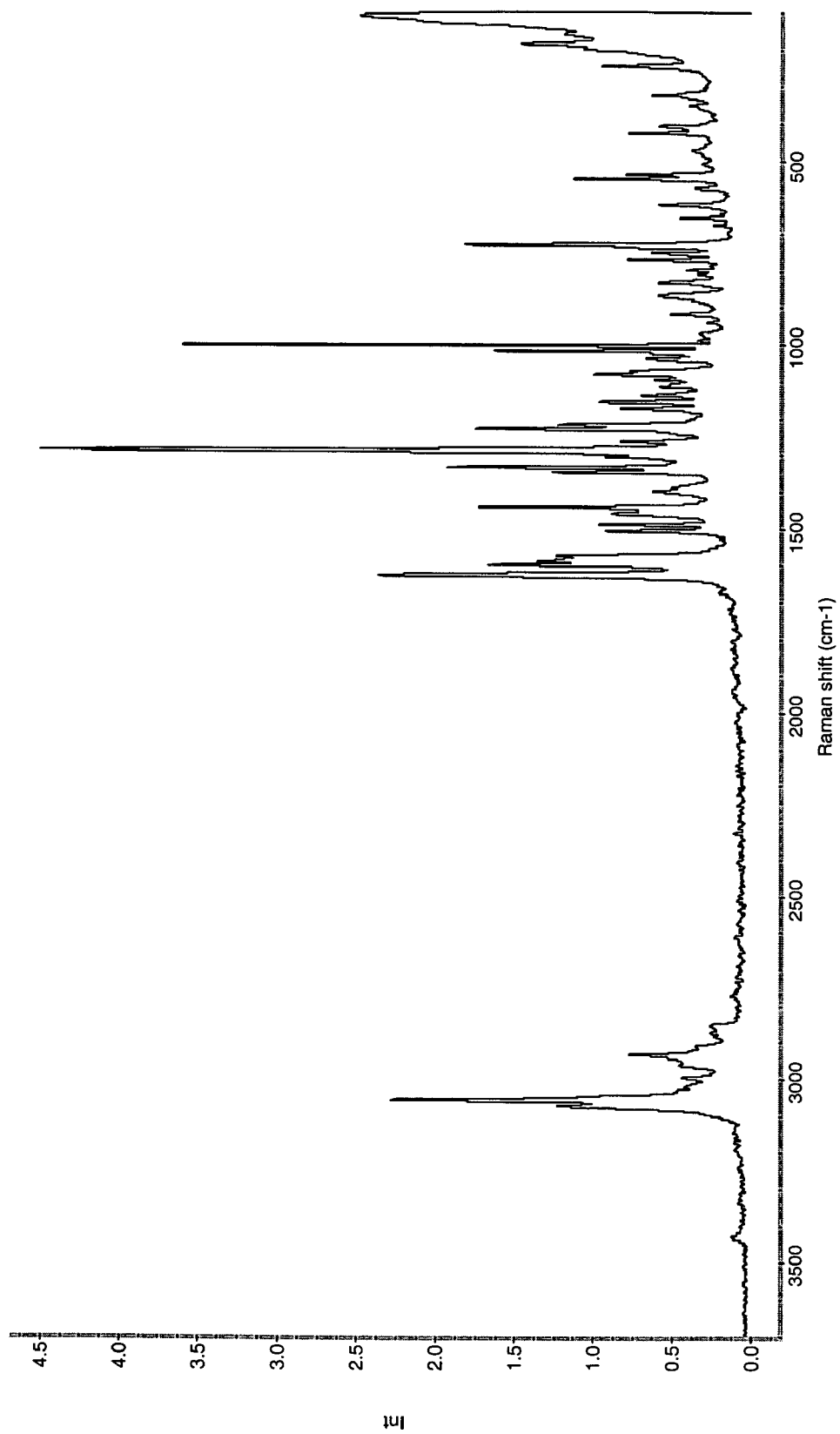

FIG. 125 is a FT-Raman spectrum of carvedilol benzoate salt.

Drug Solubility Enhancement in GI Tract

Figure 126:
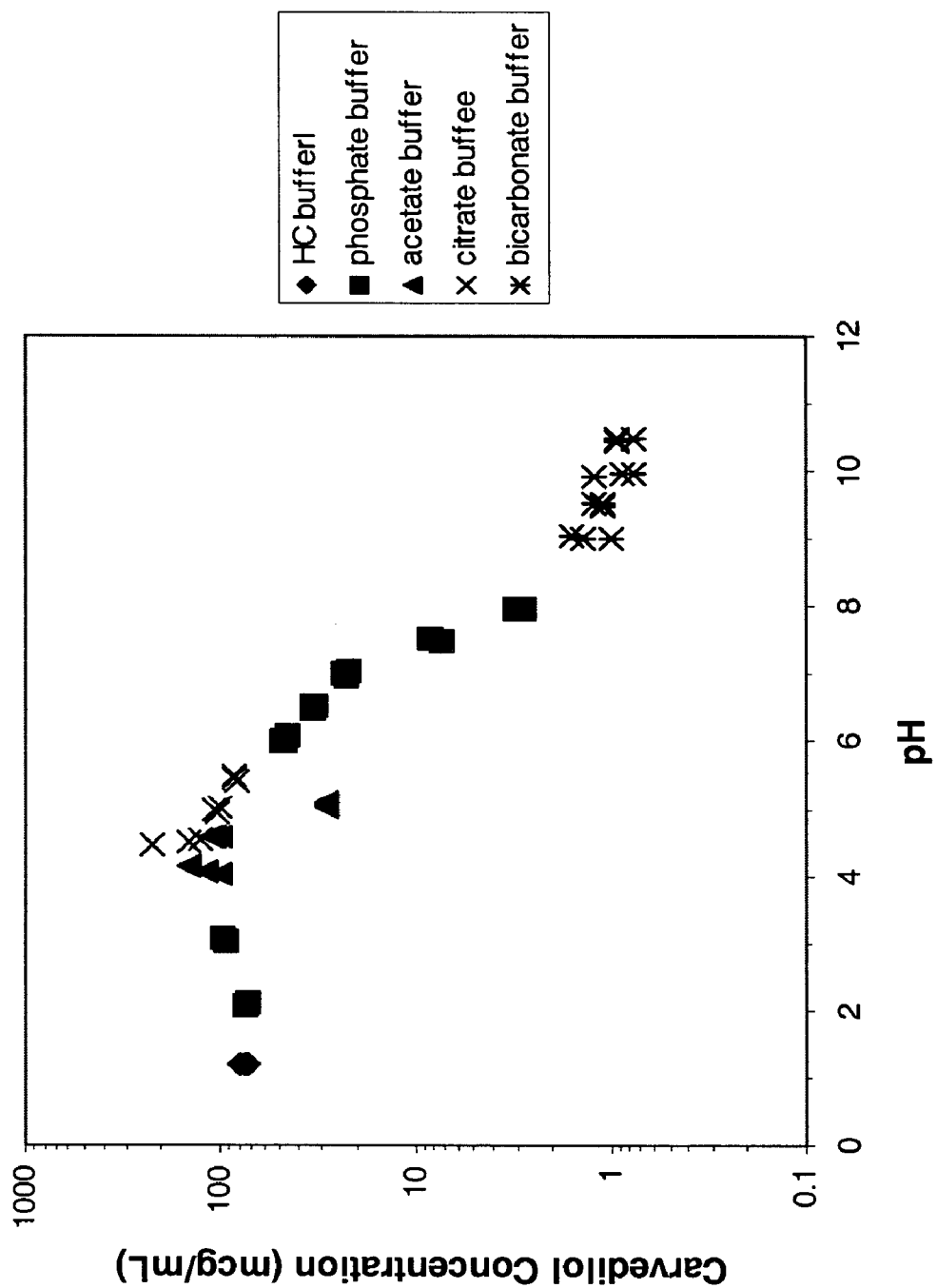

FIG. 126 depicts a pH-solubility profile for carvedilol.

Figure 127:
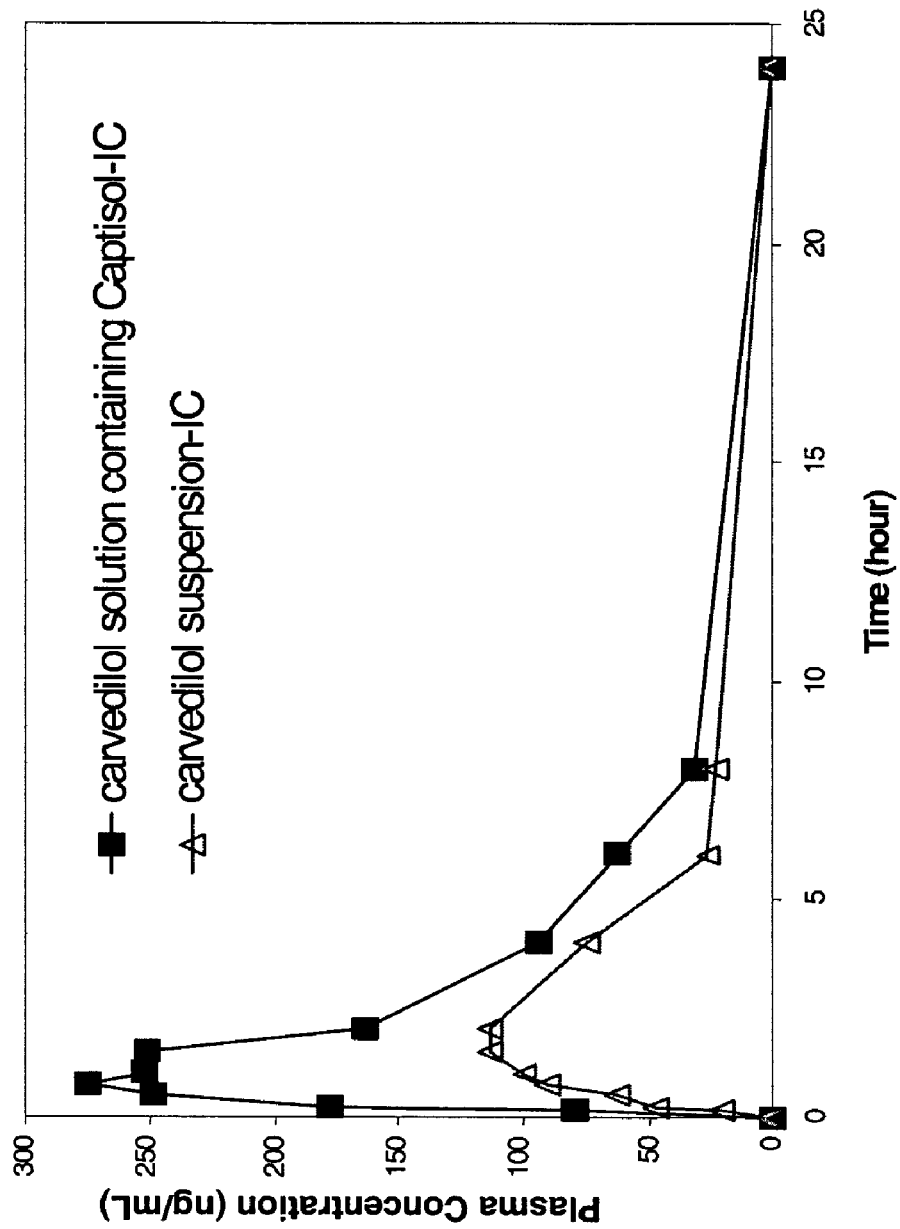

FIG. 127 depicts mean plasma profiles in beagle dogs following intra-colonic administration of a carvedilol solution containing captisol or carvedilol in aqueous suspension.

Figure 128:
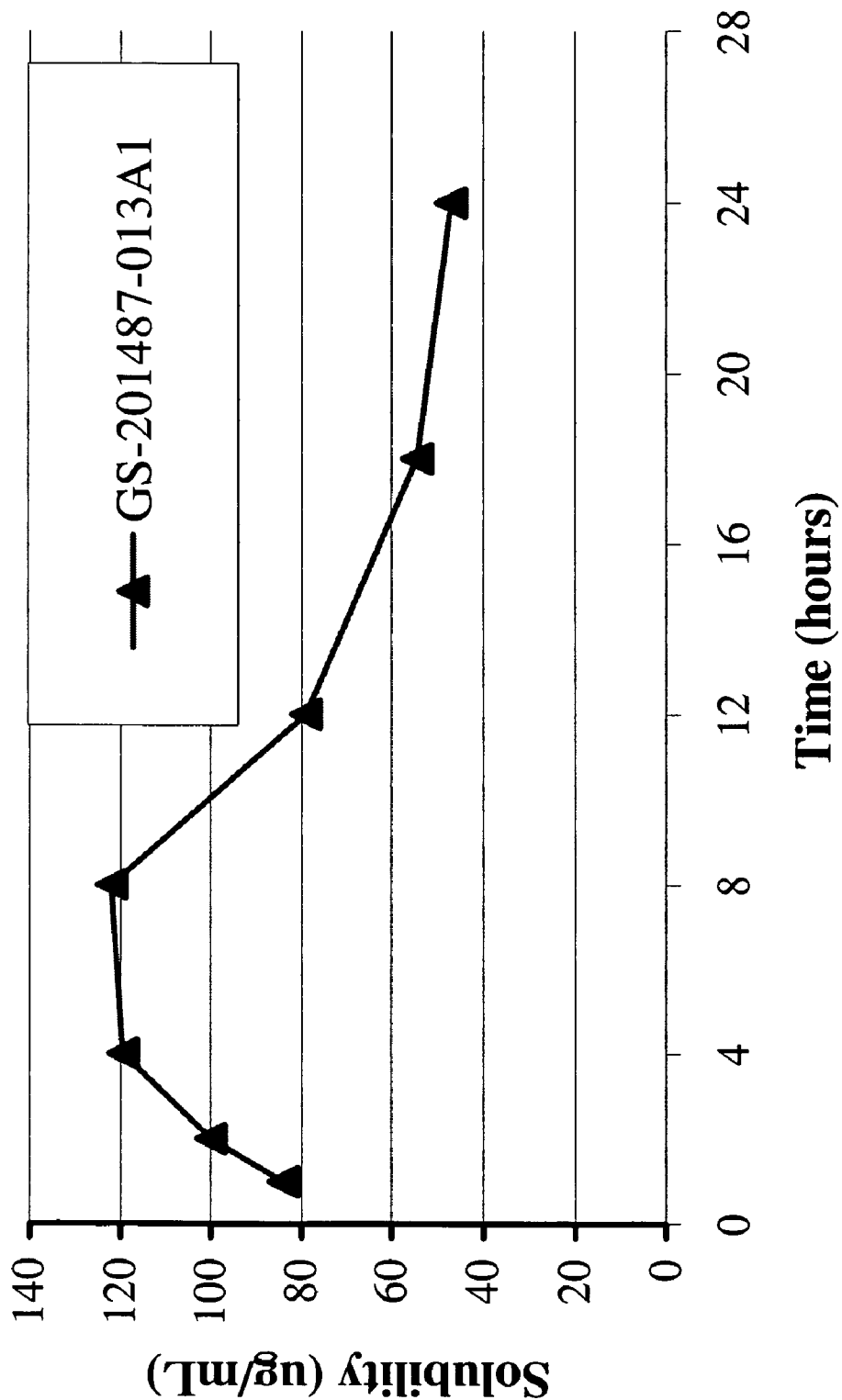

FIG. 128 depicts dissolution/solubility profile of carvedilol phosphate in pH=7.1 tris buffer.

Figure 129:
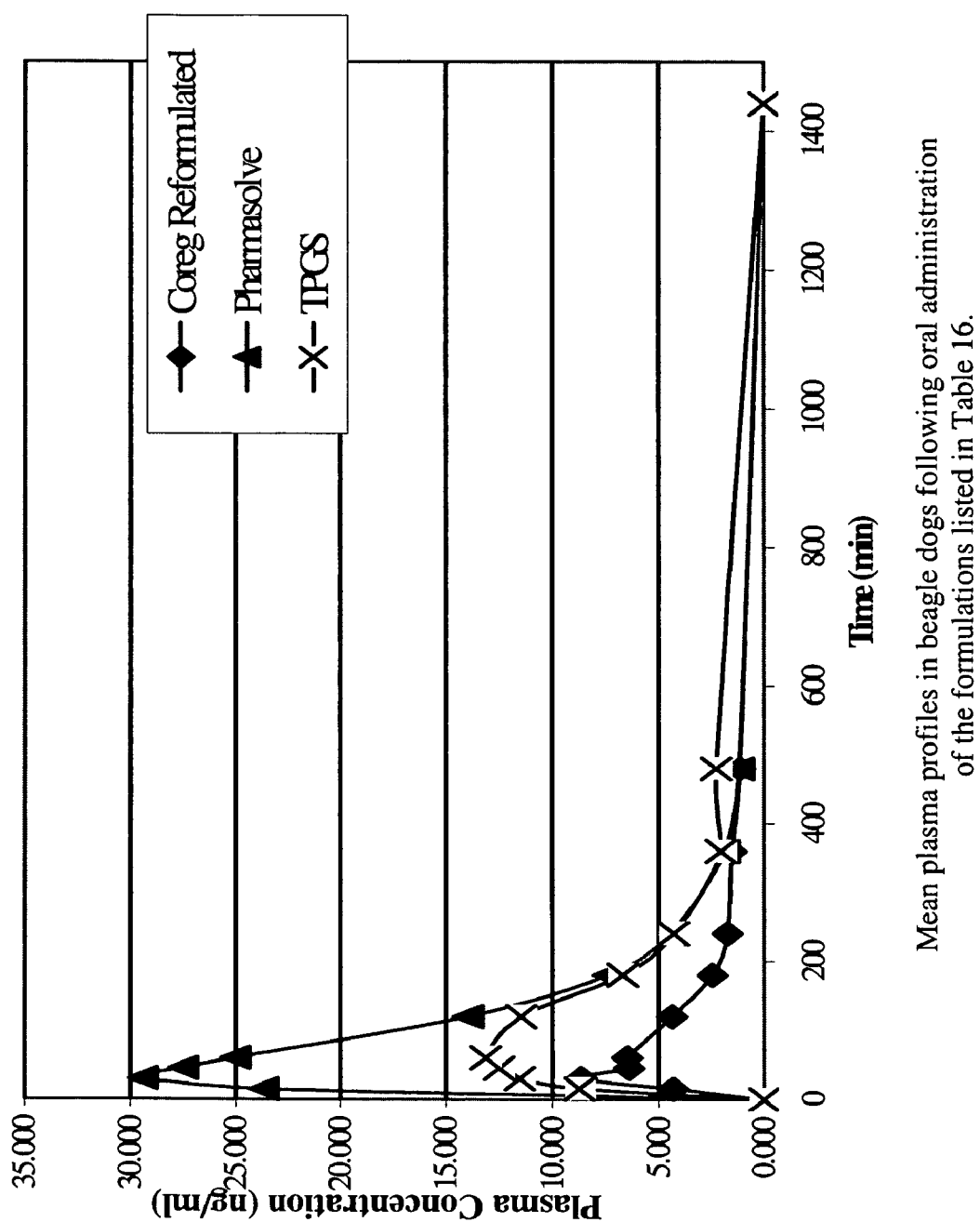

FIG. 129 depicts mean plasma profiles in beagle dogs following oral administration of the formulations listed in Table 4.

Figure 130:
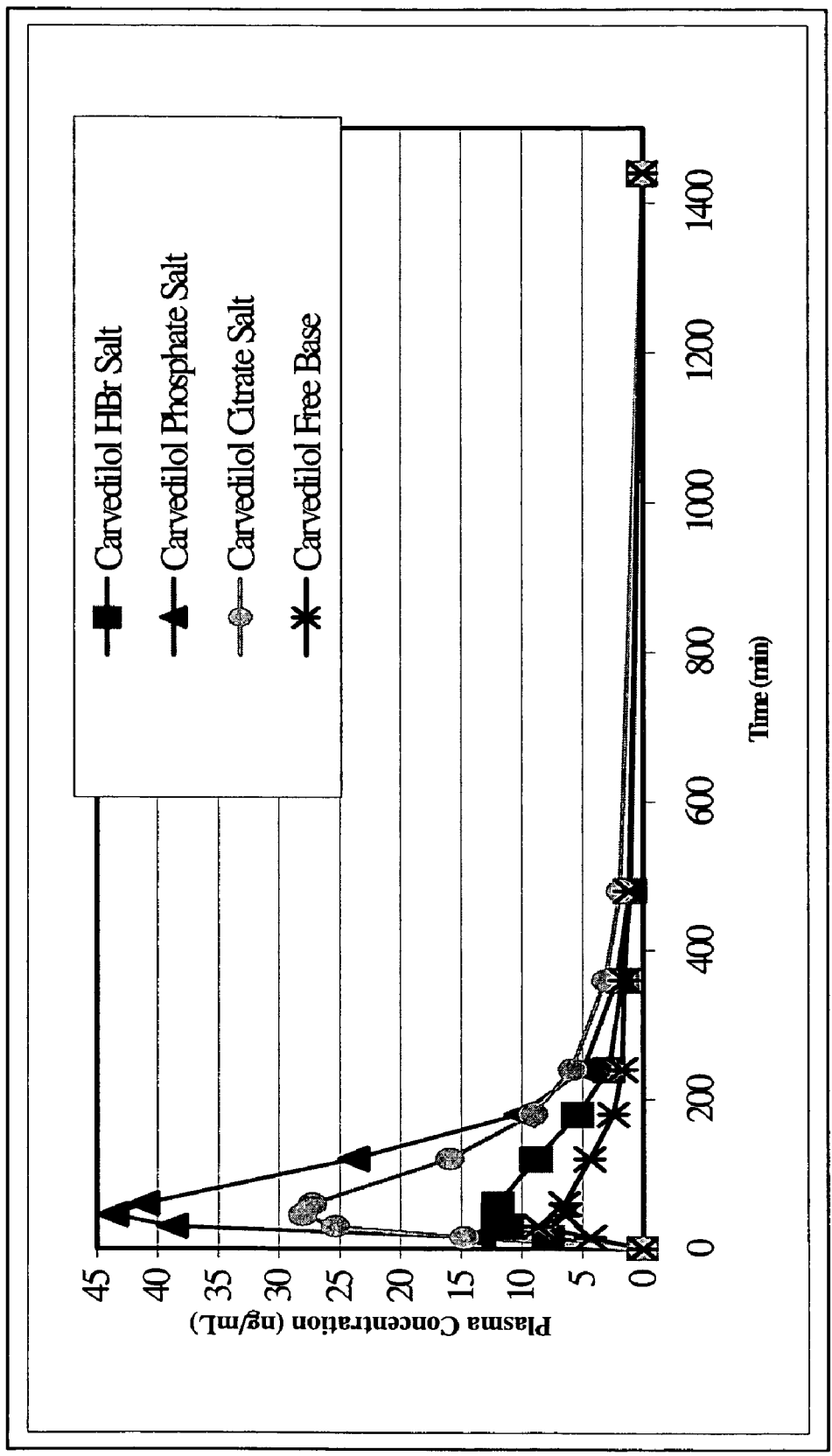

FIG. 130 depicts mean plasma profiles following oral administration of companion capsules filled with four formulations at 10 mg strength to beagle, dogs.

DETAILED DESCRIPTION OF THE INVENTION

The present invention relates to a salt of carvedilol and/or corresponding anhydrous forms or solvates thereof, compositions containing such carvedilol and/or corresponding anhydrous forms or solvates thereof, and/or methods of using the aforementioned compound(s) in the treatment of certain disease states in mammals, in particular man.

The present invention further relates to carvedilol salt forms, which may, but are not limited to include novel crystalline salt forms of carvedilol mandelate, carvedilol lactate, carvedilol maleate, carvedilol sulfate, carvedilol glutarate, carvedilol mesylate, carvedilol phosphate, carvedilol citrate, carvedilol hydrogen bromide, carvedilol oxalate, carvedilol hydrochloride, carvedilol hydrogen bromide, carvedilol benzoate, and/or corresponding anhydrous, solvates thereof.

The present invention relates to a pharmaceutical composition, which contain such aforementioned carvedilol salt forms, and/or corresponding anhydrous, solvates thereof, and/or pharmaceutically acceptable adjuvants, carriers, excipients.

The present invention further relates to a method of treating hypertension, congestive heart failure and angina, which comprises administering to a subject in need thereof an effective amount of a carvedilol salt form (which include corresponding novel crystalline forms, anhydrous forms, solvates thereof) and/or such aforementioned corresponding pharmaceutical compositions (i.e., which contain such carvedilol salt forms, anhydrous, solvates thereof).

All carvedilol salt and/or solvate compound forms suitable for use in the present invention, which include starting materials (i.e., such as carvedilol), intermediates or products, etc., are prepared as described herein, and/or by the application or adaptation of known methods, which may be methods used heretofore or described in the literature.

Carvedilol is disclosed and claimed in U.S. Pat. No. 4,503, 067 to Wiedemann et al. ("U.S. '067 patent"). Reference should be made to U.S. '067 patent for its full disclosure, which include methods of preparing and/or using the carvedilol compound. The entire disclosure of the U.S. '067 patent is incorporated hereby by reference in its entirety.

U.S. Pat. No. 6,515,010 to Franchini et al. discloses a novel salt form of carvedilol, namely carvedilol methanesulfonate salt form, pharmaceutical compositions containing carvedilol methanesulfonate and the use of the aforementioned compound in the treatment of hypertension, congestive heart failure and angina, which is hereby incorporated by reference in its entirety.

The present invention relates to a compound, which is a novel crystalline salt form of carvedilol.

In accordance with the present invention, it has been unexpectedly found that carvedilol compounds may be isolated readily as novel crystalline forms, which display much higher solubility when compared to the free base form of carvedilol.

As indicated above, the present invention relates to carvedilol salt forms, which include a novel crystalline salt forms of carvedilol mandelate, carvedilol lactate, carvedilol maleate, carvedilol sulfate, carvedilol glutarate, carvedilol mesylate, carvedilol phosphate, carvedilol citrate, carvedilol hydrogen bromide, carvedilol oxalate, carvedilol hydrochloride, carvedilol hydrogen bromide, carvedilol benzoate, and/or corresponding solvates thereof.

More particularly, the present invention relates to carvedilol salt forms, which may include, but are not limited to carvedilol hydrogen phosphate, carvedilol dihydrogen phosphate, carvedilol dihydrogen phosphate hemihydrate, carvedilol dihydrogen phosphate dihydrate, carvedilol dihydrogen phosphate methanol solvate, carvedilol hydrobromide monohydrate, carvedilol hydrobromide dioxane solvate, carvedilol hydrobromide 1-pentanol solvate, carvedilol hydrobromide 2-methyl-1-propanol solvate, carvedilol hydrobromide trifluoroethanol solvate, carvedilol hydrobromide 2-propanol solvate, carvedilol hydrobromide n-propanol solvate #1, carvedilol hydrobromide n-propanol solvate #2, carvedilol hydrobromide anhydrous forms or anhydrous, carvedilol hydrobromide ethanol solvate, carvedilol hydrobromide dioxane solvate, carvedilol monocitrate monohydrate, carvedilol mandelate, carvedilol lactate salt, carvedilol maleate, carvedilol sulfate, carvedilol glutarate, and/or corresponding anhydrous, solvates thereof.

According to one aspect of the present invention, novel crystalline carvedilol salt forms, may exist as different polymorphs, anhydrous forms, and/or solvates thereof, etc.

In light of this, crystalline carvedilol salt forms of the present invention (i.e., which may include different polymorphs, ahydrous forms, solvates, and/or hydrates thereof) may exhibit characteristic polymorphism. As conventionally understood in the art, polymorphism is defined as an ability of a compound to crystallize as more than one distinct crystalline or "polymorphic" species. A polymorph is defined as a solid crystalline phase of a compound with at least two different arrangements or polymorphic forms of that compound molecule in the solid state.

Polymorphic forms of any given compound, including those of the present invention, are defined by the same chemical formula and/or composition and are as distinct in chemical structure as crystalline structures of two different chemical compounds. Such compounds may differ in packing, geometrical arrangement of respective crystalline lattices, etc.

In light of the foregoing, chemical and/or physical properties or characteristics vary with each distinct polymorphic form, which may include variations in solubility, melting point, density, hardness, crystal shape, optical and electrical properties, vapor pressure, stability, etc.

Solvates and/or hydrates of crystalline carvedilol salt forms of the present invention also may be formed when solvent molecules are incorporated into the crystalline lattice structure of the compound molecule during the crystallization process. For example, solvate forms of the present invention may incorporate nonaqueous solvents such as methanol and the like as described herein below. Hydrate forms are solvate forms, which incorporate water as a solvent into a crystalline lattice.

Figure 9:
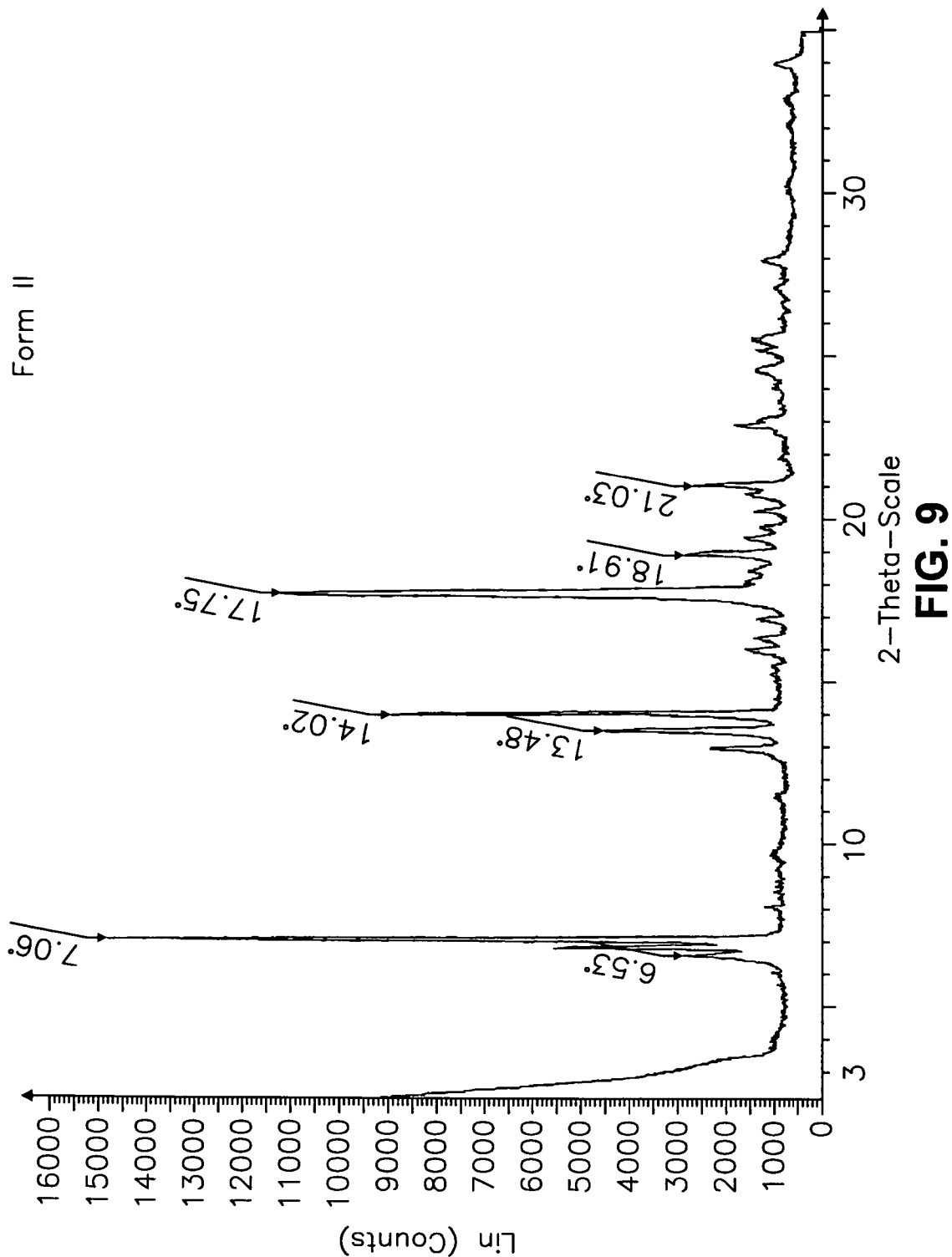
FIG. 9 is an x-ray powder diffractogram for carvedilol dihydrogen phosphate dihydrate (Form II).
Figure 10:
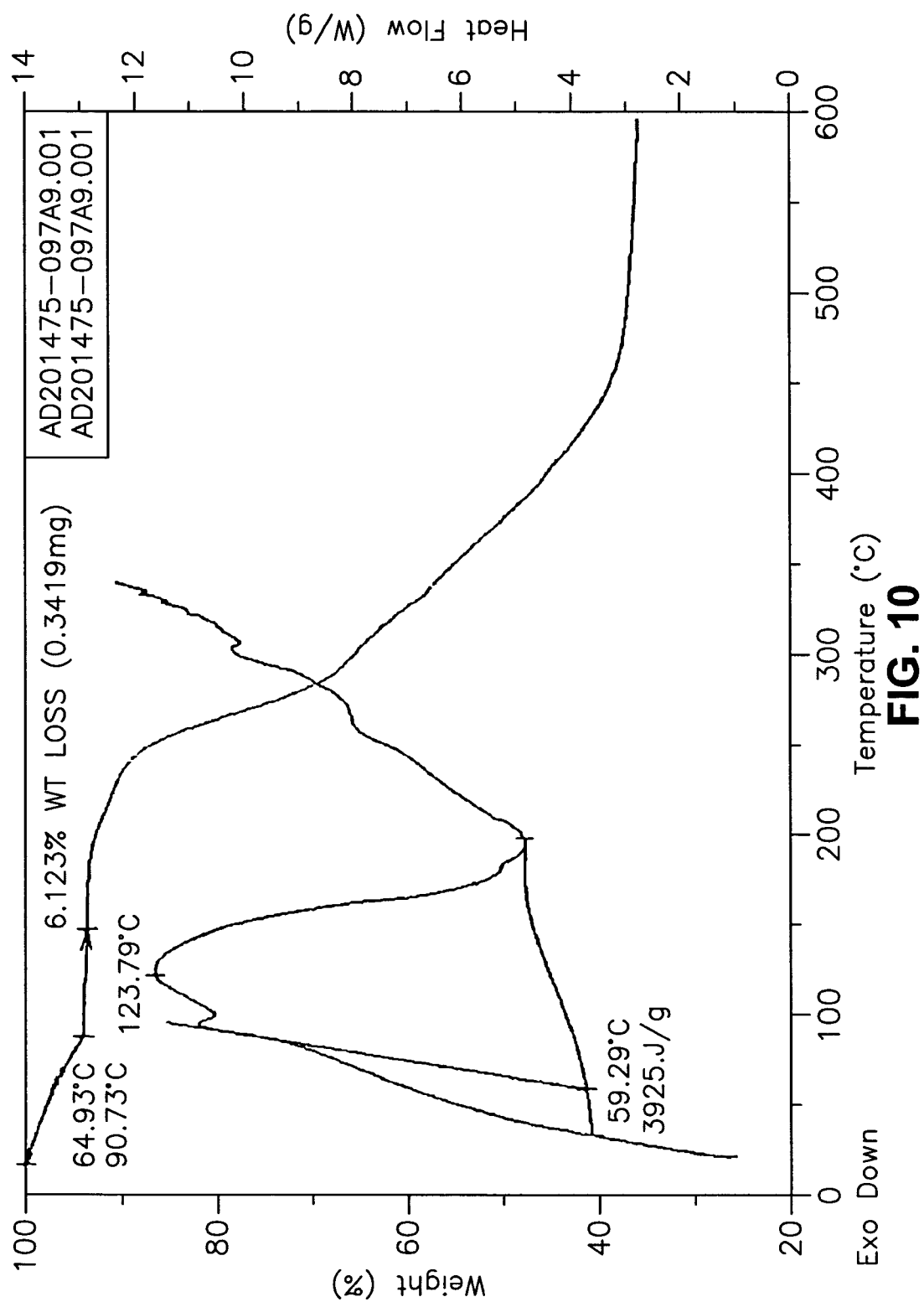
FIG. 10 shows the thermal analysis results for carvedilol dihydrogen phosphate dihydrate (Form II).
Figure 11:
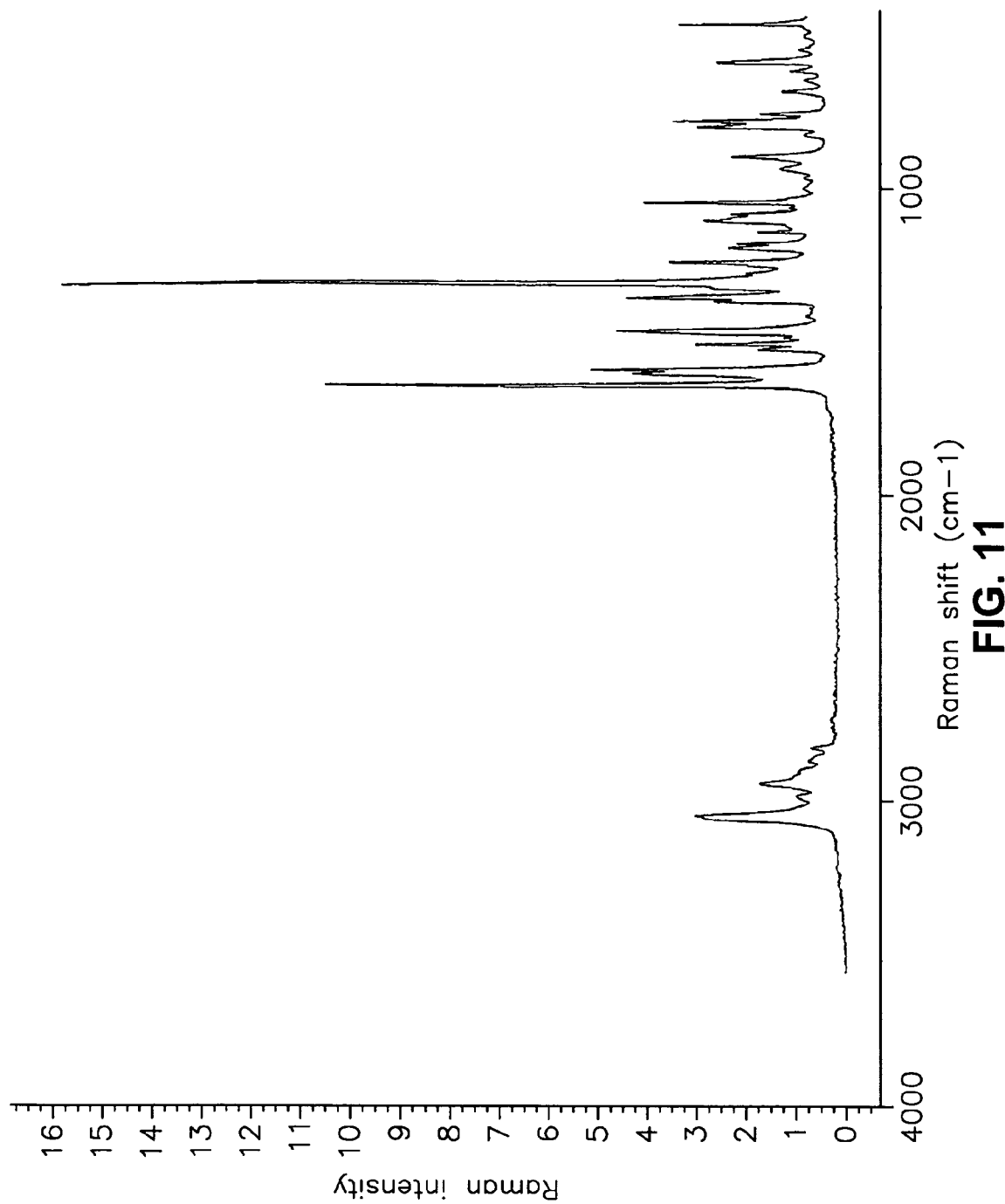
FIG. 11 is an FT-Raman spectrum for carvedilol dihydrogen phosphate dihydrate (Form II).
Figure 12:
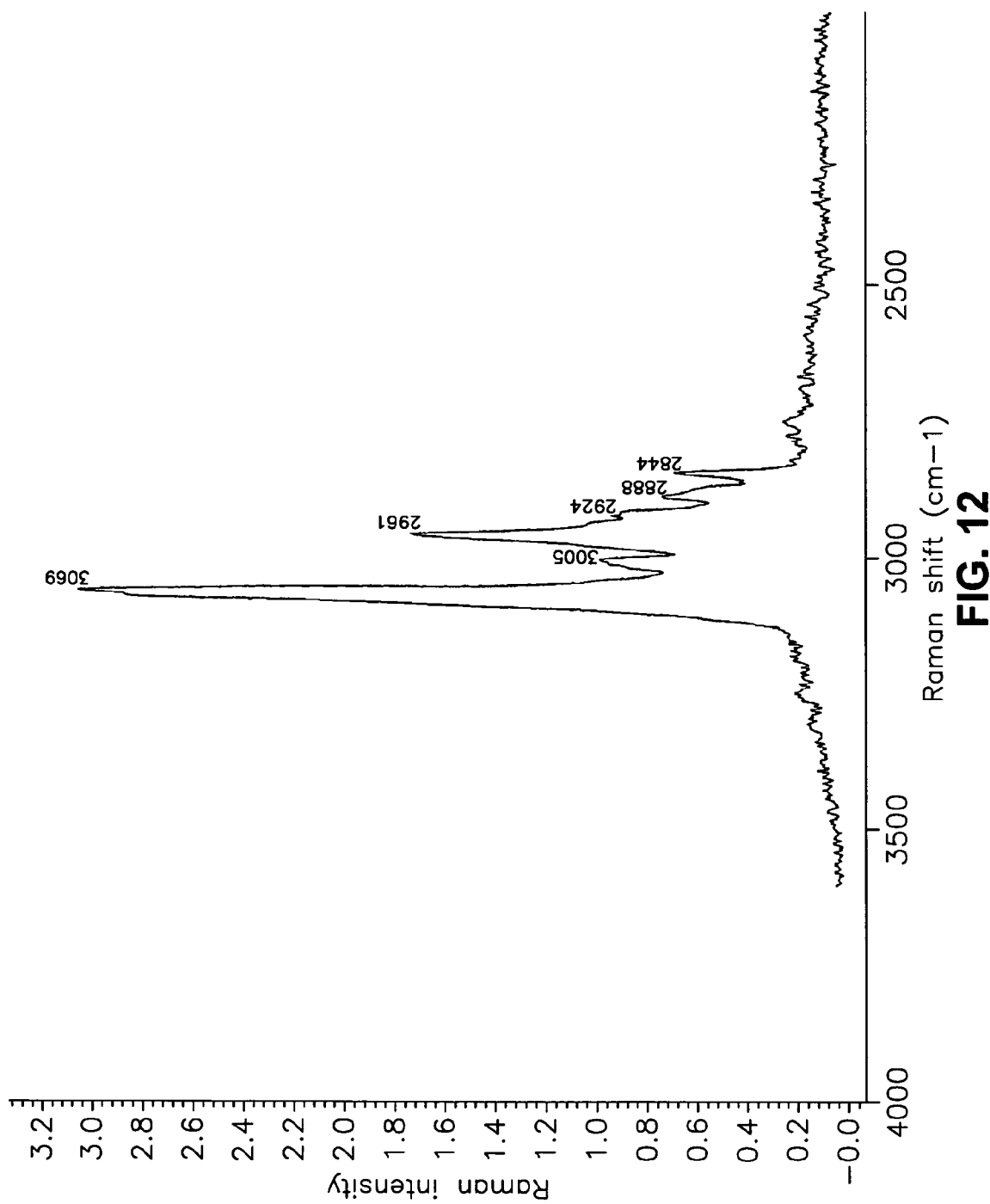
FIG. 12 is an FT-Raman spectrum for carvedilol dihydrogen phosphate dihydrate in the 4000-2000 $cm^{-1}$ region of the spectrum (Form II).
Figure 13:
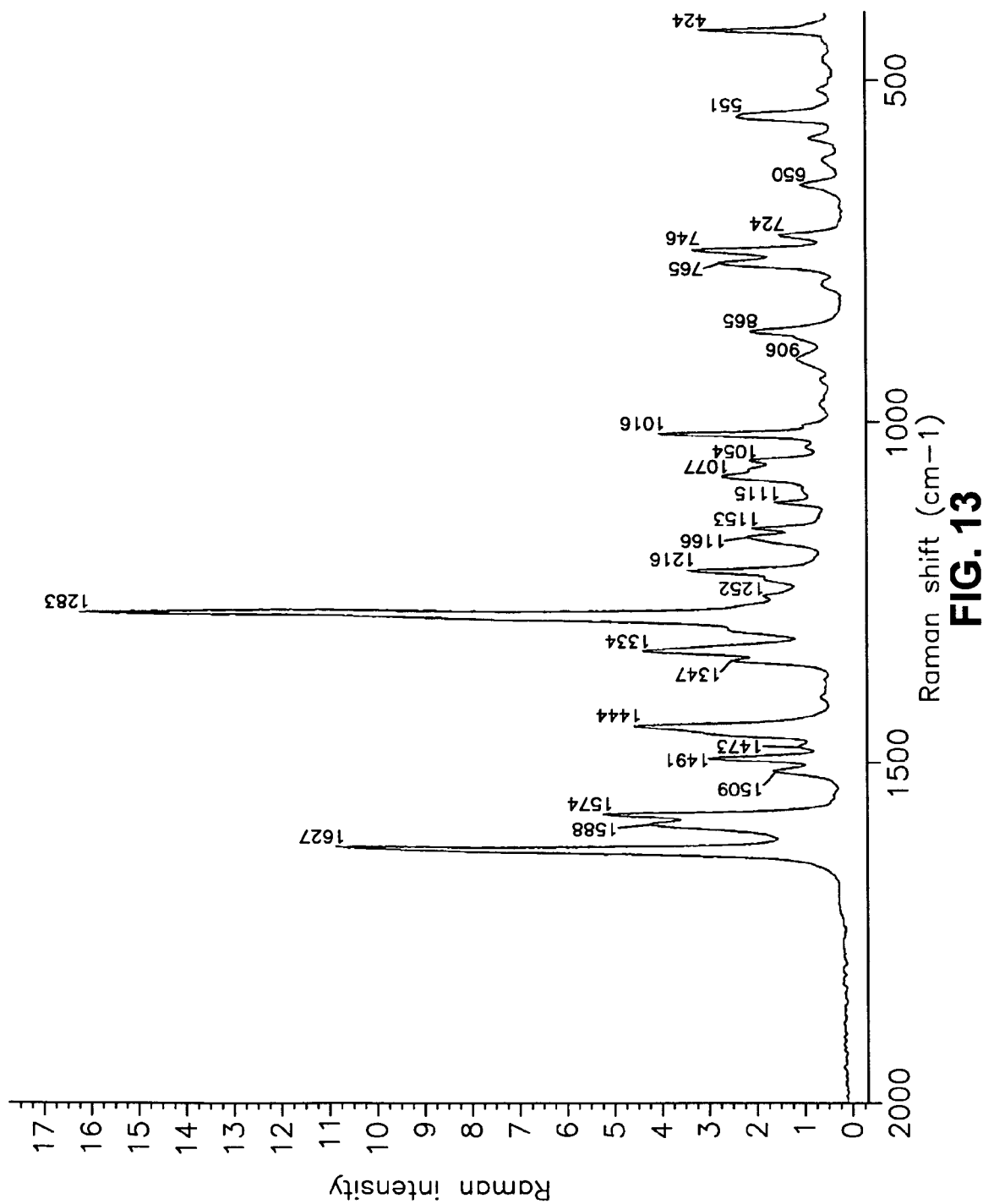
FIG. 13 is an FT-Raman spectrum for carvedilol dihydrogen phosphate dihydrate in the 2000-400 $cm^{-1}$ region of the spectrum (Form II).
Figure 14:
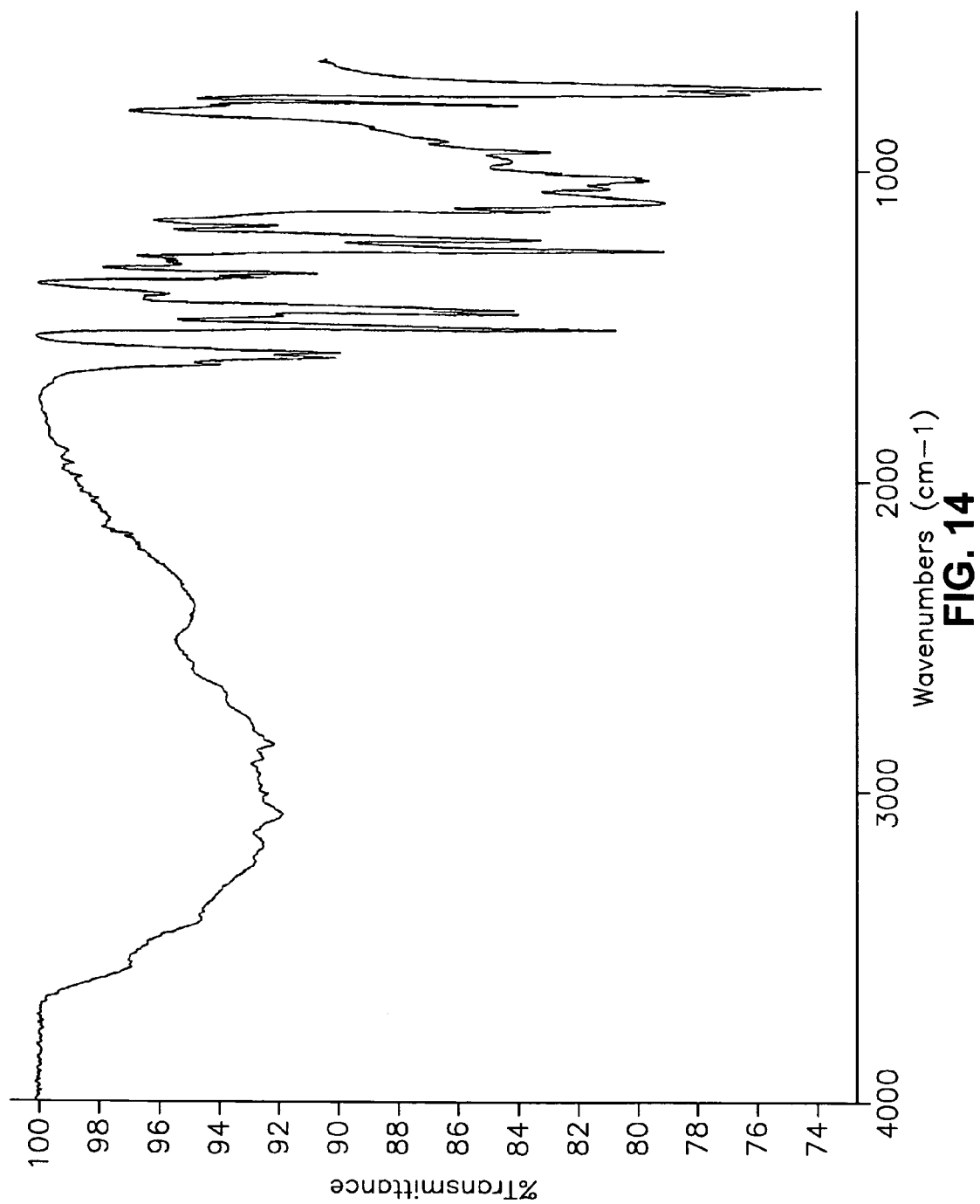
FIG. 14 is an FT-IR spectrum for carvedilol dihydrogen phosphate dihydrate (Form II).
Figure 15:
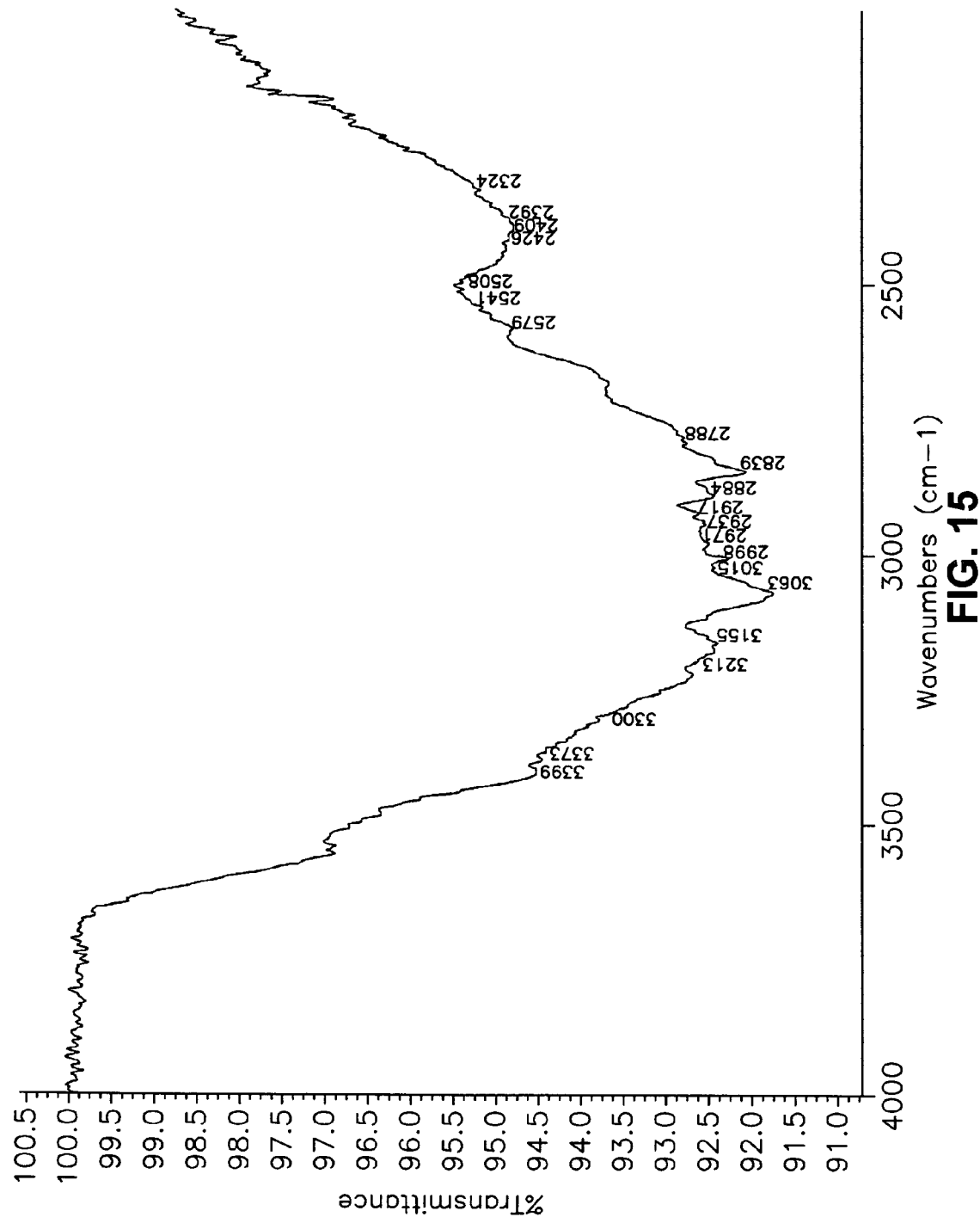
FIG. 15 is an FT-IR spectrum for carvedilol dihydrogen phosphate dihydrate in the 4000-2000 $cm^{-1}$ region of the spectrum (Form II).
Figure 16:
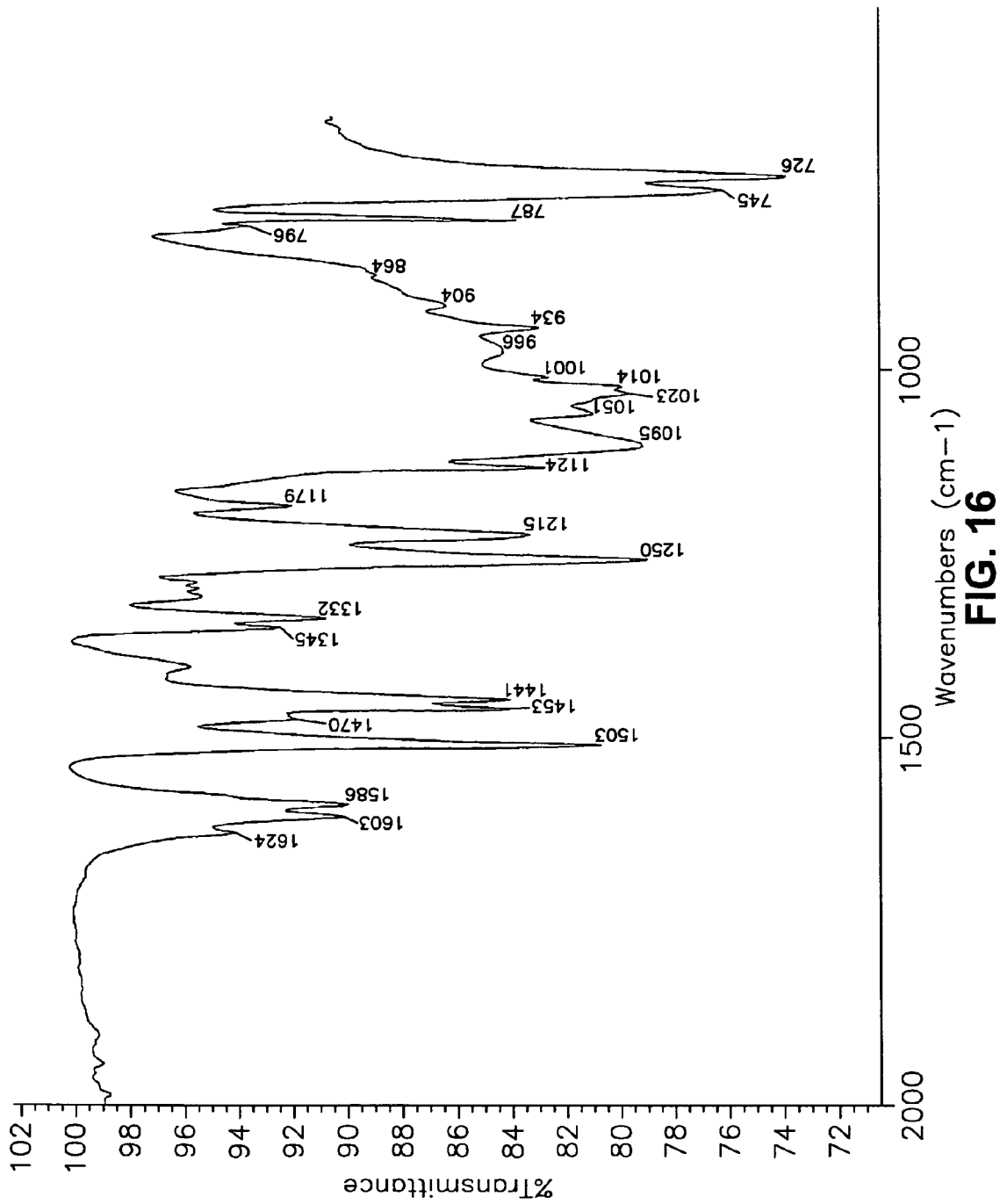
FIG. 16 is an FT-IR spectrum for carvedilol dihydrogen phosphate dihydrate in the 2000-500 $cm^{-1}$ region of the spectrum (Form II).
Figure 17:
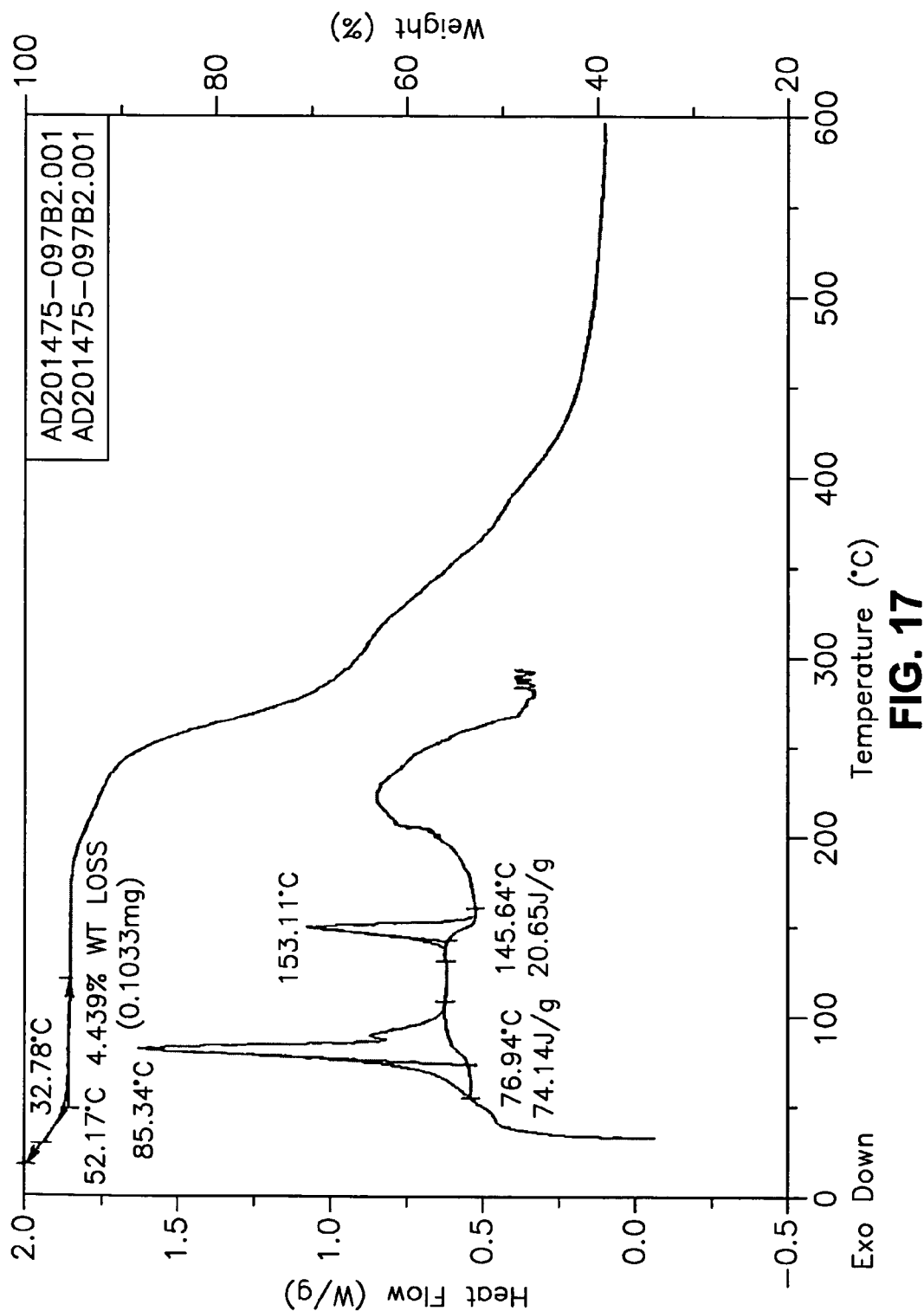
FIG. 17 shows the thermal analysis results for carvedilol dihydrogen phosphate methanol solvate (Form III).
Figure 18:
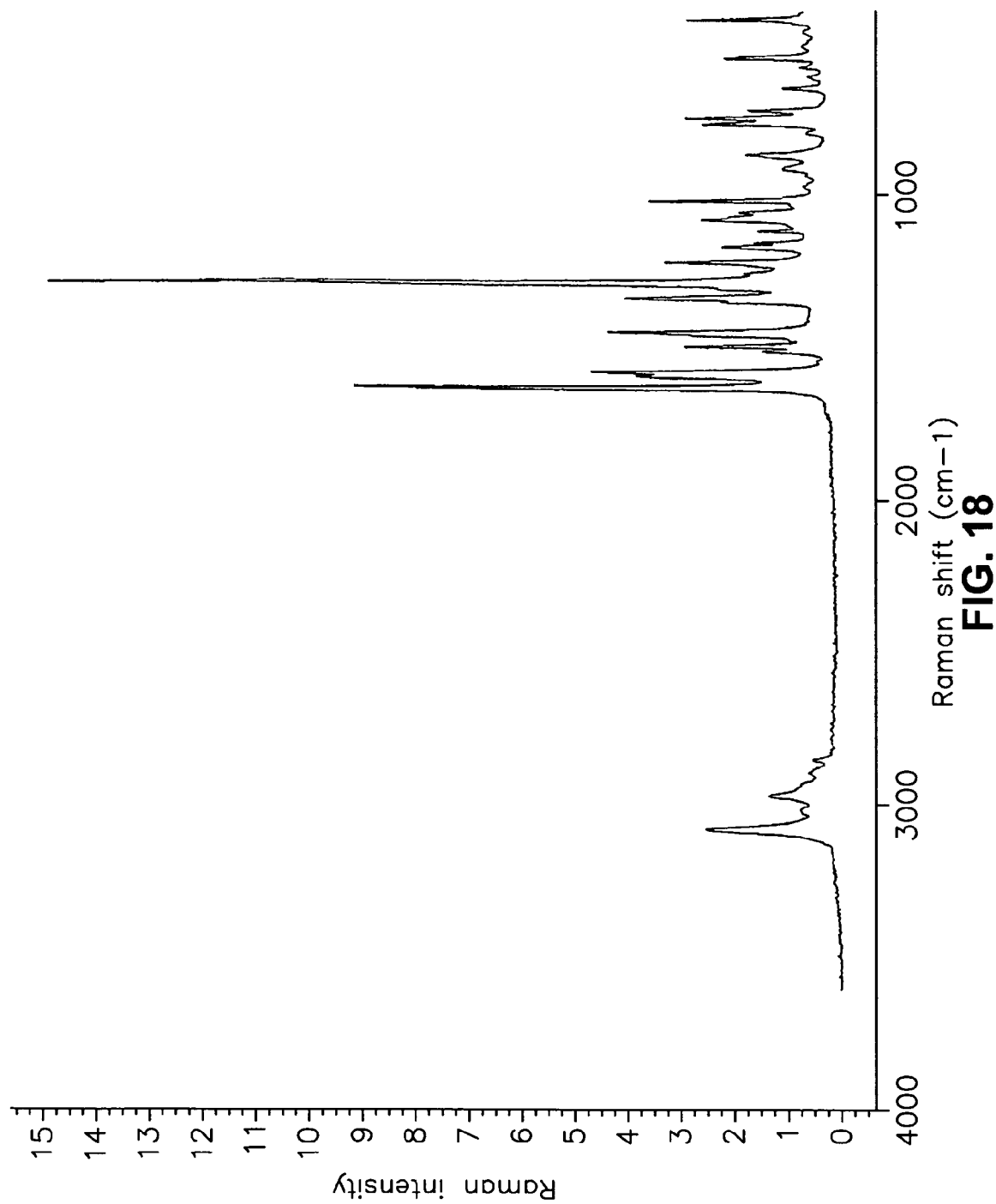
FIG. 18 is an FT-Raman spectrum for carvedilol dihydrogen phosphate methanol solvate (Form III).
Figure 19:
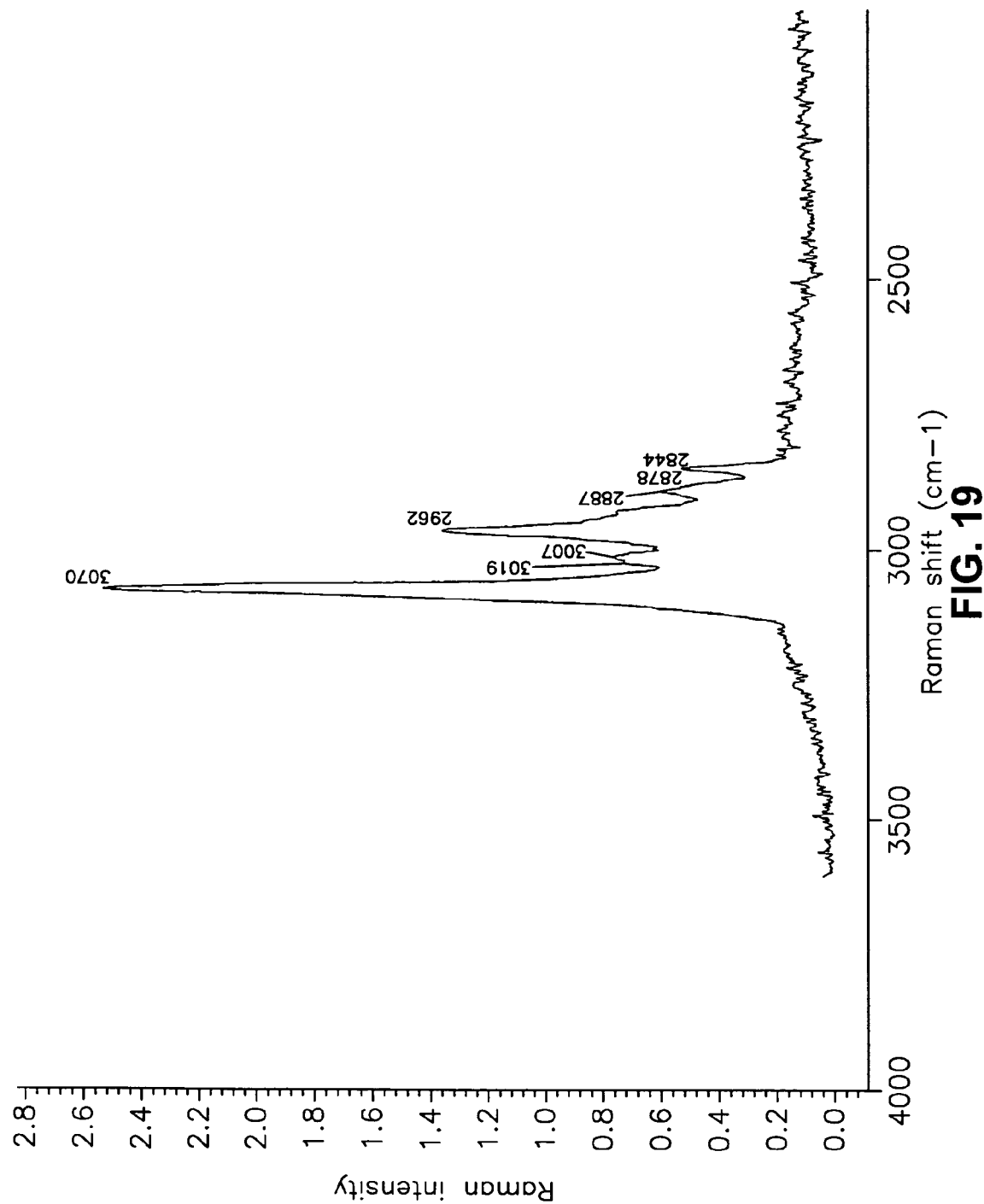
FIG. 19 is an FT-Raman spectrum for carvedilol dihydrogen phosphate methanol solvate in the 4000-2000 $cm^{-1}$ region of the spectrum (Form III).
Figure 20:
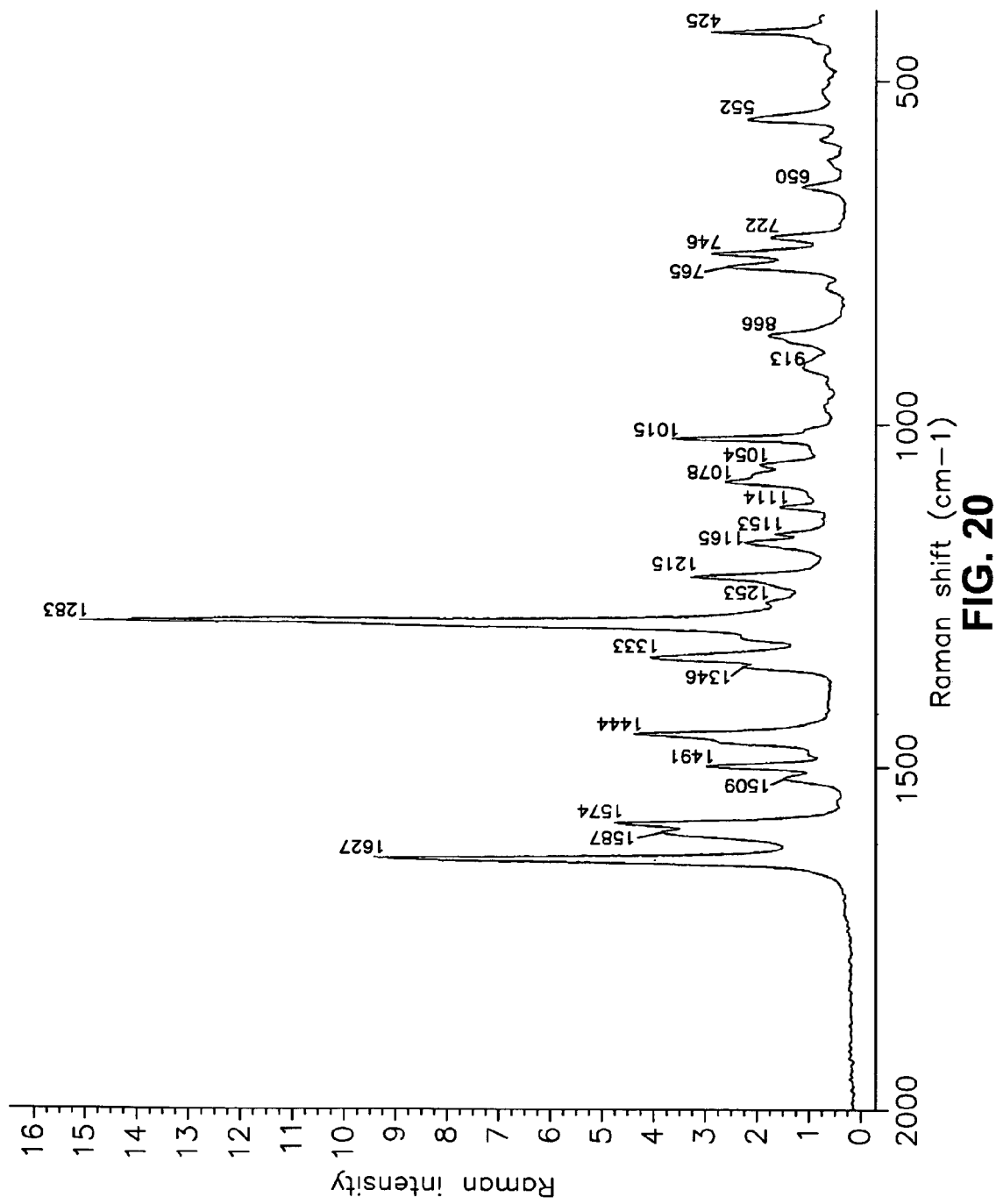
FIG. 20 is an FT-Raman spectrum for carvedilol dihydrogen phosphate methanol solvate in the 2000-400 $cm^{-1}$ region of the spectrum (Form III).
Figure 21:
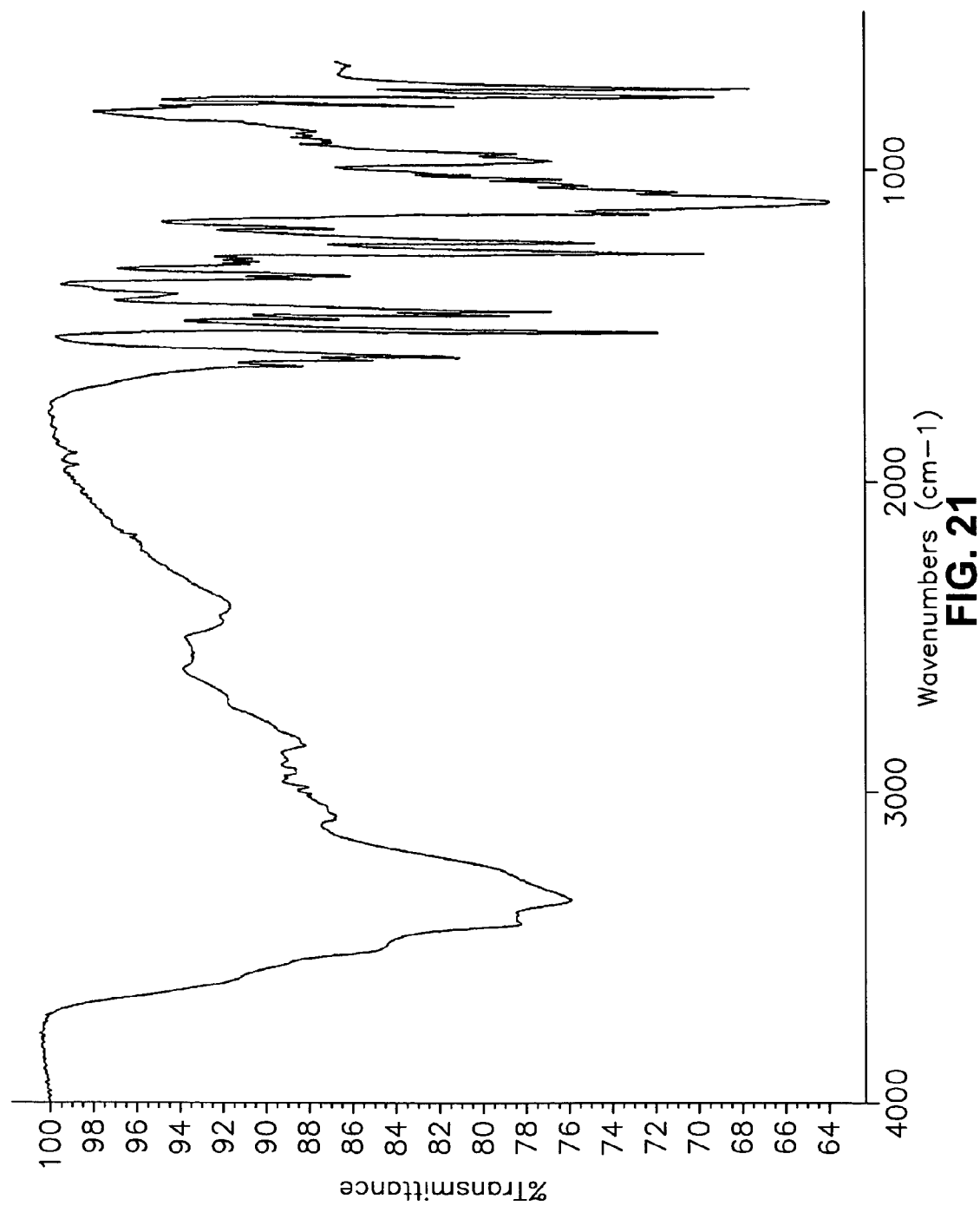
FIG. 21 is an FT-IR spectrum for carvedilol dihydrogen phosphate methanol solvate (Form III).
Figure 22:
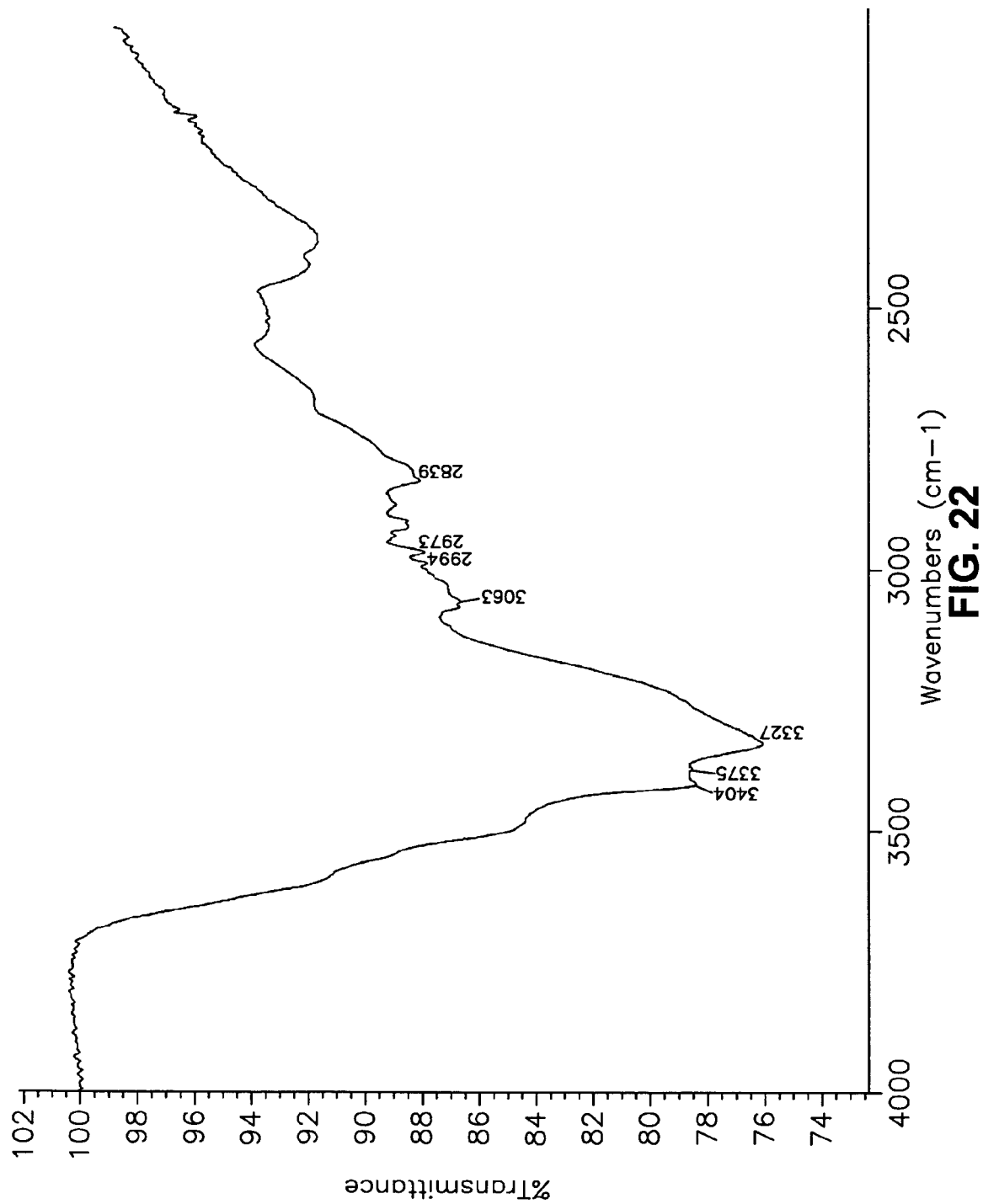
FIG. 22 is an FT-IR spectrum for carvedilol dihydrogen phosphate methanol solvate in the 4000-2000 $cm^{-1}$ region of the spectrum (Form III).
Figure 23:
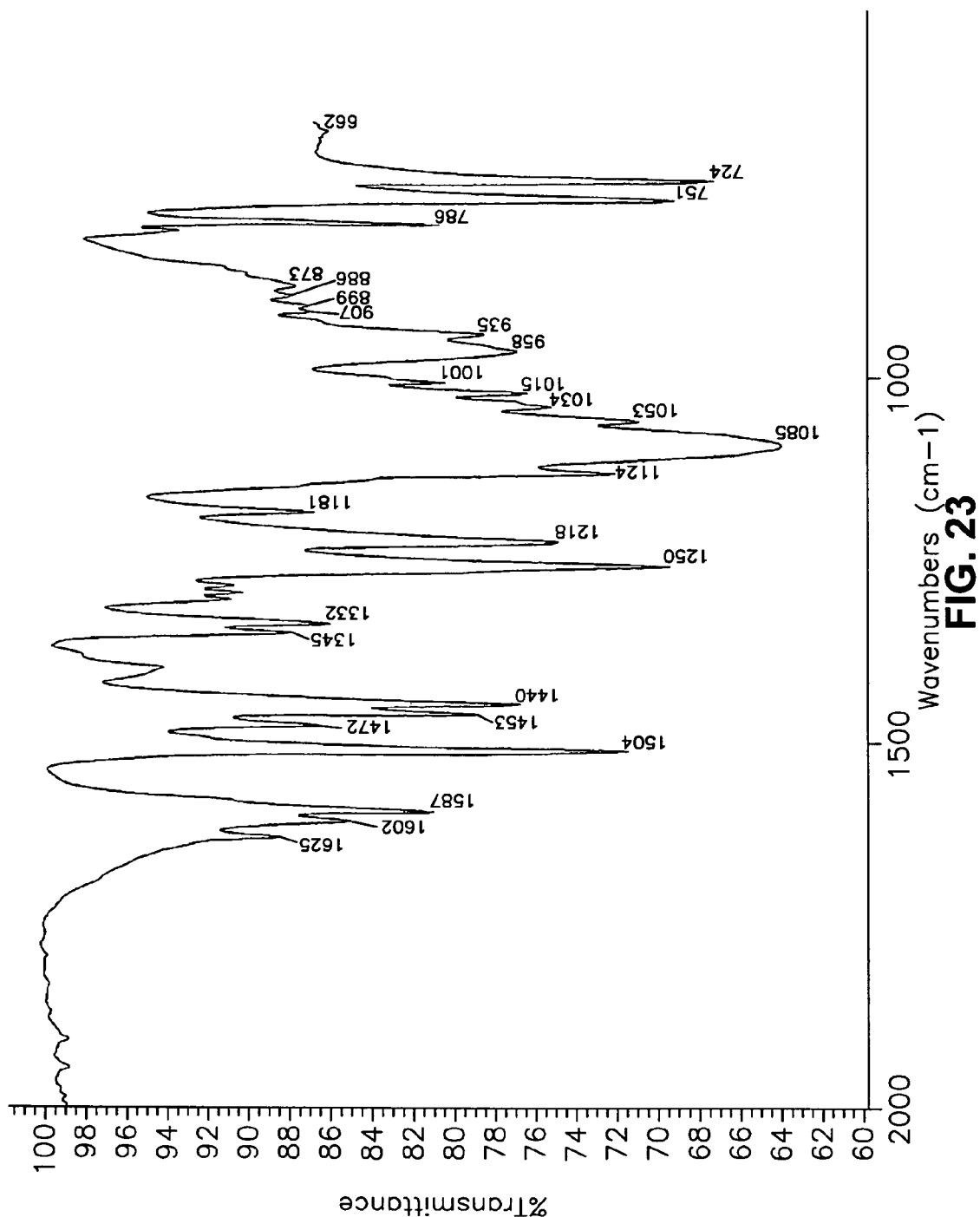
FIG. 23 is an FT-IR spectrum for carvedilol dihydrogen phosphate methanol solvate in the 2000-500 $cm^{-1}$ region of the spectrum (Form III).
Figure 25:
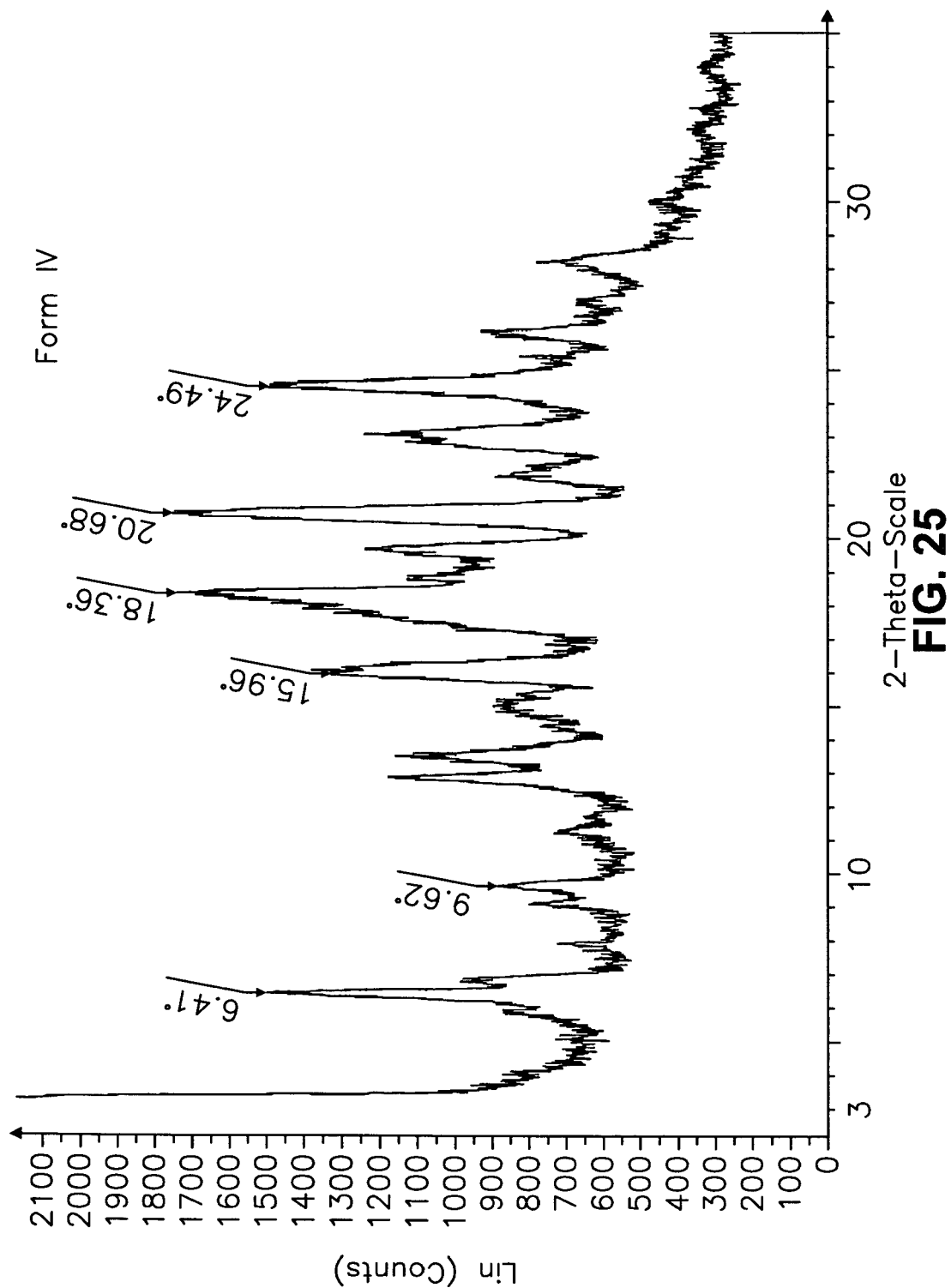
FIG. 25 is an x-ray powder diffractogram for carvedilol dihydrogen phosphate dihydrate (Form IV).

In accordance with the present invention, other salts and/or solvates of carvedilol of the present invention may be isolated as different solid and/or crystalline forms. Moreover, a specific identified species of such carvedilol salts (or a specific identified corresponding solvate species) also may be isolated in various different crystalline or solid forms, which may include anhydrous forms or solvate forms. For example, carvedilol dihydrogen phosphate, may be isolated in two different and distinct crystalline forms, Forms II and IV, respectively represented and substantially shown FIGS. 9 to 6 (for Form II) and FIG. 25 (for Form IV), which are represent spectroscopic and/or other characterizing data.

Figure 1:
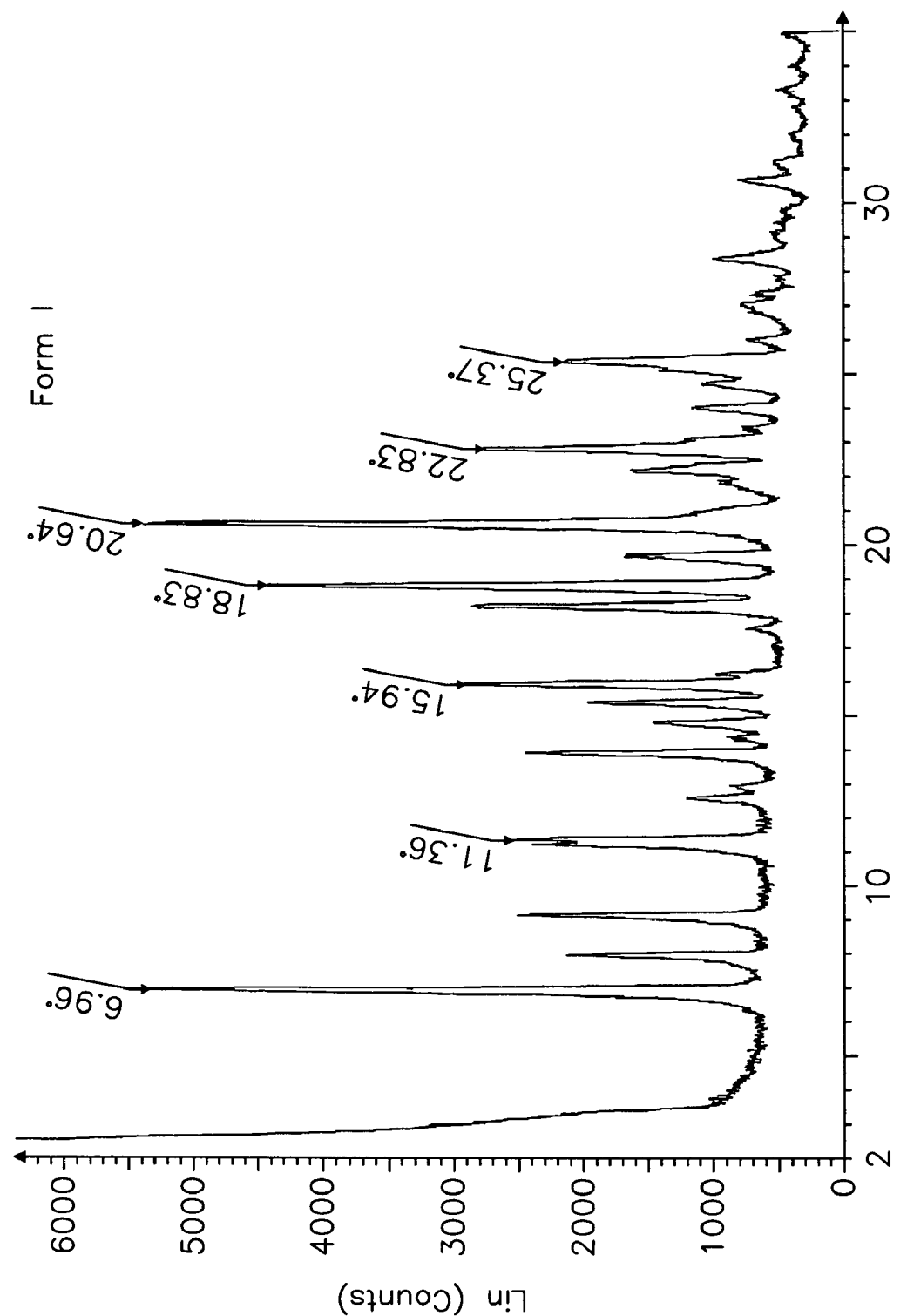
FIG. 1 is an x-ray powder diffractogram for carvedilol dihydrogen phosphate hemihydrate (Form I).

In general, FIGS. 1-125 depict spectroscopic and other characterizing data for different, specific, and distinct crystalline carvedilol salt, anhydrous, and/or solvate forms thereof. For example, carvedilol dihydrogen phosphate, may be isolated as two different and distinct crystalline forms, Forms II and IV, respectively represented and substantially shown FIGS. 9 to 6 (for Form II) and FIG. 25 (for Form IV), which represent spectroscopic and/or other characterizing data.

It is recognized that the compounds of the present invention may exist in forms as stereoisomers, regioisomers, or diastereiomers. These compounds may contain one or more asymmetric carbon atoms and may exist in racemic and optically active forms. For example, carvedilol may exist as racemic mixture of R(+) and S(−) enantiomers, or in separate respectively optical forms, i.e., existing separately as either the R(+) enantiomer form or in the S(+) enantiomer form. All of these individual compounds, isomers, and mixtures thereof are included within the scope of the present invention.

Carvedilol salts of the present invention may be prepared by various techniques, such as those exemplified below.

For example, crystalline carvedilol dihydrogen phosphate hemihydrate of the instant invention can be prepared by crystallization from an acetone-water solvent system containing carvedilol and $H_3PO_4$. Also suitable solvates of carvedilol phosphate salts of present invention may be prepared by preparing a slurrying a carvedilol phosphate salt, such as a carvedilol dihydrogen salt, in a solvent, such as methanol.

In another example, crystalline carvedilol hydrobromide monohydrate of the present invention can be prepared by crystallization from an acetone-water solvent system containing carvedilol and hydrobromic acid. Also, suitable solvates of carvedilol hydrobromide salts may be made by preparing a slurry of the carvedilol hydrobromide salt in a solvent (i.e., such as dioxane, 1-pentanol, 2-methyl-1-propanol, trifluoroethanol, 2-propanol and n-propanol. In particular, solvates of carvedilol hydrobromide as defined in the present invention, include, but are not limited to carvedilol hydrobromide 1-pentanol solvate, carvedilol hydrobromide 2-methyl-1-pentanol solvate, carvedilol hydrobromide trifluoroethanol solvate, carvedilol hydrobromide 2-propanol solvate, carvedilol hydrobromide n-propanol solvate #1, carvedilol hydrobromide n-propanol solvate #2, carvedilol hydrobromide ethanol solvate, carvedilol hydrobromide anhydrous), and/or dissolving the carvedilol hydrobromide salt in the aforementioned solvents and allowing the salt to crystallize out. Carvedilol hydrobromide anhydrous forms can be prepared by dissolving carvedilol in a solvent, such as dichloromethane, acetonitrile or isopropyl acetate, followed by the addition of anhydrous HBr (HBr in acetic acid or gaseous HBr).

In yet another example, the crystalline carvedilol citrate salt of the instant invention can be prepared by making an aqueous citric acid solution saturated with carvedilol, either by lowering the temperature of the solution, or slowly evaporating water from the solution. In addition, it can be prepared by crystallization from an acetone-water solvent system containing carvedilol and citric acid. A particularly useful and surprising characteristic of the crystalline form of carvedilol citrate salt stems from the fact that citric acid is a prochiral molecule. Consequently, a 1 to 1 ratio of racemic diasteromers are present in the crystalline carvedilol citrate salt lattice. This avoids generation of yet more optically active forms that could potentially complicate stability, dissolution rates, in vivo absorption metabolism and possibly pharmacologic effects.

According to the instant invention, the various salt forms of carvedilol and/or corresponding solvates thereof are distinguished from each other using different characterization or identification techniques. Such techniques, include solid state $^{13}$C Nuclear Magnetic Resonance (NMR), $^{31}$P Nuclear Magnetic Resonance (NMR), Infrared (IR), Raman, X-ray powder diffraction, etc. and/or other techniques, such as Differential Scanning Calorimetry (DSC) (i.e., which measures the amount of energy (heat) absorbed or released by a sample as it is heated, cooled or held at constant temperature).

In general, the aforementioned solid state NMR techniques are non-destructive techniques to yield spectra, which depict an NMR peak for each magnetically non-equivalent carbon site the solid-state For example, in identification of compounds of the present invention, $^{13}$C NMR spectrum of a powdered microcrystalline organic molecules reflect that the number of peaks observed for a given sample will depend on the number of chemically unique carbons per molecule and the number of non-equivalent molecules per unit cell. Peak positions (chemical shifts) of carbon atoms reflect the chemical environment of the carbon in much the same manner as in solution-state $^{13}$C NMR. Although peaks can overlap, each peak is in principle assignable to a single type of carbon. Therefore, an approximate count of the number of carbon sites observed yields useful information about the crystalline phase of a small organic molecule.

Based upon the foregoing, the same principles apply to phosphorus, which has additional advantages due to high sensitivity of the $^{31}$P nucleus.

Polymorphism also can be studied by comparison of $^{13}$C and $^{31}$P spectra. In the case of amorphous material, broadened peak shapes are usually observed, reflecting the range of environments experienced by the $^{13}$C or $^{31}$P sites in amorphous material types.

Specifically, novel crystalline forms of carvedilol salts, anhydrous forms or solvates thereof, are characterized substantially by spectroscopic data as described below and depicted in FIGS. 1-125.

Examples of spectroscopic data associated with specific carvedilol salt, anhydrous forms or solvate forms are described below.

For example, crystalline carvedilol dihydrogen phosphate hemihydrate (see, Example 1: Form I) is identified by an x-ray diffraction pattern as shown substantially in FIG. 1, which depicts characteristic peaks in degrees two-theta (2θ): i.e., 7.0±0.2 (2θ), 11.4±0.2 (2θ), 15.9±0.2 (2θ), 18.8±0.2 (2θ), 20.6±0.2 (2θ), 22.8±0.2 (2θ), and 25.4±0.2 (2θ).

Crystalline carvedilol dihydrogen phosphate dihydrate (see, Example 2: Form II) is identified by an x-ray diffraction pattern as shown substantially in FIG. 9, which depicts characteristic peaks in degrees two-theta (2θ): i.e., 6.5±0.2 (2θ), 7.1±0.2 (2θ), 13.5±0.2 (2θ), 14.0±0.2 (2θ), 17.8±0.2 (2θ), 18.9±0.2 (2θ), and 21.0±0.2 (2θ).

Figure 24:
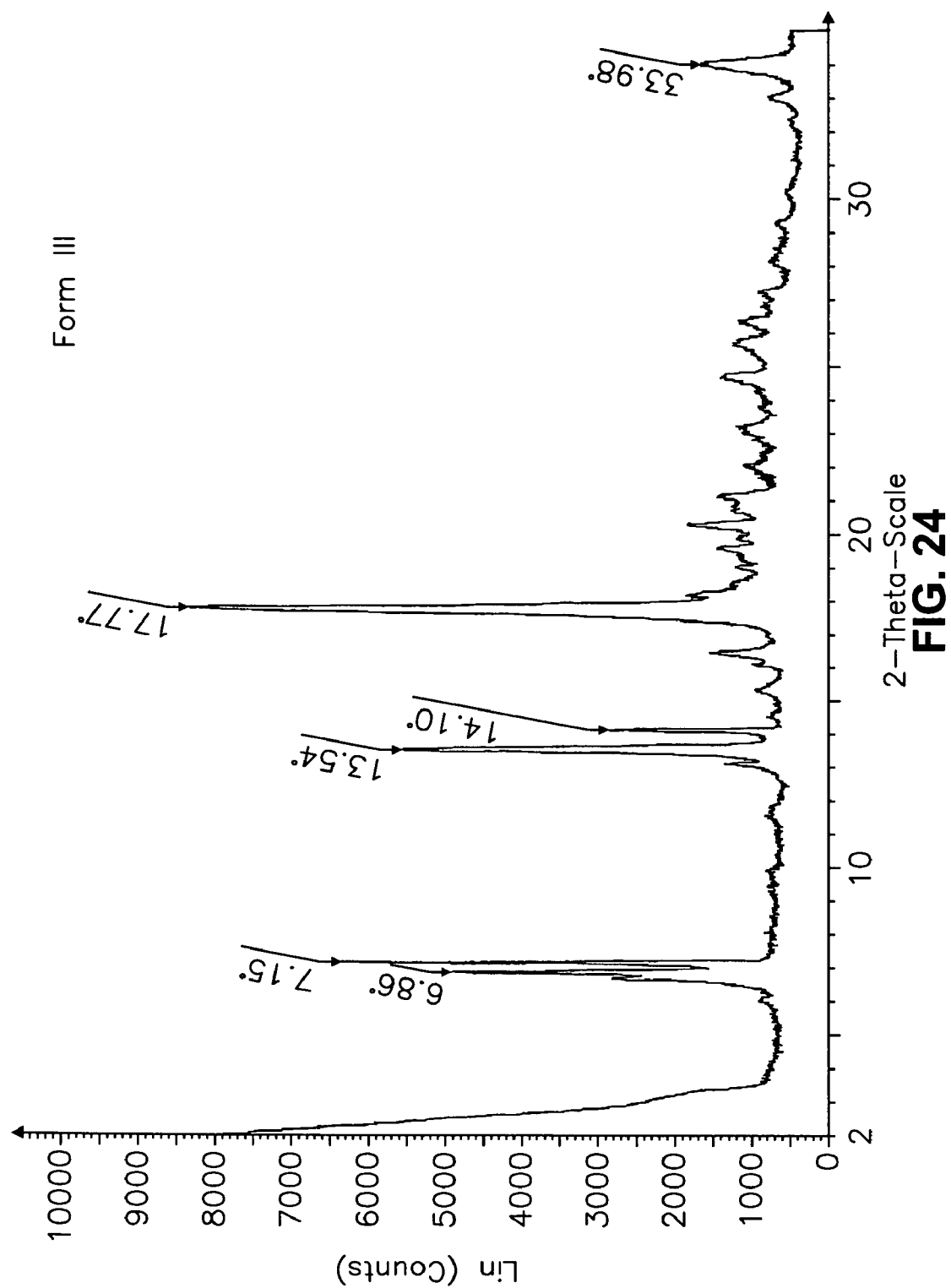
FIG. 24 is an x-ray powder diffractogram for carvedilol dihydrogen phosphate methanol solvate (Form III).

Crystalline carvedilol dihydrogen phosphate methanol solvate (see, Example 3: Form III) is identified by an x-ray diffraction pattern as shown substantially in FIG. 24, which depicts characteristic peaks in degrees two-theta (2θ): i.e., 6.9±0.2 (2θ), 7.2±0.2 (2θ), 13.5±0.2 (2θ), 14.1±0.2 (2θ), 17.8±0.2 (2θ), and 34.0±0.2 (2θ).

Crystalline carvedilol dihydrogen phosphate dihydrate (see, Example 4: Form IV) is identified by an x-ray diffraction pattern as shown substantially in FIG. 24, which depicts characteristic peaks in degrees two-theta (2θ): i.e., 6.4±0.2 (2θ), 9.6±0.2 (2θ), 16.0±0.2 (2θ), 18.4±0.2 (2θ), 20.7±0.2 (2θ), and 24.5±0.2 (2θ).

Figure 28:
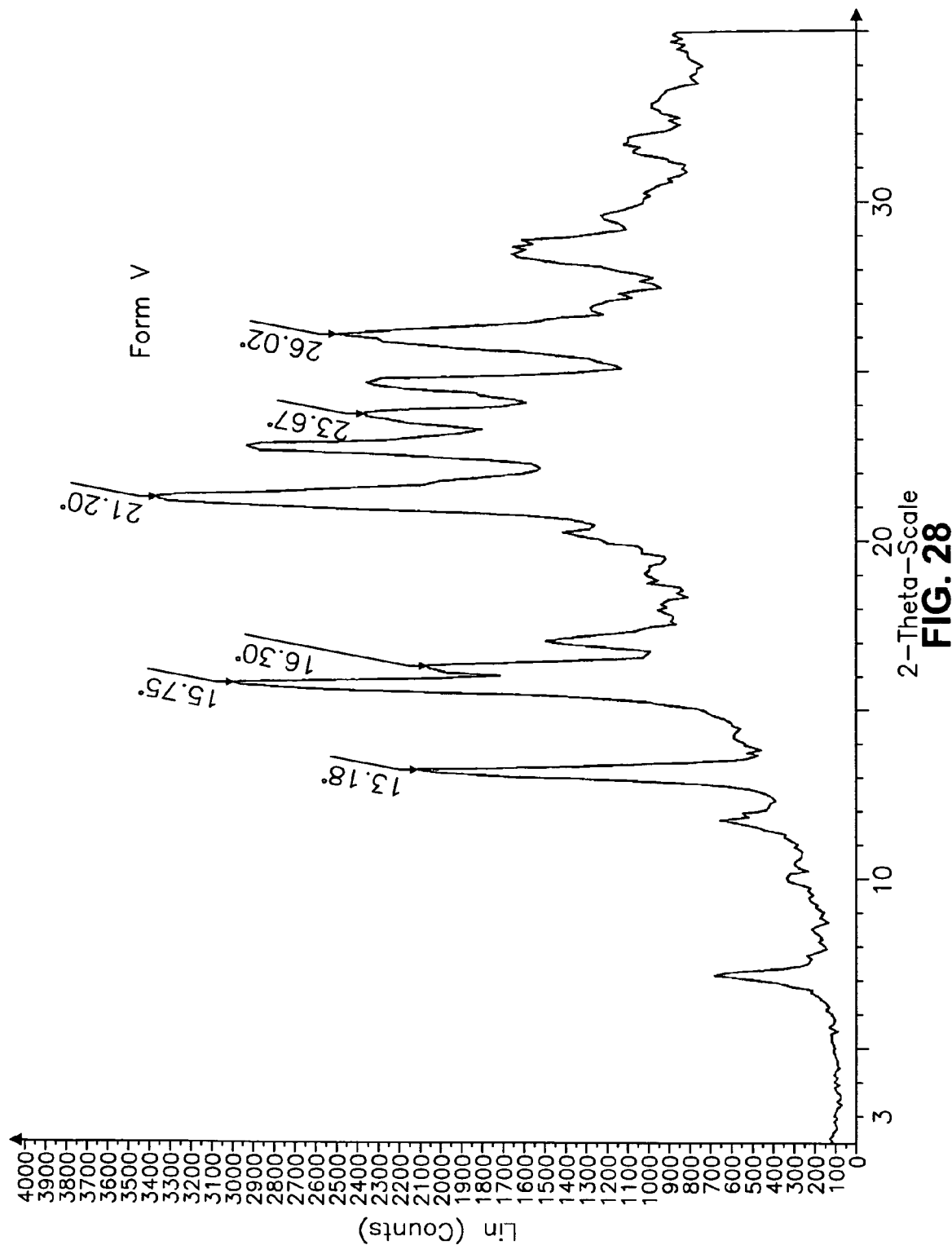
FIG. 28 is an x-ray powder diffractogram for carvedilol dihydrogen phosphate (Form V).

Crystalline carvedilol dihydrogen phosphate preparation (see, Example 5: Form V) is identified by an x-ray diffraction pattern as shown substantially in FIG. 28, which depicts characteristic peaks in degrees two-theta (2θ): i.e., 13.2±0.2 (2θ), 15.8±0.2 (2θ), 16.3±0.2 (2θ), 21.2±0.2 (2θ), 23.7±0.2 (2θ), and 26.0±0.2 (2θ).

Figure 29:
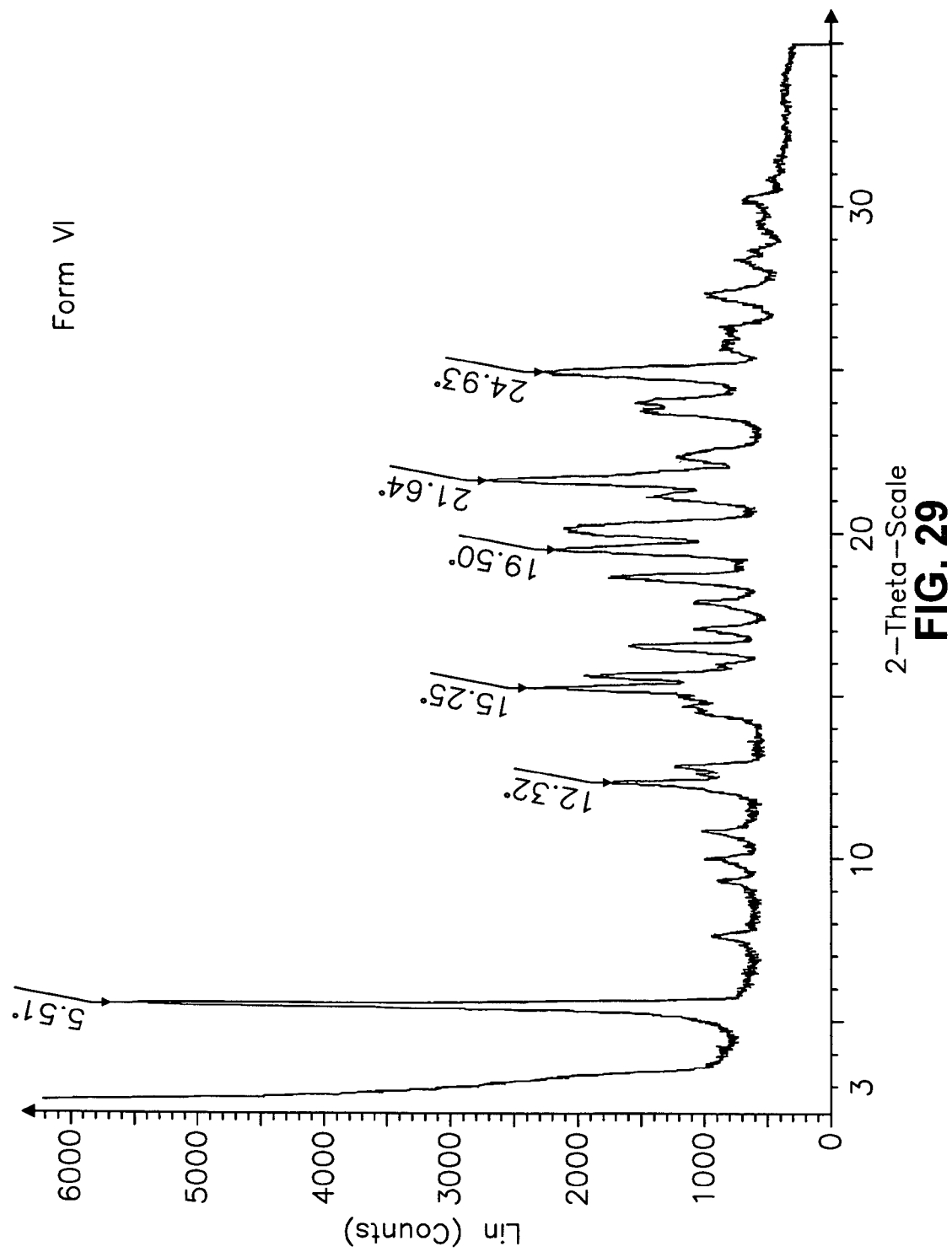
FIG. 29 is an x-ray powder diffractogram for carvedilol hydrogen phosphate (Form VI).

Crystalline carvedilol hydrogen phosphate preparation (see, Example 6: Form VI) is identified by an x-ray diffraction pattern as shown substantially in FIG. 29, which depicts characteristic peaks in degrees two-theta (2θ): i.e., 5.5±0.2 (2θ), 12.3±0.2 (2θ), 15.3±0.2 (2θ), 19.5±0.2 (2θ), 21.6±0.2 (2θ), and 24.9±0.2 (2θ).

Crystalline carvedilol hydrobromide monohydrate (see, Example 8: Form 1) is identified by an x-ray diffraction pattern as shown substantially in FIG. 1, which depicts characteristic peaks in degrees two-theta (2θ): i.e., 6.5±0.2 (2θ), 10.3±0.2 (2θ), 15.7±0.2 (2θ), 16.3±0.2 (2θ), 19.8±0.2 (2θ), 20.1±0.2 (2θ), 21.9±0.2 (2θ), 25.2±0.2 (2θ), and 30.6±0.2 (2θ).

Crystalline carvedilol hydrobromide dioxane solvate (see, Example 9: Form 2) also is identified by an x-ray diffraction pattern as shown substantially in FIG. 78, which depicts characteristic peaks in degrees two-theta (2θ): i.e., 7.7±0.2 (2θ), 8.4±0.2 (2θ), 15.6±0.2 (2θ), 17.0±0.2 (2θ), 18.7±0.2 (2θ), 19.5±0.2 (2θ), 21.4±0.2 (2θ), 23.7±0.2 (2θ), and 27.9±0.2 (2θ).

Crystalline carvedilol hydrobromide 1-pentanol solvate (see, Example 10: Form 3) also is identified by an x-ray diffraction pattern as shown substantially in FIG. 79, which depicts characteristic peaks in degrees two-theta (2θ): i.e., 77.5±0.2 (2θ), 7.8±0.2 (2θ), 15.2±0.2 (2θ), 18.9±0.2 (2θ), 22.1±0.2 (2θ), and 31.4±0.2 (2θ).

Crystalline carvedilol hydrobromide 2-methyl-1-propanol solvate (see, Example 11: Form 4) also is identified by an x-ray diffraction pattern as shown substantially in FIG. 80, which depicts characteristic peaks in degrees two-theta (2θ): i.e., 7.8±0.2 (2θ), 8.1±0.2 (2θ), 16.3±0.2 (2θ), 18.8±0.2 (2θ), 21.8±0.2 (2θ), and 28.5±0.2 (2θ).

Crystalline carvedilol hydrobromide trifluoroethanol solvate (see, Example 12: Form 5) also is identified by an x-ray diffraction pattern as shown substantially in FIG. 81, which depicts characteristic peaks in degrees two-theta (2θ): i.e., 7.7±0.2 (2θ), 8.4±0.2 (2θ), 15.6±0.2 (2θ), 16.9±0.2 (2θ), 18.9±0.2 (2θ), 21.8±0.2 (2θ), 23.8±0.2 (2θ), 23.7±0.2 (2θ), and 32.7±0.2 (2θ).

Crystalline carvedilol hydrobromide 2-propanol solvate (see, Example 13: Form 6) also is identified by an x-ray diffraction pattern as shown substantially in FIG. 82, which depicts characteristic peaks in degrees two-theta (2θ): i.e., 7.9±0.2 (2θ), 8.3±0.2 (2θ), 18.8±0.2 (2θ), 21.7±0.2 (2θ), 23.2±0.2 (2θ), 23.6±0.2 (2θ), and 32.1±0.2 (2θ).

Crystalline carvedilol hydrobromide n-propanol solvate #1 (see, Example 14: Form 7) also is identified by an x-ray diffraction pattern as shown substantially in FIG. 46, which depicts characteristic peaks in degrees two-theta (2θ): i.e., 7.9±0.2 (2θ), 8.5±0.2 (2θ), 17.0±0.2 (2θ), 18.8±0.2 (2θ), 21.6±0.2 (2θ), 23.1±0.2 (2θ), 23.6±0.2 (2θ), and 21.2±0.2 (2θ).

Crystalline carvedilol hydrobromide n-propanol solvate #2 (see, Example 15: Form 8) also is identified by an x-ray diffraction pattern as shown substantially in FIG. 54, which depicts characteristic peaks in degrees two-theta (2θ): i.e., 8.0±0.2 (2θ), 18.8±0.2 (2θ), 21.6±0.2 (2θ), 23.1±0.2 (2θ), 25.9±0.2 (2θ), 27.2±0.2 (2θ), 30.6±0.2 (2θ), and 32.2±0.2 (2θ).

Crystalline carvedilol hydrobromide anhydrous forms (see, Example 16: Form 9) also is identified by an x-ray diffraction pattern as shown substantially in FIG. 62, which depicts characteristic peaks in degrees two-theta (2θ): i.e., 6.6±0.2 (2θ), 16.1±0.2 (2θ), 17.3±0.2 (2E), 21.2±0.2 (2θ), 22.1±0.2 (2θ), 24.1±0.2 (2θ), and 27.9±0.2 (2θ).

Crystalline carvedilol hydrobromide ethanol solvate (see, Example 17: Form 10) also is identified by an x-ray diffraction pattern as shown substantially in FIG. 70, which depicts characteristic peaks in degrees two-theta (2θ): i.e., 8.1±0.2 (2θ), 8.6±0.2 (2θ), 13.2±0.2 (2θ), 17.4±0.2 (2θ), 18.6±0.2 (2θ), 21.8±0.2 (2θ), 23.2±0.2 (2θ), 23.7±0.2 (2θ), and 27.4±0.2 (2θ).

Figure 6:
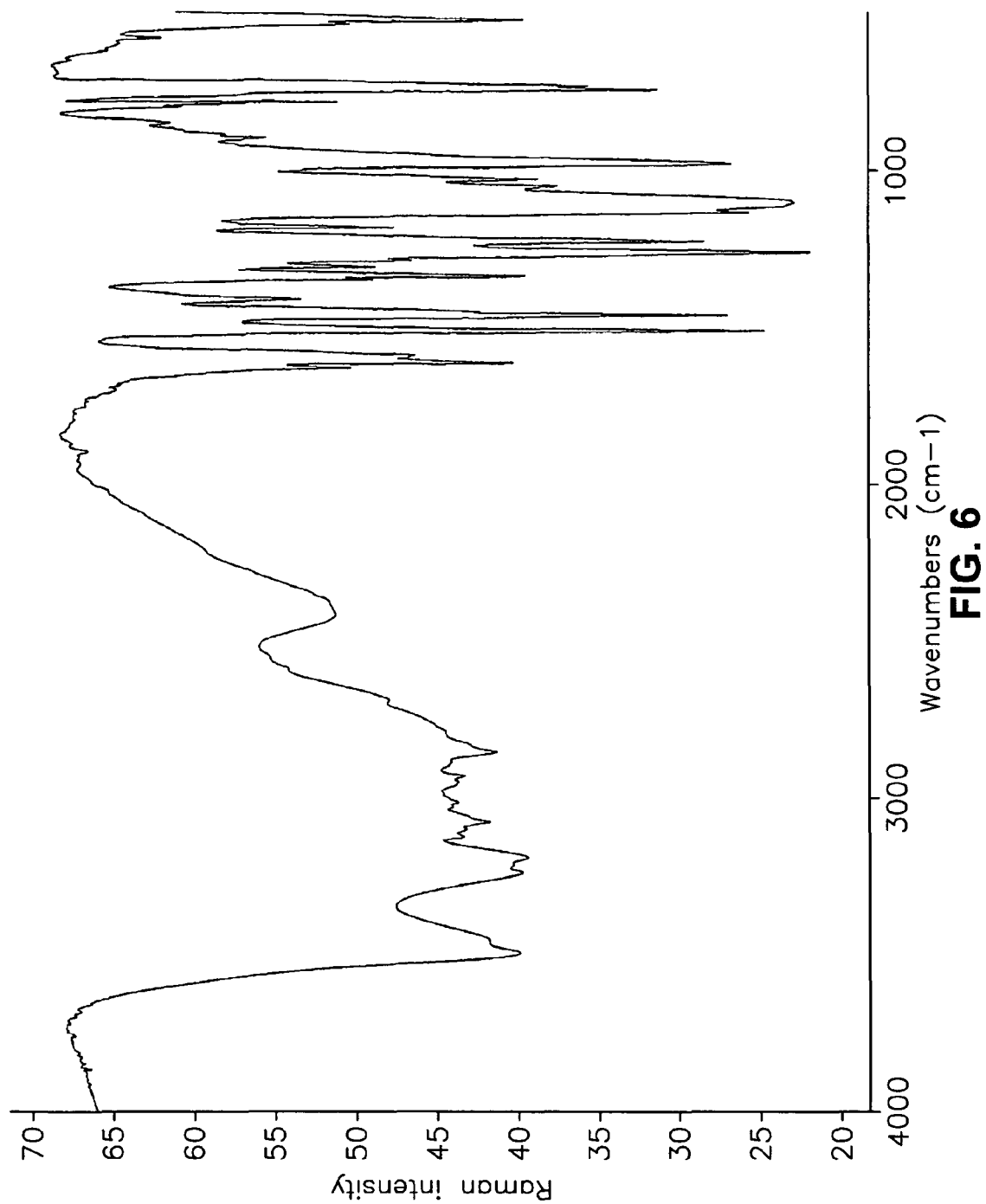
FIG. 6 is an FT-IR spectrum for carvedilol dihydrogen phosphate hemihydrate (Form I).
Figure 7:
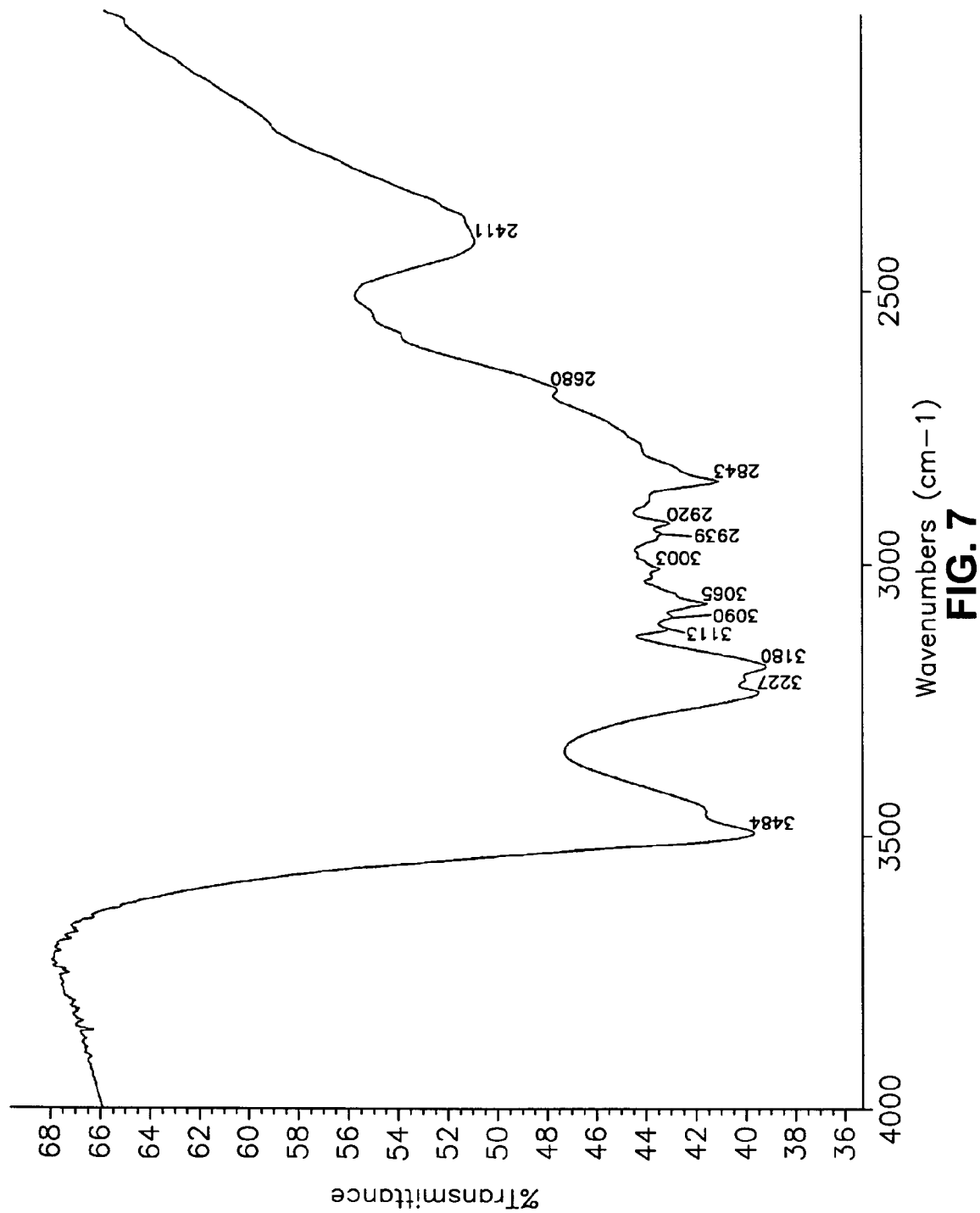
FIG. 7 is an FT-IR spectrum for carvedilol dihydrogen phosphate hemihydrate in the 4000-2000 $cm^{-1}$ region of the spectrum (Form I).
Figure 8:
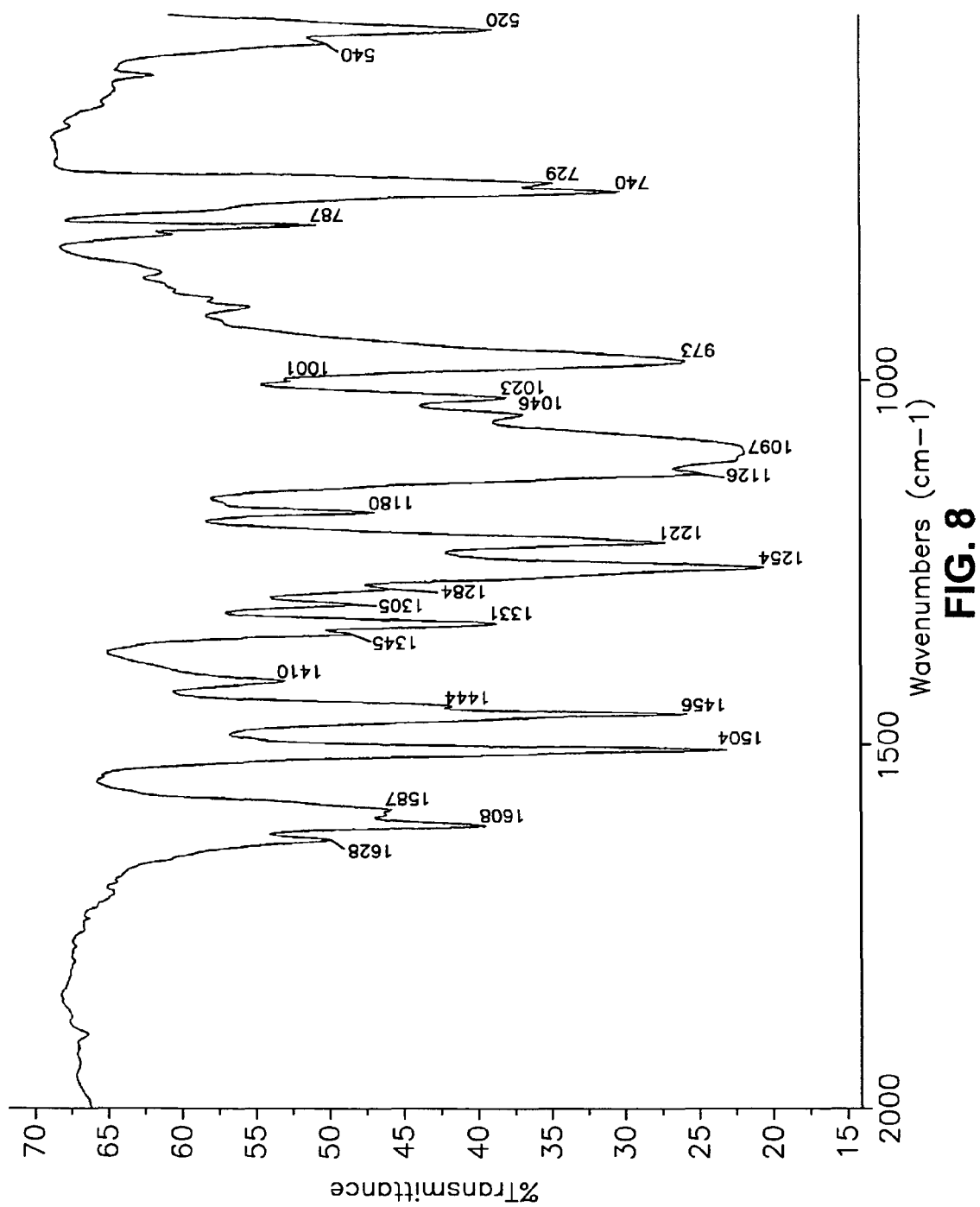
FIG. 8 is an FT-IR spectrum for carvedilol dihydrogen phosphate hemihydrate in the 2000-500 $cm^{-1}$ region of the spectrum (Form I).

Crystalline carvedilol hydrobromide monohydrate further is identified by an infrared spectrum as shown substantially in FIG. 6.

Carvedilol hydrobromide anhydrous forms also an infrared spectrum which comprises characteristic absorption bands expressed in wave numbers as shown substantially in FIG. 67.

Figure 3:
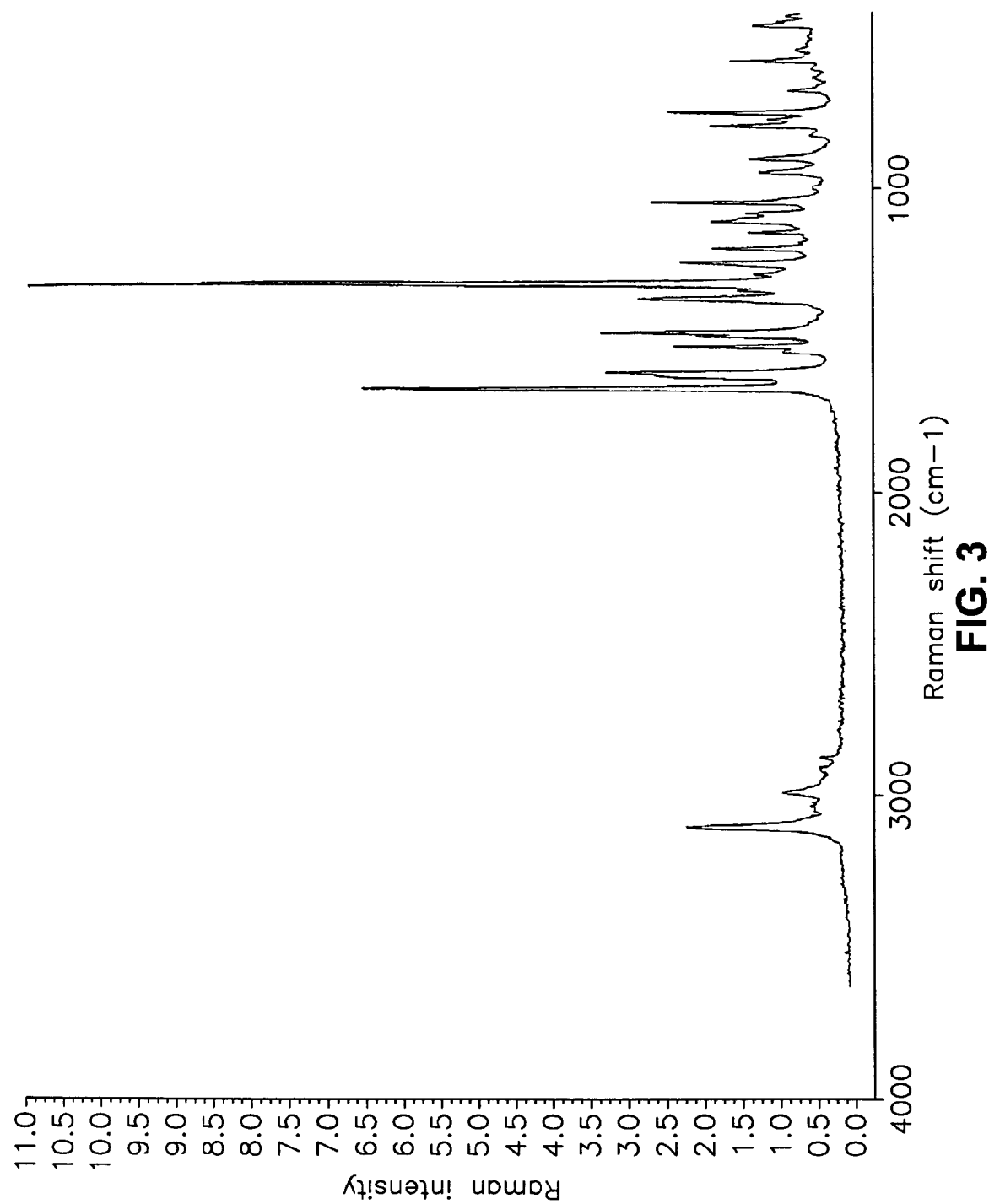
FIG. 3 is an FT-Raman spectrum for carvedilol dihydrogen phosphate hemihydrate (Form I).
Figure 4:
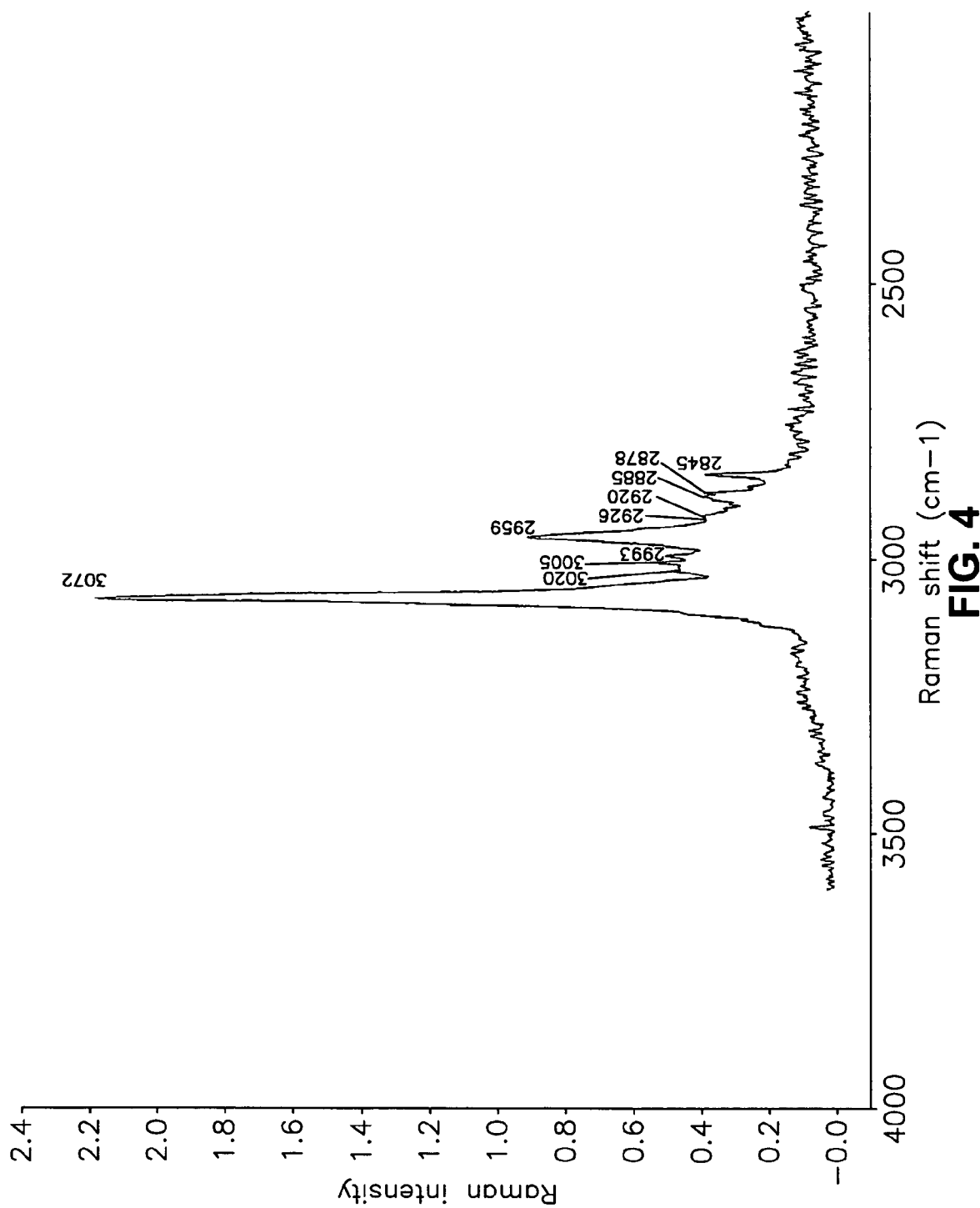
FIG. 4 is an FT-Raman spectrum for carvedilol dihydrogen phosphate hemihydrate in the 4000-2000 $cm^{-1}$ region of the spectrum (Form I).
Figure 5:
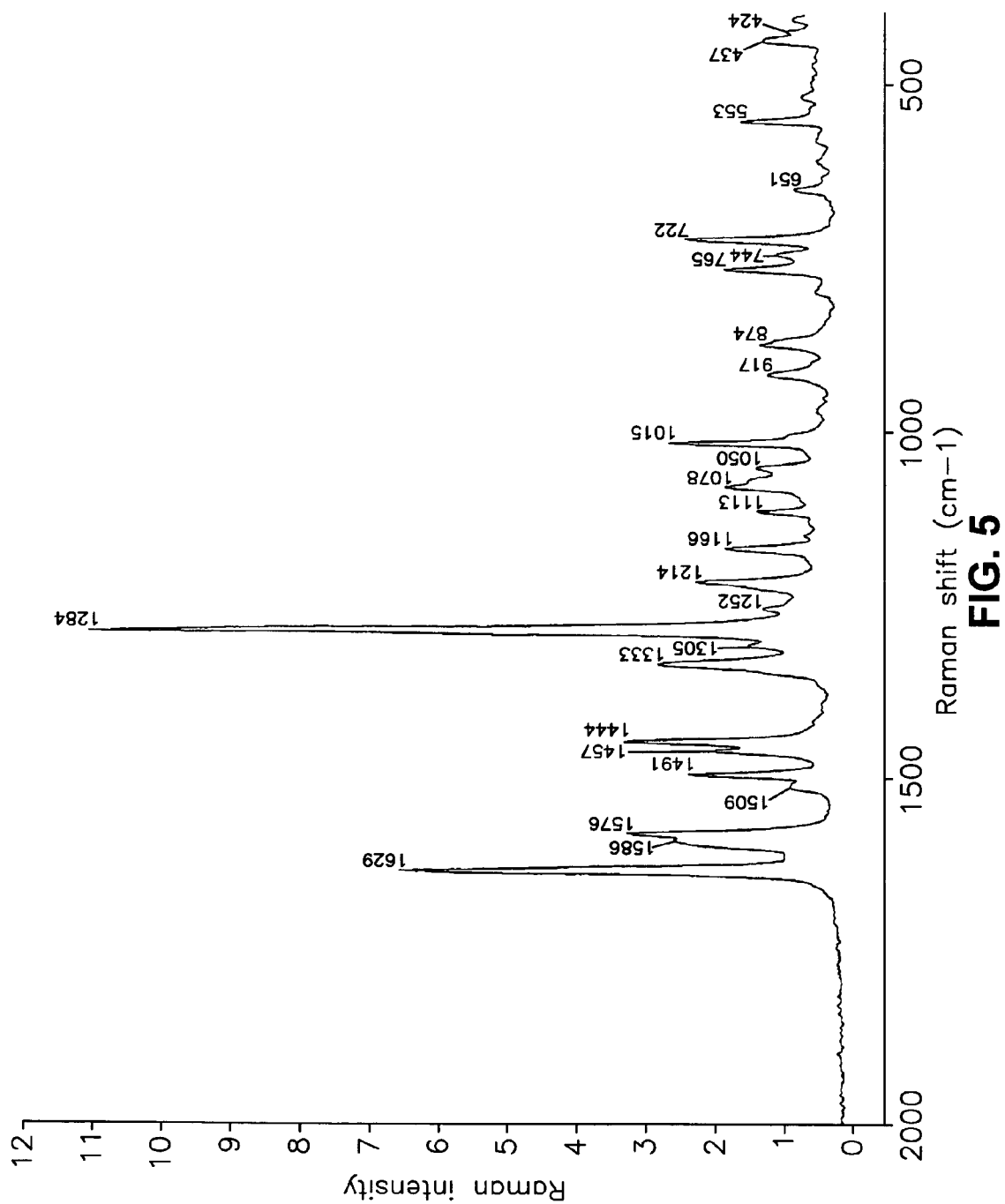
FIG. 5 is an FT-Raman spectrum for carvedilol dihydrogen phosphate hemihydrate in the 2000-400 $cm^{-1}$ region of the spectrum (Form I).

Crystalline carvedilol hydrobromide monohydrate is identified also by a Raman spectrum as shown substantially in FIG. 3.

Carvedilol hydrobromide anhydrous forms also a Raman spectrum which comprises characteristic peaks as shown substantially in FIG. 64.

Crystalline carvedilol benzoate (see, Example 22) is identified by an FT-IR spectrum pattern as shown substantially in FIG. 124, which depicts characteristic peaks in wavenumbers ($cm^{-1}$): i.e., 672 $cm^{-1}$, 718 $cm^{-1}$, 754 $cm^{-1}$, 767 $cm^{-1}$, 1022 $cm^{-1}$, 1041 $cm^{-1}$, 1106 $cm^{-1}$, 1260 $cm^{-1}$, 1498 $cm^{-1}$, 1582 $cm^{-1}$, 1604 $cm^{-1}$, 1626 $cm^{-1}$, 2932 $cm^{-1}$, 3184 $cm^{-1}$ and 3428 $cm^{-1}$. Also, crystalline carvedilol benzoate (see, Example 22) is identified by an FT-Raman spectrum pattern as shown substantially in FIG. 125, which depicts characteristic peaks in wavenumbers ($cm^{-1}$): i.e., 108 $cm^{-1}$, 244 $cm^{-1}$, 424 $cm^{-1}$, 538 $cm^{-1}$, 549 $cm^{-1}$, 728 $cm^{-1}$, 1001 $cm^{-1}$, 1015 $cm^{-1}$, 1128 $cm^{-1}$, 1286 $cm^{-1}$, 1598 $cm^{-1}$, 1626 $cm^{-1}$, 2934 $cm^{-1}$, 3058 $cm^{-1}$, and 3072 $cm^{-1}$.

Crystalline carvedilol mandelate (see, Example 23) is identified by an FT-IR spectrum pattern as shown substantially in FIG. 114, which depicts characteristic peaks in wavenumbers ($cm^{-1}$): i.e., 699 $cm^{-1}$, 723 $cm^{-1}$, 752 $cm^{-1}$, 784 $cm^{-1}$, 1053 $cm^{-1}$, 1583 $cm^{-1}$, 1631 $cm^{-1}$, 3189 $cm^{-1}$, 3246 $cm^{-1}$, and 3396 $cm^{-1}$. Also crystalline carvedilol mandelate (see, Example 23) is identified by an FT-Raman spectrum pattern as shown substantially in FIG. 115, which depicts characteristic peaks in wavenumbers ($cm^{-1}$): i.e., 233 $cm^{-1}$, 252 $cm^{-1}$, 322 $cm^{-1}$, 359 $cm^{-1}$, 423 $cm^{-1}$, 744 $cm^{-1}$, 1002 $cm^{-1}$, 1286 $cm^{-1}$, 1631 $cm^{-1}$, 3052 $cm^{-1}$, 3063 $cm^{-1}$, and 3077 $cm^{-1}$.

Crystalline carvedilol lactate (see, Example 24) is identified by an FT-IR spectrum pattern as shown substantially in FIG. 116, which depicts characteristic peaks in wavenumbers ($cm^{-1}$): i.e., 720 $cm^{-1}$, 753 $cm^{-1}$, 785 $cm^{-1}$, 1097 $cm^{-1}$, 1124 $cm^{-1}$, 1253 $cm^{-1}$, 1584 $cm^{-1}$, and 3396 $cm^{-1}$. Also, crystalline carvedilol lactate (see, Example 24) is identified by an FT-Raman spectrum pattern as shown substantially in FIG. 117, which depicts characteristic peaks in wavenumbers ($cm^{-1}$): i.e., 321 $cm^{-1}$, 422 $cm^{-1}$, 549 $cm^{-1}$, 765 $cm^{-1}$, 1015 $cm^{-1}$, 1284 $cm^{-1}$, 1626 $cm^{-1}$, 3066 $cm^{-1}$, and 3078 $cm^{-1}$.

Crystalline carvedilol sulfate (see, Example 25) is identified by an FT-IR spectrum pattern as shown substantially in FIG. 120, which depicts characteristic peaks in wavenumbers ($cm^{-1}$): i.e., 727 $cm^{-1}$, 743 $cm^{-1}$, 787 $cm^{-1}$, 1026 $cm^{-1}$, 1089 $cm^{-1}$, 1251 $cm^{-1}$, 1215 $cm^{-1}$, 1586 $cm^{-1}$, 1604 $cm^{-1}$, and 3230 $cm^{-1}$. Also, crystalline carvedilol sulfate (see, Example 25) also is identified by an FT-Raman spectrum pattern as shown substantially in FIG. 121, which depicts characteristic peaks in wavenumbers ($cm^{-1}$): i.e., 242 $cm^{-1}$, 318 $cm^{-1}$, 423 $cm^{-1}$, 549 $cm^{-1}$, 1014 $cm^{-1}$, 1214 $cm^{-1}$, 1282 $cm^{-1}$, 1627 $cm^{-1}$, 2969 $cm^{-1}$, and 3066 $cm^{-1}$.

Crystalline carvedilol maleate (see, Example 26) is identified by an FT-IR spectrum pattern as shown substantially in FIG. 118, which depicts characteristic peaks in wavenumbers ($cm^{-1}$): i.e., 725 $cm^{-1}$, 741 $cm^{-1}$, 756 $cm^{-1}$, 786 $cm^{-1}$, 1024 $cm^{-1}$, 1109 $cm^{-1}$, 1215 $cm^{-1}$, 1586 $cm^{-1}$, and 3481 $cm^{-1}$. Also, crystalline carvedilol maleate (see, Example 26) also is identified by an FT-Raman spectrum pattern as shown substantially in FIG. 119, which depicts characteristic peaks in wavenumbers ($cm^{-1}$): i.e., 249 $cm^{-1}$, 324 $cm^{-1}$, 423 $cm^{-1}$, 549 $cm^{-1}$, 751 $cm^{-1}$, 1012 $cm^{-1}$, 1216 $cm^{-1}$, 1286 $cm^{-1}$, 1629 $cm^{-1}$, and 3070 $cm^{-1}$.

Crystalline carvedilol glutarate (see, Example 27) is identified by an FT-IR spectrum pattern as shown substantially in FIG. 122, which depicts characteristic peaks in wavenumbers ($cm^{-1}$): i.e., 724 $cm^{-1}$, 743 $cm^{-1}$, 786 $cm^{-1}$, 1024 $cm^{-1}$, 1044 $cm^{-1}$, 1089 $cm^{-1}$, 1251 $cm^{-1}$, 1586 $cm^{-1}$, 1604 $cm^{-1}$, and 3229 $cm^{-1}$. Also, crystalline carvedilol glutarate (see, Example 27) is identified by an FT-Raman spectrum pattern as shown substantially in FIG. 123, which depicts characteristic peaks in wavenumbers ($cm^{-1}$): i.e., 141 $cm^{-1}$, 246 $cm^{-1}$, 322 $cm^{-1}$, 423 $cm^{-1}$, 551 $cm^{-1}$, 749 $cm^{-1}$, 1011 $cm^{-1}$, 1213 $cm^{-1}$, 1284 $cm^{-1}$, 1628 $cm^{-1}$, 2934 $cm^{-1}$, and 3073 $cm^{-1}$.

The present invention also relates to a pharmaceutical composition, which contains a salt of carvedilol, anhydrous forms and/or corresponding solvates thereof as described herein.

Importantly, the chemical and/or physical properties of carvedilol forms described herein, which include, but are not limited to the above-identified salts, anhydrous forms or solvates thereof of carvedilol indicate that those forms may be particularly suitable for inclusion in medicinal agents, pharmaceutical compositions, etc.

For example, solubility of various carvedilol salts, and/or solvates as those described herein may facilitate provision or development of a dosage form from which the drug substance becomes available for bioabsorption throughout the gastrointestinal tract (i.e., in particular the lower small intestine and colon). Parts of the gastrointestinal tract are defined to include generally the stomach (i.e. which includes the antrum and pylorus bowel), small intestine (i.e., which has three parts: the duodenum, jejunum, illeum), large intestine (i.e., which has three parts: the cecum, colon, rectum), liver, gall bladder and pancreas.

In light of the foregoing, it may be possible to develop stable controlled release dosage forms containing such carvedilol phosphate salts and/or solvates of the present invention, for once-per-day dosage, delayed release, controlled-release formulations or pulsatile release to optimize therapy by matching pharmacokinetic performance with pharmacodynamic requirements.

Compounds or compositions within the scope of this invention include all compounds or compositions, wherein the compound of the present invention is contained in an amount effective to achieve its intended purpose. While individual needs vary, determination of optimal ranges of effective amounts of each component is within the skill of the art.

In accordance with a pharmaceutical composition of the present invention as described herein, a specific embodiment may include a carvedilol free base, which may be, but is not limited to, be in a combination with a solubility enhanced carvedilol salt, solvate and/or anhydrous form or forms.

Also in accordance with a pharmaceutical composition of the present invention as described herein, a specific embodiment may include a solubility enhanced carvedilol salt, solvate and/or anhydrous form or forms selected from the group consisting of a novel crystalline salt forms of carvedilol mandelate, carvedilol lactate, carvedilol maleate, carvedilol sulfate, carvedilol glutarate, carvedilol mesylate, carvedilol phosphate, carvedilol citrate, carvedilol hydrogen bromide, carvedilol oxalate, carvedilol hydrochloride, carvedilol hydrogen bromide, carvedilol benzoate, and/or corresponding solvates thereof.

Further in accordance with a pharmaceutical composition of the present invention as described herein, a specific embodiment may include novel crystalline salt forms of carvedilol hydrogen phosphate, carvedilol dihydrogen phosphate, carvedilol dihydrogen phosphate hemihydrate, carvedilol dihydrogen phosphate dihydrate, carvedilol dihydrogen phosphate methanol solvate, carvedilol hydrobromide monohydrate, carvedilol hydrobromide dioxane solvate, carvedilol hydrobromide 1-pentanol solvate, carvedilol hydrobromide 2-methyl-1-propanol solvate, carvedilol hydrobromide trifluoroethanol solvate, carvedilol hydrobromide 2-propanol solvate, carvedilol hydrobromide n-propanol solvate #1, carvedilol hydrobromide n-propanol solvate #2, carvedilol hydrobromide anhydrous forms or anhydrous, carvedilol hydrobromide ethanol solvate, carvedilol hydrobromide dioxane solvate, carvedilol monocitrate monohydrate, carvedilol mandelate, carvedilol lactate salt, carvedilol maleate, carvedilol sulfate, carvedilol glutarate, and/or corresponding anhydrous, solvates thereof.

Also suitable for use in any of the pharmaceutical compositions of the present invention are solubility enhanced carvedilol salt, solvate and/or anhydrous form is selected from the group consisting of a novel crystalline salt forms of carvedilol hydrogen phosphate, carvedilol dihydrogen phosphate, carvedilol dihydrogen phosphate hemihydrate, carvedilol dihydrogen phosphate dihydrate, carvedilol dihydrogen phosphate methanol solvate.

In particular, in accordance with a pharmaceutical composition of the present invention as described herein, a specific embodiment may include a carvedilol salt, solvate, and/or anhydrous forms thereof, such as a carvedilol phosphate salt, which may include, but is not limited to or selected from the group consisting of a carvedilol dihydrogen phosphate hemihydrate (Form I), carvedilol dihydrogen phosphate dihydrate (Form II), carvedilol dihydrogen phosphate methanol solvate (Form III), carvedilol dihydrogen phosphate dihydrate (Form IV), carvedilol dihydrogen phosphate (Form V) and carvedilol hydrogen phosphate (Form VI), and the like.

Thus, this invention also relates to a pharmaceutical composition comprising an effective amount of carvedilol dihydrogen phosphate salts and/or solvates thereof, with any of the characteristics noted herein, in association with one or more non-toxic pharmaceutically acceptable carriers and/or diluents thereof, and if desired, other active ingredients. Also, suitable for use in any of the pharmaceutical compositions of the present invention is carvedilol dihydrogen phosphate hemihydrate.

Moreover, the quantity of the compound or composition of the present invention administered will vary depending on the patient and the mode of administration and can be any effective amount.

Treatment regimen for the administration of the compounds and/or compositions of the present invention can also be determined readily by those with ordinary skill in art. The quantity of the compound and/or composition of the present invention administered may vary over a wide range to provide in a unit dosage an effective amount based upon the body weight of the patient per day to achieve the desired effect.

In particular, a composition of the present invention is presented as a unit dose and taken preferably from 1 to 2 times daily, most preferably once daily to achieve the desired effect.

Depending upon the treatment being effected, the compounds, and/or or compositions of the present invention can be administered orally, intraperitoneally, or topically, etc. Preferably, the composition is adapted for oral administration.

In general, pharmaceutical compositions of the present invention are prepared using conventional materials and techniques, such as mixing, blending and the like.

In accordance with the present invention, compounds and/or pharmaceutical composition can also include, but are not limited to, suitable adjuvants, carriers, excipients, or stabilizers, etc. and can be in solid or liquid form such as, tablets, capsules, powders, solutions, suspensions, or emulsions, etc.

Typically, the composition will contain a compound of the present invention, such as a salt of carvedilol or active compound(s), together with the adjuvants, carriers and/or excipients. In particular, a pharmaceutical composition of the present invention comprises an effective amount of a salt of carvedilol (i.e., such as carvedilol dihydrogen phosphate salts) and/or corresponding solvates (i.e., as identified herein) thereof, with any of the characteristics noted herein, in association with one or more non-toxic pharmaceutically acceptable carriers and/or diluents thereof, and if desired, other active ingredients.

In accordance with the present invention, solid unit dosage forms can be conventional types known in the art. The solid form can be a capsule and the like, such as an ordinary gelatin type containing the compounds of the present invention and a carrier, for example, lubricants and inert fillers such as, lactose, sucrose, or cornstarch, etc. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate, etc.

The tablets, capsules, and the like can also contain a binder, such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin, etc. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both, etc. A syrup can contain, in addition to active ingredient, sucrose as a sweetening agent, methyl and propylparabens as preservatives, a dye, and flavoring such as cherry or orange flavor, etc.

For oral therapeutic administration, these active compounds can be incorporated with excipients and used in the form of tablets, capsules, elixirs, suspensions, syrups, and the like. The percentage of the compound in compositions can, of course, be varied as the amount of active compound in such therapeutically useful compositions is such that a suitable dosage will be obtained.

Typically in accordance with the present invention, the oral maintenance dose is between about 25 mg and about 70 mg, preferably given once daily. In accordance with the present invention, the preferred unit dosage forms include tablets or capsules.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet, etc.

These active compounds may also be administered parenterally. Solutions or suspensions of these active compounds for use in such parental administrations can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil, etc. In general, water, saline, aqueous dextrose and related sugar solution, and glycols such as, propylene glycol or polyethylene glycol, etc., are preferred liquid carriers, particularly for injectable solutions. Under ordinary conditions of storage and use, these preparations contain a preservative to prevent the growth of microorganisms.

The compounds and/or pharmaceutical compositions prepared according to the present invention can be used to treat warm-blooded animals, such as mammals, which include humans.

The present invention further relates to a method of treating hypertension, congestive heart failure and angina, which comprises administering to a subject in need thereof an effective amount of a carvedilol phosphate salt (which include novel crystalline forms) and/or solvates thereof or a pharmaceutical composition (i.e., which contains such salts and/or solvates of carvedilol phosphate), etc.

The present invention also relates to a method of delivering carvedilol to lower gastrointestinal tract of a subject in need thereof, which comprises administering a compound which is a crystalline salt, anhydrous forms or solvate of carvedilol.

Conventional administration methods as described in examples above may be suitable for such use in delivery or treatment methods of the present invention.

The Examples set forth below are illustrative of the present invention and are not intended to limit, in any way, the scope of the present invention.

EXAMPLES

Carvedilol Phosphate Examples

Example 1

Form I Carvedilol Dihydrogen Phosphate Hemihydrate Preparation

A suitable reactor is charged with acetone. The acetone solution is sequentially charged with carvedilol and water. Upon addition of the water, the slurry dissolves quickly. To the solution is added aqueous $H_3PO_4$. The reaction mixture is stirred at room temperature and carvedilol dihydrogen phosphate seeds are added in one portion. The solid precipitate formed is stirred, then filtered and the collected cake is washed with aqueous acetone. The cake is dried under vacuum to a constant weight. The cake is weighed and stored in a polyethylene container.

Example 2

Form II Carvedilol Dihydrogen Phosphate Dihydrate Preparation

Form I is slurried in acetone/water mixture between 10 and 30° C. for several days.

Example 3

Form III Carvedilol Dihydrogen Phosphate Methanol Solvate Preparation

Form I is slurried in methanol between 10 and 30° C. for several days.

Example 4

Form IV—Carvedilol Dihydrogen Phosphate Dihydrate Preparation

Carvedilol dihydrogen dihydrogen phosphate is dissolved in an acetone/water mixture. The acetone is removed by distillation. A solid crystallizes during acetone removal and is filtered and dried.

Example 5

Form V—Carvedilol Dihydrogen Phosphate Preparation

Carvedilol dihydrogen phosphate hemihydrate (Form I) was suspended in water, and the suspension was placed on a mechanical shaker at room temperature. After 48 hours of shaking, the solid was isolated from suspension by filtration, then dried in a desiccator under vacuum for a few days.

Example 6

Form VI—Carvedilol Hydrogen Phosphate Preparation

A suitable reactor is charged with acetone. The acetone solution is sequentially charged with SK&F 105517 and water. Upon addition of the water, the slurry dissolves quickly. To the solution is added aqueous $H_3PO_4$ (at ½ the molar quantity of Carvedilol). The reaction mixture is stirred and allowed to crystallize. The solid precipitate formed is stirred and cooled, then filtered and the collected cake is washed with aqueous acetone.

Example 7

$^{13}C$ and $^{31}P$ Solid State NMR Data Analysis of Carvedilol Dihydrogen Phosphate A sample of carvedilol dihydrogen phosphate was analyzed by solid-state $^{13}C$ NMR and $^{31}P$ NMR (i.e., to probe solid compound form structure).

Carvedilol dihydrogen phosphate (Parent MW=406.5; Salt MW=504.5) has the following structure and numbering scheme:

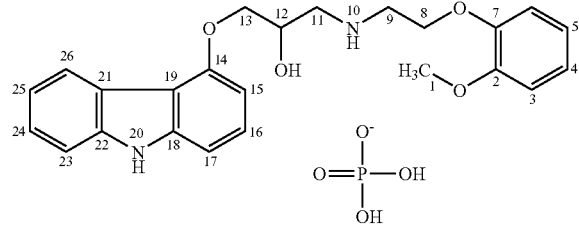

Experimental Details and $^{13}$C and $^{31}$P Analysis

The solid state $^{13}$C NMR methods used to analyze compounds of the present invention produce a qualitative picture of the types of carbon sites within the solid material. Because of variable polarization transfer rates and the need for sideband suppression, the peak intensities are not quantitative (much like the case in solution-state $^{13}$C NMR).

However, the $^{31}$P spectra are inherently quantitative.

For the $^{13}$C analysis, approximately 100 mg of sample was packed into a 7-mm O.D. magic-angle spinning rotor and spun at 5 kHz. The $^{13}$C spectrum of the sample was recorded using a CP-TOSS pulse sequence (cross-polarization with total suppression of sidebands). An edited spectrum containing only quaternary and methyl carbons was then obtained using an CP-TOSS sequence with NQS (non-quaternary suppression). The $^{13}$C spectra are referenced externally to tetramethylsilane via a sample of solid hexamethylbenzene.

For $^{31}$P Solid State NMR, approximately 40 mg of sample was packed into a 4-mm O.D. rotor and spun at 10 kHz. Both CP-MAS and single-pulse MAS $^{31}$P pulse sequences were used with $^1$H decoupling. The $^{31}$P data are externally referenced to 85% phosphoric acid by a secondary solid-state reference (triphenylphosphine oxide). The Bruker AMX2-360 spectrometer used for this work operates at $^{13}$C, $^{31}$P and $^1$H frequencies of 90.556, 145.782 and 360.097 MHz, respectively. All spectra were obtained at 298 K.

Results and Discussion

The highly sensitive $^{13}$C and $^{31}$P Solid State NMR identification methods were used for the analysis and characterization of a polymorphic form of Carvedilol phosphate, which confirms its chemical structure in the solid-state.

The form of Carvedilol dihydrogen phosphate is defined by these spectra, where both $^{13}$C and $^{31}$P spectra show clear and distinct differences.

Figure 26:
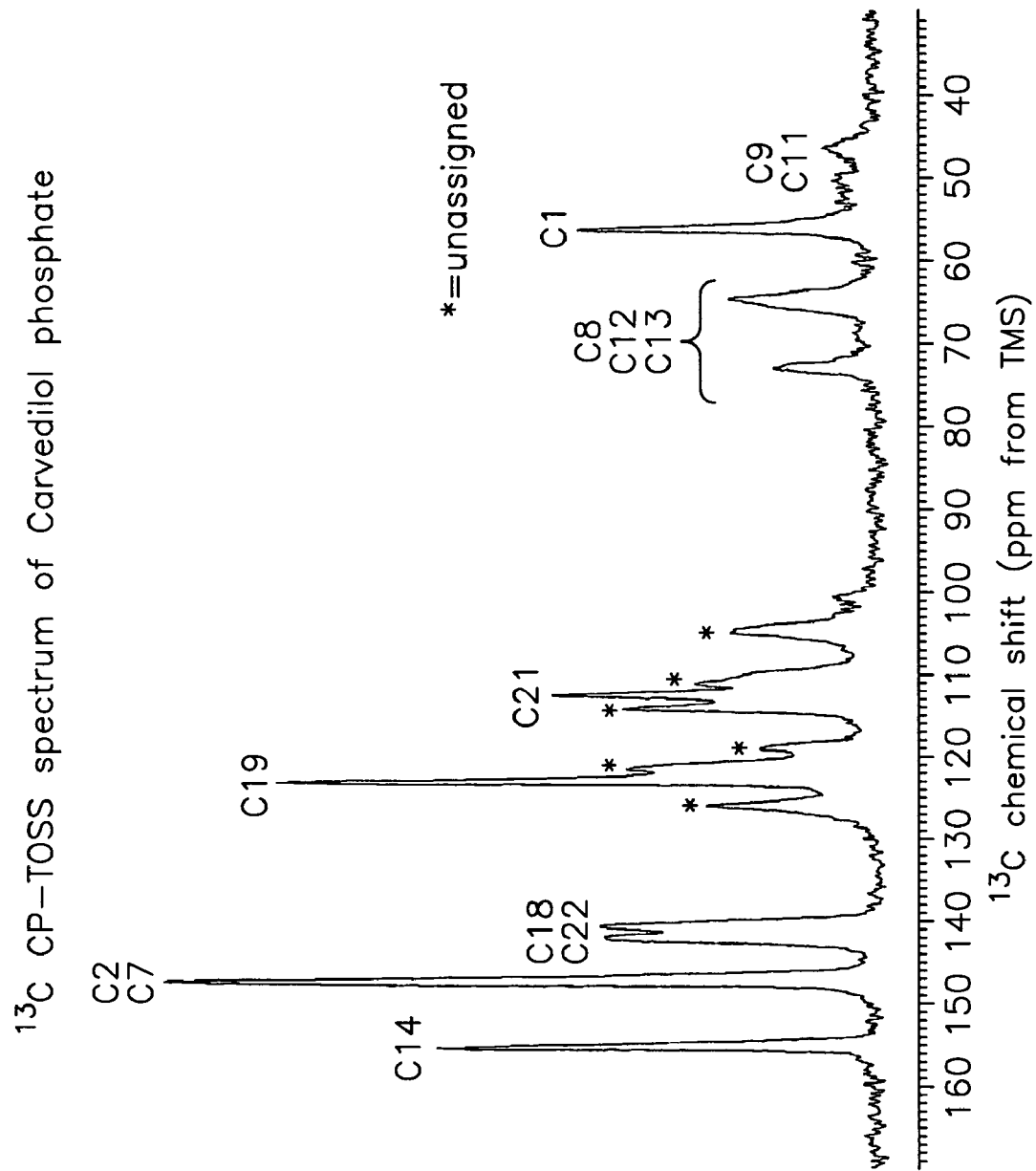
FIG. 26 is a solid state $^{13}C$ NMR for carvedilol dihydrogen phosphate dihydrate (Form I).

In particular, FIG. 26 shows the $^{13}$C CP-TOSS spectrum of carevedilol dihydrogen phosphate. An assignment of the numerous $^{13}$C resonances in FIG. 1 can be made by chemical shift assignment, the NQS spectrum and comparisons with solution-state $^{13}$C assignments. At least two non-equivalent molecules per unit cell are observed in this form of Carvedilol phosphate.

Figure 27:
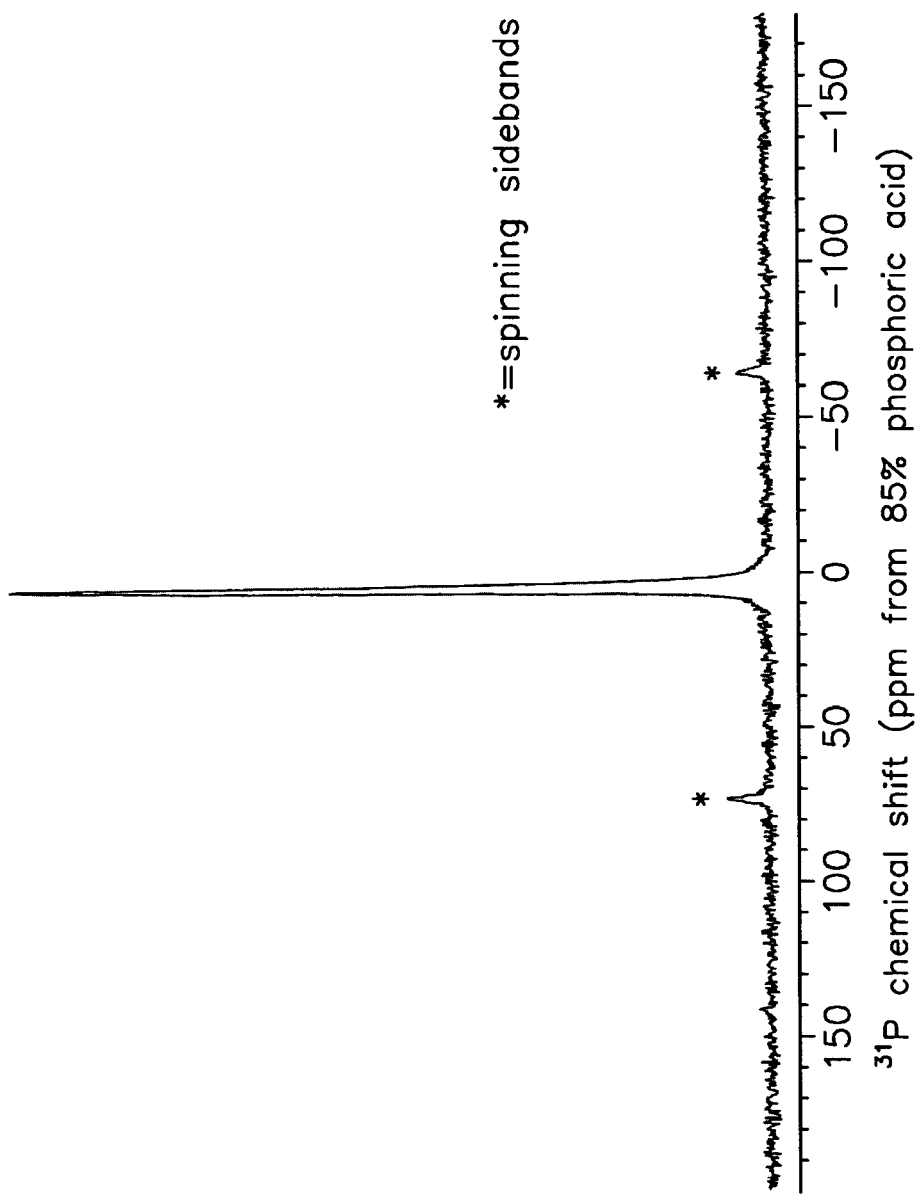
FIG. 27 is a solid state $^{31}P$ NMR for carvedilol dihydrogen phosphate dihydrate (Form I).

FIG. 27 shows the $^{31}$P MAS spectrum of carvedilol dihydrogen phosphate. A single phosphorus signal is observed at 4.7 ppm, which is characteristic of phosphate salts.

Carvedilol Hydrogen Bromide Examples

Example 8

Form 1. Carvedilol HBr Monohydrate

A suitable reactor is charged with acetone. The acetone solution is sequentially charged with carvedilol, water and 48% aqueous HBr. On addition of the water, the acetone slurry becomes a solution. The reaction mixture is stirred at room temperature. A solid precipitates during the course of the stir. The precipitate is filtered and the collected cake is washed with acetone. The cake is dried under vacuum to a constant weight. The cake is weighed and stored in a polyethylene container.

The single crystal x-ray data for carvedilol hydrobromide monohydrate is provided below.

TABLE 1

Sample and Crystal Data for Carvedilol Hydrobromide Monohydrate.

| | | |
|---|---|---|
| Crystallization solvents | Acetone, water | |
| Crystallization method | Slow cooling | |
| Empirical formula | $C_{24}H_{29}BrN_2O_5$ | |
| Formula weight | 505.40 | |
| Temperature | 150(2)K | |
| Wavelength | 0.71073 Å | |
| Crystal size | 0.18 × 0.14 × 0.08 mm | |
| Crystal habit | Clear colorless prism | |
| Crystal system | Monoclinic | |
| Space group | C2/c | |
| Unit cell dimensions | a = 18.0356(3) Å | α = 90° |
| | b = 20.8385(5) Å | β = 103.5680(10)° |
| | c = 12.9342(3) Å | γ = 90° |
| Volume | 4725.46(18) Å$^3$ | |
| Z | 8 | |
| Density (calculated) | 1.421 Mg/m$^3$ | |
| Absorption coefficient | 1.777 mm$^{-1}$ | |
| F(000) | 2096 | |

TABLE 2

Data collection and structure refinement for Carvedilol Hydrobromide Monohydrate.

| | |
|---|---|
| Diffractometer | KappaCCD |
| Radiation source | Fine-focus sealed tube, MoK$_\alpha$ |
| Data collection method | CCD; rotation images; thick slices |
| Theta range for data collection | 3.42 to 23.27° |
| Index ranges | 0 ≦ h ≦ 20, 0 ≦ k ≦ 23, −14 ≦ l ≦ 13 |
| Reflections collected | 30823 |
| Independent reflections | 3404 [R(int) = 0.042] |
| Coverage of independent reflections | 99.7% |
| Variation in check reflections | N/A |
| Absorption correction | Symmetry-related measurements |
| Max. and min. transmission | 0.8709 and 0.7404 |
| Structure solution technique | Direct methods |
| Structure solution program | SHELXTL V5.10 UNIX (Bruker, 1997) |
| Refinement technique | Full-matrix least-squares on F$^2$ |

TABLE 2-continued

Data collection and structure refinement for Carvedilol Hydrobromide Monohydrate.

| | |
|---|---|
| Refinement program | SHELXTL V5.10 UNIX (Bruker, 1997) |
| Function minimized | $\Sigma\, w(F_o^2 - F_c^2)^2$ |
| Data/restraints/parameters | 3404/11/336 |
| Goodness-of-fit on $F^2$ | 1.020 |
| $\Delta/\sigma_{max}$ | 0.000 |
| Final R indices | |
| 3071 data; $I > 2\sigma(I)$ | R1 = 0.0353, wR2 = 0.0797 |
| all data | R1 = 0.0405, wR2 = 0.0829 |
| Weighting scheme | $w = 1/[\sigma^2(F_o^2) + [(0.0304P)^2 + 14.1564P]$ where $P = [MAX(F_o^2, 0) + 2F_c^2]/3$ |
| Largest diff. peak and hole | 0.786 and −0.914 e.Å$^{-3}$ |

| | |
|---|---|
| Ordered Non-H atoms, XYZ | Freely refined |
| Ordered Non-H atoms, U | Anisotropic |
| H atoms (on carbon), XYZ | Idealized positions riding on attached atom |
| H atoms (on carbon), U | Appropriate constant times Ueq of attached atom |
| H atoms (on heteroatoms), XYZ | Freely refined |
| H atoms (on heteroatoms), U | Refined Isotropically |
| Disordered atoms, OCC | See Table 10 |
| Disordered atoms, XYZ | Refined with distance restraints |
| Disordered atoms, U | Anisotropic |

TABLE 3

Atomic Coordinates and Equivalent Isotropic Atomic Displacement Parameters (Å$^2$) for Carvedilol Hydrobromide Monohydrate.
U(eq) is defined as one third of the trace of the orthogonalized $U_{ij}$ tensor.

| | x/a | y/b | z/c | U(eq) |
|---|---|---|---|---|
| Br1 | 0.5000 | 0.22079(2) | −0.2500 | 0.04329(15) |
| Br2 | 0.0000 | 0.40821(2) | −0.2500 | 0.04510(16) |
| O1 | 0.19543(10) | 0.37037(10) | −0.00168(15) | 0.0328(5) |
| O2 | 0.08660(19) | 0.48508(15) | 0.1085(2) | 0.0312(7) |
| O2' | 0.0825(3) | 0.4816(3) | −0.0328(4) | 0.0311(13) |
| O3 | −0.19428(10) | 0.39492(10) | −0.01310(15) | 0.0347(5) |
| O4 | −0.24723(12) | 0.46974(11) | 0.11008(16) | 0.0404(5) |
| O99A | −0.0880(5) | 0.4236(3) | 0.1967(7) | 0.0430(19) |
| O99B | −0.0833(5) | 0.4514(4) | 0.1784(7) | 0.0431(19) |
| N1 | 0.34092(16) | 0.25072(13) | −0.1793(2) | 0.0390(7) |
| N2 | −0.03151(14) | 0.39706(13) | −0.0026(2) | 0.0314(6) |
| C1 | 0.26859(15) | 0.35551(14) | −0.0070(2) | 0.0301(7) |
| C2 | 0.33380(16) | 0.38188(15) | 0.0568(2) | 0.0339(7) |
| C3 | 0.40553(17) | 0.36537(16) | 0.0409(3) | 0.0402(8) |
| C4 | 0.41433(17) | 0.32249(16) | −0.0364(3) | 0.0401(8) |
| C5 | 0.34850(16) | 0.29538(15) | −0.0986(2) | 0.0343(7) |
| C6 | 0.26499(17) | 0.23737(14) | −0.2202(2) | 0.0343(7) |
| C7 | 0.23145(19) | 0.19604(15) | −0.3022(2) | 0.0401(8) |
| C8 | 0.15313(19) | 0.19096(15) | −0.3275(2) | 0.0412(8) |
| C9 | 0.10866(18) | 0.22594(14) | −0.2721(2) | 0.0364(7) |
| C10 | 0.14185(17) | 0.26731(14) | −0.1910(2) | 0.0323(7) |
| C11 | 0.22085(16) | 0.27356(13) | −0.1639(2) | 0.0300(7) |
| C12 | 0.27490(16) | 0.31103(13) | −0.0855(2) | 0.0294(6) |
| C13 | 0.18523(16) | 0.41746(14) | 0.0740(2) | 0.0301(7) |
| C14 | 0.10181(16) | 0.43671(13) | 0.0452(2) | 0.0305(7) |
| C15 | 0.05016(15) | 0.37919(14) | 0.0363(2) | 0.0289(6) |
| C16 | −0.08143(16) | 0.33991(14) | −0.0272(2) | 0.0361(7) |
| C17 | −0.16200(16) | 0.35626(16) | −0.0833(2) | 0.0380(7) |
| C18 | −0.27156(15) | 0.40680(14) | −0.0445(2) | 0.0300(6) |
| C19 | −0.30049(16) | 0.44705(14) | 0.0236(2) | 0.0316(7) |
| C20 | −0.37754(18) | 0.46060(16) | 0.0007(3) | 0.0409(8) |
| C21 | −0.42545(18) | 0.43467(17) | −0.0895(3) | 0.0499(9) |

TABLE 3-continued

Atomic Coordinates and Equivalent Isotropic Atomic Displacement Parameters (Å$^2$) for Carvedilol Hydrobromide Monohydrate.
U(eq) is defined as one third of the trace of the orthogonalized $U_{ij}$ tensor.

| | x/a | y/b | z/c | U(eq) |
|---|---|---|---|---|
| C22 | −0.39733(18) | 0.39593(17) | −0.1567(3) | 0.0504(9) |
| C23 | −0.31949(17) | 0.38199(15) | −0.1342(3) | 0.0388(7) |
| C24 | −0.2743(2) | 0.50999(17) | 0.1833(3) | 0.0482(9) |

TABLE 4

Selected Bond Lengths (Å) for Carvedilol Hydrobromide Monohydrate.

| O1—C1 | 1.373(3) | O1—C13 | 1.428(3) |
|---|---|---|---|
| O2—C14 | 1.366(4) | O2'—C14 | 1.360(6) |
| O3—C18 | 1.380(3) | O3—C17 | 1.435(3) |
| O4—C19 | 1.376(4) | O4—C24 | 1.433(4) |
| N1—C6 | 1.376(4) | N1—C5 | 1.381(4) |
| N2—C16 | 1.482(4) | N2—C15 | 1.488(4) |
| C1—C2 | 1.382(4) | C1—C12 | 1.399(4) |
| C2—C3 | 1.399(4) | C3—C4 | 1.378(5) |
| C4—C5 | 1.388(4) | C5—C12 | 1.415(4) |
| C6—C7 | 1.389(4) | C6—C11 | 1.416(4) |
| C7—C8 | 1.377(5) | C8—C9 | 1.399(4) |
| C9—C10 | 1.381(4) | C10—C11 | 1.391(4) |
| C11—C12 | 1.458(4) | C13—C14 | 1.517(4) |
| C14—C15 | 1.506(4) | C16—C17 | 1.503(4) |
| C18—C23 | 1.374(4) | C18—C19 | 1.403(4) |
| C19—C20 | 1.380(4) | C20—C21 | 1.388(5) |
| C21—C22 | 1.368(5) | C22—C23 | 1.396(4) |

TABLE 5

Selected bond angles (°) for Carvedilol Hydrobromide Monohydrate.

| C1—O1—C13 | 118.0(2) | C18—O3—C17 | 116.5(2) |
|---|---|---|---|
| C19—O4—C24 | 117.2(2) | C6—N1—C5 | 109.9(3) |
| C16—N2—C15 | 112.0(2) | O1—C1—C2 | 125.0(3) |
| O1—C1—C12 | 115.4(2) | C2—C1—C12 | 119.6(3) |
| C1—C2—C3 | 120.1(3) | C4—C3—C2 | 122.3(3) |
| C3—C4—C5 | 117.1(3) | N1—C5—C4 | 129.2(3) |
| N1—C5—C12 | 108.5(3) | C4—C5—C12 | 122.4(3) |
| N1—C6—C7 | 129.4(3) | N1—C6—C11 | 108.9(3) |
| C7—C6—C11 | 121.7(3) | C8—C7—C6 | 117.9(3) |
| C7—C8—C9 | 121.1(3) | C10—C9—C8 | 121.0(3) |
| C9—C10—C11 | 119.1(3) | C10—C11—C6 | 119.1(3) |
| C10—C11—C12 | 134.7(3) | C6—C11—C12 | 106.2(3) |
| C1—C12—C5 | 118.6(3) | C1—C12—C11 | 134.8(3) |

TABLE 5-continued

Selected bond angles (°) for Carvedilol Hydrobromide Monohydrate.

| | | | |
|---|---|---|---|
| C5—C12—C11 | 106.6(3) | O1—C13—C14 | 107.0(2) |
| O2'—C14—O2 | 83.4(3) | O2'—C14—C15 | 116.4(3) |
| O2—C14—C15 | 115.2(3) | O2'—C14—C13 | 115.6(3) |
| O2—C14—C13 | 112.0(3) | C15—C14—C13 | 111.6(2) |
| N2—C15—C14 | 111.8(2) | N2—C16—C17 | 113.0(3) |
| O3—C17—C16 | 108.1(2) | C23—C18—O3 | 125.0(3) |
| C23—C18—C19 | 120.1(3) | O3—C18—C19 | 114.9(2) |
| O4—C19—C20 | 125.4(3) | O4—C19—C18 | 115.1(2) |
| C20—C19—C18 | 119.4(3) | C19—C20—C21 | 119.8(3) |
| C22—C21—C20 | 120.9(3) | C21—C22—C23 | 119.7(3) |
| C18—C23—C22 | 120.0(3) | | |

TABLE 6

Hydrogen Bonds and Short C—H . . . X Contacts for Carvedilol Hydrobromide Monohydrate (Å and °).

| D—H . . . A | d(D-H) | d(H . . . A) | d(D . . . A) | <(DHA) |
|---|---|---|---|---|
| N1—H1N . . . Br1 | 0.76(3) | 2.53(4) | 3.269(3) | 166(3) |
| N2—H2NA . . . O99A | 0.83(4) | 2.29(4) | 3.037(10) | 149(3) |
| N2—H2NA . . . O99B | 0.83(4) | 2.13(4) | 2.943(10) | 165(4) |
| N2—H2NB . . . O2#1 | 0.89(5) | 2.17(4) | 2.873(4) | 135(4) |
| O2'—H2O' . . . Br2 | 0.67(5) | 2.65(7) | 3.237(6) | 149(12) |
| O99A—H99A . . . Br1#2 | 0.94(3) | 2.49(4) | 3.395(8) | 163(6) |
| O99B—H99B . . . Br2#1 | 0.94(3) | 2.38(3) | 3.320(8) | 173(6) |
| C15—H15A . . . O1 | 0.99 | 2.38 | 2.783(3) | 103.2 |
| C15—H15B . . . Br1#2 | 0.99 | 2.85 | 3.738(3) | 149.3 |
| C16—H16A . . . Br1#2 | 0.99 | 2.88 | 3.760(3) | 148.2 |

Symmetry transformations used to generate equivalent atoms:
1 −x, −y+1, −z
2 −x+½, −y+½, −z

TABLE 7

Selected torsion angles (°) for Carvedilol Hydrobromide Monohydrate.

| | | | |
|---|---|---|---|
| C13—O1—C1—C2 | 1.2(4) | C13—O1—C1—C12 | −177.5(2) |
| O1—C1—C2—C3 | −177.0(3) | C12—C1—C2—C3 | 1.7(4) |
| C1—C2—C3—C4 | −0.8(5) | C2—C3—C4—C5 | −0.5(5) |
| C6—N1—C5—C4 | −179.7(3) | C6—N1—C5—C12 | 0.8(3) |
| C3—C4—C5—N1 | −178.6(3) | C3—C4—C5—C12 | 0.8(4) |
| C5—N1—C6—C7 | 179.4(3) | C5—N1—C6—C11 | −0.9(3) |
| N1—C6—C7—C8 | 179.5(3) | C11—C6—C7—C8 | −0.1(4) |
| C6—C7—C8—C9 | −0.4(5) | C7—C8—C9—C10 | 0.8(5) |
| C8—C9—C10—C11 | −0.6(4) | C9—C10—C11—C6 | 0.0(4) |
| C9—C10—C11—C12 | −179.9(3) | N1—C6—C11—C10 | −179.4(3) |
| C7—C6—C11—C10 | 0.3(4) | N1—C6—C11—C12 | 0.6(3) |
| C7—C6—C11—C12 | −179.7(3) | O1—C1—C12—C5 | 177.4(2) |
| C2—C1—C12—C5 | −1.4(4) | O1—C1—C12—C11 | −2.4(5) |
| C2—C1—C12—C11 | 178.8(3) | N1—C5—C12—C1 | 179.6(2) |
| C4—C5—C12—C1 | 0.1(4) | N1—C5—C12—C11 | −0.5(3) |
| C4—C5—C12—C11 | 180.0(3) | C10—C11—C12—C1 | −0.3(6) |
| C6—C11—C12—C1 | 179.8(3) | C10—C11—C12—C5 | 179.9(3) |
| C6—C11—C12—C5 | −0.1(3) | C1—O1—C13—C14 | 166.1(2) |
| O1—C13—C14—O2' | −82.6(4) | O1—C13—C14—O2 | −175.8(2) |
| O1—C13—C14—C15 | 53.4(3) | C16—N2—C15—C14 | 171.3(2) |
| O2'—C14—C15—N2 | −38.6(4) | O2—C14—C15—N2 | 56.6(3) |
| C13—C14—C15—N2 | −174.2(2) | C15—N2—C16—C17 | −170.5(2) |
| C18—O3—C17—C16 | −170.7(2) | N2—C16—C17—O3 | −63.3(3) |
| C17—O3—C18—C23 | 3.3(4) | C17—O3—C18—C19 | −177.3(3) |
| C24—O4—C19—C20 | 1.0(4) | C24—O4—C19—C18 | −178.7(3) |
| C23—C18—C19—O4 | −179.2(3) | O3—C18—C19—O4 | 1.4(4) |
| C23—C18—C19—C20 | 1.0(4) | O3—C18—C19—C20 | −178.3(3) |
| O4—C19—C20—C21 | 179.9(3) | C18—C19—C20—C21 | −0.4(5) |
| C19—C20—C21—C22 | −0.3(5) | C20—C21—C22—C23 | 0.3(6) |
| O3—C18—C23—C22 | 178.2(3) | C19—C18—C23—C22 | −1.1(5) |
| C21—C22—C23—C18 | 0.4(5) | | |

TABLE 8

Anisotropic Atomic Displacement Parameters (Å$^2$) for Carvedilol Hydrobromide Monohydrate.
The anisotropic atomic displacement factor exponent takes the form:
$-2\pi^2 [h^2 a^{*2} U_{11} + \ldots + 2hka^* b^* U_{12}]$

| | $U_{11}$ | $U_{22}$ | $U_{33}$ | $U_{23}$ | $U_{13}$ | $U_{12}$ |
|---|---|---|---|---|---|---|
| Br1 | 0.0484(3) | 0.0447(3) | 0.0464(3) | 0.000 | 0.0306(2) | 0.000 |
| Br2 | 0.0707(3) | 0.0413(3) | 0.0234(2) | 0.000 | 0.0111(2) | 0.000 |
| O1 | 0.0272(11) | 0.0408(12) | 0.0323(11) | 0.0067(9) | 0.0108(9) | −0.0009(9) |
| O2 | 0.0416(18) | 0.0306(18) | 0.0215(17) | −0.0006(14) | 0.0077(15) | 0.0059(14) |
| O2' | 0.038(3) | 0.028(3) | 0.031(3) | 0.001(3) | 0.014(3) | 0.000(3) |
| O3 | 0.0254(11) | 0.0473(13) | 0.0308(11) | −0.0091(9) | 0.0058(9) | −0.0001(9) |
| O4 | 0.0400(12) | 0.0500(14) | 0.0323(11) | −0.0076(10) | 0.0108(10) | 0.0019(10) |
| O99A | 0.042(3) | 0.044(5) | 0.040(4) | −0.004(4) | 0.004(3) | 0.002(4) |
| O99B | 0.033(3) | 0.061(6) | 0.035(4) | −0.004(4) | 0.007(2) | −0.010(4) |

TABLE 8-continued

Anisotropic Atomic Displacement Parameters (Å$^2$) for Carvedilol Hydrobromide Monohydrate.
The anisotropic atomic displacement factor exponent takes the form:
$$-2\pi^2 [h^2 a^{*2} U_{11} + \ldots + 2hka^* b^* U_{12}]$$

|     | U$_{11}$    | U$_{22}$    | U$_{33}$    | U$_{23}$     | U$_{13}$     | U$_{12}$     |
|-----|-------------|-------------|-------------|--------------|--------------|--------------|
| N1  | 0.0384(17)  | 0.0449(17)  | 0.0393(16)  | 0.0053(13)   | 0.0203(14)   | 0.0112(13)   |
| N2  | 0.0270(13)  | 0.0341(15)  | 0.0332(15)  | 0.0015(13)   | 0.0075(12)   | 0.0033(11)   |
| C1  | 0.0283(16)  | 0.0324(16)  | 0.0321(16)  | 0.0078(13)   | 0.0124(13)   | 0.0005(12)   |
| C2  | 0.0321(17)  | 0.0381(17)  | 0.0327(16)  | 0.0056(13)   | 0.0100(13)   | −0.0014(13)  |
| C3  | 0.0301(17)  | 0.048(2)    | 0.0412(18)  | 0.0104(16)   | 0.0051(14)   | −0.0044(14)  |
| C4  | 0.0290(17)  | 0.0471(19)  | 0.0470(19)  | 0.0133(16)   | 0.0148(15)   | 0.0064(14)   |
| C5  | 0.0324(17)  | 0.0390(17)  | 0.0343(16)  | 0.0113(14)   | 0.0132(14)   | 0.0065(14)   |
| C6  | 0.0391(18)  | 0.0334(17)  | 0.0339(17)  | 0.0099(14)   | 0.0161(14)   | 0.0088(14)   |
| C7  | 0.056(2)    | 0.0324(17)  | 0.0362(18)  | 0.0011(14)   | 0.0204(16)   | 0.0098(15)   |
| C8  | 0.055(2)    | 0.0337(18)  | 0.0357(18)  | −0.0020(14)  | 0.0119(16)   | 0.0003(15)   |
| C9  | 0.0411(18)  | 0.0344(17)  | 0.0348(17)  | 0.0030(14)   | 0.0111(14)   | −0.0009(14)  |
| C10 | 0.0362(17)  | 0.0321(16)  | 0.0323(16)  | 0.0038(13)   | 0.0155(14)   | 0.0022(13)   |
| C11 | 0.0377(17)  | 0.0275(15)  | 0.0277(15)  | 0.0079(12)   | 0.0136(13)   | 0.0040(13)   |
| C12 | 0.0305(16)  | 0.0309(16)  | 0.0295(15)  | 0.0085(13)   | 0.0122(13)   | 0.0017(12)   |
| C13 | 0.0311(16)  | 0.0331(16)  | 0.0265(15)  | −0.0019(12)  | 0.0078(12)   | −0.0021(12)  |
| C14 | 0.0325(16)  | 0.0307(16)  | 0.0290(16)  | 0.0010(13)   | 0.0083(13)   | 0.0015(13)   |
| C15 | 0.0263(15)  | 0.0327(16)  | 0.0289(15)  | 0.0031(13)   | 0.0090(12)   | 0.0043(12)   |
| C16 | 0.0322(16)  | 0.0347(17)  | 0.0390(18)  | −0.0078(14)  | 0.0036(14)   | 0.0016(13)   |
| C17 | 0.0298(16)  | 0.0477(19)  | 0.0342(17)  | −0.0106(15)  | 0.0031(13)   | 0.0023(14)   |
| C18 | 0.0246(15)  | 0.0317(16)  | 0.0337(16)  | 0.0031(13)   | 0.0069(13)   | −0.0014(12)  |
| C19 | 0.0299(16)  | 0.0352(17)  | 0.0313(16)  | 0.0063(13)   | 0.0103(13)   | −0.0031(13)  |
| C20 | 0.0379(18)  | 0.0382(18)  | 0.051(2)    | 0.0048(15)   | 0.0194(16)   | 0.0033(15)   |
| C21 | 0.0245(17)  | 0.050(2)    | 0.073(3)    | 0.0038(19)   | 0.0059(17)   | 0.0012(15)   |
| C22 | 0.0326(18)  | 0.053(2)    | 0.057(2)    | −0.0075(18)  | −0.0052(16)  | −0.0012(16)  |
| C23 | 0.0317(17)  | 0.0407(18)  | 0.0407(18)  | −0.0045(14)  | 0.0021(14)   | −0.0004(14)  |
| C24 | 0.065(2)    | 0.050(2)    | 0.0325(18)  | −0.0027(15)  | 0.0176(17)   | 0.0098(17)   |

TABLE 9

Hydrogen Atom Coordinates and Isotropic Atomic Displacement Parameters (Å$^2$) for Carvedilol Hydrobromide Monohydrate.

|       | x/a        | y/b        | z/c       | U         |
|-------|------------|------------|-----------|-----------|
| H2O   | 0.086(3)   | 0.471(3)   | 0.155(4)  | 0.047     |
| H2O'  | 0.082(6)   | 0.465(5)   | −0.077(6) | 0.047     |
| H99A  | −0.073(4)  | 0.3802(19) | 0.201(6)  | 0.064     |
| H99B  | −0.060(4)  | 0.490(2)   | 0.205(6)  | 0.065     |
| H99   | −0.1344(19)| 0.4409(13) | 0.157(3)  | 0.065     |
| H1N   | 0.373(2)   | 0.2411(16) | −0.205(3) | 0.039(10) |
| H2NA  | −0.043(2)  | 0.4188(18) | 0.045(3)  | 0.058(12) |
| H2NB  | −0.036(2)  | 0.422(2)   | −0.060(4) | 0.077(14) |
| H2A   | 0.3299     | 0.4112     | 0.1114    | 0.041     |
| H3A   | 0.4497     | 0.3844     | 0.0850    | 0.048     |
| H4A   | 0.4633     | 0.3119     | −0.0468   | 0.048     |
| H7A   | 0.2616     | 0.1720     | −0.3395   | 0.048     |
| H8A   | 0.1289     | 0.1632     | −0.3836   | 0.049     |
| H9A   | 0.0548     | 0.2212     | −0.2906   | 0.044     |
| H10A  | 0.1112     | 0.2912     | −0.1543   | 0.039     |
| H13A  | 0.2180     | 0.4552     | 0.0713    | 0.036     |
| H13B  | 0.1990     | 0.3994     | 0.1468    | 0.036     |
| H14   | 0.0925     | 0.4552     | −0.0281   | 0.037     |
| H14'  | 0.0943     | 0.4596     | 0.1099    | 0.037     |
| H15A  | 0.0642     | 0.3477     | −0.0132   | 0.035     |
| H15B  | 0.0576     | 0.3585     | 0.1069    | 0.035     |
| H16A  | −0.0819    | 0.3172     | 0.0400    | 0.043     |
| H16B  | −0.0599    | 0.3103     | −0.0723   | 0.043     |
| H17A  | −0.1625    | 0.3802     | −0.1496   | 0.046     |
| H17B  | −0.1922    | 0.3165     | −0.1021   | 0.046     |
| H20A  | −0.3977    | 0.4876     | 0.0466    | 0.049     |
| H21A  | −0.4785    | 0.4439     | −0.1048   | 0.060     |
| H22A  | −0.4306    | 0.3786     | −0.2183   | 0.060     |
| H23A  | −0.2996    | 0.3553     | −0.1809   | 0.047     |
| H24A  | −0.2310    | 0.5242     | 0.2397    | 0.072     |
| H24B  | −0.3101    | 0.4858     | 0.2148    | 0.072     |
| H24C  | −0.3002    | 0.5475     | 0.1455    | 0.072     |

TABLE 10

Site Occupation Factors that Deviate from Unity for Carvedilol Hydrobromide Monohydrate.

| Atom  | sof  | Atom  | sof  | Atom  | sof  |
|-------|------|-------|------|-------|------|
| Br1   | 1    | Br2   | 1    | O1    | 1    |
| O2    | 0.65 | H2O   | 0.65 | O2'   | 0.35 |
| H2O'  | 0.35 | O99A  | 0.50 | H99A  | 0.50 |
| O99B  | 0.50 | H99B  | 0.50 | H99   | 1    |
| H14   | 0.65 | H14'  | 0.35 |       |      |

Example 9

Form 2. Carvedilol HBr (dioxane solvate)

Form 1 is slurried in dioxane between 0 and 40° C. for 2 days. The product is filtered and mildly dried.

Example 10

Form 3. Carvedilol HBr (1-pentanol solvate)

Form 1 is slurried in 1-pentanol between 0° C. and 40° C. for 2 days. The product is filtered and mildly dried.

Example 11

Form 4. Carvedilol HBr (2-Methyl-1-Propanol solvate)

Form 1 is slurried in 2-Methyl-1-Propanol between 0° C. and 40° C. for 2 days. The product is filtered and mildly dried.

Example 12

Form 5. Carvedilol HBr (trifluoroethanol solvate)

Form 1 is slurried in trifluoroethanol between 0° C. and 40° C. for 2 days. The product is filtered and mildly dried.

Example 13

Form 6. Carvedilol HBr (2-propanol solvate)

Form 1 is slurried in 2-propanol between 0° C. and 40° C. for 2 days. The product is filtered and mildly dried.

Example 14

Form 7. Carvedilol HBr (n-propanol solvate #1)

Carvedilol free base is dissolved in n-propanol/water (95:5), and stoichiometric hydrobromic acid is added. The solution is cooled, and crystallization ensues. The product is filtered, washed with process solvent, and dried.

Example 15

Form 8. Carvedilol HBr (n-propanol solvate #2)

Carvedilol HBr monohydrate (Form 1) is dissolved in n-propanol at ambient temperature. The n-propanol is slowly evaporated off, giving a white solid.

Example 16

Form 9. Carvedilol HBr (anhydrous forms and solvent free)

Carvedilol free base is dissolved in a solvent (dichloromethane, isopropyl acetate, and acetonitrile have been used) and anhydrous forms HBr is added (HBr in acetic acid or gaseous HBr). The solution is cooled, and crystallization ensues. The product is filtered, washed with process solvent, and dried.

Example 17

Form 10. Carvedilol HBr (ethanol solvate)

Carvedilol free base is dissolved in ethanol, and anhydrous forms HBr is added (HBr in acetic acid). The solution is cooled, and crystallization ensues. The product is filtered, washed with process solvent, and dried.

Carvedilol Monocitrate Monohydrate

Example 18

Carvedilol Monocitrate Monohydrate Preparation

In a 150 mL glass beaker, 100 gram of 20% w/w citric acid solution was prepared and 2.2 gram of carvedilol was added. The solution became slightly brownish after 15 minutes stirring, with only a little solid sticking on the bottom of the beaker. The beaker was then placed in a fume hood for evaporation. After staying in the hood overnight, large single crystals appeared in the beaker. The solid crystals were isolated and dried in a desiccator under vacuum. Similarly single crystals of citrate salt could be obtained by slow evaporation of carvedilol/citric acid solutions (containing citric acid 5%, 10% or 20% w/w) in Petri dishes (150 mm diameter) placed in a desiccator connected to a house vacuum.

Example 19

Carvedilol Monocitrate Monohydrate Preparation

A 250 mL three-necked flask equipped with stirrer bar, thermometer, and an addition funnel is charged with acetone (20 mL, 2.5 volumes). The solution is sequentially charged with carvedilol (8 g, 19.7 mmol), and 2 M citric acid solution (40 mL, 5 volumes). Upon addition of the citric acid solution, the slurry dissolves quickly. The solution is filtered through a Buchner funnel fitted with Whatman filter paper and the solution is returned to a 250 mL flask fitted with a stirrer. To the light brown solution is added water (20 mL, 2.5 volumes). No exotherm is noted. The reaction mixture becomes cloudy but disappears upon stirring (heating up to 40° C. maybe needed to remove cloudiness). The mixture is stirred at room temperature and when judged clear is charged with carvedilol monocitrate monohydrate seeds (80 mgs) in one portion. An immediate cloudiness is observed (solid starts to precipitate out over 12-24 hours). The precipitate formed is stirred for 24-48 hours and is filtered through a Buchner funnel fitted with Whatman filter paper and the collected cake is washed with water (2×16 mL). The cake is dried in the oven under house vacuum at 50° C. to a constant weight. The cake (7.95 g, 67%) is weighed and stored in a polyethylene container.

Example 20

Carvedilol Monocitrate Monohydrate Preparation

A suitable reactor is charged with acetone. The solution is sequentially charged with carvedilol, and aqueous citric acid solution. Upon addition of the citric acid solution, the slurry dissolves quickly. To the solution is added water. The mixture is stirred at room temperature and is charged with carvedilol seeds in one portion. The precipitate formed is stirred for a period of time, filtered and the collected cake is washed with water. The cake is dried under vacuum to a constant weight and stored in a polyethylene container.

Example 21

Characterization of Carvedilol Monocitrate Monohydrate Preparation

The HPLC assay and $^1$H-NMR revealed that the molar ratio of carvedilol and citric acid in carvedilol citrate salt prepared was approximately 1:1. The characterization by several other techniques are listed below:

Scanning Electron Microscopy (SEM)

The SEM used for the study was a Hitachi S-3500N. SEM was performed using an acceleration voltage of 5 kV. The samples were gold sputtered.

The carvedilol monocitrate salt consists of crystals with plate-shape, and various sizes depending on the preparation method. Crystals as large as 1 mm width and length were observed.

Differential Scanning Calorimetry (DSC)

DSC measurements were performed with a MDSC 2920 (TA Instruments, Inc.). Approximately 5 mg of the sample was placed in an open aluminum pan. The sample was scanned at 10° C./min. An endothermic event was observed with an onset temperature near 82-83° C. The heat of fusion was calculated as 63 kJ/mol.

Fourier Transform Infrared Spectroscopy (FT-IR)

Approximately 2 mg of sample was diluted with 300 mg of dried potassium bromide (KBr). The mixture was ground with a mortar and pestle, then transferred to a die that is placed under high pressure for 3 minutes. The instrument was a PerkinElmer Spectrum GX FTIR instrument. Forty scans were collected at 4 cm$^{-1}$ resolution. The typical FT-IR spectrum of carvedilol monocitrate salt is shown in FIG. 1. The characteristic peaks in the 1800 to 600 cm$^{-1}$ region are found at about 1727, 1709, 1636, 1625, 1604, 1586, 1508, 1475, 1454, 1443, 1396, 1346, 1332, 1305, 1256, 1221, 1129, 1096, 1077, 1054, 1021, 1008, 984, 939, 919, 902, 826, 787, 755, 749, 729, 676, 664, 611 cm$^{-1}$.

X-Ray Powder Diffraction (XRPD)

Figure 2:
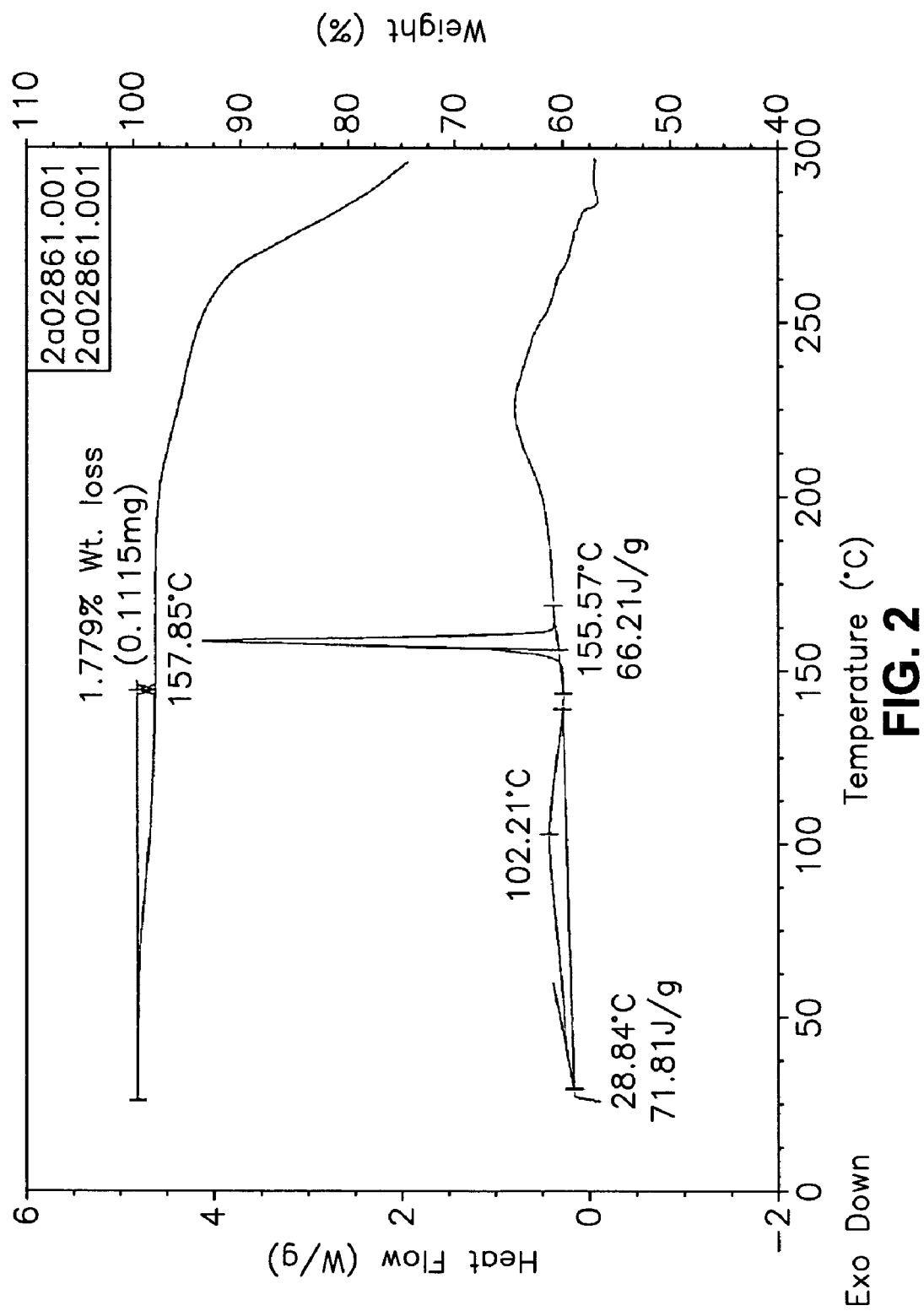
FIG. 2 shows the thermal analysis results for carvedilol dihydrogen phosphate hemihydrate (Form I).

XRPD patterns were collected using a Philips X'Pert Pro Diffractometer. Approximately 30 mg of sample was gently flattened on a silicon sample holder and scanned from 2-35 degrees two-theta, at 0.02 degrees two-theta per step and a step time of 2.5 seconds. The sample was rotated at 25 rpm. The XRPD patterns of two different batches of Carvedilol monocitrate salt are shown in FIG. 2.

Solubility in Water

Glass vials containing water and excess amount of carvedilol salts were shaken by a mechanical shaker at ambient conditions. Aliquots were taken out at various time-point, filtered through 0.45 μm Acrodisc GHP filter. The pH of the filtered solutions was measured and suitable dilution was performed prior to UV-Vis analysis of carvedilol concentration.

The solubility of carvedilol monocitrate salt in water at room temperature was determined. The drug concentrations and pH values at different time-points are presented in Table 11. This crystalline form of carvedilol monocitrate salt exhibited high solubility in water (1.63 mg/mL at 1 hour and 1.02 mg/mL at 48 hour).

TABLE 11

Aqueous Solubility (expressed as mg of carvedilol free base/mL of solution) over time at 25° C. for Carvedilol Free Base and Its Monocitrate Salt.

| Time, hr | Carvedilol Free Base | Carvedilol Mono-Citrate Salt |
|---|---|---|
| 1 | 0.0098 | 1.63 (pH = 3.5) |
| 4 |  | 1.47 (pH = 3.4) |
| 24 | 0.0116 | 1.07 (pH = 3.0) |
| 48 |  | 1.02 (pH = 3.0) |

Carvedilol monocitrate salt has two free carboxylic acid groups in one unit salt, which contributes the low pH value (near pH 3) observed for monocitrate salt when dissolved in water. This may potentially lead to improved formulations by providing a low pH microenvironment within the formulation as it traverses the GI tract. This may provide an environment at a molecular level that is more conductive to dissolution, particularly in the lower GI tract, where the pH of the environment is near neutral pH and the intrinsic solubility of the drug substance is limited. Such a microenvironmental pH should lead to greater dissolution rate because of higher solubility in the solid/liquid interface, leading to improved absorption of drug in the lower GI tract thereby sustaining overall absorption and, in consequence providing prolonged blood levels and allowing less frequent dosing. Therefore, a once-per-day carvedilol formulation may be possible by incorporating carvedilol monocitrate salt, Such a unit is more convenient for patients and result in higher patient compliance with the dosage regimen and hence a better therapeutic effect.

Crystalline Structure of Carvedilol Monocitrate Salt

The crystalline structure of carvedilol citrate salt was determined by Single Crystal X-Ray Diffraction analysis on the large crystals formed by evaporation. The result indicated that the salt form was a carvedilol monocitrate, where the molar ratio of carvedilol and citric acid was 1:1. Surprisingly, the hydroxyl of carvedilol is disordered in the crystalline packing. In other words, the monocitrate salt has both R(+) and S(−) carvedilol enantiomers at 1:1 molar ratio, and the two enantiomers are randomly distributed, without any specific order.

This crystalline packing habit is very unusual for a salt formed between a chiral compound and a chiral counter-ion (monocitrate). Typically, chiral counter-ion tends to differentiate the two stereoisomers of the compound when forming crystals. However, in the case of the monocitrate salt, there seems to be enough space in the crystal packing to allow the carbonyl group of the terminal carboxylic acid group of citrate to form equivalent hydrogen bond with the hydroxyl from either the R(+) or the S(−) carvedilol stereoisomer.

This avoids generation of yet more optically active forms that could potentially complicate stability, dissolution rates and possibly in vivo absorption and pharmacologic effects.

The above data demonstrates that a novel crystalline form of carvedilol monocitrate monohydrate can be prepared with a unique crystalline packing habit, which exhibits high aqueous solubility and can provide a low pH microenvironment for enhanced dissolution.

Example 22

Crystalline Carvedilol Benzoate Preparation

A suitable reactor is charged with acetone. The solution is sequentially charged with carvedilol (4.1 grams, 0.1 moles), and benzoic acid solution. Upon addition of the benzoic acid (1.4 grams, 0.011 moles) solution, all material dissolves into the solution. To the stirred solution is added tert-butyl methyl ether (60 ml). The precipitate formed is stirred for a period of time, filtered and the collected cake is washed with water. The cake is dried under vacuum to a constant weight and stored in a polyethylene container.

Example 23

Crystalline Carvedilol Mandelate Preparation

A suitable reactor is charged with acetone (38 mL). The acetone solution is sequentially charged with carvedilol (11.08 grams) and water (8 mL). Upon addition of the water, the slurry dissolves completely with heating. To the solution, 1N Mandelic acid in methanol (1 Equiv. 27.3 mL.) is added. The resulting mixture is stirred at the range between 17° C. and 35° C., and the solid precipitate is formed over 10 hours to 24 hours. Later, the mixture filtered and the cake is washed with a mixture of acetone and water (10 to 1) at 3 volumes or 33 mL. The cake is then dried under vacuum to a constant weight. The final weight is 8.34 g, 54.5% yield.

Example 24

Crystalline Carvedilol Lactate Preparation

A suitable reactor is charged with acetone (50 mL). The acetone solution is sequentially charged with carvedilol (15.0 grams) and water (7 mL). Upon addition of the water, the slurry dissolves completely with heating. To the solution is added 1N aqueous D, L-Lactic acid (1 equiv., 36.9 mL). The reaction mixture is stirred at between 17° C. and 35° C. and seeded in one portion. The solid precipitate is formed over 10 hours to 24 hours. Later, the mixture is filtered and the cake is washed with a mixture of acetone and water (10 to 1) at 2 volume or 30 mL. The cake is dried under vacuum to a constant weight. The final weight is 9.16 grams.

Example 25

Crystalline Carvedilol Sulfate Preparation

A suitable reactor is charged with acetone (38 mL). The acetone solution is sequentially charged with carvedilol (10.25 grams) and water (6 mL). Upon addition of the water, the slurry dissolves completely with heating. To the solution, 1N aqueous sulfuric acid (1 equiv., 25.2 mL) is added. The reaction mixture is stirred at between 17° C. and 35° C. and the solid precipitate is formed over 10 hours to 24 hours. Later, the mixture is filtered and the cake is washed with a mixture of acetone and water at 2 volumes or 20.5 mL. The cake is then added a mixture of acetone and water (10 to 1) for ripening between 20° C.-35° C. over 24 hours to 48 hours. The slurry is filtered and the cake is dried under vacuum to a constant weight. The final weight is 5.48 grams.

Example 26

Crystalline Carvedilol Maleate Preparation

A suitable reactor is charged with acetone (56 mL). The acetone solution is sequentially charged with carvedilol (15.0 grams) and water (8 mL). Upon addition of the water, the slurry dissolves completely with heating. To the solution is added 1 M of aqueous Maleic acid (1 Equiv. 36.9 mL.) The reaction mixture is stirred at between 17° C. and 35° C. The solid precipitate is formed over 10 hours to 24 hours. Later, the mixture is filtered and the cake is washed with a mixture of acetone and water (10 to 1) at 3 volume or 45.0 mL. The cake is dried under vacuum to a constant weight. The final weight is 14.08 grams.

Example 27

Crystalline Carvedilol Glutarate Preparation

A suitable reactor is charged with 2 grams of carvedilol and a mixture of acetone and water (in a 7 to 1 ratio) at 8 mL. The contents were warmed to 35° C. to 40° C. to a clear solution. 1N D,L-Glutaric acid in water (1 equivalent. 4.9 mL.) is added to the solution. The resulting mixture is stirred at the temperature between 17° C. and 35° C. until the solid precipitate is formed over 10 hours to 24 hours. Subsequently, the mixture filtered and the cake is washed with a mixture of acetone and water (in a 10 to 1) at about 5 mL. The cake is then dried under vacuum to a constant weight. The final weight is 1.35 grams.

Example 28

Solubility Enhancement in the GI Tract

Background:
Drug absorption following oral dosage requires that drug first dissolves in the gastrointestinal milieu. In most cases such dissolution is primarily a function of drug solubility. If solubility is affected by pH it is likely that absorption will vary in different regions of the gastro intestinal tract, because pH varies from acidic in the stomach to more neutral values in the intestine.

Such pH-dependent solubility can complicate dosage form design when drug absorption needs to be prolonged, delayed or otherwise controlled, to evince a sustained or delayed action effect. Variations in solubility can lead to variable dissolution, absorption and subsequent therapeutic effect.

Carvedilol is a drug used to treat hypertension and congestive heart failure, being usually administered twice daily. For chronic diseases such as these a once-daily dosage regimen is desirable, to enhance patient compliance and reduce "pill burden". However, the dose response and time course of carvedilol in the body is such that a conventional dosage form, releasing all the drug immediately on ingestion does not provide once-a-day therapy. Release from the dosage form needs to be slowed down so that absorption and subsequent systemic residence is prolonged. This however requires that release and dissolution occurs along the GI tract, not just in the stomach.

The pH-dependent solubility of the currently used form of carvedilol (free base) is such that, while gastric solubility is adequate, solubility is much poorer at pH values encountered in the small intestine and beyond (see, FIG. 126), which depicts a pH-solubility profile for carvedilol.

Consequently, while drug dissolution rate and extent from an immediate release dosage form is likely to be acceptable (such dissolution occurring in the stomach) it could be inadequate in regions beyond the stomach, with absorption compromised as a consequence.

However, when drug is administered as a solution (in cyclodextrin in this example), directly to the colon it can be seen that absorption is significantly improved (FIG. 127, which depicts mean plasma profiles in beagle dogs following intra-colonic administration of a carvedilol solution containing Captisol or carvedilol in aqueous suspension). All this information suggests that absorption throughout the GI tract could be significant, provided that drug can be solubilised.

Moreover, solubilization may mean that drug stability is compromised. The secondary amino group of carvedilol is prone to chemically react with excipients normally included in a dosage form to aid manufacture, maintain quality or enhance dissolution rate. For example, this type of amine groups can react with aldehydes or ester functional groups through nucleophilic reactions. Many excipients have ester functional groups. Furthermore, aldehydes and other such residues are common residues in excipients. This often results in marginal or unacceptable chemical stability of conventionally formulated carvedilol dosage forms, where drug is simply blended with excipients before being compressed to tablets. As drug-excipient interactions are likely to be even faster in the solvated state it follows that solubilization does not provide facile resolution of dissolution-limited absorption challenges. This is illustrated in Table 12. Solutions of carvedilol in oleic acid degraded rapidly. Other approaches to solubilization evince the same effect. Thus solubilization might enhance absorption but is not a practical approach because of the destabilising effect.

TABLE 12

Drug content (mg/g) in carvedilol/Oleic acid solution during storage.

|  | Initial | 1 month at 25° C. | 3 months at 25° C. |
|---|---|---|---|
| 7.788% w/w carvedilol solution in Oleic acid | 76.6 | 71.3 | 64.3 |

It has now been unexpectedly shown that salts of carvedilol afford significant improvement in absorption from the lower GI tract in dogs over that seen when carvedilol base is used. There is no reason to believe that this surprising effect does not also apply to humans and it may be feasible as a consequence to design dosage forms that enable drug to be absorbed as the unit traverses the gastrointestinal tract. This ought to provide more gradual absorption and prolonged plasma profiles that facilitate once-a-day dosage.

The better absorption may be partially due to the better solubilities of salts of carvedilol. It can be seen from the data in Table 13 that citrate, hydrobromide and phosphate salts have much better aqueous solubility than the free base.

TABLE 13

Aqueous Solubility (expressed as mg of Carvedilol free base/mL of solution) at 25° C. for Carvedilol free base and three salts.

| Time | Free Base | Citrate salt | Phosphate salt | HBr salt |
|---|---|---|---|---|
| 1 hr | — | 1.64 (pH = 3.3) | 2.35 (pH = 3.0) | 0.62 (pH = 6.1) |
| 4 hr | — | 1.74 (pH = 3.2) | 2.25 (pH = 3.0) | 0.61 (pH = 6.3) |
| 24 hr | 0.024 (pH = 7.0) | 1.46 (pH = 3.2) | 2.21 (pH = 3.0) | 0.61 (pH = 6.2) |

Ostensibly, it can be claimed that these acidic salts simply generate low pH when dissolved in water (Table 13), leading to solubility enhancement (because of the pH/solubility relationship shown in FIG. 126). However, it is also possible that any pH-lowering effect contributed by the modest amounts of drug (that would be included in a dosage form to provide a therapeutic effect) would be readily swamped in the in vivo situation, with pH soon reverting to that of the general intestinal milieu. Consequently, any short term solubilization would be quickly negatived. However, it has been surprisingly shown that when pH is adjusted to neutral, the solubilities of salts remain higher than free base for a significant period, rather than equilibrating rapidly. Such prolonged solubility could be crucial in vivo, allowing dissolution and absorption to occur more readily at neutral pH than for free base (FIG. 128, which depicts dissolution/solubility profile of carvedilol phosphate in pH=7.1 Tris buffer (for comparison, carvedilol free base has a solubility of ~20-30 ug/mL at this pH).

Furthermore, it has been shown that, if carvedilol salts are dissolved in solubilizing agents, stability is much better than when free base is used in the same system (Table 14). Thus, if solubilizing agents were to be required in the formulation, to provide even greater solubility enhancement, salts would be preferred to the base because of such better stability.

TABLE 14

Chemical stability data of carvedilol/Vitamin E TPGS granulation containing carvedilol free base or carvedilol HBr salt.

| | Assay/Impurity after 1 month's storage at 40° C./75% RH (open vials) | |
|---|---|---|
| Formulation | % of initial level* | Total Impurities (% peak area) |
| Carvedilol free base granulation containing Vitamin E TPGS (Lot 200412-144) | 81.5* | 7.77 |
| Carvedilol HBr salt granulation containing Vitamin E TPGS (Lot 200746-102) | 89.9* | 0.15 |

*Lower % of nominal due to additional moisture in the system.

The foregoing facts and considerations suggest but do not provide conclusive proof that forms of carvedilol with superior solubility, whether effected by using a solvent to dissolve carvedilol base, or by using a carvedilol salt have better potential than conventionally formulated base for prolonged absorption along the GI tract. To provide stronger evidence that solubilization enhances absorption, formulations containing carvedilol base, formulated in a conventional manner, and also fully solvated by dissolving in n-methyl pyrrolidone were dosed to beagle dogs in units that were activated to make drug available after the dosage unit had passed the pyloric sphincter separating the stomach from the duodenum. Intestinal absorption efficiency was determined by monitoring plasma levels of carvedilol following such dosage. Results are provided in Table 5 and FIG. 128 (which depicts mean plasma profiles in beagle dogs following oral administration of the formulations listed in Table 15).

TABLE 15

Pharmacokinetic values following dosage of 10 mg carvedilol (base) to three fasted beagle dogs.

| Formulation | Solubility in pH 6.8 Phosphate Buffer Over 4-hour Period (ug/mL) | $C_{max}$ (ng/mL) | $T_{max}$ (min) | AUC (0-t) (ug · min/mL) |
|---|---|---|---|---|
| Carvedilol Pharmasolve ® Granulation | 86-120 | 31.32 ± 3.43 (n = 3) | $15^{b\text{-}}$, 30, $45^a$ (n = 3) | 4.03 ± 1.34 (n = 3) |
| Carvedilol Vitamin ETPGS Granulation | 108-94 | 16.26 ± 1.20 (n = 3) | 30, 120, $45^a$ (n = 3) | 2.75 ± 0.55 (n = 3) |
| Carvedilol in conventional granules | 29-36 | 13.08, 12.74, $2.89^a$ (n = 3) | 45, 30, $120^a$ (n = 3) | 2.14, 1.19, $0.60^a$ (n = 3) |

$^a$= values listed individually due to large variability; animals always listed in the same order. AUC(0-t) refers to the area from time 0 to the last quantifiable concentration.
$^b$= Pharmasolve ® capsule was leaking slightly before firing in-vivo.

It can be seen that, when drug was fully dissolved absorption was rapid and high, contrasting with lower concentrations in dogs that were dosed intraduodenally with base in a conventional solid dosage unit. These findings indicated that bioavailability from carvedilol base in the small intestine is constrained by its low solubility at neutral pH. When units introduced to the stomach the low gastric pH can be expected to facilitate dissolution and absorption but this will not be the case in the more neutral small intestine or beyond.

A further dog study utilised salts of carvedilol, formulated using conventional (non-solubilizing) excipients. The mode of dosage was the same as for the first dog study, the formulations being delivered such that drug did not become available until units were beyond the gastric milieu. Results are provided in Table 16 and FIG. 129 (which depicts mean plasma profiles following oral administration of Companion capsules filled with four formulations at 10 mg strength to Beagle dogs).

TABLE 16

Pharmacokinetic analysis of 10 mg dose formulations in three fasted beagle dogs from study DM18086-38.

| Formulation | $C_{max}$ (ng/mL) | $T_{max}$ (min) | AUC (0-t)[a] (ug · min/mL) | AUC (0-inf) (ug · min/mL) |
|---|---|---|---|---|
| Carvedilol HBr Salt granules | 12.9 ± 7.11 | 45 ± 15 | 2.22 ± 1.37 | 2.35 ± 1.46 |
| Carvedilol Phosphate Salt Granules[b] | 61.8, 28.4 | 45, 60 | 6.69, 4.56 | 6.75, 4.90 |
| Carvedilol Citrate Salt Granules | 30.4 ± 16.9 | 45 ± 15 | 4.41 ± 2.43 | 4.66 ± 2.54 |
| Carvedilol Base Granulesx[c] | 13.08, 12.74, 2.89 | 45, 30, 120 | 2.14, 1.19, 0.60 | — |

[a]AUC(0-t) refers to the area from time 0 to the last quantifiable concentration
[b]n = 2 only, due to malfunction of one InteliSite ® Companion capsule; animals always listed in the same order
[c]data from dog study DI01251; values listed individually due to large variability; animals always listed in the same order.

The findings from the second dog study, illustrated graphically in FIG. 130 conclusively showed that drug, administered in salt form was rapidly and more completely absorbed than the free base form.

It is to be understood that the invention is not limited to the embodiments illustrated hereinabove and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A compound which is a carvedilol mandelate salt.

2. The compound according to claim 1 having an FT-IR spectrum pattern which comprises characteristic peaks in wavenumbers (cm$^{-1}$) as substantially shown in FIG. 114.

3. The compound according to claim 2 having characteristic peaks from 0 wavenumbers (cm$^{-1}$) to 4000 wavenumbers (cm$^{-1}$) at about 699 cm$^{-1}$, 723 cm$^{-1}$, 752 cm$^{-1}$, 784 cm$^{-1}$, 1053 cm$^{-1}$, 1583 cm$^{-1}$, 1631 cm$^{-1}$, 3189 cm$^{-1}$, 3246 cm$^{-1}$, and 3396 cm$^{-1}$.

4. The compound according to claim 1 having an FT-Raman spectrum pattern which comprises characteristic peaks in wavenumbers (cm$^{-1}$) as substantially shown in FIG. 115.

5. The compound according to claim 4 having characteristic peaks from 0 wavenumbers (cm$^{-1}$) to 4000 wavenumbers (cm$^{-1}$) at about 233 cm$^{-1}$, 252 cm$^{-1}$, 322 cm$^{-1}$, 359 cm$^{-1}$, 423 cm$^{-1}$, 744 cm$^{-1}$, 1002 cm$^{-1}$, 1286 cm$^{-1}$, 1631 cm$^{-1}$, 3052 cm$^{-1}$, 3063 cm$^{-1}$, and 3077 cm$^{-1}$.

6. A compound which is a carvedilol lactate salt.

7. The compound according to claim 6 having an FT-IR spectrum pattern which comprises characteristic peaks in wavenumbers (cm$^{-1}$) as substantially shown in FIG. 116.

8. The compound according to claim 7 having characteristic peaks from 0 wavenumbers (cm$^{-1}$) to 4000 wavenumbers (cm$^{-1}$) at about 720 cm$^{-1}$, 753 cm$^{-1}$, 785 cm$^{-1}$, 1097 cm$^{-1}$, 1124 cm$^{-1}$, 1253 cm$^{-1}$, 1584 cm$^{-1}$, and 3396 cm$^{-1}$.

9. The compound according to claim 6 having an FT-Raman spectrum pattern which comprises characteristic peaks in wavenumbers (cm$^{-1}$) as substantially shown in FIG. 117.

10. The compound according to claim 9 having characteristic peaks from 0 wavenumbers (cm$^{-1}$) to 4000 wavenumbers (cm$^{-1}$) at about 321 cm$^{-1}$, 422 cm$^{-1}$, 549 cm$^{-1}$, 765 cm$^{-1}$, 1015 cm$^{-1}$, 1284 cm$^{-1}$, 1626 cm$^{-1}$, 3066 cm$^{-1}$, and 3078 cm$^{-1}$.

11. A compound which is a carvedilol maleate salt.

12. The compound according to claim 11 having an FT-IR spectrum pattern which comprises characteristic peaks in wavenumbers (cm$^{-1}$) as substantially shown in FIG. 118.

13. The compound according to claim 12 having characteristic peaks from 0 wavenumbers (cm$^{-1}$) to 4000 wavenumbers (cm$^{-1}$) at about 725 cm$^{-1}$, 741 cm$^{-1}$, 756 cm$^{-1}$, 786 cm$^{-1}$, 1024 cm$^{-1}$, 1109 cm$^{-1}$, 1215 cm$^{-1}$, 1586 cm$^{-1}$, and 3481 cm$^{-1}$.

14. The compound according to claim 11 having an FT-Raman spectrum pattern which comprises characteristic peaks in wavenumbers (cm$^{-1}$) as substantially shown in FIG. 119.

15. The compound according to claim 14 having characteristic peaks from 0 wavenumbers (cm$^{-1}$) to 4000 wavenumbers (cm$^{-1}$) at about 249 cm$^{-1}$, 324 cm$^{-1}$, 423 cm$^{-1}$, 549 cm$^{-1}$, 751 cm$^{-1}$, 1012 cm$^{-1}$, 1216 cm$^{-1}$, 1286 cm$^{-1}$, 1629 cm$^{-1}$, and 3070 cm$^{-1}$.

16. A compound which is a carvedilol sulfate salt.

17. The compound according to claim 16 having an FT-IR spectrum pattern which comprises characteristic peaks in wavenumbers (cm$^{-1}$) as substantially shown in FIG. 120.

18. The compound according to claim 17 having characteristic peaks from 0 wavenumbers (cm$^{-1}$) to 4000 wavenumbers (cm$^{-1}$) at about 727 cm$^{-1}$, 743 cm$^{-1}$, 787 cm$^{-1}$, 1026 cm$^{-1}$, 1089 cm$^{-1}$, 1251 cm$^{-1}$, 1215 cm$^{-1}$, 1586 cm$^{-1}$, 1604 cm$^{-1}$, and 3230 cm$^{-1}$.

19. The compound according to claim 16 having an FT-Raman spectrum pattern which comprises characteristic peaks in wavenumbers (cm$^{-1}$) as substantially shown in FIG. 121.

20. The compound according to claim 19 having characteristic peaks from 0 wavenumbers (cm$^{-1}$) to 4000 wavenumbers (cm$^{-1}$) at about 242 cm$^{-1}$, 318 cm$^{-1}$, 423 cm$^{-1}$, 549 cm$^{-1}$, 1014 cm$^{-1}$, 1214 cm$^{-1}$, 1282 cm$^{-1}$, 1627 cm$^{-1}$, 2969 cm$^{-1}$, and 3066 cm$^{-1}$.

21. A compound which is a carvedilol glutarate salt.

22. The compound according to claim 21 having an FT-IR spectrum pattern which comprises characteristic peaks in wavenumbers (cm$^{-1}$) as substantially shown in FIG. 122.

23. The compound according to claim 22 having characteristic peaks from 0 wavenumbers (cm$^{-1}$) to 4000 wavenumbers (cm$^{-1}$) at about 724 cm$^{-1}$, 743 cm$^{-1}$, 786 cm$^{-1}$, 1024 cm$^{-1}$, 1044 cm$^{-1}$, 1089 cm$^{-1}$, 1251 cm$^{-1}$, 1586 cm$^{-1}$, 1604 cm$^{-1}$, and 3229 cm$^{-1}$.

24. The compound according to claim 21 having an FT-Raman spectrum pattern which comprises characteristic peaks in wavenumbers (cm$^{-1}$) as substantially shown in FIG. 123.

25. The compound according to claim 24 having characteristic peaks from 0 wavenumbers (cm$^{-1}$) to 4000 wavenumbers (cm$^{-1}$) at about 141 cm$^{-1}$, 246 cm$^{-1}$, 322 cm$^{-1}$, 423 cm$^{-1}$, 551 cm$^{-1}$, 749 cm$^{-1}$, 1011 cm$^{-1}$, 1213 cm$^{-1}$, 1284 cm$^{-1}$, 1628 cm$^{-1}$, 2934 cm$^{-1}$, and 3073 cm$^{-1}$.

26. A compound which is a carvedilol benzoate salt.

27. The compound according to claim 21 having an FT-IR spectrum pattern which comprises characteristic peaks in wavenumbers (cm$^{-1}$) as substantially shown in FIG. 124.

28. The compound according to claim 22 having characteristic peaks from 0 wavenumbers (cm$^{-1}$) to 4000 wavenumbers (cm$^{-1}$) at about 672 cm$^{-1}$, 718 cm$^{-1}$, 754 cm$^{-1}$, 767 cm$^{-1}$, 1022 cm$^{-1}$, 1041 cm$^{-1}$, 1106 cm$^{-1}$, 1260 cm$^{-1}$, 1498 cm$^{-1}$, 1582 cm$^{-1}$, 1604 cm$^{-1}$, 1626 cm$^{-1}$, 2932 cm$^{-1}$, 3184 cm$^{-1}$, and 3428 cm$^{-1}$.

29. The compound according to claim 21 having an FT-Raman spectrum pattern which comprises characteristic peaks in wavenumbers (cm$^{-1}$) as substantially shown in FIG. 125.

30. The compound according to claim 24 having characteristic peaks from 0 wavenumbers (cm$^{-1}$) to 4000 wavenumbers (cm$^{-1}$) at about 108 cm$^{-1}$, 244 cm$^{-1}$, 424 cm$^{-1}$, 538 cm$^{-1}$, 549 cm$^{-1}$, 728 cm$^{-1}$, 1001 cm$^{-1}$, 1015 cm$^{-1}$, 1128 cm$^{-1}$, 1286 cm$^{-1}$, 1598 cm$^{-1}$, 1626 cm$^{-1}$, 2934 cm$^{-1}$, 3058 cm$^{-1}$, and 3072 cm$^{-1}$.

31. A pharmaceutical composition comprising the compound according to claim 1 and a pharmaceutically acceptable adjuvant, carrier, diluent, and/or excipient.

32. A pharmaceutical composition comprising the compound according to claim 6 and a pharmaceutically acceptable adjuvant, carrier, diluent, and/or excipient.

33. A pharmaceutical composition comprising the compound according to claim 11 and a pharmaceutically acceptable adjuvant, carrier, diluent, and/or excipient.

34. A pharmaceutical composition comprising the compound according to claim 16 and a pharmaceutically acceptable carrier.

35. A pharmaceutical composition comprising the compound according to claim 21 and a pharmaceutically acceptable carrier.

36. A pharmaceutical composition comprising the compound according to claim 26 and a pharmaceutically acceptable carrier.

37. A method of treating hypertension, congestive heart failure or angina which comprises administering to a subject in need thereof an effective amount of the compound according to claim 1.

38. A method of treating hypertension, congestive heart failure or angina which comprises administering to a subject in need thereof an effective amount of the compound according to claim 6.

39. A method of treating hypertension, congestive heart failure or angina which comprises administering to a subject in need thereof an effective amount of the compound according to claim 11.

40. A method of treating hypertension, congestive heart failure or angina which comprises administering to a subject in need thereof an effective amount of the compound according to claim 16.

41. A method of treating hypertension, congestive heart failure or angina which comprises administering to a subject in need thereof an effective amount of the compound according to claim 21.

42. A method of treating hypertension, congestive heart failure or angina which comprises administering to a subject in need thereof an effective amount of the compound according to claim 26.

43. A method of treating hypertension, congestive heart failure or angina which comprises administering to a subject in need thereof an effective amount of the pharmaceutical composition according to claim 31.

44. A method of treating hypertension, congestive heart failure or angina which comprises administering to a subject in need thereof an effective amount of the pharmaceutical composition according to claim 32.

45. A method of treating hypertension, congestive heart failure or angina which comprises administering to a subject in need thereof an effective amount of the pharmaceutical composition according to claim 33.

46. A method of treating hypertension, congestive heart failure or angina which comprises administering to a subject in need thereof an effective amount of the pharmaceutical composition according to claim 34.

47. A method of treating hypertension, congestive heart failure or angina which comprises administering to a subject in need thereof an effective amount of the pharmaceutical composition according to claim 35.

48. A method of treating hypertension, congestive heart failure or angina which comprises administering to a subject in need thereof an effective amount of the pharmaceutical composition according to claim 36.

* * * * *